US011707522B2

(12) United States Patent
Rainey et al.

(10) Patent No.: US 11,707,522 B2
(45) Date of Patent: Jul. 25, 2023

(54) HUMAN ANTIBODIES TO TN ANTIGEN

(71) Applicant: Boehringer Ingelheim International GmbH, Ingelheim am Rhein (DE)

(72) Inventors: Godfrey Jonah Anderson Rainey, San Diego, CA (US); Wolfgang Walter Scholz, San Diego, CA (US); Ritsuko Sawada, San Diego, CA (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 755 days.

(21) Appl. No.: 16/158,688

(22) Filed: Oct. 12, 2018

(65) Prior Publication Data

US 2019/0111164 A1    Apr. 18, 2019

Related U.S. Application Data

(60) Provisional application No. 62/657,661, filed on Apr. 13, 2018, provisional application No. 62/656,933, filed on Apr. 12, 2018, provisional application No. 62/572,383, filed on Oct. 13, 2017.

(51) Int. Cl.
| | |
|---|---|
| *A61K 39/395* | (2006.01) |
| *C07K 16/30* | (2006.01) |
| *C07K 16/44* | (2006.01) |
| *A61K 47/68* | (2017.01) |
| *A61K 47/64* | (2017.01) |
| *A61P 35/00* | (2006.01) |
| *A61K 51/10* | (2006.01) |

(52) U.S. Cl.
CPC .... *A61K 39/39558* (2013.01); *A61K 47/6415* (2017.08); *A61K 47/6803* (2017.08); *A61K 51/1072* (2013.01); *A61P 35/00* (2018.01); *C07K 16/3015* (2013.01); *C07K 16/3092* (2013.01); *C07K 16/44* (2013.01); *C07K 2317/21* (2013.01); *C07K 2317/34* (2013.01); *C07K 2317/565* (2013.01); *C07K 2317/732* (2013.01); *C07K 2317/77* (2013.01); *C07K 2317/92* (2013.01)

(58) Field of Classification Search
CPC .......................... C07K 16/30; A61K 39/39558
See application file for complete search history.

(56) References Cited

PUBLICATIONS

Bendig M. M. (Methods: A Companion to Methods in Enzymology, 1995; 8:83-93) (Year: 1995).*
Portolano (The Journal of Immunology, vol. 150, No. 3, p. 880-887, 1993) (Year: 1993).*
Johnson and Wu (Methods in Molecular Biology, Antibody Engineering: Methods and Protocols, vol. 248, p. 11-25, 2004) (Year: 2004).*
Rudikoff et al. (Proc Natl Acad Sci USA 79: 1979-1983, 1982) (Year: 1982).*
Paul (Fundamental Immunology, 3rd Edition, 1993, pp. 292-295) (Year: 1993).*
Wall (Theriogenology, vol. 45, p. 57-68, 1996) (Year: 1996).*
Houdebine (Journal of Biotechnology, vol. 34, p. 269- 287, 1994) (Year: 1994).*
Kappell (Current Opinions in Biotechnology, vol. 3, p. 548-553, 1992) (Year: 1992).*
Eavarone, Siamab, Novel Humanized, anti-Sialyl-Tn, anti-CD3 bispecific antibiodies demonstrate tumor and T-cell specificity for immune activation at the tumor site, 2014.
Persson, Chemical Biology, Epitope Mapping of a new anti-Tn antibodydetecting gastric cancer cells, 2017.
Borgert, National Institute of Health, Deciphering Structural Elements of Mucin Glycoprotein, 2012.
Posey, Immunity, Engineered CAR T cellstargeting the Cancer-Associated Tn-Glycoform of the Membrane Mucin MUC1 control Adenocarcinoma, 2016.
Sakai, J. Biochem, Isolation and characterization of antibodies against three consectutive Tn antigen clusters, vol. 147, 2010.
Zhang, Int. J. Cancer, Selection of Tumor Antigens as targets for Immune attack, vol. 73, 1997.
Shi, Molecular Immunolgy, CD3/DC28 dynabeads induce expression of Tn antigen in human T cells, vol. 90, 2007.
Van vliet, Journal of Biological Chem, Human T cell acitvation results in extracellular signal related kinase, vol. 288, 2013.
Blixt, Glycobiology, Analysis of Tn antigenicity with a panel with a new IgM and IgG1 monoclonal antibodies, vol. 22, 2012.
Matsumoto, Identification of Tn antigen O-GalNAc-expressing glycoproteins in human carcinomas using novel anti-Tn recombinant antibodies, Glycobiology, vol. 30, 2019, p. 282-300.

* cited by examiner

*Primary Examiner* — Michael Allen
(74) *Attorney, Agent, or Firm* — Wendy M. Gombert

(57) ABSTRACT

The present invention provides compositions for the production of an antibody or functional fragment thereof directed against Tn antigen or sTn antigen. The compositions disclosed herein include isolated antibody or functional fragments thereof that binds to Tn antigen or sTn antigen and polynucleotides encoding the heavy chain and/or a light chain variable domains of such antibody or functional fragment. The invention also provides methods of treating or preventing a disease, such as cancer or tumor formation, wherein the antibody or functional fragment includes a variable heavy chain domain and a variable light chain domain that has an amino acid sequence provided herein. The invention further provides a conjugate of an antibody or functional fragment thereof conjugated or recombinantly fused to a localizing agent, detectable agent or therapeutic agent, and methods of treating, preventing or diagnosing a disease in a subject in need thereof.

15 Claims, 43 Drawing Sheets
Specification includes a Sequence Listing.

| | | | | | |
|---|---|---|---|---|---|
| 2F3   | EVQLLESGGG | LVQPGGSLRL | SCAASGFTFD | SYAMSWVRQA | PGKGLEWVSA |
| 3A7   | QVQLVQSGGG | LVQPGETLRL | SCEASGFTFR | SYYMSWVRQA | PRKGLEWVAS |
| 1G10  | QVQLVQSGAE | VKKPGASVKV | SCKASGYTFT | SYDINWVRQA | TGQGLEWMGW |
| 2A8   | QVQLVGSGAE | VKKPGASVKV | SCKASGYTFT | SYDINWVRQA | TGQGLEWMGW |
| 1E2b  | QVQLQQSGAE | VKKPGASVKV | SCKATGYTFT | SYGISWVRQA | PGQGLEWMGW |
| 1A4   | QLQLVESGGG | LVQPGGSLRL | SCAASGFTFS | DGYMDWIRQA | PGKGLEWVGR |
| 1A12b | QVQLVESGGG | LVQPGGSLRL | SCAVSGFTFS | DHYMDWVRQA | PGKGLEWVGR |

| | | | | | |
|---|---|---|---|---|---|
| 2F3   | I..SGSGDST | YYADSVKGRF | SISRDNSKNT | LYLQMNSLRA | EDTAVYYCAI |
| 3A7   | I..NQHGSEK | YYVDSVKGRF | TISRDNAKNS | LYLQMISLRA | EDTAVYYCAR |
| 1G10  | M..NPNSGNT | GYAQKFQGRV | TMTRNTSIST | AYMELSSLRS | EDTAVYYCAR |
| 2A8   | M..NPNSGNT | GYAQKFQGRV | TMTRNTSIST | AYMELSSLRS | EDTAVYYCAR |
| 1E2b  | I..SAYNGNT | NYAQKLQGRV | TMTTDTSTST | AYMELRSLRS | DDTAVYYCAR |
| 1A4   | IRNKANRYTT | DYAASVKGRF | IISRDDSKNS | LYLQMNRLRI | EDTAVYYCVR |
| 1A12b | IRNKANSYTT | EYAASVKGRF | TISRDESKRS | LYLQMNSLKT | EDTAVYYCAR |

| | | | | | |
|---|---|---|---|---|---|
| 2F3   | RREYSGYA.. | ..PFDYWGQG | TLVTVSSGSA | SAPTLFPLVS | CENSPSDTSS |
| 3A7   | DGDRTT.... | ......DYWGQG | TLVTVSSRSA | SAPTLFPLVS | CENSPSDTSS |
| 1G10  | GWRYSSSWYR | KVRFDPWGQG | TLVTVSSGSA | SAPTLFPLVS | CENSPSDTSS |
| 2A8   | ANRKGA...R | TRAFDYWGQG | TLVTVSSGSA | SAPTLFPLVS | CENSPSDTSS |
| 1E2b  | GGGTTVLDYY | RYGMDVWGQG | TTVTVSSGSA | SAPTLFPLVS | CENSPSDTSS |
| 1A4   | VTAVAL.... | ......DYWGQG | TLVTVSSGSA | SAPTLFPLVS | CENSPSDTSS |
| 1A12b | VSYYAM.... | ......DVWGQG | TTVTVSSAST | KGPSVFPLAP | SSKSTSG.GT |

| | | | | | |
|---|---|---|---|---|---|
| 2F3   | VAVGCLAQDF | LPDSITFSWK | YKNNSDISST | RGFPSVLRGG | KYAATSQVLL |
| 3A7   | VAVGCLAQDF | LPDSITFSWK | YKNNSDISST | RGFPSVLRGG | KYAATSQVLL |
| 1G10  | VXVGCLAQDF | LPDSITFSWK | YKNNSDISST | RGFPSVLRGG | KYAATSQVLL |
| 2A8   | VAVGCLAQDF | LPDSITFSWK | YKNNSDISST | RGFPSVLRGG | KYAATSQVLL |
| 1E2b  | VAVGCLAQDF | LPDSITFSWK | YKNNSDISST | RGFPSVLRGG | KYAATSQVLL |
| 1A4   | VAVGCLAQDF | LPDSITFSWK | YKNNSDISST | RGFPSVLRGG | KYAATSQVLL |
| 1A12b | AALGCLVKDY | FPEPVTVSWN | ..SGALTSGV | HTFPAVLQSS | GLYSLSSVVT |

| | | | | |
|---|---|---|---|---|
| 2F3   | PSKDVMQGTD | EHVVCKVQHP | NGNKEKNVPL | PV (SEQ ID NO: 77) |
| 3A7   | PSKDVMQGTD | EHVVCKVQHP | NGNKEKNVPL | PV (SEQ ID NO: 78) |
| 1G10  | PSKDVMQGTD | EHVVCKVQHP | NGNKEKNVPL | PV (SEQ ID NO: 75) |
| 2A8   | PSKDVMQGTD | EHVVCKVQHP | NGNKEKNVPL | PV (SEQ ID NO: 76) |
| 1E2b  | PSKDVMQGTD | EHVVCKVQHP | NGNKEKNVPL | PV (SEQ ID NO: 74) |
| 1A4   | PSKDVMQGTD | EHVVCKVQHP | NGNKEKNVPL | PV (SEQ ID NO: 73) |
| 1A12b | VPSSSLGTQT | YICNVNHKPS | NTKVDKKVEP | KS (SEQ ID NO: 72) |

Fig. 1

```
1A12b       EIVLTQSPSS LSASVGDRVT ITC░░░░░ ░░░░░░░░W YQQKPGKAPK
2F3         DIVMTQTPSS LSASVGDRVT ITC░░░░░ ░░░░░░░░W YQQKPEKAPR
1A4         DVVMTQSPAT LSLSPGERAT LSC░░░░░ ░░░░░░░░W YQQKPGQAPT
3A7         ETTLTQSPAT LSLSPGDRAT LSC░░░░░ ░░░░░░░░W YQQKFGQAPR
1G10        ETTLTQSPLS LPVTPGEPAS ISC░░░░░ ░░░░░░░░W YLQKPGQSPQ
1E2b        .QSVLTQPPS LSASPGASAS LTC░░░░░ ░░░░░░░░W YQQKPGSPPQ
2A8\L17     .QSVLIQPPS VSAAPGQKVT ISC░░░░░ ░░░░░░░░W YQQLPGTAPK

1A12b       LLIY....░░ ░░░░░GVPSR FSGSGSGTDF T..LTISSLQ PEDFATYYC░
2F3         SLIY....░░ ░░░░░GVPSR FSGSGSGTDF T..LTISSLQ PEDFATYYC░
1A4         LLIY....░░ ░░░░░GIPAR FSGRGSGTDF T..LTISSLE PEDFAVYYC░
3A7         LLIY....░░ ░░░░░GIPAR FSGSGSGTDF T..LTISSLE PEDFAVYYC░
1G10        LLIY....░░ ░░░░░GVPDR FSGSGSGTDF T..LKISRVE AEDVGVYYC░
1E2b        YLLR░░░░░░ ░░░░░GVPSR FSGSKDASAN AGILLISGLQ SEDEADYYC░
2A8         LLIY....░░ ░░░░░GIPVR FSGSKSGTSA T..LGITGLQ TGDEADYYC░

1A12b       ░░░░░░░░░F GQGTKVEI.K RAVAAPSVFI FPPSDEQLKS GTASVVCLLN
2F3         ░░░░░░░░░F GQGTKLEI.K RTVAAPSVFI FPPSDEQLKS GTASVVCLLN
1A4         ░░░░░░░░░F GQGTRLEI.K RTVAAPSVFI FPPSDEQLKS GTASVVCLLN
3A7         ░░░░░░░░░F GPGTKVDI.K RTVAAPSVFI FPPSDEQLKS GTASVVCLLN
1G10        ░░░░░░░░░F GQGTRLEI.K RTVAAPSVFI FPPSDEQLKS GTASVVCLLN
1E2b        ░░░░░░░░░F GGGTKLTVLG QPKAAPSVTL FPPSSEELQA NKATLVCLIS
2A8         ░░░░░░░░░F GTGTKVTVLG QPKANPTVTL FPPSSEELQA NKATLVCLIS

1A12b       NFYPREAKVQ WKVDNALQSG NSQESVTEQD SKDSTYSLSS TLTLSKADYE
2F3         NFYPREAKVQ WKVDNALQSG NSQESVTEQD SKDSTYSLSS TLTLSKADYE
1A4         NFYPREAKVQ WKVDNALQSG NSQESVTEQD SKDSTYSLSS TLTLSKADYE
3A7         NFYPREAKVQ WKVDNALQSG NSQESVTEQD SKDSTYSLSS TLTLSKADYE
1G10        NFYPREAKVQ WKVDNALQSG NSQESVTEQD SKDSTYSLSS TLTLSKADYE
1E2b        DFYPGAVTVA WKADSSPVKA GV.ETTTPSK QSNNKYAASS YLSLTPEQWK
2A8         DFYPGAVTVA WKADSSPVKA GV.ETTTPSK QSNNKYAASS YLSLTPEQWK

1A12b       KHKVYACEVT HQGLSSPVTK SFNRGEC  (SEQ ID NO: 79)
2F3         KHKVYACEVT HQGLSSPVTK SFNRGEC  (SEQ ID NO: 84)
1A4         KHKVYACEVT HQGLSSPVTK SFNRGEC  (SEQ ID NO: 80)
3A7         KHKVYACEVT HQGLSSPVTK SFNRGEC  (SEQ ID NO: 85)
1G10        KHKVYACEVT HQGLSSPVTK SFNRGEC  (SEQ ID NO: 82)
1E2b        SHRSYSCQVT HEGSTVEKTV APTEC..  (SEQ ID NO: 81)
2A8         SHRSYSCQVT HEGSTVEKTV APTECS.  (SEQ ID NO: 83)
```

Fig. 2

```
                         1           2           3           4           5
               1         0           0           0           0           0
2F3#289        EVQLLESGGG  LVQPGGSLRL  SCAASGFTFD  SYAMSWVRQA  PGKGLEWVSA
2F3\Original   QITLRESGGG  LVQPGGSLRL  SCAASGFTFD  SYAMSWVRQA  PGKGLEWVSA 555         6           7           8 88888      9
               223         0           0           0 22223      0
               A                                     ABC
2F3#289        ISGSGDSTYY  ADSVKGRFSI  SRDNSKNTLY  LQMNSLRAED  TAVYYCAIRR
2F3\Original   ISGSGDSTYY  ADSVKGRFSI  SRDNSKNTLY  LQMNSLRAED  TAVYYCAIRR 111111      1  1
               000000      1  1
               000001      0  3
               ABCD
2F3#289        EYSGYAPFDY  WGQGTLVTVS  S  (SEQ ID NO: 114)
2F3\Original   EYSGYAPFDY  WGQGTLVTVS  S  (SEQ ID NO: 105)
```

Fig. 3

```
                         1           2           3           4           5
           1             0           0           0           0           0
2F3#27     QVTLKESGGG  LVQPGGFLRL  SCAASGFTFD  SYAMSWVRQA  PGKGLEWVSA
2F3#51     QVTLKESGGG  LVQPGGSLRL  SCAASGFTFD  SYAMSWVRQA  PGKGLEWVSA
2F3#17     QITLRESGGG  LVQPGGSLRL  SCAASGFTFD  SYAMSWVRQA  PGKGLEWVSA
2F3#33     QITLRESGGG  LVQPGGSLRL  SCAASGFTFD  SYAMSWVQQA  PGKGLEWVSA
2F3#80     QITLKESGGG  LVQPGGSLRL  SCAASGFTFD  SYAMSWIRQA  PGKGLEWVSA
2F3#75     QVQLVESGGG  LVQPGGSLRL  SCAASGFTFD  SYAMSWVRQA  PGKGLEWVSA
2F3#50     QVTLRESVGG  LVQPGGSLRL  SCAASGFTFD  SYAMSWVRQA  PGKGLEWVSA
2F3#289    EVQLLESGGG  LVQPGGSLRL  SCAASGFTFD  SYAMSWVRQA  PGKGLEWVSA
2F3#6      QVQLLESGGG  LVQPGGSLRL  SCAASGFTFD  SYAMSWVRQA  PGKGLEWVSA 555         6           7           8 88888     9
                         223         0           0           0 22223     0
                         A                                     ABC
2F3#27     ISGSGDSTYY  ADSVKGRFSI  SRDNSKNTLY  LQMNSLRAED  TAVYYCAIRR
2F3#51     ISGSGDSTYY  ADSVKGRFSI  SRDNSKNTLY  LQMNSLRAED  TAVYYCAIRR
2F3#17     ISGSGHSTYY  ADSVKGRFSI  SRDNSKNTLY  LQMNNLRAED  TAVYYCAIRR
2F3#33     ISGSGDSTYY  ADSVKGRFSI  SRDNSKNTLY  LQMNSLRAED  TAVYYCAIRR
2F3#80     ISGSGDSTYY  ANSVKGRFSI  SRDNSKNTLY  LQMNSLRAED  TAVYYCAIRR
2F3#75     ISGSGDSTYY  ADSVKGRFSI  SRDNSKNTLY  LQMNSLRAED  AAVYYCAIRR
2F3#50     ISGSGDSTYY  ADSMKGRFSI  SRDNSKNTLY  LQMNSLRAED  TAVYYCAIRR
2F3#289    ISGSGDSTYY  ADSVKGRFSI  SRDNSKNTLY  LQMNSLRAED  TAVYYCAIRR
2F3#6      ISGSGASTYY  ADSVKGRFSI  SRDNSKNTLY  LQMNSLRAED  TAVYYCAIRR 111111      1           1
                         000000      1           1
                         000001      0           3
                         ABCD
2F3#27     EYSGYAPFDY  WGQGTLVTVS  S  (SEQ ID NO: 115)
2F3#51     EYSGYAPFDY  WGKGTLVTVS  S  (SEQ ID NO: 116)
2F3#17     EYSGYAPFDY  WGQGTLVT..  .  (SEQ ID NO: 117)
2F3#33     EYSGYTPFDY  WGQGTLVTVS  S  (SEQ ID NO: 118)
2F3#80     EYSGYAPFDY  WGQGTLVTVS  S  (SEQ ID NO: 119)
2F3#75     EYSGYAPFDY  WGQGTLVTVS  S  (SEQ ID NO: 120)
2F3#50     EYSGYAPFDY  WGQGTLVTVS  S  (SEQ ID NO: 121)
2F3#289    EYSGYAPFDY  WGQGTLVTVS  S  (SEQ ID NO: 114)
2F3#6      EYSGYAPFDY  WGQGTLVIVS  S  (SEQ ID NO: 122)
```

Fig. 4

```
                  1           2           3           4           5
           1      0           0           0           0           0
2F3#17     QITLRESGGG  LVQPGGSLRL  SCAAS GFTFD  SYA MSWVRQA  PGKGLEWVSA
2F3#17V2   QITLRESGGG  LVQPGGSLRL  SCAAS GFTFD  SYA MSWVRQA  PGKGLEWVSA 555         6           7           8 88888       9
           223         0           0           0 22223       0
           A                                     ABC
2F3#17     ISGSGHST YY  ADSVKGRFSI  SRDNSKNTLY  LQMNNLRAED  TAVYYC AIRR
2F3#17V2   ISGSGHST YY  ADSVKGRFSI  SRDNSKNTLY  LQMNNLRAED  TAVYYC AIRR 111111      1   1
           000000      1   1
           000001      0   3
           ABCD
2F3#17     EYSGYAPFDY  WGQGTLVT. . .  (SEQ ID NO: 117)
2F3#17V2   EYSGYAPFDY  WGQGTLVTVS  S  (SEQ ID NO: 123)
```

Fig. 5

```
                    1          2          3          4          5
           1        0          0          0          0          0
2F3CDR2R   EVQLLESGGG LVQPGGSLRL SCAAS GFTFD SYA MSWVRQA PGKGLEWVSA
2F3CDR2Y   EVQLLESGGG LVQPGGSLRL SCAAS GFTFD SYA MSWVRQA PGKGLEWVSA
2F3CDR2F   EVQLLESGGG LVQPGGSLRL SCAAS GFTFD SYA MSWVRQA PGKGLEWVSA
2F3#289    EVQLLESGGG LVQPGGSLRL SCAAS GFTFD SYA MSWVRQA PGKGLEWVSA
2F3#6      QVQLLESGGG LVQPGGSLRL SCAAS GFTFD SYA MSWVRQA PGKGLEWVSA
2F3#17V2   QITLRESGGG LVQPGGSLRL SCAAS GFTFD SYA MSWVRQA PGKGLEWVSA 555        6          7          8 88888    9
           223        0          0          0 22223    0
           A                                ABC
2F3CDR2R   ISGSGRST YY ADSVKGRFSI SRDNSKNTLY LQMNSLRAED TAVYYC AIRR
2F3CDR2Y   ISGSGYST YY ADSVKGRFSI SRDNSKNTLY LQMNSLRAED TAVYYC AIRR
2F3CDR2F   ISGSGFST YY ADSVKGRFSI SRDNSKNTLY LQMNSLRAED TAVYYC AIRR
2F3#289    ISGSGIST YY ADSVKGRFSI SRDNSKNTLY LQMNSLRAED TAVYYC AIRR
2F3#6      ISGSGAST YY ADSVKGRFSI SRDNSKNTLY LQMNSLRAED TAVYYC AIRR
2F3#17V2   ISGSGHST YY ADSVKGRFSI SRDNSKNTLY LQMNNLRAED TAVYYC AIRR 111111     1  1
           000000     1  1
           000001     0  3
           ABCD
2F3CDR2R   EYSGYAPFDY WGQGTLVTVS S (SEQ ID NO: 124)
2F3CDR2Y   EYSGYAPFDY WGQGTLVTVS S (SEQ ID NO: 125)
2F3CDR2F   EYSGYAPFDY WGQGTLVTVS S (SEQ ID NO: 126)
2F3#289    EYSGYAPFDY WGQGTLVTVS S (SEQ ID NO: 114)
2F3#6      EYSGYAPFDY WGQGTLVTVS S (SEQ ID NO: 122)
2F3#17V2   EYSGYAPFDY WGQGTLVTVS S (SEQ ID NO: 123)
```

Fig. 6

```
                            1          2          3           4           5
                   1        0          0          0           0           0
2F3#1733    QITLRESGGG LVQPGGSLRL SCAASGFTFD  SYAMSWVRQA PGKGLEWVSA
2F3#17V2    QITLRESGGG LVQPGGSLRL SCAASGFTFD  SYAMSWVRQA PGKGLEWVSA
2F3#680     QITLKESGGG LVQPGGSLRL SCAASGFTFD  SYAMSWIRQA PGKGLEWVSA
2F3#80      QITLKESGGG LVQPGGSLRL SCAASGFTFD  SYAMSWIRQA PGKGLEWVSA
2F3#1780    QITLKESGGG LVQPGGSLRL SCAASGFTFD  SYAMSWIRQA PGKGLEWVSA
2F3#289     EVQLLESGGG LVQPGGSLRL SCAASGFTFD  SYAMSWVRQA PGKGLEWVSA
2F3#633     EVQLLESGGG LVQPGGSLRL SCAASGFTFD  SYAMSWVRQA PGKGLEWVSA
2F3#6       QVQLLESGGG LVQPGGSLRL SCAASGFTFD  SYAMSWVRQA PGKGLEWVSA
2F3#33      QVQLVESGGG LVQPGGSLRL SCAASGFTFD  SYAMSWVCQA PGKGLEWVSA 555        6          7          8 88888      9
                   223        0          0          0 22223      0
                   A                                ABC
2F3#1733    ISGSGHSTYY ADSVKGRFSI SRDNSKNTLY LQMNNLRAED TAVYYCAIRR
2F3#17V2    ISGSGHSTYY ADSVKGRFSI SRDNSKNTLY LQMNNLRAED TAVYYCAIRR
2F3#680     ISGSGASTYY AYSVKGRFSI SRDNSKNTLY LQMNSLRAED TAVYYCAIRR
2F3#80      ISGSGDSTYY AYSVKGRFSI SRDNSKNTLY LQMNSLRAED TAVYYCAIRR
2F3#1780    ISGSGHSTYY AYSVKGRFSI SRDNSKNTLY LQMNSLRAED TAVYYCAIRR
2F3#289     ISGSGDSTYY ADSVKGRFSI SRDNSKNTLY LQMNSLRAED TAVYYCAIRR
2F3#633     ISGSGASTYY ADSVKGRFSI SRDNSKNTLY LQMNSLRAED TAVYYCAIRR
2F3#6       ISGSGASTYY ADSVKGRFSI SRDNSKNTLY LQMNSLRAED TAVYYCAIRR
2F3#33      ISGSGDSTYY ADSVKGRFSI SRDNSKNTLY LQMNSLRAED TAVYYCAIRR 111111     1    1
                   000000     1    1
                   000001     0    3
                   ABCD
2F3#1733    EYSGYTPFDY WGQGTLVTVS S (SEQ ID NO: 127)
2F3#17V2    EYSGYAPFDY WGQGTLVTVS S (SEQ ID NO: 123)
2F3#680     EYSGYAPFDY WGQGTLVTVS S (SEQ ID NO: 128)
2F3#80      EYSGYAPFDY WGQGTLVTVS S (SEQ ID NO: 119)
2F3#1780    EYSGYAPFDY WGQGTLVTVS S (SEQ ID NO: 129)
2F3#289     EYSGYAPFDY WGQGTLVTVS S (SEQ ID NO: 114)
2F3#633     EYSGYTPFDY WGQGTLVTVS S (SEQ ID NO: 130)
2F3#6       EYSGYAPFDY WGQGTLVTVS S (SEQ ID NO: 122)
2F3#33v2    EYSGYTPFDY WGQGTLVTVS S (SEQ ID NO: ~~118~~158)
```

Fig. 7

| Clone ID | Screened against | Specificity by ELISA | PBS | GM2-PAA | GD2-PAA | GD3-PAA | Globo-H | Tn-PAA | sTn-PAA | TF-PAA | sLeA-PAA | EtOH | GM2-cer | GD2-cer | GD3-cer | F-GM1-cer | GM3-cer |
|---|---|---|---|---|---|---|---|---|---|---|---|---|---|---|---|---|---|
| | | | | | | | | Experiment 1 | | | | | | | | | |
| 1E2bG3 | Tn-PAA | Tn-PAA (GM2/GD2/GD3-PAA) | 0.21 | 0.41 | 0.38 | 0.39 | 0.23 | 0.69 | 0.20 | 0.29 | 0.19 | 0.13 | 0.12 | 0.11 | 0.12 | 0.12 | 0.12 |
| | | | | | | | | Experiment 2 | | | | | | | | | |
| 3A7G3 | Tn-PAA | Tn-PAA (sTn-PAA) | 0.25 | 0.18 | 0.16 | 0.14 | 0.14 | 2.53 | 0.35 | 0.17 | 0.15 | 0.11 | 0.09 | 0.09 | 0.11 | 0.09 | 0.10 |
| | | | | | | | | Experiment 3 | | | | | | | | | |
| 1A4G3 | Tn-PAA | Tn-PAA/sTn-PAA | 0.42 | 0.40 | 0.40 | 0.31 | 0.38 | 3.73 | 3.74 | 0.48 | 0.43 | 0.18 | 0.17 | 0.22 | 0.19 | 0.16 | 0.22 |
| 1A12G3 | GD2-PAA | GD2-PAA (GD3-PAA), GD2-cer | 0.37 | 0.33 | 3.82 | 0.96 | 0.32 | 0.40 | 0.30 | 0.32 | 0.32 | 0.19 | 0.18 | 3.73 | 0.38 | 0.20 | 0.35 |
| | | | | | | | | Experiment 4 | | | | | | | | | |
| 2F3 | Tn/Tf-PAA | Tn/Tn-PAA | 0.09 | 0.09 | 0.09 | 0.09 | 0.09 | 3.68 | 1.99 | 0.09 | 0.09 | 0.09 | 0.09 | 0.09 | 0.08 | 0.09 | 0.09 |
| | | | | | | | | Experiment 5 | | | | | | | | | |
| 1G10 | sTn-PAA | (GD2-PAA) | 0.32 | 0.31 | 0.47 | 0.35 | 0.35 | 0.21 | 0.21 | 0.27 | 0.32 | 0.10 | 0.10 | 0.09 | 0.09 | 0.10 | 0.10 |
| 2A8 | sTn-PAA | (sTn-PAA, GM3-cer, GD3-cer) | 0.17 | 0.18 | 0.20 | 0.21 | 0.18 | 0.19 | 0.24 | 0.13 | 0.22 | 0.09 | 0.11 | 0.11 | 0.19 | 0.10 | 0.28 |

Fig. 8

| mAb ID | SEC (%) | Primary Screening, EC50 (nM) | | ELISA, EC50 (nM) | | | | | | | |
|---|---|---|---|---|---|---|---|---|---|---|---|
| | | Total IgG | Tn-PAA | Total IgG, EC50 | Tn-PAA-biotin | Tn-Cluster-Biotin | sTn-PAA-biotin | TF-PAA-biotin | MUC1-1 | MUC1-1-5G | DiTn-MUC1 | BSM |
| 2F3#6 | 97.8 | 0.158 | 1.260 | 0.328 | 1.416 | 0.711 | 63.947 | NB | NB | 5.929 | NB | 14.987 |
| 2F3#17V2 | 96.3 | 0.287 | 0.230 | 0.372 | 0.593 | 0.756 | 106.133 | NB | NB | 37.547 | NB | 36.320 |
| 2F3#1733 | 96.9 | 0.159 | 0.167 | 0.393 | 0.322 | 0.260 | 48.993 | NB | NB | 12.680 | NB | 11.313 |
| 2F3 CDR2Y | 98.6 | 0.243 | 0.218 | 0.420 | 0.202 | 0.044 | 139.400 | NB | NB | 14.080 | NB | 41.347 |
| 2F3G CDR2R | 98.4 | 0.208 | 0.026 | 0.387 | 0.135 | 1.385 | 60.613 | NB | NB | 9.187 | NB | 30.107 |
| 2F3#633 | 97.5 | 0.149 | 0.884 | 0.394 | 0.421 | 0.401 | 51.927 | NB | NB | 7.533 | NB | 9.673 |
| 2F3#6 CDR3 A10S | 98.5 | 0.243 | 0.640 | 0.416 | 0.384 | 0.923 | 182.000 | NB | NB | 13.947 | NB | 15.920 |
| 2F3#6 CDR3 A10R | 97 | 0.203 | 0.599 | 0.362 | 0.318 | 1.774 | 64.147 | NB | NB | 26.720 | NB | 33.193 |
| 2F3#680 | 98.1 | 0.218 | 0.317 | 0.377 | 0.302 | 0.984 | 74.267 | NB | NB | 18.480 | NB | 22.567 |
| 2F3#1780 | 98.2 | 0.201 | 0.300 | 0.373 | 0.408 | 0.635 | 70.067 | NB | NB | 27.287 | NB | 36.040 |

Fig. 12

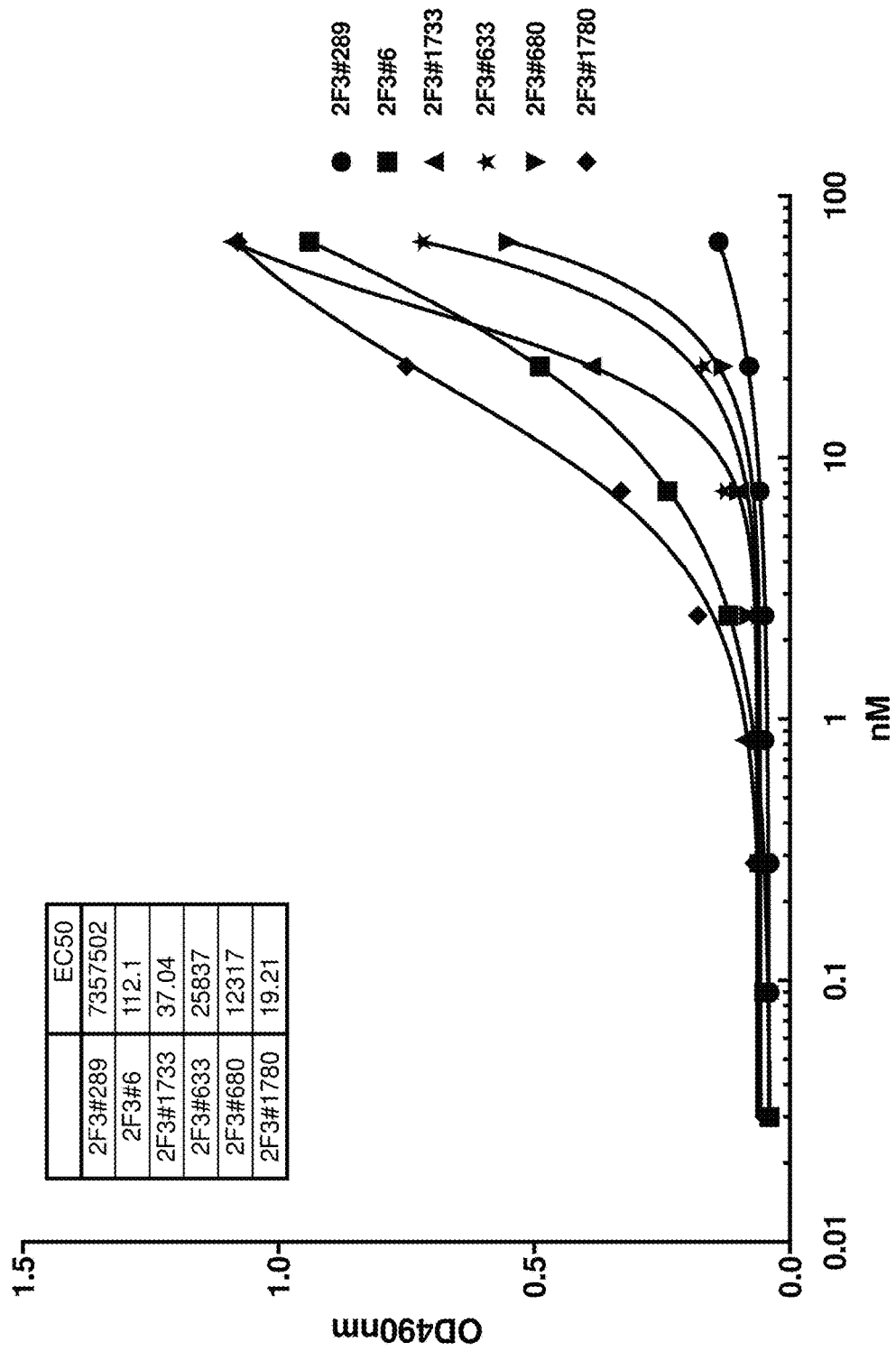

MUC1 di-Tn Peptide    PAPGSTAPPAHGVTSAPDTRPAPG
MUC1-1-5G Peptide     HGVTSAPDTRPAPGSTAPPA Underlined residues are modified with Tn Sussex Research Sng-01-087
MSKCC

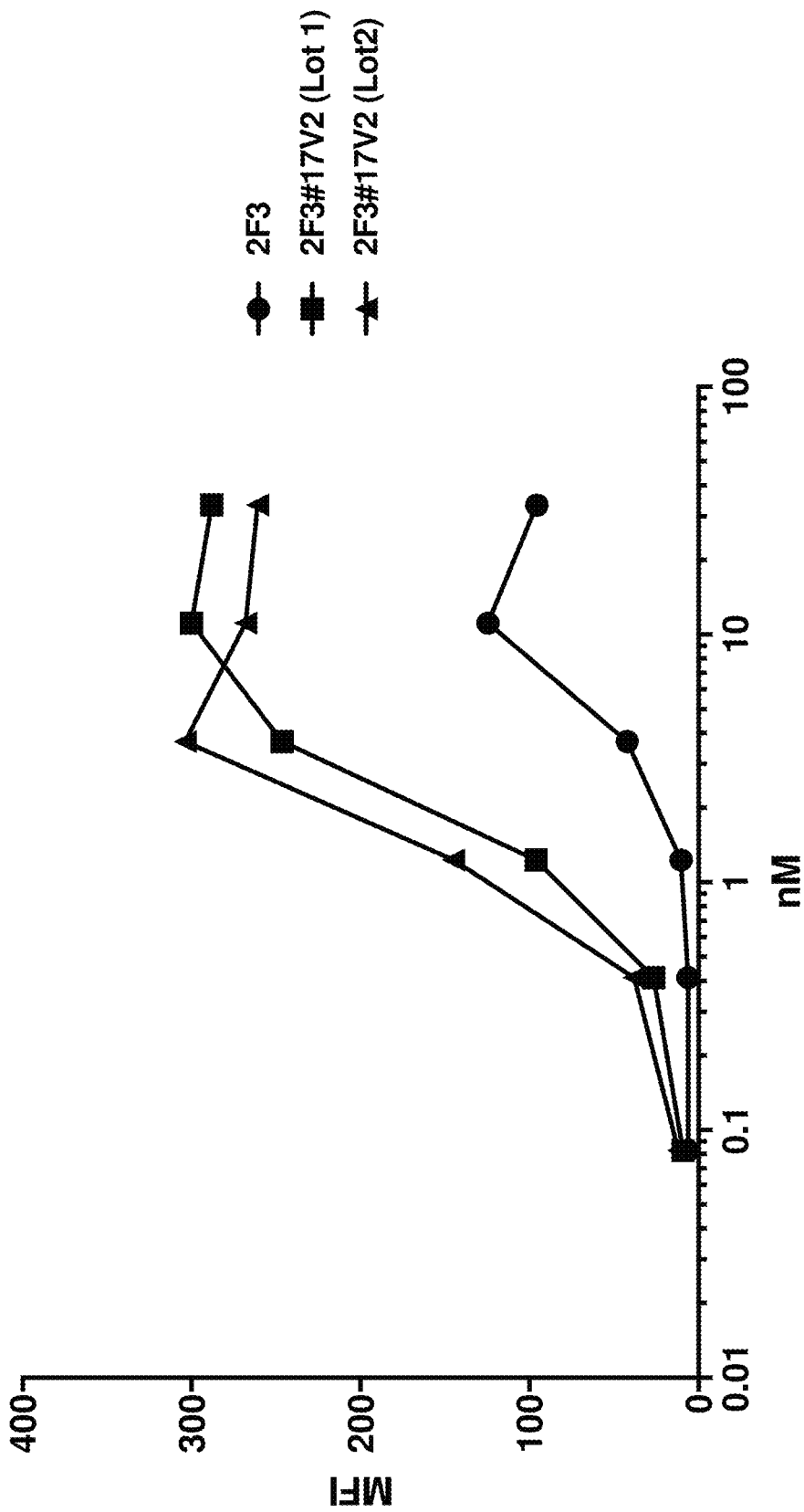

2F3#6-pHAb
10µg/mL
pH7.0

2F3#6-pHAb
10µg/mL
pH5.5

Zhang, et al

| Tumor | % positive |
|---|---|
| Breast | 50% |
| Ovarian | 20-80% |
| Colon | 50-100% |
| Lung | 40-60% |
| Prostate | 60-100% |
| Pancreatic | 40% |

Internal TMA data

| Tumor | Pos/total cores | % positive |
|---|---|---|
| Lung (SCLC) | 3/80 | 4% |
| Ovarian | 35/75 | 47% |
| Breast | 107/142 | 75% |
| TNBC | 24/27 | 89% |
| Colon (malignant) | 6/20 | 30% |
| Colon (metastatic) | 10/20 | 50% |

Fig. 22

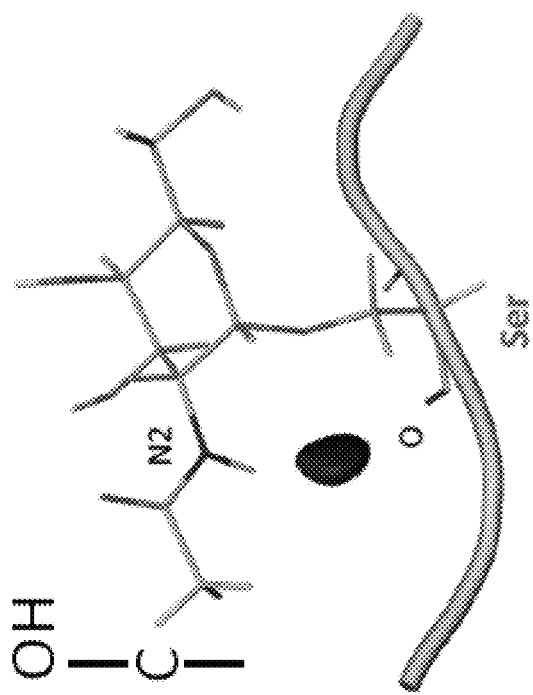
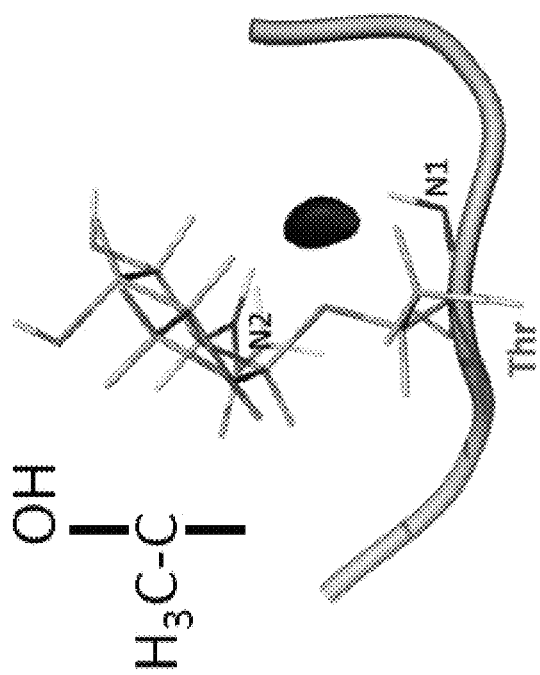
Fig. 27

HUMAN ANTIBODIES TO TN ANTIGEN

SEQUENCE LISTING

The instant application contains a Sequence Listing which has been submitted electronically in ASCII format and is hereby incorporated by reference in its entirety. Said ASCII copy, created on Jun. 2, 2022, is named 02-0496-US-4_SL.txt and is 109,665 bytes in size.

The present invention relates generally to antibodies directed against carbohydrate antigens, and more specifically to antibodies or fragments thereof that bind to Thomsen-nouvelle (Tn) antigen or a sialylated form thereof (sTn antigen), and methods related thereto.

BACKGROUND OF INVENTION

Passive administration of antibodies directed against tumor specific antigens may eliminate tumor cells and early metastases during cancer development. This treatment may also have a significant impact on cancer recurrence. Antibodies directed against tumor specific carbohydrates may be useful candidates in this cancer treatment. For example, many tumor-restricted monoclonal antibodies resulting from immunization of mice with human cancer cells have been shown to be directed against carbohydrate antigens expressed at the cell surface as glycolipids, glycoproteins, or proteoglycans.

The Tn antigen is a carbohydrate antigen that is present on a broad array of tumor types, but is not found on the cell surface of normal tissues. The sTn antigen, a closely-related sialylated form of the Tn antigen, is also a promising tumor antigen. Tn is a single sugar residue that is added to serine or threonine during the first step of O-glycosylation. Normally, subsequent saccharides are added to make a complex mature glycan. In many cancers, however, O-glycoproteins with the immature Tn precursor find their way to the cell surface where they can be exploited as tumor antigens.

Thus, there exists a need for identifying and generating antibodies that specifically recognize tumor specific carbohydrates, such as Tn and sTn, for the treatment of cancers and for detecting malignant lesions and metastases. This application discloses human antibodies against carbohydrate antigens such as the Tn antigen or sTn antigen, which satisfy this need and provide related advantages.

SUMMARY OF INVENTION

In accordance with the present invention, provided herein are compositions and methods for targeting antibodies or functional fragments thereof to carbohydrate antigens, specifically to a Tn antigen or an sTn antigen. The compositions disclosed herein include an isolated antibody or functional fragment thereof, wherein the antibody or functional fragment thereof binds to Tn antigen or sTn antigen. The methods disclosed herein include methods of making the isolated antibody or functional fragment thereof provided herein, methods of treating or prevent a disease associated with Tn antigen or sTn antigen using an isolated antibody, functional fragment thereof or conjugate provided herein, and methods for detecting a tumor that has Tn antigen or sTn antigen on the surface of its cells in a subject using a conjugate provided herein.

In some embodiments, the invention provides an isolated antibody or functional fragment thereof that binds Tn antigen or sTn antigen, wherein the antibody or functional fragment thereof includes a VH domain having VH CDR1, VH CDR2, and VH CDR3 regions provided herein. In other embodiments, the invention provides an isolated antibody or functional fragment thereof that binds Tn antigen or sTn antigen, wherein the antibody or functional fragment thereof includes a VH domain having an amino acid sequence provided herein.

In some embodiments, the invention provides an isolated antibody or functional fragment thereof that binds Tn antigen or sTn antigen, wherein the antibody or functional fragment thereof includes a VL domain having VL CDR1, VL CDR2, and VL CDR3 regions provided herein. In other embodiments, the invention provides an isolated antibody or functional fragment thereof that binds Tn antigen or sTn antigen, wherein the antibody or functional fragment thereof includes a VL domain having an amino acid sequence provided herein.

In some embodiments, the invention provides an isolated antibody or functional fragment thereof that binds to Tn antigen or sTn antigen, wherein the antibody or functional fragment thereof includes both a VH domain and a VL domain, wherein the VH domain and the VL domain respectively include an amino acid sequence for the respective VH and VL domains provided herein.

In some embodiments, the antibody or functional fragment thereof provided herein has distinct features. For example, in some aspects, the antibody or functional fragment thereof binds to a Tn antigen or an sTn antigen and has one or more of the following features:

- binds to two Tn antigen molecules, wherein the two Tn antigen molecules are each located on an amino acid residue of a protein, and wherein the two Tn antigen molecules are separated by 10 or fewer consecutive amino acid residues;
- binds to two Tn antigen molecules, wherein the two Tn antigen molecules are located on adjacent amino acid residues of a protein;
- greater than 10 fold higher avidity for Tn antigen than sialyl Le$^a$, globo H, or a ganglioside selected from the group consisting of F-GM1, GM2, GM3, GD2, and GD3; greater than 10 fold higher avidity for Tn antigen than Thomsen-Friedenreich (TF) antigen;
- does not bind sialyl Le$^a$, globo H, or a ganglioside selected from the group consisting of F-GM1, GM2, GM3, GD2, and GD3 above a background control in an enzyme-linked immunosorbant assay;
- does not bind TF antigen above a background control in an enzyme-linked immunosorbant assay;
- has an EC50 value for binding to Tn antigen of less than 50 nM;
- has an EC50 value for binding to Tn antigen of less than 20 nM; or has an EC50 value for binding to Tn antigen of less than 10 nM;
- preferentially binds a Tn or sTn antigen, wherein the Tn or sTn antigen is on a serine residue;
- specifically binds a Tn or sTn antigen, wherein the Tn or sTn antigen is on a serine residue.
- preferentially binds a Tn or sTn antigen, wherein the Tn or sTn antigen is on a cancer cell, and the Tn or sTn antigen is on a seine residue;
- specifically binds a Tn or sTn antigen, wherein the Tn or sTn antigen is on a cancer cell, and the Tn or sTn antigen is on a seine residue.

The compositions provided herein also include an isolated polynucleotide encoding the VH domain, the VL domain, or both the VH and VL domains of an antibody or a functional fragment thereof provided herein, an expression vector that includes such a polynucleotide, and a host cell that contains such an expression vector. Also provided are methods of using such compositions for making an antibody or functional fragment provided herein. Such a method can include culturing the host cell provided herein in a medium, and obtaining the antibody or functional fragment expressed therein.

In some embodiments, the invention provides a conjugate having an antibody or functional fragment provided herein that is conjugated or recombinantly fused to a localizing agent, a detectable agent or a therapeutic agent. In some aspects disclosed herein, a conjugate disclosed herein that includes a localizing agent or a detectable agent can be used in a method for detecting and/or diagnosing tumor formation in a subject. Such methods can include administering an effective amount of the conjugate to a subject in need thereof.

In some embodiments, the invention provides pharmaceutical compositions having one or more antibody or functional fragment disclosed herein and a pharmaceutically acceptable carrier. In some embodiments, the invention provides pharmaceutical compositions having one or more conjugates disclosed herein and a pharmaceutically acceptable carrier. In some aspects, the invention also provides a method for treating or preventing a disease in a subject in need thereof, by administering a therapeutically effective amount of a pharmaceutical composition disclosed herein. In still another aspect, the invention provides administering a second therapeutic agent concurrently or successively with an antibody or functional fragment disclosed herein.

BRIEF DESCRIPTION OF THE DRAWINGS

FIG. 1 shows an alignment of Fab amino acid sequences having the variable heavy chain domains for the seven initially identified antibody clonal isolates 2F3 (SEQ ID NO:77), 3A7 (SEQ ID NO:78), 1G10 (SEQ ID NO:75), 2A8 (SEQ ID NO:76), 1E2b (SEQ ID NO:74), 1A4 (SEQ ID NO:73), and 1A12b (SEQ ID NO:72). Shaded residue represent the CDR sequences according to the Kabat numbering system, whereas the boxed residues represent the CDR sequences according to the IMGT numbering system.

FIG. 2 shows an alignment of Fab amino acid sequences having the variable light chain domains for the seven initially identified antibody clonal isolates 2F3 (SEQ ID NO:84), 3A7 (SEQ ID NO:85), 1G10 (SEQ ID NO:82), 2A8 (SEQ ID NO:83), 1E2b (SEQ ID NO:81), 1A4 (SEQ ID NO:80), and 1A12b (SEQ ID NO:79). Shaded residue represent the CDR sequences according to the Kabat numbering system, whereas the boxed residues represent the CDR sequences according to the IMGT numbering system.

FIG. 3 shows an alignment of variable heavy chain amino acid sequences of clonal isolate 2F3 (SEQ ID NO:105) and the reverted germline variant #289 of 2F3 (SEQ ID NO:114). Boxed residues represent the CDR sequences according to the IMGT numbering system. Numbering of the residues is according to the Kabat system.

FIG. 4 shows an alignment of variable heavy chain amino acid sequences of several exemplary 2F3 variants (#27 (SEQ ID NO:115), #51 (SEQ ID NO:116), #17 (SEQ ID NO:117), #33 (SEQ ID NO:118), #80 (SEQ ID NO:119), #75 (SEQ ID NO:120), #50 (SEQ ID NO:121), #289 (SEQ ID NO:114), and #6 (SEQ ID NO:122)). Boxed residues represent the CDR sequences according to the IMGT numbering system. Shaded residues represent variant amino acid residues across the aligned sequences. Numbering of the residues is according to the Kabat system.

FIG. 5 shows an alignment of 2F3 variant #17 (2F3 #17) (SEQ ID NO:117) and version 2 of 2F3 variant #17 (2F3 #17v2) (SEQ ID NO:123). Boxed residues represent the CDR sequences according to the IMGT numbering system. Numbering of the residues is according to the Kabat system.

FIG. 6 shows an alignment of 2F3 variants having specific VH CDR2 amino acid variants R (SEQ ID NO:124), Y (SEQ ID NO:125), or F (SEQ ID NO:126), at position 55 according to the Kabat numbering system and other 2F3 variants (2F3 #289 (SEQ ID NO:114), 2F3 #6 (SEQ ID NO:122) and 2F3 #17v2 (SEQ ID NO:123). Boxed residues represent the CDR sequences according to the IMGT numbering system. Numbering of the residues is according to the Kabat system. Shaded residues represent variant amino acid residues across the aligned sequences.

FIG. 7 shows an alignment of several 2F3 variants (#1733 (SEQ ID NO:127), #17v2 (SEQ ID NO:123), #680 (SEQ ID NO:128), #80 (SEQ ID NO:119), #1780 (SEQ ID NO:129), #289 (SEQ ID NO:114), #633 (SEQ ID NO:130), #6 (SEQ ID NO:122) and #33v2 (SEQ ID NO:158)). Boxed residues represent the CDR sequences according to the IMGT numbering system. Shaded residues represent variant amino acid residues across the aligned sequences. Numbering of the residues is according to the Kabat system.

FIG. 8 shows selection of potent human monoclonal antibodies to Tn antigen or sTn antigen. Supernatants from 7 positive hybridomas tested interacted with Tn or sTn. V genes were isolated from these hybridomas and cloned in the context of human IgG1 or 3/kappa sequences. Purified antibodies were screened for reactivity with a panel of carbohydrate antigens to determine breadth of specificity. Antigens were immobilized on ELISA plates. The solvent for the first set of antigens, PBS, was tested as a negative control. The solvent for the second set of antigens, EtOH, was tested as a second negative control. Specificity of interaction is indicated in the "Specificity by ELISA" column, and OD numbers indicating these specificities are indicated on the right-hand 15 columns.

FIG. 12 shows a summary table of favorable mutants from affinity maturation binding profiles to model antigens.

FIG. 13A-13D shows determination of relative improvement over parent and the impact of increased affinity on specificity for five mutants that were selected and bound to model antigens. Data was not shown for the absence of binding by any variants to TF-PAA, GalNac-beta-PAA (in which Tn is GalNac-alpha-linked), monomeric Tn, and monomeric sTn.

FIG. 15A-15D shows binding of original 2F3 parent and selected affinity variants to Tn-positive T47-D cells demonstrated by FACS analysis, a down-shift in EC50 value showing higher binding affinity and an up-shift in the maximal binding indicating ability to occupy more available sites at equilibrium.

FIG. 22 shows evidence from literature and internal tumor microarray studies demonstrating broad expression of Tn antigen in a variety of tissue types, particularly representing approximately 50% or higher staining of primary human tumors in ovary, breast (including triple negative breast cancer (TNBC)) and colon cancers. The table on the left summarizes staining results obtained from Zhang et al, IJC 73:50-56 (1997) in which 2 sTn and one Tn antibody were used to profile panels of diverse tumor types. The ranges indicate the lowest and highest percent positive across this set of antibodies. Internal data were also obtained.

FIG. 23D discloses SEQ ID NO: 156. FIG. 23E discloses SEQ ID NO: 157. FIG. 23F discloses SEQ ID NO: 155.

FIG. 27 shows the structural variation between Tn-Ser and Tn-Thr.

DETAILED DESCRIPTION OF THE INVENTION

Figure 9:
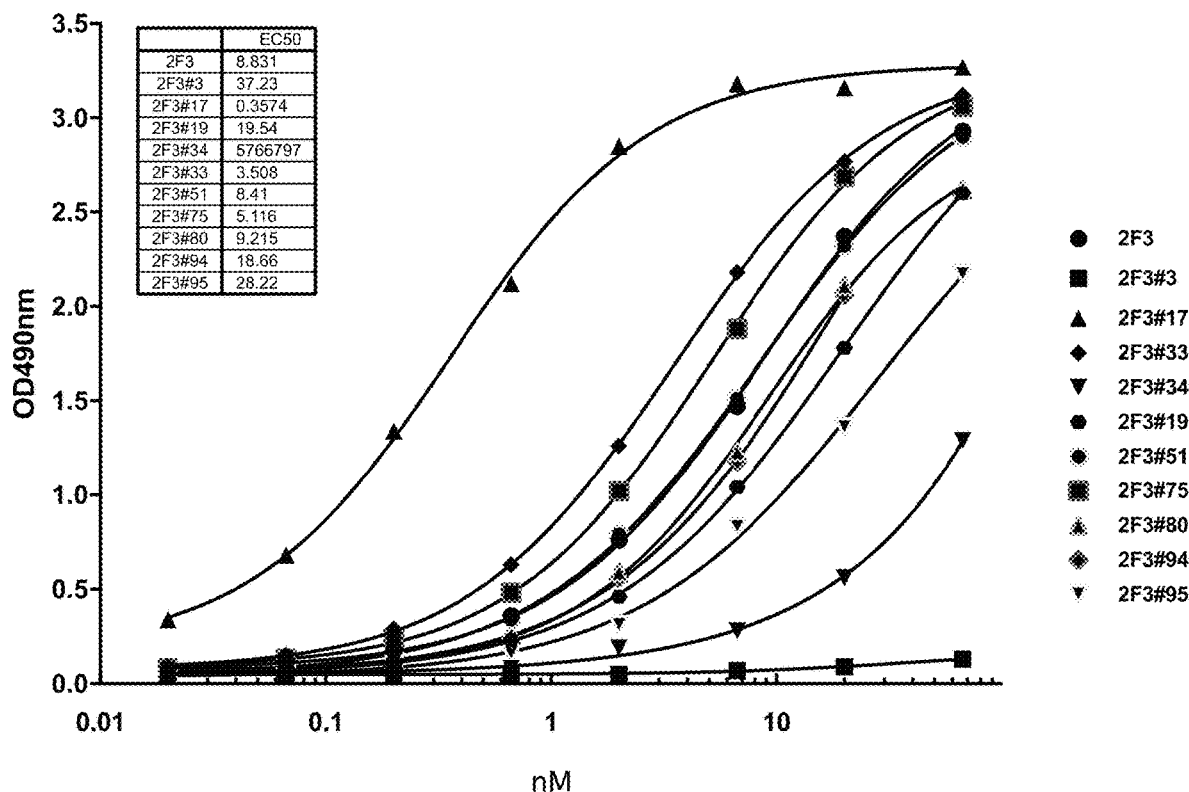
FIG. 9 shows selection of one of the lead antibodies, 2F3, for affinity optimization. Error prone PCR was employed to generate mutants and mutants were screened by ELISA. Unpurified cell supernatants were quantitated and used to bind to Tn-PAA to determine impact of mutations on binding.

Carbohydrates expressed on the tumor cell surface can be targets for cancer immunotherapy. The compositions provided herein are based, at least in part, on the identification and characterization of human antibodies that were generated from B cells of individuals immunized with either: 1) a Tn modified Muc1 keyhole limpet hemocyanin (Tn-modified-Muc1-KLH) conjugate vaccine in the presence of other antigens (Globo H, GM2, and a peptide-assembled TF cluster) and treatment with bevacizumab; or 2) a unimolecular vaccine including Globo H, GM2, sTn, TF, and Tn all conjugated to KLH. At least seven candidate antibodies (clonal isolates named 1A12b, 1A4, 1E2b, 1G10, 2A8, 2F3, and 3A7) were identified, expressed as recombinant antibodies, and further characterized in in vitro assays. Each of the identified antibodies preferentially bound to certain antigens as disclosed herein, with certain clonal isolates having a specific preference for Tn antigen or sTn antigen (1A4, 2F3, and 3A7). Of these antibodies identified and tested, one antibody (2F3) was selected for further optimization leading to several 2F3 variants having improved features, including improved avidity, cytotoxicity, and/or internalization into cells having Tn and/or sTn antigens.

As used herein, the term "antibody" is intended to mean a polypeptide product of B cells within the immunoglobulin class of polypeptides that is able to bind to a specific molecular antigen and is composed of two identical pairs of polypeptide chains, wherein each pair has one heavy chain (about 50-70 kDa) and one light chain (about 25 kDa) and each amino-terminal portion of each chain includes a variable region of about 100 to about 130 or more amino acids and each carboxy-terminal portion of each chain includes a constant region (See Borrebaeck (ed.) (1995) *Antibody Engineering*, Second Edition, Oxford University Press.; Kuby (1997) *Immunology*, Third Edition, W.H. Freeman and Company, New York). In the context of the present invention, the specific molecular antigen that can be bound by an antibody disclosed herein includes a Tn antigen or an sTn antigen.

An "antigen" is a predetermined antigen to which an antibody can selectively bind. A target antigen may be a polypeptide, carbohydrate, nucleic acid, lipid, hapten or other naturally occurring or synthetic compound. In the context of certain embodiments, the target antigen is a Tn antigen or an sTn antigen. In some embodiments, the target antigen is a Tn or sTn antigen on a serine residue.

The term "bispecific" when used in reference to an antibody or functional fragment thereof refers to an antibody or functional fragment thereof that has specificity for two different structures, epitopes or antigenic determinants. Bispecific antibodies can simultaneously bind to two different structures, epitopes or antigenic determinants.

The term "human" when used in reference to an antibody or a functional fragment thereof refers an antibody or functional fragment thereof that has a human variable region and, if applicable, a human constant region or a portion thereof corresponding to human germline immunoglobulin sequences. Such human germline immunoglobulin sequences are described by Kabat et al. (1991) *Sequences of Proteins of Immunological Interest*, Fifth Edition, U.S. Department of Health and Human Services, NIH Publication No. 91-3242. A human antibody, in the context of the present invention, can include an antibody that binds to Tn antigen or sTn antigen and is encoded by a nucleic acid sequence that is a naturally occurring somatic variant of the human germline immunoglobulin nucleic acid sequence. Exemplary methods of producing human antibodies are provided in the Examples provided herein, but any method well known to those skilled in the art can be used.

The term "monoclonal antibody" refers to an antibody that is the product of a single cell clone or hybridoma or a population of cells derived from a single cell. A monoclonal antibody also is intended to refer to an antibody produced by recombinant methods from heavy and light chain encoding immunoglobulin genes to produce a single molecular immunoglobulin species. Amino acid sequences for antibodies within a monoclonal antibody preparation are substantially homogeneous and the binding activity of antibodies within such a preparation exhibit substantially the same antigen binding activity. In contrast, polyclonal antibodies are obtained from different B cells within a population, which are a combination of immunoglobulin molecules that bind a specific antigen. Each immunoglobulin of the polyclonal antibodies can bind a different epitope of the same antigen. Methods for producing both monoclonal antibodies and polyclonal antibodies are well known in the art (Harlow and Lane., *Antibodies: A Laboratory Manual*, Cold Spring Harbor Laboratory Press (1989) and Borrebaeck (ed.), *Antibody Engineering: A Practical Guide*, W.H. Freeman and Co., Publishers, New York, pp. 103-120 (1991)).

As used herein, the term "functional fragment" when used in reference to an antibody is intended to refer to a portion of the antibody including heavy and/or light chain polypeptides that retains some or all of the binding activity as the antibody from which the fragment was derived. Such functional fragments can include, for example, an Fd, Fv, Fab, Fab', F(ab')$_2$, single chain Fv (scFv), diabody, triabody, tetrabody, minibody and single-domain antibody (sdAB). Other functional fragments can include, for example, heavy or light chain polypeptides, variable region polypeptides or CDR polypeptides or portions thereof so long as such functional fragments retain binding activity. Such antibody binding fragments can be found described in, for example, Harlow and Lane, *Antibodies: A Laboratory Manual*, Cold Spring Harbor Laboratory, New York (1989); Myers (ed.), *Molec. Biology and Biotechnology: A Comprehensive Desk Reference*, New York: VCH Publisher, Inc.; Huston et al., *Cell Biophysics,* 22:189-224 (1993); Plückthun and Skerra, *Meth. Enzymol.,* 178:497-515 (1989) and in Day, E. D., *Advanced Immunochemistry*, Second Ed., Wiley-Liss, Inc., New York, N.Y. (1990).

The term "heavy chain" when used in reference to an antibody refers to a polypeptide chain of about 50-70 kDa, wherein the amino-terminal portion includes a variable region of about 120 to 130 or more amino acids and a carboxy-terminal portion that includes a constant region. The constant region can be one of five distinct types, referred to as alpha ($\alpha$), delta ($\delta$), epsilon ($\varepsilon$), gamma ($\gamma$) and mu ($\mu$), based on the amino acid sequence of the heavy chain constant region. The distinct heavy chains differ in size: $\alpha$, $\delta$ and $\gamma$ contain approximately 450 amino acids, while $\mu$ and $\varepsilon$ contain approximately 550 amino acids. When combined with a light chain, these distinct types of heavy chains give rise to five well known classes of antibodies, IgA, IgD, IgE, IgG and IgM, respectively, including four subclasses of IgG, namely IgG1, IgG2, IgG3 and IgG4. Further, IgA and IgM may associate with J chain. A heavy chain can be a human heavy chain.

The term "light chain" when used in reference to an antibody refers to a polypeptide chain of about 25 kDa, wherein the amino-terminal portion includes a variable region of about 100 to about 110 or more amino acids and a carboxy-terminal portion that includes a constant region. The approximate length of a light chain is 211 to 217 amino acids. There are two distinct types, referred to as kappa ($\kappa$) or lambda ($\lambda$) based on the amino acid sequence of the constant domains. Light chain amino acid sequences are well known in the art. A light chain can be a human light chain.

The term "variable domain" or "variable region" refers to a portion of the light or heavy chains of an antibody that is generally located at the amino-terminal of the light or heavy chain and has a length of about 120 to 130 amino acids in the heavy chain and about 100 to 110 amino acids in the light chain, and are used in the binding and specificity of each particular antibody for its particular antigen. The variable domains differ extensively in sequence between different antibodies. The variability in sequence is concentrated in the CDRs while the less variable portions in the variable domain are referred to as framework regions (FR). The CDRs of the light and heavy chains are primarily responsible for the interaction of the antibody with antigen. Numbering of amino acid positions used herein is according to the EU Index, as in Kabat et al. (1991) *Sequences of proteins of immunological interest*. (U.S. Department of Health and Human Services, Washington, D.C.) $5^{th}$ ed. A variable region can be a human variable region.

A "complementarity-determining region" or "CDR" refers to one of three hypervariable regions (H1, H2 or H3) within the non-framework region of the immunoglobulin (Ig or antibody) VH β-sheet framework (also referred to herein as VH CDR1, VH CDR2 or VH CDR3, respectively), or one of three hypervariable regions (L1, L2 or L3) within the non-framework region of the antibody VL β-sheet framework (also referred to herein as VL CDR1, VL CDR2 or VL CDR3, respectively). Accordingly, CDRs are variable region sequences interspersed within the framework region sequences. CDR sequences are well known to those skilled in the art and have been defined by, for example, Kabat as the regions of most hypervariability within the antibody variable (V) domains (Kabat et al., J. Biol. Chem. 252:6609-6616 (1977); Kabat, Adv. Prot. Chem. 32:1-75 (1978)). CDR sequences also have been defined structurally by Chothia as those residues that are not part of the conserved β-sheet framework, and thus are able to adapt different conformations (Chothia and Lesk, J. Mol. Biol. 196:901-917 (1987)). Both terminologies are well recognized in the art. CDR sequences have also been defined by AbM, Contact and IMGT. CDR sequences applicable to the antibodies disclosed herein are illustrated in FIGS. 1-7 and Tables 2-4. The positions of CDRs within a canonical antibody variable region have been determined by comparison of numerous structures (Al-Lazikani et al., J. Mol. Biol. 273:927-948 (1997); Morea et al., Methods 20:267-279 (2000)). Because the number of residues within a hypervariable region varies in different antibodies, additional residues relative to the canonical positions are conventionally numbered with a, b, c and so forth next to the residue number in the canonical variable region numbering scheme (Al-Lazikani et al., supra (1997)). Such nomenclature is similarly well known to those skilled in the art.

The term hypervariable region, HVR, or HV, when used herein refers to the regions of an antibody variable region that are hypervariable in sequence and/or form structurally defined loops. Generally, antibodies comprise six hypervariable regions; three in the VH (H1, H2, H3), and three in the VL (L1, L2, L3). A number of hypervariable region delineations are in use and are encompassed herein. The Kabat Complementarity Determining Regions (CDRs) are based on sequence variability and are the most commonly used (see, e.g., Kabat et al., Sequences of Proteins of Immunological Interest, 5th Ed. Public Health Service, National Institutes of Health, Bethesda, Md. (1991)). Chothia refers instead to the location of the structural loops (see, e.g., Chothia and Lesk, J. Mol. Biol. 196:901-917 (1987)). The end of the Chothia CDR-H1 loop when numbered using the Kabat numbering convention varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34). The AbM hypervariable regions represent a compromise between the Kabat CDRs and Chothia structural loops, and are used by Oxford Molecular's AbM antibody modeling software (see, e.g., Martin, in Antibody Engineering, Vol. 2, Chapter 3, Springer Verlag). The "contact" hypervariable regions are based on an analysis of the available complex crystal structures (Honegger and Plückthun, J. Mol. Biol. 309: 657-670 (2001)). The residues from each of these hypervariable regions or CDRs are noted below.

Recently, a universal numbering system has been developed and widely adopted, ImMunoGeneTics (IMGT) Information System® (Lafranc et al., Dev. Comp. Immunol. 27(1):55-77 (2003)). IMGT is an integrated information system specializing in immunoglobulins (IG), T cell receptors (TR) and major histocompatibility complex (MHC) of human and other vertebrates. Herein, the CDRs are referred to in terms of both the amino acid sequence and the location within the light or heavy chain. As the "location" of the CDRs within the structure of the immunoglobulin variable domain is conserved between species and present in structures called loops, by using numbering systems that align variable domain sequences according to structural features, CDR and framework residues and are readily identified. This information can be used in grafting and replacement of CDR residues from immunoglobulins of one species into an acceptor framework from, typically, a human antibody. An additional numbering system (AHon) has been developed by Honegger and Plückthun, supra. Correspondence between the numbering system, including, for example, the Kabat numbering and the IMGT unique numbering system, is well known to one skilled in the art (see, e.g., Kabat, supra; Chothia and Lesk, supra; Martin, supra; Lefranc et al., supra) and is also illustrated in FIGS. 1-7. Exemplary CDR residues, as defined by the various systems, are set forth in Table 1.

TABLE 1

CDR residues using different numbering systems

| | IMGT | Kabat | AbM | Chothia | Contact |
|---|---|---|---|---|---|
| VH CDR1 | 27-38 | 31-35 | 26-35 | 26-32 | 30-35 |
| VH CDR2 | 56-65 | 50-65 | 50-58 | 53-55 | 47-58 |
| VH CDR3 | 105-117 | 95-102 | 95-102 | 96-101 | 93-101 |
| VL CDR1 | 27-38 | 24-34 | 24-34 | 26-32 | 30-36 |
| VL CDR2 | 56-65 | 50-56 | 50-56 | 50-52 | 46-55 |
| VL CDR3 | 105-117 | 89-97 | 89-97 | 91-96 | 89-96 |

Hypervariable regions may comprise "extended hypervariable regions" as follows: 24-36 or 24-34 (L1), 46-56 or 50-56 (L2) and 89-97 or 89-96 (L3) in the VL and 26-35 or 26-35A (H1), 50-65 or 49-65 (H2) and 93-102, 94-102, or 95-102 (H3) in the VH. As used herein, the terms "HVR" and "CDR" are used interchangeably.

The term constant region or constant domain refers to a carboxy terminal portion of the light and heavy chain which is not directly involved in binding of the antibody to antigen but exhibits various effector function, such as interaction with the Fc receptor. The terms refer to the portion of an immunoglobulin molecule having a more conserved amino acid sequence relative to the other portion of the immunoglobulin, the variable region, which contains the antigen binding site. The constant region may contain the CH1, CH2 and CH3 regions of the heavy chain and the CL region of the light chain.

The term framework or FR residues are those variable region residues flanking the CDRs. FR residues are present, for example, in chimeric, humanized, human, domain antibodies, diabodies, and bispecific antibodies.

As used herein, the term "isolated" when used in reference to an antibody, antibody functional fragment or polynucleotide is intended to mean that the referenced molecule is free of at least one component as it is found in nature. The term includes an antibody, antibody functional fragment or polynucleotide that is removed from some or all other components as it is found in its natural environment. Components of an antibody's natural environment include, for example, erythrocytes, leukocytes, thrombocytes, plasma, proteins, nucleic acids, salts and nutrients. Components of an isolated antibody functional fragment's or polynucleotide's natural environment include, for example, lipid membranes, cell organelles, proteins, nucleic acids, salts and nutrients. An antibody, antibody functional fragment or polynucleotide disclosed herein can also be free or all the way to substantially free from all of these components or any other component of the cells from which it is isolated or recombinantly produced.

As used herein, "isotype" refers to the antibody class that is encoded by heavy chain constant region genes. The heavy chains of a given antibody or functional fragment determine the class of that antibody or functional fragment: IgM, IgG, IgA, IgD or IgE. Each class can have either κ or λ light chains. The term "subclass" refers to the minor differences in amino acid sequences of the heavy chains that differentiate the subclasses. In humans there are two subclasses of IgA (subclasses IgA1 and IgA2) and there are four subclasses of IgG (subclasses IgG1, IgG2, IgG3 and IgG4). Such classes and subclasses are well known to those skilled in art.

The terms "binds" or "binding" as used herein refer to an interaction between molecules to form a complex. Interactions can be, for example, non-covalent interactions including hydrogen bonds, ionic bonds, hydrophobic interactions, and/or van der Waals interactions. A complex can also include the binding of two or more molecules held together by covalent or non-covalent bonds, interactions or forces. Binding of an antibody or functional fragment thereof can be detected using, for example, an enzyme-linked immunosorbant assay, a method provided in the Examples provided herein or any one of a number of methods that are well known to those skilled in the art.

The strength of the total non-covalent interactions between a single antigen-binding site on an antibody or functional fragment and a single epitope of a target molecule, such as Tn antigen or sTn antigen, is the "affinity" of the antibody or functional fragment for that epitope. The ratio of association ($k_1$) to dissociation ($k_{-1}$) of an antibody or functional fragment thereof to a monovalent antigen ($k_1/k_{-1}$) is the equilibrium dissociation constant K, which is a measure of affinity. The value of K varies for different complexes of antibody or functional fragment and antigen and depends on both $k_1$ and $k_{-1}$. The dissociation constant K for an antibody or functional fragment disclosed herein can be determined using any method provided herein or any other method well known to those skilled in the art. (For example Hearty et al. 2012. Methods Mol Biol. 907:411-42).

The affinity at one binding site does not always reflect the true strength of the interaction between an antibody or functional fragment and an antigen. When complex antigens containing multiple, repeating antigenic determinants, such as a polyvalent Tn antigen or sTn antigen, come in contact with antibodies containing multiple binding sites, the interaction of antibody or functional fragment with antigen at one site will increase the probability of a reaction at a second site. The strength of such multiple interactions between a multivalent antibody and antigen is called the "avidity." The avidity of an antibody or functional fragment can be a better measure of its binding capacity than is the affinity of its individual binding sites. For example, high avidity can compensate for low affinity as is sometimes found for pentameric or hexameric IgM antibodies, which can have a lower affinity than IgG, but the high avidity of IgM, resulting from its multivalence, enables it to bind antigen effectively. As used herein, the term "avidity" refers to the overall stability of the complex between a population of immunoglobulins and an antigen, that is, the cumulative strength of an immunoglobulin mixture with the antigen. Avidity is related to both the affinity of individual antibody molecules in the population with specific epitopes, and also the valencies of the immunoglobulins and the antigen.

The specificity of an antibody or functional fragment thereof refers to the ability of an individual antibody or functional fragment thereof to react with only one antigen. An antibody or functional fragment can be considered specific when it can distinguish differences in the primary, secondary or tertiary structure of an antigen or isomeric forms of an antigen. The antibody can be cross-reactive if the binding epitope is present on other antigens.

For example, in any of the embodiments described herein, the most effective antibody may be determined based on the functional affinity and/or avidity with which the antibody, antibody fragment or antigen binding unit binds a Tn antigen, a sTn antigen, or both. In an embodiment, for example, the functional affinity or avidity of one Tn/sTn antibody may be comparably higher or lower relative to another Tn/sTn antibody such that the responsiveness of a cell expressing the Tn/sTn antigen is affected upon antibody binding. The relative avidity can be assayed by methods generally known by those skilled in the art, for example, with a chromium release assay, where SD50 values are correlated to the concentration of antibody needed to achieve maximal specific lysis. An antibody with a higher avidity for example, would be one with a lower SD50, i.e. a lower concentration of antibody will be required to achieve maximal specific lysis. The avidity of a Tn/sTn antibody can be a function of both the affinity of the anti-Tn/sTn antibody epitope with the specific-Tn/sTn antibody, and also the binding time of the antibody with the Tn/sTn epitope.

Furthermore, the antibodies according to the present invention may comprise substitution, deletion, addition, and/or insertion of one or more amino acids in their CDR sequences as long as the resulting antibodies are functionally equivalent to the starting material or CDR regions prior to modification(s). In the present invention, the term "functionally equivalent" refers to being comparable in functional affinity and/or avidity for the Tn/sTn antigen. In the present invention, the term "equivalent" refers to having at least 50%, preferably 70%, more preferably 90% or higher activity, compared with the claimed antibodies.

Potential therapeutic antibody candidates are screened for antibody-dependent cell-mediated cytotoxity (ADCC) activity to find those that will have the most potent anti-cancer abilities. One of ordinary skill in the art will appreciate various methods can be used to measure the cytotoxicity mediated by the Tn/sTn antibody and/or Tn/sTn-CD3 engager binding proteins of the present invention. To assess ADCC activity an variant protein of interest is added to target cells in combination with immune effector cells, which may be activated by the antigen antibody complexes resulting in cytolysis of the target cell. Cytolysis is generally detected by the release of label (e.g. radioactive substrates, fluorescent dyes or natural intracellular proteins) from the lysed cells. Useful effector cells for such assays include peripheral blood mononuclear cells (PBMC) and Natural Killer (NK) cells. Specific examples of in vitro ADCC assays are described in Wisecarver et al., 1985 79:277-282 Bruggemann et al., 1987, J Exp Med 166:1351-1361; Wilkinson et al., 2001, J Immunol Methods 258:183-191; Patel et al., 1995 J Immunol Methods 184:29-38. ADCC activity of the Fc variant protein of interest may also be assessed in vivo, e.g., in an animal model such as that disclosed in Clynes et. al., 1998, Proc. Natl. Acad. Sci. USA 95:652-656.

In embodiments of the invention, a variant protein is described as having enhanced ADCC activity relative to a comparable molecule, for example a variant protein has ADCC activity that is at least 2 fold, or at least 3 fold, or at least 5 fold or at least 10 fold or at least 50 fold or at least 100 fold greater than that of a comparable molecule, In one example, cytotoxicity can be measured using Calcein-AM (Thermo Fisher). Very generally, Tn/sTn positive cells lines are co-cultured with effectors cells with increasing concentration of Tn/sTn Ab and/or Tn/sTn-CD3 binding proteins for 3-24 hours at an effector to target cell ratio, for example 20:1. Effector cells can be e.g. stimulated or unstimulated (human or cynomolgus monkey) T cells or their subsets (e.g. CD4, CD8) or unstimulated (human or cynomolgus monkey) peripheral blood mononuclear cells (PBMCs). The target cells express Tn/sTn and can be cells with endogenous (natural) Tn/sTn expression, such as the human ovarian adenocarcinoma-cell line CAOV3. Cytotoxic activity of Tn/sTn and/or Tn/sTn-CD3 binding molecules is determined e.g. release of the fluorescent dye calecin AM after 2-48 hours of incubation with effector cells in the presence of specific antibody. Modifications in incubation time and read-out used for determination of cytotoxicity are possible and known to the skilled person.

The term "polynucleotide" refers to a polymeric form of nucleotides of any length, either deoxyribonucleotides or ribonucleotides or analogs thereof. The sequence of a polynucleotide is composed of four nucleotide bases: adenine (A); cytosine (C); guanine (G); thymine (T); and uracil (U) for thymine when the polynucleotide is RNA. Thus, the terms "nucleotide sequence" or "nucleic acid sequence" is the alphabetical representation of a polynucleotide. A polynucleotide can include a gene or gene fragment (for example, a probe, primer, EST or SAGE tag), exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes and primers. Polynucleotide also refers to both double- and single-stranded molecules. Unless otherwise specified or required, any embodiment of this invention that is a polynucleotide encompasses both the double-stranded form and each of two complementary single-stranded forms known or predicted to make up the double-stranded form. It is understood that the isolated polynucleotides and nucleic acids described herein are directed to non naturally occurring polynucleotides and nucleic acids or polynucleotides that encode amino acid sequences that are assembled with amino acid sequences encoded by non naturally occurring polynucleotides. Non-naturally occurring polynucleotides and nucleic acids can include, but not limit to, cDNA and chemically synthesized molecules.

The term "encode" or grammatical equivalents thereof as it is used in reference to polynucleotides refers to a polynucleotide in its native state or when manipulated by methods well known to those skilled in the art that can be transcribed to produce mRNA, which is then translated into a polypeptide and/or a fragment thereof. The antisense strand is the complement of such a polynucleotide, and the encoding sequence can be deduced therefrom.

The phrase "second therapeutic agent" refers to any agent that can be used in the treatment, management or amelioration of a disease associated with expression of Tn antigen or sTn antigen and/or a symptom related thereto. In certain embodiments, a second therapeutic agent refers to an antibody or functional fragment disclosed herein. In other embodiments, a second therapeutic agent refers to an agent other than an antibody or functional fragment disclosed herein. A second therapeutic agent can be an agent which is well known to be useful for, or has been or is currently being used for the treatment, management or amelioration of a disease associated with expression of Tn antigen or sTn antigen and/or one or more symptoms related thereto. Non-limiting examples of second therapeutic agents that can be used in or with the embodiments disclosed herein include chemotherapeutic agents and immunotherapeutic agents.

The phrase "triple negative breast cancer" or "TNBC" refers to a form of breast cancer that tests negative for estrogen receptors (ER⁻), progesterone receiptors (PR⁻) and HER2 (HER2⁻).

The term "Thomsen-nouvelle antigen" or "Tn antigen" refers to the monosaccharide structure N-acetylgalactosamine (GalNAc) linked to serine or threonine by a glycosidic bond (GalNAcα-O-serine/threonine) or other biologically derived macromolecules.

The term "sTn antigen" refers to a sialylated form of Tn antigen that is formed by elongation of the Tn antigen with sialic acid (NeuAcα2→6GalNAcα-O-serine/threonine) rather than galactose.

The term "Thomsen-Friedenreich antigen," "TF antigen," "T antigen" or "Core 1" refers to Tn antigen with an additional galactose monosaccharide that creates a disaccharide antigen (Galβ1→3GalNAcα-O-serine/threonine).

The term "ganglioside" refers to molecule composed of a glycosphingolipid (ceramide and oligosaccharide) with one or more sialic acids (e.g., n-acetylneuraminic acid, NANA) linked on the sugar chain. More than 60 gangliosides are known, which differ from each other mainly in the position and number of NANA residues. Non-limiting examples of gangliosides include ganglisides having one NANA (e.g., GM1, including fucosyl-GM1 (F-GM1), GM2, and GM3), two NANAs (e.g., GD1a, GD1b, GD2, and GD3), three NANAs (e.g., GT1b and GT3), and four NANAs (e.g., GQ1).

The term "globo H" or "globohexaosylceramide" refers to a hexasaccharide formed from the pentasaccharide precursor, SSEA3 (stage-specific embryonic antigen 3). Globo H is a member of a family of antigenic carbohydrates expressed on the surface of cancer cells as glycolipids and glycoproteins.

The term "sialyl Le$^a$" (sLe$^a$), also known as, Sialyl-Lewis$^a$, Sialyl-Lewis A, Sialylated Lewis a and CA 19.9, is a tetrasaccharide with a molecular formula of $C_{31}H_{52}N_2O_{23}$ and a molar mass of 820.74 g/mol. The structure of sLe$^a$ can include Neu5Acα2-3Galβ1-3(Fucα1-4)GlcNAcβ and Neu5Gcα2-3Galβ1-3(Fucα1-4)GlcNAcβ. sLe$^a$ is widely expressed on tumors of the gastrointestinal tract and is used as a tumor marker in pancreatic and colon cancer. sLe$^a$ is also a known ligand for E-selection, also known as endothelial leukocyte adhesion molecule (ELAM).

The phrase "localizing agent" refers to a substance administered to a subject that aids in the diagnosis or treatment of a disease. Such substances can be used to reveal, pinpoint, and/or define the localization of a disease causing process. Such substances can also be used to localize a second therapeutic agent to a location that a conjugate including the localizing agent is bound. In certain embodiments, a localizing agent includes a substance that is conjugated to an antibody or functional fragment disclosed herein, that when administered to a subject or contacted to a sample from a subject aids in the diagnosis or treatment of cancer or tumor formation.

The phrase "detectable agent" refers to a substance that can be used to ascertain the existence or presence of a desired molecule, such as an antibody or functional fragment disclosed herein, in a sample or subject. A detectable agent can be a substance that is capable of being visualized or a substance that is otherwise able to be determined and/or measured (e.g., by quantitation).

The phrase "therapeutic agent," when used in reference to a conjugate, refers to any agent that can be used with an antibody or functional fragment disclosed herein, when conjugated or recombinantly fused with the antibody or functional fragment, in the treatment, management or amelioration of a disease associated with expression of Tn antigen or sTn antigen and/or a symptom related thereto.

An "effective amount" is an amount sufficient to effect beneficial or desired results. An effective amount can be administered in one or more administrations, applications or dosages. Such delivery is dependent on a number of variables including the time period for which the individual dosage unit is to be used, the bioavailability of the agent, the route of administration, etc.

The phrase "therapeutically effective amount" as used herein refers to the amount of a therapeutic agent (e.g., an antibody or functional fragment provided herein or any other therapeutic agent provided herein) which is sufficient to stabilize, reduce and/or ameliorate the severity and/or duration of a given disease and/or a symptom related thereto. A therapeutically effective amount of a therapeutic agent can be an amount necessary for the stabilization, reduction or amelioration of the advancement or progression of a given disease, reduction or amelioration of the recurrence, development or onset of a given disease, and/or to improve or enhance the prophylactic or therapeutic effect of another therapy (e.g., a therapy other than the administration of an antibody or functional fragment provided herein).

The term "tumor antigen" refers to an antigenic substance produced in or on a tumor cell, which can trigger an immune response in the host or be targeted by immunological pharmaceutical agents. Exemplary tumor antigens include any protein or modification thereof produced in a tumor cell that has an abnormal structure due to mutation, abnormal protein production caused by protooncogenes and tumor suppressors, tumor-associated antigens caused by mutation of other genes unrelated to the tumor formation, tissue differentiation antigens, mutant protein antigens, oncogenic viral antigens, cancer-testis antigens, vascular or stromal specific antigens, oncofetal antigens, and other substances like cell surface glycolipids and glycoproteins that have an abnormal structure in tumor cells.

A "co-inhibitory molecule" (also known as a "negative checkpoint regulator" or "NCR") refers to a molecule that down-regulates immune responses (e.g., T-cell activation) by delivery of a negative signal to T-cells following their engagement by ligands or counter-receptors. Exemplary functions of a co-inhibitory molecule is to prevent out-of-proportion immune activation, minimize collateral damage, and/or maintain peripheral self-tolerance. In some aspects, a co-inhibitory molecule is a ligand or receptor expressed by an antigen presenting cell or a T-cell. In aspects, a co-inhibitory molecule is a ligand or receptor expressed by both an antigen presenting cell and a T-cell.

A "co-stimulatory molecule" refers to a molecule that up-regulates immune responses (e.g., T-cell activation) by delivery of a positive signal to T-cells following their engagement by ligands or counter-receptors. For a T-cell to become fully activated, two signals are required: 1) an antigen-specific signal is provided through the T-cell receptor interacting with peptide-MHC molecules on an antigen presenting cell; and 2) a co-stimulatory signal, which is antigen nonspecific, and is provided by the interaction between co-stimulatory molecules expressed on the membrane of an antigen presenting cell and the T-cell. T-cell co-stimulation provides for T-cell proliferation, differentiation and survival. In some aspects, a co-stimulatory molecule is a ligand or receptor expressed by an antigen presenting cell or a T-cell. In some aspects, a co-stimulatory molecule is a ligand or receptor expressed by both an antigen presenting cell and a T-cell.

The term "administer" or "administration" refers to the act of injecting or otherwise physically delivering a substance as it exists outside the body (e.g., an antibody or functional fragment thereof as described herein) into a patient, such as by mucosal, intradermal, intravenous, intramuscular delivery and/or any other method of physical delivery described herein or known in the art. When a disease is being treated, administration of the substance typically occurs after the onset of the disease. When a disease is being prevented, administration of the substance typically occurs before the onset of the disease thereof.

The term "EC50" or "half maximal effective concentration" refers to the concentration of an antibody or functional fragment thereof described herein that induces a response halfway between the baseline and maximum after a specified exposure concentration.

The term "synthetic Tn antigen" refers to a monosaccharide structure N-acetylgalactosamine (GalNAc) of a Tn antigen that is attached to any substrate by a glycosidic bond. Non-limiting exemplary synthetic Tn antigens include a-GalNAc-O(CH$_2$)$_3$NHCO(CH$_2$)$_5$NH-biotin (GlycoTech; Cat #02-010) and α-GalNAc-PAA-biotin (GlycoTech; Cat #01-001, wherein PAA is a polyacrylamide backbone. Another exemplary synthetic Tn antigen is a Tn "cluster" according to the following structure, whereby KLH denotes keyhole limpet hemocyanin, which does not form part of the Tn antigen:

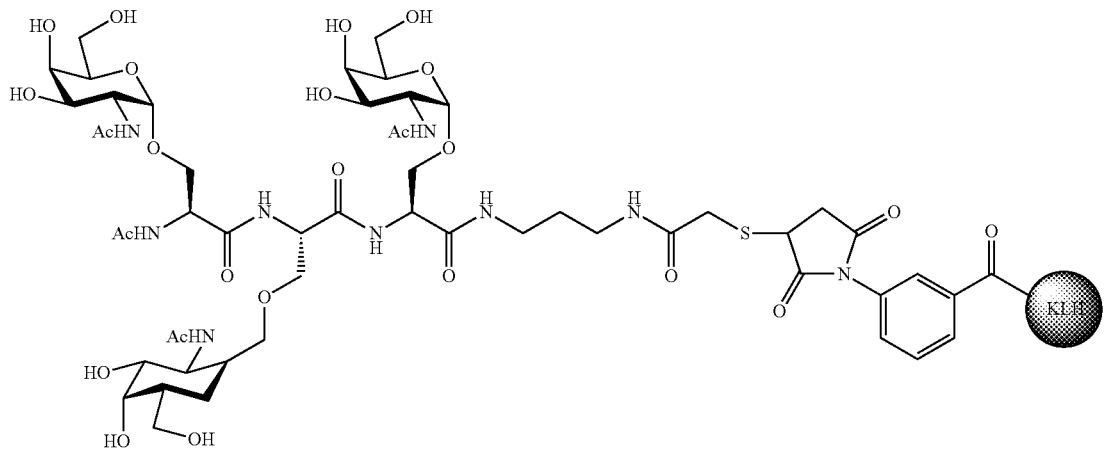

The term "Tn-modified peptide" according to the invention refers to an isolated peptide that has two or more serine or threonine residues, e.g. 2, 3, 4, 5, 6, 7, 8, 9 or 10 serine or threonine residues, or e.g. from about 10, 15, 20, 25, 30, 35, 40, 45, 50 to about 60, 75, 80, 90, 95, 100 serine or threonine residues, or e.g. from about 3, 4, 5, 6, 7, 8, 9 to about 10, 15, 20, 25, 30, 35, 40, 45, 50 serine or threonine residues modified to have a monosaccharide structure N-acetylgalactosamine (GalNAc) attached by a glycosidic bond, wherein the modified serine or threonine residues are separated by 10 or fewer consecutive amino acid residues, e.g. by 2, 3, 4, 5, 6, 7, 8, or 9 consecutive amino acid residues, wherein the serine or threonine residues that are modified to form an Tn or sTn antigen my be positioned adjacent to each other, e.g. serine followed by threonine, or threonine followed by serine. A non-limiting example of a Tn-modified peptide is a Muc1-1-5G peptide having the following amino acid sequence: HGVTSAPDTRPAPG STAPPA (SEQ ID NO: 155), wherein the residues in bold and underline text have been modified to be a Tn antigen.

The term "Tn-modified protein" according to the invention when used in reference to a protein that is expressed by a cell refers to protein expressed by a cell that has two or more serine or threonine residues modified to have a monosaccharide structure N-acetylgalactosamine (GalNAc) attached by a glycosidic bond, wherein the modified serine or threonine residues are separated by 10 or fewer consecutive amino acid residues, including wherein at least two amino acid residues that are modified are adjacent to each other. Such modifications can occur by growth of the cell in culture such that enzymes, which are expressed by such a cell, produce the modified protein on the surface of the cell.

In some embodiments, the invention provides an isolated antibody or functional fragment thereof, wherein the antibody heavy or light chain or functional fragment thereof has one or more of the CDRs from the clonal isolates named 1A12b, 1A4, 1E2b, 1G10, 2A8, 2F3, 3A7 and the 2F3 variants described herein. Accordingly, in some aspects, the antibody heavy or light chain or functional fragment thereof has one or more of the CDRs depicted in Table 2-4 and FIGS. 1-7. An antibody or functional fragment thereof that includes one or more of the CDRs depicted in Table 2-4 and FIGS. 1-7 can specifically bind to a target antigen as described herein, such as specifically a Tn antigen or sTn antigen as described herein. An antibody or functional fragment thereof according to the invention that includes one or more of the CDRs, in particular CDR3, can specifically bind to Tn antigen or sTn antigen as described herein. Specific binding to a Tn antigen or sTn antigen can include the specificity, affinity and/or avidity as provided in Examples provided herein for any of the inventive antibodies provided herein. In some embodiments, the inventive antibody binds Tn or sTn on threonine and/or serine residues. In some embodiments, the antibody preferentially binds Tn or sTn on serine residues. In some embodiments, the antibody specifically binds Tn or sTn on serine residues. Such anti-Tn or anti-sTn antibodies showing preferential or specific binding include, for example, antibody 2F3 and variants #289, #6, #1733, #633, #680-4, #1780-2 and #17v2. Specific binding includes distinguishing the primary, secondary or tertiary structure of the serine linked Tn or sTn antigen compared to threonine linked Tn or sTn. The greater the binding is distinguishing the more specific the antibody is to serine linked Tn or sTn. Preferential binding includes serine specific Tn or sTn antibodies, but can also show cross-reactivity with threonine linked Tn or sTn.

TABLE 2

CDRs of variable heavy chains from seven initial clonal isolates

| Clone | VH CDR1 IMGT | VH CDR1 Kabat | VH CDR2 IMGT | VH CDR2 Kabat | VH CDR3 IMGT | VH CDR3 Kabat |
|---|---|---|---|---|---|---|
| 1A12b | GFTFSDHY (SEQ ID NO: 1) | DHYMD (SEQ ID NO: 7) | IRNKANSYTT (SEQ ID NO: 13) | RIRNKANSYT TEYAASVKG (SEQ ID NO: 19) | ARVSYYAMDV (SEQ ID NO: 25) | VSYYAMDV (SEQ ID NO: 32) |
| 1A4 | GFTFSDQY (SEQ ID NO: 2) | DQYMD (SEQ ID NO: 8) | IRNKANRYTT (SEQ ID NO: 14) | RIRNKANRYT TDYAASVKG (SEQ ID NO: 20) | VRVTAVALDY (SEQ ID NO: 26) | VTAVALDY (SEQ ID NO: 33) |
| 1E2b | GYTFTSYG (SEQ ID NO: 3) | SYGIS (SEQ ID NO: 9) | ISAYNGNT (SEQ ID NO: 15) | WISAYNGNTN YAQKLQG (SEQ ID NO: 21) | ARGGGTTVLD YYRYGMDV (SEQ ID NO: 27) | GGGTTVLD MYYRYGDV (SEQ ID NO: 34) |
| 1G10 | GYTFTSYD (SEQ ID NO: 4) | SYDIN (SEQ ID NO: 10) | MNPNSGNT (SEQ ID NO: 16) | WMNPNSGNT GYAQKFQG (SEQ ID NO: 22) | ARGWRYSSS WYRKVRFDP (SEQ ID NO: 28) | GWRYSSSW YRKVRFDP (SEQ ID NO: 35) |
| 2A8 | GYTFTSYD (SEQ ID NO: 4) | SYDIN (SEQ ID NO: 10) | MNPNSGNT (SEQ ID NO: 16) | WMNPNSGNT GYAQKFQG (SEQ ID NO: 22) | ARANRKGAR TRAFDY (SEQ ID NO: 29) | ANRKGART RAFDY (SEQ ID NO: 36) |
| 2F3 | GFTFDSYA (SEQ ID NO: 5) | SYAMS (SEQ ID NO: 11) | ISGSGDST (SEQ ID NO: 17) | AISGSGDST YYADSVKG (SEQ ID NO: 23) | AIRREYSGY APFDY (SEQ ID NO: 30) | RREYSGYA PFDY (SEQ ID NO: 37) |
| 3A7 | GFTFRSYY (SEQ ID NO: 6) | SYYMS (SEQ ID NO: 12) | INQHGSEK (SEQ ID NO: 18) | SINQHGSEKY YVDSVKG (SEQ ID NO: 24) | ARDGDRTTDY (SEQ ID NO: 31) | DGDRTTDY (SEQ ID NO: 38) |

TABLE 3

CDRs of variable light chains from seven initial clonal isolates

| Clone | VL CDR1 IMGT | VL CDR1 Kabat | VL CDR2L IMGT | VL CDR2L Kabat | VL CDR3 IMGT | VL CDR3 Kabat |
|---|---|---|---|---|---|---|
| 1A12b | QSISSY (SEQ ID NO: 39) | RASQSISSYLN (SEQ ID NO: 46) | AAS (SEQ ID NO: 53) | AASSLQS (SEQ ID NO: 58) | QQSYSTPRT (SEQ ID NO: 65) | QQSYSTPRT (SEQ ID NO: 65) |
| 1A4 | QSVSTY (SEQ ID NO: 40) | RASQSVSTYLA (SEQ ID NO: 47) | DAS (SEQ ID NO: 54) | DASNRAT (SEQ ID NO: 59) | HQRSDWPPVT (SEQ ID NO: 66) | HQRSDWPPVT (SEQ ID NO: 66) |
| 1E2b | SGINVGTYR (SEQ ID NO: 41) | TLRSGINVGTYRIY (SEQ ID NO: 48) | YKSDSDK (SEQ ID NO: 55) | YKSDSDKQQGS (SEQ ID NO: 60) | MIWHSSAVV (SEQ ID NO: 67) | MIWHSSAVV (SEQ ID NO: 67) |
| 1G10 | QSLLHSNGYNY (SEQ ID NO: 42) | RSSQSLLHSNGYNYLD (SEQ ID NO: 49) | LGS (SEQ ID NO: 56) | LGSNRAS (SEQ ID NO: 61) | MQALQTPIT (SEQ ID NO: 68) | MQALQTPIT (SEQ ID NO: 68) |
| 2A8 | SSSNIGNNY (SEQ ID NO: 43) | SGSSSNIGNNYVS (SEQ ID NO: 50) | DNN (SEQ ID NO: 57) | DNNKRPS (SEQ ID NO: 62) | GTWDSSLSAV (SEQ ID NO: 69) | GTWDSSLSAV (SEQ ID NO: 69) |
| 2F3 | QGISSW (SEQ ID NO: 44) | RASQGISSWLA (SEQ ID NO: 51) | AAS (SEQ ID NO: 53) | AASSLQS (SEQ ID NO: 63) | QQYISYPYT (SEQ ID NO: 70) | QQYISYPYT (SEQ ID NO: 70) |
| 3A7 | QSVSSY (SEQ ID NO: 45) | RASQSVSSYLV (SEQ ID NO: 52) | AAS (SEQ ID NO: 53) | AASNRAA (SEQ ID NO: 64) | QQRSNWPIT (SEQ ID NO: 71) | QQRSNWPIT (SEQ ID NO: 71) |

TABLE 4

CDRs of variable heavy chains from 2F3 variants

| Clone | VH CDR1 | VH CDR2 IMGT | VH CDR3 |
|---|---|---|---|
| 2F3 Original | GFTFDSYA (SEQ ID NO: 5) | ISGSGDST (SEQ ID NO: 17) | AIRREYSGYAPFDY (SEQ ID NO: 30) |
| 2F3#289 | GFTFDSYA (SEQ ID NO: 5) | ISGSGDST (SEQ ID NO: 17) | AIRREYSGYAPFDY (SEQ ID NO: 30) |
| 2F3#27 | GFTFDSYA (SEQ ID NO: 5) | ISGSGDST (SEQ ID NO: 17) | AIRREYSGYAPFDY (SEQ ID NO: 30) |
| 2F3#51 | GFTFDSYA (SEQ ID NO: 5) | ISGSGDST (SEQ ID NO: 17) | AIRREYSGYAPFDY (SEQ ID NO: 30) |
| 2F3#17 | GFTFDSYA (SEQ ID NO: 5) | ISGSGHST (SEQ ID NO: 149) | AIRREYSGYAPFDY (SEQ ID NO: 30) |
| 2F3#33 | GFTFDSYA (SEQ ID NO: 5) | ISGSGDST (SEQ ID NO: 17) | AIRREYSGYTPFDY (SEQ ID NO: 154) |
| 2F3#80 | GFTFDSYA (SEQ ID NO: 5) | ISGSGDST (SEQ ID NO: 17) | AIRREYSGYAPFDY (SEQ ID NO: 30) |
| 2F3#75 | GFTFDSYA (SEQ ID NO: 5) | ISGSGDST (SEQ ID NO: 17) | AIRREYSGYAPFDY (SEQ ID NO: 30) |
| 2F3#50 | GFTFDSYA (SEQ ID NO: 5) | ISGSGDST (SEQ ID NO: 17) | AIRREYSGYAPFDY (SEQ ID NO: 30) |
| 2F3#6 | GFTFDSYA (SEQ ID NO: 5) | ISGSGAST (SEQ ID NO: 150) | AIRREYSGYAPFDY (SEQ ID NO: 30) |
| 2F3#17V2 | GFTFDSYA (SEQ ID NO: 5) | ISGSGHST (SEQ ID NO: 149) | AIRREYSGYAPFDY (SEQ ID NO: 30) |
| 2F3CDR2R | GFTFDSYA (SEQ ID NO: 5) | ISGSGRST (SEQ ID NO: 151) | AIRREYSGYAPFDY (SEQ ID NO: 30) |

TABLE 4-continued

CDRs of variable heavy chains from 2F3 variants

| Clone | VH CDR1 | VH CDR2 IMGT | VH CDR3 |
|---|---|---|---|
| 2F3CDR2Y | GFTFDSYA (SEQ ID NO: 5) | ISGSGYST (SEQ ID NO: 152) | AIRREYSGYAPFDY (SEQ ID NO: 30) |
| 2F3CDR2F | GFTFDSYA (SEQ ID NO: 5) | ISGSGFST (SEQ ID NO: 153) | AIRREYSGYAPFDY (SEQ ID NO: 30) |
| 2F3#1733 | GFTFDSYA (SEQ ID NO: 5) | ISGSGHST (SEQ ID NO: 149) | AIRREYSGYTPFDY (SEQ ID NO: 154) |
| 2F3#680 | GFTFDSYA (SEQ ID NO: 5) | ISGSGAST (SEQ ID NO: 150) | AIRREYSGYAPFDY (SEQ ID NO: 30) |
| 2F3#1780 | GFTFDSYA (SEQ ID NO: 5) | ISGSGHST (SEQ ID NO: 149) | AIRREYSGYAPFDY (SEQ ID NO: 30) |
| 2F3#633 | GFTFDSYA (SEQ ID NO: 5) | ISGSGAST (SEQ ID NO: 150) | AIRREYSGYTPFDY (SEQ ID NO: 154) |

In some embodiments, an antibody or functional fragment thereof disclosed herein has one or more of the following features:
- binds to two Tn antigen molecules, wherein the two Tn antigen molecules are each located on an amino acid residue of a protein, and wherein the two Tn antigen molecules are separated by 10 or fewer consecutive amino acid residues;
- binds to two Tn antigen molecules, wherein the two Tn antigen molecules are located on adjacent amino acid residues of a protein;
- greater than 10 fold higher avidity for Tn antigen than sialyl Le$^a$, globo H, or a ganglioside selected from the group consisting of F-GM1, GM2, GM3, GD2, and GD3;
- greater than 10 fold higher avidity for Tn antigen than Thomsen-Friedenreich (TF) antigen;
- does not bind sialyl Le$^a$, globo H, or a ganglioside selected from the group consisting of F-GM1, GM2, GM3, GD2, and GD3 above a background control in an enzyme-linked immunosorbant assay;
- does not bind TF antigen above a background control in an enzyme-linked immunosorbant assay;
- has an EC50 value for binding to Tn antigen of less than 50 nM;
- has an EC50 value for binding to Tn antigen of less than 20 nM;
- has an EC50 value for binding to Tn antigen of less than 10 nM; or
- preferentially binds a Tn or sTn antigen, wherein the Tn or sTn antigen is on a serine residue;
- specifically binds a Tn or sTn antigen, wherein the Tn or sTn antigen is on a serine residue;
- preferentially binds a Tn or sTn antigen, wherein the Tn or sTn antigen is on a cancer cell, and the Tn or sTn antigen is on a seine residue;
- specifically binds a Tn or sTn antigen, wherein the Tn or sTn antigen is on a cancer cell, and the Tn or sTn antigen is on a seine residue.

In some aspects, features described above for inventive antibody or functional fragment thereof as disclosed herein is determined using Tn antigen that is a synthetic Tn antigen; part of a Tn-modified peptide; or part of a Tn-modified protein expressed by a cell. In some aspects, the Tn antigen is expressed by a cancer cell. Methods for assessing any of the above features of an antibody or functional fragment thereof described herein are well known in the art and exemplary methods are provided herein.

The present invention further includes an antibody or functional fragment thereof that binds preferentially or specifically to a Tn antigen or a sTn antigen on one or more serine residues. This preferential or specific binding to Tn or sTn on one or more serine residues may, for example, facilitate distinguishing target cells such as cancer compared to non-target cells such as normal immune cells. Additionally, the antibodies provided herein having preferential or specific to Tn or sTn on one or more serine residues are IgG isotypes, including IgG1 isotypes, which have distinguishing characteristics compared to, for example, IgM isotypes. Therefore, in some embodiments the present invention may, for example, facilitate target versus non-target selectivity using the antibodies or functional fragment thereof that binds preferentially or specifically to a Tn antigen or a sTn antigen on one or more serine residues to provide. In certain embodiments, the present invention provides a method to specifically target the cancer cell expressing Tn antigen through targeting serine linked Tn or sTn compared to theorine linked Tn or sTn.

In some embodiments, the antibody or functional fragment thereof disclosed herein includes less than six CDRs. In some embodiments, the antibody or functional fragment thereof includes one, two, three, four, or five CDRs selected from the group consisting of VH CDR1, VH CDR2, VH CDR3, VL CDR1, VL CDR2, and/or VL CDR3. In specific embodiments, the antibody or functional fragment thereof includes one, two, three, four, or five CDRs selected from the group consisting of VH CDR1, VH CDR2, VH CDR3, VL CDR1, VL CDR2, and/or VL CDR3 of clonal isolates 1A12b, 1A4, 1E2b, 1G10, 2A8, 2F3, or 3A7, including the 2F3 variants, described herein. Such CDRs are depicted in Table 2-4 and FIGS. 1-7.

In some embodiments, the present invention provides an isolated antibody or functional fragment thereof that binds to a Tn antigen or an sTn antigen, wherein the antibody or functional fragment thereof includes: (a) a VH domain, wherein the VH domain includes: a VH CDR1 having an amino acid sequence selected from the group consisting of SEQ ID NOS: 2, 5, 6, 8, 11, and 12; a VH CDR2 having an amino acid sequence selected from the group consisting of SEQ ID NOS: 14, 17, 18, 20, 23, 24, 149, 150, 151, 152, and 153; and a VH CDR3 having an amino acid sequence selected from the group consisting of SEQ ID NOS: 26, 30, 31, 33, 37, 38, and 154; and/or (b) a VL domain, wherein the VL domain includes: a VL CDR1 having an amino acid sequence selected from the group consisting of SEQ ID NOS: 40, 44, 45, 47, 51, and 52; a VL CDR2 having an amino acid sequence selected from the group consisting of SEQ ID NOS: 54, 53, 59, 63, and 64; and a VL CDR3 having an amino acid sequence selected from the group consisting of SEQ ID NOS: 66, 70, and 71.

In some embodiments, the present invention provides an isolated antibody or functional fragment thereof that binds to a Tn antigen or an sTn antigen, wherein the antibody or functional fragment thereof includes: (a) a VH domain, wherein the VH domain includes: a VH CDR1 having an amino acid sequence selected from the group consisting of SEQ ID NOS: 2, 5, 6, 8, 11, and 12; a VH CDR2 having an amino acid sequence selected from the group consisting of SEQ ID NOS: 14, 17, 18, 20, 23, 24, 149, 150, 151, 152, and 153; and a VH CDR3 having an amino acid sequence selected from the group consisting of SEQ ID NOS: 26, 30, 31, 33, 37, 38, and 154.

In some embodiments, the present invention provides an isolated antibody or functional fragment thereof that binds to a Tn antigen or an sTn antigen, wherein the antibody or functional fragment thereof includes: (a) a VL domain, wherein the VL domain includes: a VL CDR1 having an amino acid sequence selected from the group consisting of SEQ ID NOS: 40, 44, 45, 47, 51, and 52; a VL CDR2 having an amino acid sequence selected from the group consisting of SEQ ID NOS: 54, 53, 59, 63, and 64; and a VL CDR3 having an amino acid sequence selected from the group consisting of SEQ ID NOS: 66, 70, and 71.

In some embodiments, the present invention provides an isolated antibody or functional fragment thereof that binds to a Tn antigen or an sTn antigen, wherein the antibody or functional fragment thereof includes: a VH domain and a VL domain, wherein the VH domain includes: a VH CDR1 having an amino acid sequence selected from the group consisting of SEQ ID NOS: 2 and 8; a VH CDR2 having an amino acid sequence selected from the group consisting of SEQ ID NOS: 14 and 20; and a VH CDR3 having an amino acid sequence selected from the group consisting of SEQ ID NOS: 26 and 33; and the VL domain includes: a VL CDR1 having an amino acid sequence selected from the group consisting of SEQ ID NOS: 40 and 47; a VL CDR2 having an amino acid sequence selected from the group consisting of SEQ ID NOS: 54 and 59; and a VL CDR3 having an amino acid sequence of SEQ ID NO: 66.

In some embodiments, the present invention provides an isolated antibody or functional fragment thereof that binds to a Tn antigen or an sTn antigen, wherein the antibody or functional fragment thereof includes: a VH domain and a VL domain, wherein the VH domain includes: a VH CDR1 having an amino acid sequence selected from the group consisting of SEQ ID NOS: 5 and 11; a VH CDR2 having an amino acid sequence selected from the group consisting of SEQ ID NOS: 17, 23, 149, 150, 151, 152, and 153; and a VH CDR3 having an amino acid sequence selected from the group consisting of SEQ ID NOS: 30, 37, and 154; and the VL domain includes: a VL CDR1 having an amino acid sequence selected from the group consisting of SEQ ID NOS: 44 and 51; a VL CDR2 having an amino acid sequence selected from the group consisting of SEQ ID NOS: 53 and 63; and a VL CDR3 having an amino acid of SEQ ID NO: 70.

In some embodiments, the antibody or functional fragment thereof described herein comprises a VH and a VL domain, wherein the (i) VH domain comprises a VH CDR1 of SEQ ID NO: 5, a VH CDR2 of SEQ ID NO: 17 and a VH CDR3 of SEQ ID NO: 30 and the VL domain comprises a VL CDR1 of SEQ ID NO: 44, a VL CDR2 of SEQ ID NO: 53 and a VL CDR3 of SEQ ID NO: 70; or (ii) the VH domain comprises a VH CDR1 of SEQ ID NO: 5, a VH CDR2 of SEQ ID NO: 149, and a VH CDR3 of SEQ ID NO: 30 and the VL domain comprises a VL CDR1 of SEQ ID NO: 44, a VL CDR2 of SEQ ID NO: 53 and a VL CDR3 of SEQ ID NO: 70; or (iii) the VH domain comprises a VH CDR1 of SEQ ID NO: 5, a VH CDR2 of SEQ ID NO: 17 and a VH CDR3 of SEQ ID NO: 154 and the VL domain comprises a VL CDR1 of SEQ ID NO: 44, a VL CDR2 of SEQ ID NO: 53 and a VL CDR3 of SEQ ID NO: 70; or (iv) the VH domain comprises a VH CDR1 of SEQ ID NO: 5, a VH CDR2 of SEQ ID NO: 150 and a VH CDR3 of SEQ ID NO: 30 and the VL domain comprises a VL CDR1 of SEQ ID NO: 44, a VL CDR2 of SEQ ID NO: 53 and a VL CDR3 of SEQ ID NO: 70; or (v) the VH domain comprises a VH CDR1 of SEQ ID NO: 5, a VH CDR2 of SEQ ID NO: 151 and a VH CDR3 of SEQ ID NO: 30 and the VL domain comprises a VL CDR1 of SEQ ID NO: 44, a VL CDR2 of SEQ ID NO: 53 and a VL CDR3 of SEQ ID NO: 70; or (vi) the VH domain comprises a VH CDR1 of SEQ ID NO: 5, a VH CDR2 of SEQ ID NO: 152 and a VH CDR3 of SEQ ID NO: 30 and the VL domain comprises a VL CDR1 of SEQ ID NO: 44, a VL CDR2 of SEQ ID NO: 53 and a VL CDR3 of SEQ ID NO: 70; or (vii) the VH domain comprises a VH CDR1 of SEQ ID NO: 5, a VH CDR2 of SEQ ID NO: 153 and a VH CDR3 of SEQ ID NO: 30 and the VL domain comprises a VL CDR1 of SEQ ID NO: 44, a VL CDR2 of SEQ ID NO: 53 and a VL CDR3 of SEQ ID NO: 70; or (viii) the VH domain comprises a VH CDR1 of SEQ ID NO: 5, a VH CDR2 of SEQ ID NO: 149 and a VH CDR3 of SEQ ID NO: 154 and the VL domain comprises a VL CDR1 of SEQ ID NO: 44, a VL CDR2 of SEQ ID NO: 53 and a VL CDR3 of SEQ ID NO: 70; or (ix) the VH domain comprises a VH CDR1 of SEQ ID NO: 5, a VH CDR2 of SEQ ID NO: 150 and a VH CDR3 of SEQ ID NO: 154 and the VL domain comprises a VL CDR1 of SEQ ID NO: 44, a VL CDR2 of SEQ ID NO: 53 and a VL CDR3 of SEQ ID NO: 70.

In some embodiments, the present invention provides an isolated antibody or functional fragment thereof that binds to a Tn antigen or an sTn antigen, wherein the antibody or functional fragment thereof includes: a VH domain and a VL domain, wherein the VH domain includes: a VH CDR1 having an amino acid sequence selected from the group consisting of SEQ ID NOS: 6 and 12; a VH CDR2 having an amino acid sequence selected from the group consisting of SEQ ID NOS: 18 and 24; and a VH CDR3 having an amino acid sequence selected from the group consisting of SEQ ID NOS: 31 and 38; and the VL domain includes: a VL CDR1 having an amino acid sequence selected from the group consisting of SEQ ID NOS: 45 and 52; a VL CDR2 having an amino acid sequence selected from the group consisting of SEQ ID NOS: 53 and 64; and a VL CDR3 having an amino acid sequence of SEQ ID NO: 71.

In some embodiments, the present invention provides an isolated antibody or functional fragment having a VH domain with the amino acid sequence of the VH domain for the clonal isolate 1A12b, 1A4, 1E2b, 1G10, 2A8, 2F3, or 3A7, including the 2F3 variants, as described herein. Such VH domain sequences are depicted in Tables 5 and 6 and FIGS. 1 and 3-7.

In some embodiments, the present invention provides an isolated antibody or functional fragment having a VL domain with the amino acid sequence of the VL domain for the clonal isolate 1A12b, 1A4, 1E2b, 1G10, 2A8, 2F3, or 3A7, including the 2F3 variants, described herein. Such VH domain sequences are depicted in Table 5 and FIG. 2.

In some embodiments, the present invention provides an isolated antibody or functional fragment having a VH domain and a VL domain with the amino acid sequence of the VH domain and VL domain for the clonal isolate 1A12b, 1A4, 1E2b, 1G10, 2A8, 2F3, or 3A7, including the 2F3 variants, described herein. Such VH domain and VL domain sequences are depicted in Table 5 and 6 and FIGS. 1-7.

TABLE 5

Amino acid sequences of the heavy chain and light chain variable regions of the seven initial antibody candidates

| Clone | Heavy Chain Variable Region | Light Chain Variable Region |
| --- | --- | --- |
| 1A12b | QVQLVESGGGLVQPGGSLRLSCAVSGFTFS DHYMDWVRQAPGKGLEWVGRIRNKANSY TTEYAASVKGRFTISRDESKRSLYLQMNSL KTEDTAVYYCARVSYYAMDVWGQGTTVT VSS (SEQ ID NO: 100) | EIVLTQSPSSLSASVGDRVTITCRASQSISSYL NWYQQKPGKAPKLLIYAASSLQSGVPSRFSG SGSGTDFTLTISSLQPEDFATYYCQQSYSTPR TFGQGTKVEIK (SEQ ID NO: 107) |
| 1A4 | QLQLVESGGGLVQPGGSLRLSCAASGFTFS DQYMDWIRQAPGKGLEWVGRIRNKANRYT TDYAASVKGRFIISRDDSKNSLYLQMNRLRI EDTAVYYCVRVTAVALDYWGQGTLVTVSS (SEQ ID NO: 101) | DVVMTQSPATLSLSPGERATLSCRASQSVST YLAWYQQKPGQAPTLLIYDASNRATGIPARF SGRGSGTDFTLTISSLEPEDFAVYYCHQRSD WPPVTFGQGTRLEIK (SEQ ID NO: 108) |
| 1E2b | QVQLQQSGAEVKKPGASVKVSCKATGYTF TSYGISWVRQAPGQGLEWMGWISAYNGNT NYAQKLQGRVTMTTDTSTSTAYMELRSLRS DDTAVYYCARGGGTTVLDYYRYGMDVWG QGTTVTVSS (SEQ ID NO: 102) | QSVLTQPPSLSASPGASASLTCTLRSGINVGT YRIYWYQQKPGSPPQYLLRYKSDSDKQQGS GVPSRFSGSKDASANAGILLISGLQSEDEADY YCMIWHSSAVVFGGGTKLTVL (SEQ ID NO: 109) |
| 1G10 | QVQLVQSGAEVKKPGASVKVSCKASGYTF TSYDINWVRQATGQGLEWMGWMNPNSGN TGYAQKFQGRVTMTRNTSISTAYMELSSLR SEDTAVYYCARGWRYSSSWYRKVRFDPW GQGTLVTVSS (SEQ ID NO: 103) | ETTLTQSPLSLPVTPGEPASISCRSSQSLLHSN GYNYLDWYLQKPGQSPQLLIYLGSNRASGV PDRFSGSGSGTDFTLKISRVEAEDVGVYYCM QALQTPITFGQGTRLEIK (SEQ ID NO: 110) |
| 2A8 | QVQLVGSGAEVKKPGASVKVSCKASGYTF TSYDINWVRQATGQGLEWMGWMNPNSGN TGYAQKFQGRVTMTRNTSISTAYMELSSLR SEDTAVYYCARANRKGARTRAFDYWGQG TLVTVSS (SEQ ID NO: 104) | QSVLIQPPSVSAAPGQKVTISCSGSSSNIGNN YVSWYQQLPGTAPKLLIYDNNKRPSGIPVRF SGSKSGTSATLGITGLQTGDEADYYCGTWDS SLSAVFGTGTKVTVL (SEQ ID NO: 111) |
| 2F3 | QITLRESGGGLVQPGGSLRLSCAASGFTFDS YAMSWVRQAPGKGLEWVSAISGSGDSTYY ADSVKGRFSISRDNSKNTLYLQMNSLRAED TAVYYCAIRREYSGYAPFDYWGQGTLVTV SS (SEQ ID NO: 105) | DIVMTQTPSSLSASVGDRVTITCRASQGISSW LAWYQQKPEKAPRSLIYAASSLQSGVPSRFS GSGSGTDFTLTISSLQPEDFATYYCQQYISYP YTFGQGTKLEIK (SEQ ID NO: 112) |
| 3A7 | QVQLVQSGGGLVQPGETLRLSCEASGFTFR SYYMSWVRQAPRKGLEWVASINQHGSEKY YVDSVKGRFTISRDNAKNSLYLQMISLRAE DTAVYYCARDGDRTTDYWGQGTLVTVSS (SEQ ID NO: 106) | ETTLTQSPATLSLSPGDRATLSCRASQSVSSY LVWYQQKFGQAPRLLIYAASNRAAGIPARFS GSGSGTDFTLTISSLEPEDFAVYYCQQRSNW PITFGPGTKVDIK (SEQ ID NO: 113) |

TABLE 6

Amino acid sequences of the heavy chain variable regions of 2F3 variants

| Clone | SEQ ID NO. | SEQUENCE |
|---|---|---|
| 2F3#289 | 114 | EVQLLESGGGLVQPGGSLRLSCAASGFTFDSYAMSWVRQAPGKGLEWVSAISGSGDSTYYADSVKGRFSISRDNSKNTLYLQMNSLRAEDTAVYYCAIRREYSGYAPFDYWGQGTLVTVSS |
| 2F3#27 | 115 | QVTLKESGGGLVQPGGFLRLSCAASGFTFDSYAMSWVRQAPGKGLEWVSAISGSGDSTYYADSVKGRFSISRDNSKNTLYLQMNSLRAEDTAVYYCAIRREYSGYAPFDYWGQGTLVTVSS |
| 2F3#51 | 116 | QVTLKESGGGLVQPGGSLRLSCAASGFTFDSYAMSWVRQAPGKGLEWVSAISGSGDSTYYADSVKGRFSISRDNSKNTLYLQMNSLRAEDTAVYYCAIRREYSGYAPFDYWGKGTLVTVSS |
| 2F3#17 | 117 | QITLRESGGGLVQPGGSLRLSCAASGFTFDSYAMSWVRQAPGKGLEWVSAISGSGHSTYYADSVKGRFSISRDNSKNTLYLQMNNLRAEDTAVYYCAIRREYSGYAPFDYWGQGTLVT... |
| 2F3#33 | 118 | QITLRESGGGLVQPGGSLRLSCAASGFTFDSYAMSWVCQAPGKGLEWVSAISGSGDSTYYADSVKGRFSISRDNSKNTLYLQMNSLRAEDTAVYYCAIRREYSGYTPFDYWGQGTLVTVSS |
| 2F3#80 | 119 | QITLKESGGGLVQPGGSLRLSCAASGFTFDSYAMSWIRQAPGKGLEWVSAISGSGDSTYYAYSVKGRFSISRDNSKNTLYLQMNSLRAEDTAVYYCAIRREYSGYAPFDYWGQGTLVTVSS |
| 2F3#75 | 120 | QVQLVESGGGLVQPGGSLRLSCAASGFTFDSYAMSWVRQAPGKGLEWVSAISGSGDSTYYADSVKGRFSISRDNSKNTLYLQMNSLRAEDAAVYYCAIRREYSGYAPFDYWGQGTLVTVSS |
| 2F3#50 | 121 | QVTLRESVGGLVQPGGSLRLSCAASGFTFDSYAMSWVRQAPGKGLEWVSAISGSGDSTYYADSMKGRFSISRDNSKNTLYLQMNSLRAEDTAVYYCAIRREYSGYAPFDYWGQGTLVTVSS |
| 2F3#6 | 122 | QVQLLESGGGLVQPGGSLRLSCAASGFTFDSYAMSWVRQAPGKGLEWVSAISGSGASTYYADSVKGRFSISRDNSKNTLYLQMNSLRAEDTAVYYCAIRREYSGYAPFDYWGQGTLVIVSS |
| 2F3#17V2 | 123 | QITLRESGGGLVQPGGSLRLSCAASGFTFDSYAMSWVRQAPGKGLEWVSAISGSGHSTYYADSVKGRFSISRDNSKNTLYLQMNNLRAEDTAVYYCAIRREYSGYAPFDYWGQGTLVTVSS |
| 2F3CDR2R | 124 | EVQLLESGGGLVQPGGSLRLSCAASGFTFDSYAMSWVRQAPGKGLEWVSAISGSGRSTYYADSVKGRFSISRDNSKNTLYLQMNSLRAEDTAVYYCAIRREYSGYAPFDYWGQGTLVTVSS |
| 2F3CDR2Y | 125 | EVQLLESGGGLVQPGGSLRLSCAASGFTFDSYAMSWVRQAPGKGLEWVSAISGSGYSTYYADSVKGRFSISRDNSKNTLYLQMNSLRAEDTAVYYCAIRREYSGYAPFDYWGQGTLVTVSS |
| 2F3CDR2F | 126 | EVQLLESGGGLVQPGGSLRLSCAASGFTFDSYAMSWVRQAPGKGLEWVSAISGSGFSTYYADSVKGRFSISRDNSKNTLYLQMNSLRAEDTAVYYCAIRREYSGYAPFDYWGQGTLVTVSS |
| 2F3#1733 | 127 | QITLRESGGGLVQPGGSLRLSCAASGFTFDSYAMSWVRQAPGKGLEWVSAISGSGHSTYYADSVKGRFSISRDNSKNTLYLQMNNLRAEDTAVYYCAIRREYSGYTPFDYWGQGTLVTVSS |
| 2F3#680 | 128 | QITLKESGGGLVQPGGSLRLSCAASGFTFDSYAMSWIRQAPGKGLEWVSAISGSGASTYYAYSVKGRFSISRDNSKNTLYLQMNSLRAEDTAVYYCAIRREYSGYAPFDYWGQGTLVTVSS |
| 2F3#1780 | 129 | QITLKESGGGLVQPGGSLRLSCAASGFTFDSYAMSWIRQAPGKGLEWVSAISGSGHSTYYAYSVKGRFSISRDNSKNTLYLQMNSLRAEDTAVYYCAIRREYSGYAPFDYWGQGTLVTVSS |
| 2F3#633 | 130 | EVQLLESGGGLVQPGGSLRLSCAASGFTFDSYAMSWVRQAPGKGLEWVSAISGSGASTYYADSVKGRFSISRDNSKNTLYLQMNSLRAEDTAVYYCAIRREYSGYTPFDYWGQGTLVTVSS |

In some embodiments, the present invention provides an isolated antibody or functional fragment thereof that binds to a Tn antigen or an sTn antigen, wherein the antibody or functional fragment thereof includes a VH domain having an amino acid sequence selected from the group consisting of SEQ ID NOS: 101, 105, 106 and 114, 115, 116, 117, 118, 119, 129, 121, 122, 123, 124, 125, 126, 127, 128, 129, and 130.

In some embodiments, the present invention provides an isolated antibody or functional fragment thereof that binds to a Tn antigen or an sTn antigen, wherein the antibody or functional fragment thereof includes a VL domain having an amino acid sequence selected from the group consisting of SEQ ID NOS: 108, 112 and 113.

In some embodiments, the present invention provides an isolated antibody or functional fragment thereof that binds to a Tn antigen or an sTn antigen, wherein the antibody or functional fragment thereof includes a VH domain and a VL domain, wherein the VH domain includes the amino acid sequence of SEQ ID NO: 101 and the VL domain includes the amino acid sequence of SEQ ID NO: 108.

In some embodiments, the present invention provides an isolated antibody or functional fragment thereof that binds to a Tn antigen or an sTn antigen, wherein the antibody or functional fragment thereof includes a VH domain and a VL domain, wherein the VH domain includes an amino acid sequence selected from the group consisting of SEQ ID NOS: 105 and the VL domain includes the amino acid sequence of SEQ ID NO: 112.

In some embodiments, the present invention provides an isolated antibody or functional fragment thereof that binds to a Tn antigen or an sTn antigen, wherein the antibody or functional fragment thereof includes a VH domain and a VL domain, wherein the VH domain includes an amino acid sequence selected from the group consisting of SEQ ID NOS: 114 and the VL domain includes the amino acid sequence of SEQ ID NO: 112.

In some embodiments, the present invention provides an isolated antibody or functional fragment thereof that binds to a Tn antigen or an sTn antigen, wherein the antibody or functional fragment thereof includes a VH domain and a VL domain, wherein the VH domain includes an amino acid sequence selected from the group consisting of SEQ ID NOS: 115 and the VL domain includes the amino acid sequence of SEQ ID NO: 112.

In some embodiments, the present invention provides an isolated antibody or functional fragment thereof that binds to a Tn antigen or an sTn antigen, wherein the antibody or functional fragment thereof includes a VH domain and a VL domain, wherein the VH domain includes an amino acid sequence selected from the group consisting of SEQ ID NOS: 116 and the VL domain includes the amino acid sequence of SEQ ID NO: 112.

In some embodiments, the present invention provides an isolated antibody or functional fragment thereof that binds to a Tn antigen or an sTn antigen, wherein the antibody or functional fragment thereof includes a VH domain and a VL domain, wherein the VH domain includes an amino acid sequence selected from the group consisting of SEQ ID NOS: 117 and the VL domain includes the amino acid sequence of SEQ ID NO: 112.

In some embodiments, the present invention provides an isolated antibody or functional fragment thereof that binds to a Tn antigen or an sTn antigen, wherein the antibody or functional fragment thereof includes a VH domain and a VL domain, wherein the VH domain includes an amino acid sequence selected from the group consisting of SEQ ID NOS: 105 and 114-130 and the VL domain includes the amino acid sequence of SEQ ID NO: 112.

In some embodiments, the present invention provides an isolated antibody or functional fragment thereof that binds to a Tn antigen or an sTn antigen, wherein the antibody or functional fragment thereof includes a VH domain and a VL domain, wherein the VH domain includes an amino acid sequence selected from the group consisting of SEQ ID NOS: 118 and the VL domain includes the amino acid sequence of SEQ ID NO: 112.

In some embodiments, the present invention provides an isolated antibody or functional fragment thereof that binds to a Tn antigen or an sTn antigen, wherein the antibody or functional fragment thereof includes a VH domain and a VL domain, wherein the VH domain includes an amino acid sequence selected from the group consisting of SEQ ID NOS: 119 and the VL domain includes the amino acid sequence of SEQ ID NO: 112.

In some embodiments, the present invention provides an isolated antibody or functional fragment thereof that binds to a Tn antigen or an sTn antigen, wherein the antibody or functional fragment thereof includes a VH domain and a VL domain, wherein the VH domain includes an amino acid sequence selected from the group consisting of SEQ ID NOS: 105 and 114-130 and the VL domain includes the amino acid sequence of SEQ ID NO: 112.

In some embodiments, the present invention provides an isolated antibody or functional fragment thereof that binds to a Tn antigen or an sTn antigen, wherein the antibody or functional fragment thereof includes a VH domain and a VL domain, wherein the VH domain includes an amino acid sequence selected from the group consisting of SEQ ID NOS: 120 and the VL domain includes the amino acid sequence of SEQ ID NO: 112.

In some embodiments, the present invention provides an isolated antibody or functional fragment thereof that binds to a Tn antigen or an sTn antigen, wherein the antibody or functional fragment thereof includes a VH domain and a VL domain, wherein the VH domain includes an amino acid sequence selected from the group consisting of SEQ ID NOS: 121 and the VL domain includes the amino acid sequence of SEQ ID NO: 112.

In some embodiments, the present invention provides an isolated antibody or functional fragment thereof that binds to a Tn antigen or an sTn antigen, wherein the antibody or functional fragment thereof includes a VH domain and a VL domain, wherein the VH domain includes an amino acid sequence selected from the group consisting of SEQ ID NOS: 122 and the VL domain includes the amino acid sequence of SEQ ID NO: 112.

In some embodiments, the present invention provides an isolated antibody or functional fragment thereof that binds to a Tn antigen or an sTn antigen, wherein the antibody or functional fragment thereof includes a VH domain and a VL domain, wherein the VH domain includes an amino acid sequence selected from the group consisting of SEQ ID NOS: 123 and the VL domain includes the amino acid sequence of SEQ ID NO: 112.

In some embodiments, the present invention provides an isolated antibody or functional fragment thereof that binds to a Tn antigen or an sTn antigen, wherein the antibody or functional fragment thereof includes a VH domain and a VL domain, wherein the VH domain includes an amino acid sequence selected from the group consisting of SEQ ID NOS: 124 and the VL domain includes the amino acid sequence of SEQ ID NO: 112.

In some embodiments, the present invention provides an isolated antibody or functional fragment thereof that binds to a Tn antigen or an sTn antigen, wherein the antibody or functional fragment thereof includes a VH domain and a VL domain, wherein the VH domain includes an amino acid sequence selected from the group consisting of SEQ ID NOS: 125 and the VL domain includes the amino acid sequence of SEQ ID NO: 112.

In some embodiments, the present invention provides an isolated antibody or functional fragment thereof that binds to a Tn antigen or an sTn antigen, wherein the antibody or functional fragment thereof includes a VH domain and a VL domain, wherein the VH domain includes an amino acid sequence selected from the group consisting of SEQ ID NOS: 126 and the VL domain includes the amino acid sequence of SEQ ID NO: 112.

In some embodiments, the present invention provides an isolated antibody or functional fragment thereof that binds to a Tn antigen or an sTn antigen, wherein the antibody or functional fragment thereof includes a VH domain and a VL domain, wherein the VH domain includes an amino acid sequence selected from the group consisting of SEQ ID NOS: 127 and the VL domain includes the amino acid sequence of SEQ ID NO: 112.

In some embodiments, the present invention provides an isolated antibody or functional fragment thereof that binds to a Tn antigen or an sTn antigen, wherein the antibody or functional fragment thereof includes a VH domain and a VL domain, wherein the VH domain includes an amino acid sequence selected from the group consisting of SEQ ID NOS: 128 and the VL domain includes the amino acid sequence of SEQ ID NO: 112.

In some embodiments, the present invention provides an isolated antibody or functional fragment thereof that binds to a Tn antigen or an sTn antigen, wherein the antibody or functional fragment thereof includes a VH domain and a VL domain, wherein the VH domain includes an amino acid sequence selected from the group consisting of SEQ ID NOS: 129 and the VL domain includes the amino acid sequence of SEQ ID NO: 112.

In some embodiments, the present invention provides an isolated antibody or functional fragment thereof that binds to a Tn antigen or an sTn antigen, wherein the antibody or functional fragment thereof includes a VH domain and a VL domain, wherein the VH domain includes an amino acid sequence selected from the group consisting of SEQ ID NOS: 130 and the VL domain includes the amino acid sequence of SEQ ID NO: 112.

In some embodiments, the present invention provides an isolated antibody or functional fragment thereof that binds to a Tn antigen or an sTn antigen, wherein the antibody or functional fragment thereof includes a VH domain and a VL domain, wherein the VH domain includes the amino acid sequence of SEQ ID NOS: 106 and the VL domain includes the amino acid sequence of SEQ ID NO: 113.

In yet another embodiment, the present invention provides an isolated antibody or functional fragment thereof described herein having a VH domain with one or more amino acid residue substitutions at select positions. Accordingly, in some aspects, the isolated antibody or functional fragment thereof of the invention as described herein has, based on Kabat numbering, a VH domain with one or more amino acid variants selected from: a serine or a phenylalanine at position 17; a valine or an isoleucine at position 37; an aspartic acid, a histidine or an alanine at position 55; an aspartic acid or a tyrosine at position 61; a valine or a methionine at position 63; a serine or an asparagine at position 82B; a threonine or an alanine at position 87; an alanine or a threonine at position 100B; a glutamine or lysine at position 105; or a threonine or an isoleucine at position 110. In yet an additional embodiment, the VH domain includes 2 or more, 3 or more, 4 or more, 5 or more, 6 or more, 7 or more, 8 or more, 9 or more or all 10 of the variants described herein.

In some embodiments, the invention provides an isolated polynucleotide encoding an antibody or functional fragment thereof described herein, wherein the antibody heavy or light chain or functional fragment thereof has one or more of the CDRs from the clonal isolates named 1A12b, 1A4, 1E2b, 1G10, 2A8, 2F3, 3A7 and the 2F3 variants described herein. Accordingly, in some aspects, the isolated polynucleotides encodes an antibody heavy or light chain or functional fragment thereof has one or more of the CDRs depicted in Table 2-4 and FIGS. 1-7.

In some embodiments, the isolated polynucleotide according to the invention as provided herein encodes an antibody or functional fragment thereof disclosed herein that includes less than six CDRs. In some embodiments, the antibody or functional fragment encoded by the polynucleotide includes one, two, three, four, or five CDRs selected from the group consisting of VH CDR1, VH CDR2, VH CDR3, VL CDR1, VL CDR2, and/or VL CDR3. In specific embodiments, the antibody or functional fragment thereof encoded by the inventive polynucleotide includes one, two, three, four, or five CDRs selected from the group consisting of VH CDR1, VH CDR2, VH CDR3, VL CDR1, VL CDR2, and/or VL CDR3 of clonal isolates 1A12b, 1A4, 1E2b, 1G10, 2A8, 2F3, or 3A7, including the 2F3 variants, described herein. Such CDRs are depicted in Table 2-4 and FIGS. 1-7.

In some embodiments, the present invention provides an isolated polynucleotide encoding an antibody or functional fragment thereof that binds to a Tn antigen or an sTn antigen, wherein the antibody or functional fragment thereof includes: (a) a variable heavy chain (VH) domain, wherein the VH domain includes: a VH CDR1 having an amino acid sequence selected from the group consisting of SEQ ID NOS: 2, 5, 6, 8, 11, and 12; a VH CDR2 having an amino acid sequence selected from the group consisting of SEQ ID NOS: 14, 17, 18, 20, 23, 24, 149, 150, 151, 152, and 153; and a VH CDR3 having an amino acid sequence selected from the group consisting of SEQ ID NOS: 26, 30, 31, 33, 37, 38, and 154; and/or (b) a variable light chain (VL) domain, wherein the VL domain includes: a VL CDR1 having an amino acid sequence selected from the group consisting of SEQ ID NOS: 40, 44, 45, 47, 51, and 52; a VL CDR2 having an amino acid sequence selected from the group consisting of SEQ ID NOS: 54, 53, 59, 63, and 64; and a VL CDR3 having an amino acid sequence selected from the group consisting of SEQ ID NOS: 66, 70, and 71.

In some embodiments, the present invention provides an isolated polynucleotide encoding an antibody or functional fragment thereof that binds to a Tn antigen or an sTn antigen, wherein the antibody or functional fragment thereof includes: (a) a variable heavy chain (VH) domain, wherein the VH domain includes: a VH CDR1 having an amino acid sequence selected from the group consisting of SEQ ID NOS: 2, 5, 6, 8, 11, and 12; a VH CDR2 having an amino acid sequence selected from the group consisting of SEQ ID NOS: 14, 17, 18, 20, 23, 24, 149, 150, 151, 152, and 153; and a VH CDR3 having an amino acid sequence selected from the group consisting of SEQ ID NOS: 26, 30, 31, 33, 37, 38, and 154.

In some embodiments, the present invention provides an isolated polynucleotide encoding an antibody or functional fragment thereof that binds to a Tn antigen or an sTn antigen, wherein the antibody or functional fragment thereof includes: (a) a variable light chain (VL) domain, wherein the VL domain includes: a VL CDR1 having an amino acid sequence selected from the group consisting of SEQ ID NOS: 40, 44, 45, 47, 51, and 52; a VL CDR2 having an amino acid sequence selected from the group consisting of SEQ ID NOS: 54, 53, 59, 63, and 64; and a VL CDR3 having an amino acid sequence selected from the group consisting of SEQ ID NOS: 66, 70, and 71.

In some embodiments, the present invention provides an isolated polynucleotide encoding an antibody or functional fragment thereof that binds to a Tn antigen or an sTn antigen, wherein the antibody or functional fragment thereof includes: a VH domain and a VL domain, wherein the VH domain includes: a VH CDR1 having an amino acid sequence selected from the group consisting of SEQ ID NOS: 2 and 8; a VH CDR2 having an amino acid sequence selected from the group consisting of SEQ ID NOS: 14 and 20; and a VH CDR3 having an amino acid sequence selected from the group consisting of SEQ ID NOS: 26 and 33; and the VL domain includes: a VL CDR1 having an amino acid sequence selected from the group consisting of SEQ ID NOS: 40 and 47; a VL CDR2 having an amino acid sequence selected from the group consisting of SEQ ID NOS: 54 and 59; and a VL CDR3 having an amino acid sequence of SEQ ID NO: 66.

In some embodiments, the present invention provides an isolated polynucleotide encoding an antibody or functional fragment thereof that binds to a Tn antigen or an sTn antigen, wherein the antibody or functional fragment thereof includes: a VH domain and a VL domain, wherein the VH domain includes: a VH CDR1 having an amino acid sequence selected from the group consisting of SEQ ID NOS: 5 and 11; a VH CDR2 having an amino acid sequence selected from the group consisting of SEQ ID NOS: 17, 23, 149, 150, 151, 152, and 153; and a VH CDR3 having an amino acid sequence selected from the group consisting of SEQ ID NOS: 30, 37, and 154; and the VL domain includes: a VL CDR1 having an amino acid sequence selected from the group consisting of SEQ ID NOS: 44 and 51; a VL CDR2 having an amino acid sequence selected from the group consisting of SEQ ID NOS: 53 and 63; and a VL CDR3 having an amino acid of SEQ ID NO: 70.

In some embodiments, the present invention provides an isolated polynucleotide encoding an antibody or functional fragment thereof that binds to a Tn antigen or an sTn antigen, wherein the antibody or functional fragment thereof includes: a VH domain and a VL domain, wherein the VH domain includes: a VH CDR1 having an amino acid sequence selected from the group consisting of SEQ ID NOS: 6 and 12; a VH CDR2 having an amino acid sequence selected from the group consisting of SEQ ID NOS: 18 and 24; and a VH CDR3 having an amino acid sequence selected from the group consisting of SEQ ID NOS: 31 and 38; and the VL domain includes: a VL CDR1 having an amino acid sequence selected from the group consisting of SEQ ID NOS: 45 and 52; a VL CDR2 having an amino acid sequence selected from the group consisting of SEQ ID NOS: 53 and 64; and a VL CDR3 having an amino acid sequence of SEQ ID NO: 71.

In some embodiments, the present invention provides an isolated polynucleotide encoding an antibody or functional fragment having a VH domain with the amino acid sequence of the VH domain for the clonal isolate 1A12b, 1A4, 1E2b, 1G10, 2A8, 2F3, or 3A7, including the 2F3 variants, described herein. Such VH domain sequences are depicted in Tables 5 and 6 and FIGS. 1 and 3-7.

In some embodiments, the present invention provides an isolated polynucleotide encoding an antibody or functional fragment having a VL domain with the amino acid sequence of the VL domain for the clonal isolate 1A12b, 1A4, 1E2b, 1G10, 2A8, 2F3, or 3A7, including the 2F3 variants, described herein. Such VL domain sequences are depicted in Table 5 and FIG. 2.

In some embodiments, the present invention provides an isolated polynucleotide encoding an antibody or functional fragment having a VH domain and a VL domain with the amino acid sequence of the VH domain and VL domain for the clonal isolate 1A12b, 1A4, 1E2b, 1G10, 2A8, 2F3, or 3A7, including the 2F3 variants, described herein. Such VH domain and VL domain sequences are depicted in Table 5 and 6 and FIGS. 1-7.

In some embodiments, the present invention provides an isolated polynucleotide encoding an antibody or functional fragment thereof that binds to a Tn antigen or an sTn antigen, wherein the antibody or functional fragment thereof includes a VH domain having an amino acid sequence selected from the group consisting of SEQ ID NOS: 101, 105, 106 and 114-130.

In some embodiments, the present invention provides an isolated polynucleotide encoding an antibody or functional fragment thereof that binds to a Tn antigen or an sTn antigen, wherein the antibody or functional fragment thereof includes a VL domain having an amino acid sequence selected from the group consisting of SEQ ID NOS: 108, 112 and 113.

In some embodiments, the present invention provides an isolated polynucleotide encoding an antibody or functional fragment thereof that binds to a Tn antigen or an sTn antigen, wherein the antibody or functional fragment thereof includes a VH domain and a VL domain, wherein the VH domain includes the amino acid sequence of SEQ ID NO: 101 and the VL domain includes the amino acid sequence of SEQ ID NO: 108.

In some embodiments, the present invention provides an isolated polynucleotide encoding an antibody or functional fragment thereof that binds to a Tn antigen or an sTn antigen, wherein the antibody or functional fragment thereof includes a VH domain and a VL domain, wherein the VH domain includes an amino acid sequence selected from the group consisting of SEQ ID NOS: 105, 114, 115, 116, 117, 118, 119, 129, 121, 122, 123, 124, 125, 126, 127, 128, 129 and 130 and the VL domain includes the amino acid sequence of SEQ ID NO: 112.

In some embodiments, the present invention provides an isolated polynucleotide encoding an antibody or functional fragment thereof that binds to a Tn antigen or an sTn antigen, wherein the antibody or functional fragment thereof includes a VH domain and a VL domain, wherein the VH domain includes the amino acid sequence of SEQ ID NOS: 106 and the VL domain includes the amino acid sequence of SEQ ID NO: 113.

In yet another embodiment, the present invention provides an isolated polynucleotide encoding an antibody or functional fragment thereof described herein having a VH domain with one or more amino acid residues at select positions. Accordingly, in some aspects, the isolated polynucleotide encoding antibody or functional fragment thereof described herein has, based on Kabat numbering, a VH domain with one or more amino acid variants selected from: a serine or a phenylalanine at position 17; a valine or an isoleucine at position 37; an aspartic acid, a histidine or an alanine at position 55; an aspartic acid or a tyrosine at position 61; a valine or a methionine at position 63; a serine or an asparagine at position 82B; a threonine or an alanine at position 87; an alanine or a threonine at position 100B; a glutamine or lysine at position 105; or a threonine or an isoleucine at position 110. Accordingly, in yet other embodiments, the isolated polynucleotide encoding antibody or functional fragment thereof described herein has, based on Kabat numbering, a VH domain with one or more of the amino acid variants selected from the group consisting of: a serine, a threonine, or an arginine at position 30; a glycine at position 56; an asparagine or a threonine at position 57; a glutamine at position 62; a lysine at position 63; and a lysine at position 98. In yet an additional embodiment, the VH domain includes 2 or more, 3 or more, 4 or more, 5 or more, 6 or more, 7 or more, 8 or more, 9 or more or all 10 of the variants described herein.

In another embodiment, the isolated polynucleotide endcoding antibody or functional fragment thereof described herein has, based on Kabat numbering, a VL domain with one or more of the amino acid variants selected from the group consisting of: an asparginine or a lysine at position 31; and a glycine at position 41. In yet an additional aspect, the VL domain includes 1 or more of the variants described herein. Polynucleotide variants encode the amino acid changes and therefore by extension are reflected as amino acid variants of the different clones.

In another embodiment, the invention provides a variant of the polynucleotides provided herein. A variant when used in reference to a polynucleotide includes a polynucleotide having one or more modified nucleotides, such as, but not limited to, a methylated nucleotide or a nucleotide analog. Additionally, a variant polynucleotide can include a polynucleotide that is interrupted by non-nucleotide components. Modifications to a polynucleotide can be imparted before or after assembly of the polynucleotide using methods well known to those skilled in the art. For example, a polynucleotide can be modified after polymerization by conjugation with a labeling component using either enzymatic or chemical techniques (e.g., as described in Gottfried and Weinhold, 2011, *Biochem. Soc. Trans.*, 39(2):523-628; Paredes et al., 2011, *Methods*, 54(2):251-259).

The polynucleotides can be obtained, and the nucleotide sequence of the polynucleotides determined, by any method well known in the art. Since the amino acid sequences of the variable heavy and light chain domains of the identified clonal isolates 1A12b, 1A4, 1E2b, 1G10, 2A8, 2F3, 3A7 and 2F3 variants (e.g., Tables 5 and 6) are described herein, nucleotide sequences encoding antibodies and modified versions of these antibodies can be determined using methods well known in the art, i.e., nucleotide codons known to encode particular amino acids are assembled in such a way to generate a nucleic acid that encodes the antibody. Such a polynucleotide encoding the antibody can be assembled from chemically synthesized oligonucleotides (e.g., as described in Kutmeier et al., 1994, *BioTechniques* 17:242), which, briefly, involves the synthesis of overlapping oligonucleotides containing portions of the sequence encoding the antibody, fragments, or variants thereof, annealing and ligating of those oligonucleotides, and then amplification of the ligated oligonucleotides by PCR.

A polynucleotide encoding an antibody or a functional fragment thereof disclosed herein can be generated using the nucleic acid sequence of the variable heavy and/or light chain domains of clonal isolates 1A12b, 1A4, 1E2b, 1G10, 2A8, 2F3, 3A7 and 2F3 variants (e.g., Tables 5 and 6). A nucleic acid encoding the antibody or functional fragment can be chemically synthesized or obtained from a suitable source (e.g., cDNA isolated from cells expressing the antibody or functional fragment thereof, such as hybridoma cells selected to express the antibody or functional fragment thereof) by PCR amplification using synthetic primers hybridizable to the 3' and 5' ends of the sequence or by cloning using an oligonucleotide probe specific for the particular nucleic acid sequence. Amplified nucleic acids generated by PCR can then be cloned into replicable cloning vectors using any method well known in the art.

Due to the degeneracy of the genetic code, it will be appreciated by one of ordinary skill in the art that each of the polypeptide sequences depicted herein are also encoded by a large number of other polynucleotide sequences besides those provided. For example, heavy chain variable domains provided herein in may be encoded by the specific polynucleotide sequences described herein in addition to others because a single amino acid may be coded for by more than one codon. Thus the present application provides adequate written description and enablement for each degenerate nucleotide sequence encoding each antigen binding protein. Changes in the nucleotide sequence which do not result in modifications to the amino acid sequence are silent, and are therefore not considered "variants". On the otherhand, sequences described herein as "variants" have polynucleotide changes to the originally isolated "parental clone" sequence. Modifications made to the parental sequence, and which produced a binding molecule with an altered functional characteristic were further studied as "variants" as the encoded amino acid sequence was changed. Thus "variant" can be used to describe both changes in the polynucleotide and amino acid sequence, but is generally linked to sequences which encode a protein with a changed functional or "variant" characteristic.

In some embodiments disclosed herein, the isolated antibody or functional fragment thereof is a monoclonal antibody. In some aspects disclosed herein, the isolated antibody or functional fragment thereof provided herein is an IgG or IgM isotype. In a further aspect disclosed herein, the antibody or function fragment thereof is an antibody of the IgG1 subclass. In a further aspect disclosed herein, the antibody or function fragment thereof is an antibody of the IgG including, for example, an IgG1 subclass and binds to Tn or sTn on a cancer cell.

In some embodiments disclosed herein, the isolated antibody or functional fragment thereof is a bispecific antibody. Bispecific antibodies are antibodies that have binding specificities for at least two different epitopes. Exemplary bispecific antibodies bind to two different epitopes, for example a Tn/sTn binding arm may be combined with an arm which binds to a triggering molecule on a leukocyte such as a T cell receptor molecule (e.g., CD2 or CD3), or Fc receptors for IgG (FcγR), so as to focus cellular defense mechanisms to the Tn/sTn expressing cell. Bispecific antibodies may also be used to localize cytotoxic agents to the Tn/sTN expressing cell (e.g., saporin, anti-interferon-α, vinca alkaloid, ricin A chain, methola-exate or radioactive isotope hapten). Bispecific antibodies can be prepared as full-length antibodies or antibody fragments (e.g., F(ab): bispecific antibodies).

Methods for making bispecific antibodies are known in the art. (See, for example, Millstein et al., Nature, 305:537-539 (1983): Traunecker et al., EMBO J., 10:3655-3659 (1991); Suresh et al., Methods in Enzymology, 121:210 (1986): Kostelny et al., J. Immunol., 148(5):1547-1553 (1992): Hollinger et al., Proc. Natl Acad. Sci. USA, 90:6444-6448 (1993); Gruber et al., J. Immunol., 152:5368 (1994). U.S. Pat. Nos. 4,474,893; 4,714,681; 4,925,648; 5,573,920; 5,601,81; 95,731,168; 4,676,980; and 4,676,980, WO 94/04690; WO 91/00360; WO 92/200373; WO 93/17715; WO 92/08802; and WO 96/27011.)

Accordingly, in some embodiments the isolated antibody or functional fragment thereof of the invention provided herein binds to not only Tn antigen or sTn antigen, but also binds to a second antigen. The second antigen can be any antigen suitable for further targeting an antibody or functional fragment thereof to a desired target (e.g., Tn antigen or sTn antigen) and/or recruiting additional components to the desired target (e.g., immune regulatory cells). Thus, in some aspects, the bispecific antibody provided herein binds to Tn antigen or sTn antigen and a tumor antigen. In some embodiments, a tumor antigen is a Adipophilin, AIM-2, ALDH1AI, BCLX (L), BING-4, CALCA, CD45, CPSF, cyclin D1, DKKI, ENAH (hMcna), Ga733 (EpCAM), EphA3, EZH2, FGF5, glypican-3, G250/MN/CAIX, HER-2/neu, IDO1, IGF2B3, IL13Ralpha2, Intestinal carboxyl esterase, alpha-foetoprotein, Kallikrein 4, KIF20A, Lengsin, M-CSF, MCSP, mdm-2, Meloe, MMP-2, MMP-7, MUC1, MUC5AC, p53 (non-mutant), PAX5, PBF, PRAME, PSMA, RAGE, RAGE-1, RGS5, RhoC, RNF43, RU2AS, secernin 1, SOX1O, STEAP1 (six-transmembrane epithelial antigen of the prostate 1), survivinn, Telomerase, VEGF, WT1, EGF-R, CEA, CD20, CD33, CD52, glycoprotein 100 (GP100 or gp 100 protein), MELANA/MART1, MART2, NY-ESO-1, p53, MAGE A1, MAGE A3, MAGE-4, MAGE-5, MAGE-6, CDK4, alpha-actinin-4, ARTC1, BCR-ABL, BCR-ABL fusion protein (b3a2), B-RAF, CASP-5, CASP-8, beta-catenin, Cdc27, CDK4, CDKN2A, CLPP, COA-1, dek-can fusion protein, EFTUD2, Elongation factor 2, ETV6-AML, ETV6-AML1 fusion protein, FLT3-ITD, FN1, GPNMB, LDLR-fucosyltransferaseAS fusion protein, NFYC, OGT, OS-9, pml-RARalpha fusion protein, PRDX5, PTPRK, H-ras, K-ras (V-Ki-ras2 Kirsten rat sarcoma viral oncogene), N-ras, RBAF600, SIRT2, SNRPD1, SSX, SSX2, SYT-SSX1 or- SSX2 fusion protein, TGF-betaRll, Triose-phosphate isomerase, ormdm-2, LMP2, HPV E6/E7, EGFRvIII (epidermal growth factor variant III), Idiotype, Ras-mutant, p53 (mutant), Proteinase3 (PR1), Tyrosinase, PSA, hTERT, Sarcoma translocation breakpoints, EphA2, prostatic acid phosphatase PAP, neo-PAP, ML-IAP, AFP, ERG (TMPRSS2 ETS Fusion gene), NA17, PAX3, ALK, Androgen Receptor, Cyclin B1, Polysialic acid, MYCN, TRP2, TRP2-Int2, Fucosyl GM1, Mesothelin, PSCA, sLe (a), cyp1B1, PLAC1, BORIS, globoH, NY-BR-1, SART3, Carbonic Anhydrase IX, OY-TES1, Sperm protein 17, LCK, high molecular weight melanoma-associated antigen (HMWMAA), AKAP-4, SSX2, XAGE 1, B7H3, Legumain, Tie 2, Page4, VEGFR2, MAD-CT-1, FAP, PDGFR-beta, MAD-CT-2, For-related antigen 1, TRP1, CA-125, CA19-9, Calretinin, Epithelial membrane antigen (EMA), Epithelial tumor antigen (ETA), CD19, CD34, CD99, CD117, Chromogranin, Cytokeratin, Desmin, Glial fibrillary acidic protein (GFAP), gross cystic disease fluid protein (GCDFP-15), HMB-45 antigen, Myo-D1, muscle-specific actin (MSA), neurofilament, neuron-specific enolase (NSE), placental alkaline phosphatase, synaptophysin, thyroglobulin, thyroid transcription factor-1, dimeric form of the pyruvate kinase isoenzyme type M2 (tumor M2-PK), BAGE BAGE-1, CAGE, CTAGE, FATE, GAGE, GAGE-1, GAGE-2, GAGE-3, GAGE-4, GAGE-5, GAGE-6, GAGE-7, HCA661, HOM-TES-85, MAGEA, MAGEB, MAGEC, NA88, NY-SAR-35, SPANXB1, SPA17, SSX, SYCP1, TPTE, a carbohydrate, a glycan, Le$^a$, sialyl Le$^a$, Le$^b$, Le$^x$, polyfucosyl-Le$^x$, Le$^y$, a ganglioside, GM1, GM2, GM3, GD2, GD3, CA 15-3 (CA 27.29\BCAA), CA 195, CA 242, CA 50, CAM 43, CEA, EBNA, EF2, Epstein-Ban virus antigen, HLA-A2, HLA-A11, HSP70-2, KIAAO205, MUM-1, MUM-2, MUM-3, Myosin class I, GnTV, Herv-K-mel, LAGE-1, LAGE-2, (sperm protein) SP17, SCP-1, P15(58), Hom/Mel-40, E2A-PRL, H4-RET, IGH-IGK, MYL-RAR, TSP-180, P185erbB2, p180erbB-3, c-met, nm-23H1, TAG-72, TAG-72-4, CA-72-4, CAM 17.1, NuMa, 13-catenin, P16, TAGE, CT7, 43-9F, 5T4, 791Tgp72, 13HCG, BCA225, BTAA, CD68\KP1, CO-029, HTgp-175, M344, MG7-Ag, MOV18, NB\70K, NY-CO-1, RCAS1, SDCCAG16, TA-90, TAAL6, TLP, TPS, CD22, CD27, CD30, CD70, CD73 (5'-NT; ecto-5'-nucleotidase; NTSE), prostein, TARP (T cell receptor gamma alternate reading frame protein), Trp-p8, integrin avf33 (CD61), galactin, or Ral-B, CD123, CLL-1, CD38, CS-1, CD138, stimulator of interferon genes protein (STING) agonist, or ROR1.

In another aspects, the bispecific antibody provided herein binds to Tn antigen or sTn antigen and a protein expressed by a T lymphocyte, a natural killer cell, a neutrophil, a leukocyte, a monocyte, a macrophage, or a myeloid-derived suppressor cell. In some embodiments, such a protein is CD16, a protein of the T-cell receptor (CD3δ/ε, CD3γ/ε and CD247ζ/ζ or ζ/η), C2, CD4, CD8, LFA-1, CD45, FasL, TRAIL, TNF, PRTN3, MPO, BPI, HLA-A, HLA-B, HLA-C, CD14, IL-12, CD40, CD23, CD31, CD38, CD44, CD45, CD69, LFA-3, ARG1, NOS2, CD11b, PD-L1, PSGL-1, LY-6G, CCR2, CCR2, CD43, or L-Selectin. In some embodiments, the bispecific antibody provided herein binds to Tn antigen or sTn antigen and to CD3 (e.g. CD3δ/ε, CD3γ/ε). Through simultaneously binding to CD3 on T cells and tumor cells, such bispecific antibody forces formation of a cytolytic synapse between the two cells, thereby redirecting the T cell activity selectively to the targeted tumor cells. For example, the bispecific antibody binds to (i) Tn antigen or sTn antigen via any one of the VH and VL domains defined by the CDR and/or VH/VL sequences of clonal isolates 1A4, 3A7 and 2F3 and its variants (e.g. CDR and/or VH/VL sequences as shown in Tables 2, 3, 4, 5 and 6 for clonal isolates 1A4, 3A7 and 2F3 and its variants) and (ii) to CD3 (e.g. CD3δ/ε, CD3γ/δ).

Targeting Tn/sTn with a bispecific T cell engaging approach is expected to provide advantages over an ADC approach, as redirecting T cells is not influenced by resistance to chemotherapy and low expression levels on the cell surface are less critical for this mode of action. Through simultaneous binding to T effector cells and tumor cells, the T cell engagers force formation of a cytolytic synapse between the two cells and so, redirect the T cell activity selectively to the targeted tumor cells.

In one aspect, the invention provides a multi-specific binding protein (e.g. a bispecific antibody) comprising a first antigen binding unit specifically binding to Tn/sTn and a second antigen binding unit specifically binding to CD3, said first antigen binding unit specifically binding to Tn/sTn comprising a first light chain variable (VL) domain and a first heavy chain variable domain (VH) with the amino acid sequence of the VH domain and VL domain for the clonal isolate 1A12b, 1A4, 1E2b, 1G10, 2A8, 2F3, or 3A7, including the 2F3 variants, described herein.

In embodiments of the invention, the first antigen binding unit specifically binding to Tn/sTn is selected from VL and VH domains, paired respectively, wherein
  (i) a VL domain has the amino acid sequence of the VL domain for the clonal isolate 1A12b, 1A4, 1E2b, 1G10, 2A8, 2F3, or 3A7, including the 2F3 variants, e.g. as depicted in Table 5 and 7, and FIG. 2; and/or
  (ii) the VL domain includes one, two, or three, VL CDRs (VL CDR1, VL CDR2, and/or VL CDR3) having the amino acid sequence of any one of the VL CDRs, e.g. as depicted in Table 3 or FIGS. 1-7; and
  (iii) a VH domain has the amino acid sequence of the VH domain for the clonal isolate 1A12b, 1A4, 1E2b, 1G10, 2A8, 2F3, or 3A7, including the 2F3 variants, e.g. as depicted in Table 5 or 6 or FIG. 1, or 3-7; and/or (iv) the VH domain includes one, two, or three, VH CDRs (VH CDR1, VH CDR2, VH CDR3) having the amino acid sequence of any one of the VH CDRs, e.g. as depicted in Tables 2 or 4.

In one aspect, the invention provides a multi-specific binding protein (e.g. a bispecific antibody) comprising a first antigen binding unit specifically binding to Tn/sTn and a second antigen binding unit specifically binding CD3, wherein the first antigen binding unit binding to Tn/sTn comprises a VH domain comprising the amino acid sequence of SEQ ID NO: 101 and a VL domain comprising the amino acid sequence of SEQ ID NO: 108.

In another embodiment, the invention provides a multi-specific binding protein (e.g. a bispecific antibody) comprising a first antigen binding unit specifically binding to Tn/sTn and a second antigen binding unit specifically binding CD3, wherein the first antigen binding unit binding to Tn/sTn comprises a VH and a VL domain, wherein the (i) VH domain comprises a VH CDR1 of SEQ ID NO: 5, a VH CDR2 of SEQ ID NO: 17 and a VH CDR3 of SEQ ID NO: 30 and the VL domain comprises a VL CDR1 of SEQ ID NO: 44, a VL CDR2 of SEQ ID NO: 53 and a VL CDR3 of SEQ ID NO: 70; or (ii) the VH domain comprises a VH CDR1 of SEQ ID NO: 5, a VH CDR2 of SEQ ID NO: 149, and a VH CDR3 of SEQ ID NO: 30 and the VL domain comprises a VL CDR1 of SEQ ID NO: 44, a VL CDR2 of SEQ ID NO: 53 and a VL CDR3 of SEQ ID NO: 70; or (iii) the VH domain comprises a VH CDR1 of SEQ ID NO: 5, a VH CDR2 of SEQ ID NO: 17 and a VH CDR3 of SEQ ID NO: 154 and the VL domain comprises a VL CDR1 of SEQ ID NO: 44, a VL CDR2 of SEQ ID NO: 53 and a VL CDR3 of SEQ ID NO: 70; or (iv) the VH domain comprises a VH CDR1 of SEQ ID NO: 5, a VH CDR2 of SEQ ID NO: 150 and a VH CDR3 of SEQ ID NO: 30 and the VL domain comprises a VL CDR1 of SEQ ID NO: 44, a VL CDR2 of SEQ ID NO: 53 and a VL CDR3 of SEQ ID NO: 70; or (v) the VH domain comprises a VH CDR1 of SEQ ID NO: 5, a VH CDR2 of SEQ ID NO: 151 and a VH CDR3 of SEQ ID NO: 30 and the VL domain comprises a VL CDR1 of SEQ ID NO: 44, a VL CDR2 of SEQ ID NO: 53 and a VL CDR3 of SEQ ID NO: 70; or (vi) the VH domain comprises a VH CDR1 of SEQ ID NO: 5, a VH CDR2 of SEQ ID NO: 152 and a VH CDR3 of SEQ ID NO: 30 and the VL domain comprises a VL CDR1 of SEQ ID NO: 44, a VL CDR2 of SEQ ID NO: 53 and a VL CDR3 of SEQ ID NO: 70; or (vii) the VH domain comprises a VH CDR1 of SEQ ID NO: 5, a VH CDR2 of SEQ ID NO: 153 and a VH CDR3 of SEQ ID NO: 30 and the VL domain comprises a VL CDR1 of SEQ ID NO: 44, a VL CDR2 of SEQ ID NO: 53 and a VL CDR3 of SEQ ID NO: 70; or (viii) the VH domain comprises a VH CDR1 of SEQ ID NO: 5, a VH CDR2 of SEQ ID NO: 149 and a VH CDR3 of SEQ ID NO: 154 and the VL domain comprises a VL CDR1 of SEQ ID NO: 44, a VL CDR2 of SEQ ID NO: 53 and a VL CDR3 of SEQ ID NO: 70; or (ix) the VH domain comprises a VH CDR1 of SEQ ID NO: 5, a VH CDR2 of SEQ ID NO: 150 and a VH CDR3 of SEQ ID NO: 154 and the VL domain comprises a VL CDR1 of SEQ ID NO: 44, a VL CDR2 of SEQ ID NO: 53 and a VL CDR3 of SEQ ID NO: 70.

In yet another embodiment, the invention provides a multi-specific binding protein (e.g. a bispecific antibody) comprising a first antigen binding unit specifically binding to Tn/sTn and a second antigen binding unit specifically binding CD3, wherein the first antigen binding unit binding to Tn/sTn comprises a VH domain comprising an amino acid sequence selected from the group consisting of SEQ ID NOS: 105, 114, 115, 116, 117, 118, 119, 120, 121, 122, 123, 124, 125, 126, 127, 128, 129 and 130 and a VL domain comprising the amino acid sequence of SEQ ID NO: 112.

In yet another embodiment, the invention provides a multi-specific binding protein (e.g., a bispecific antibody) comprising a first antigen binding unit specifically binding to Tn/sTn and a second antigen binding unit specifically binding CD3, wherein the first antigen binding unit binding to Tn/sTn comprises a VH domain comprising the amino acid sequence of SEQ ID NO: 106 and a VL domain comprising the amino acid sequence of SEQ ID NO: 113.

Thus in one non-limiting example of a bi-specific antibody, the present invention provides a protein comprising a first polypeptide chain specifically binding to Tn/sTn and a second polypeptide chain, wherein the first chain comprises a first light chain covalently linked to a first linker, which is itself covalently linked to a first heavy chain, and wherein the second chain specifically binding to CD3 comprises a second light chain covalently linked to a second linker, which is itself covalently linked to a second heavy chain.

In one exemplary embodiment, starting from its N-terminus, the first chain comprises a first light chain variable region specifically binding to Tn/sTn (e.g., a VL domain comprising the amino acid sequence of SEQ ID NO: 112), a first light chain constant region, a first linker, a first heavy chain variable region specific for Tn/sTn (e.g., a VH domain comprising an amino acid sequence selected from the group consisting of SEQ ID NOS: 105, 114, 115, 116, 117, 118, 119, 129, 121, 122, 123, 124, 125, 126, 127, 128, 129 and 130) and a first heavy chain constant region. In some embodiments, starting from its N-terminus, the second chain comprises a second light chain variable region specifically binding to CD3, a second light chain constant region, a second linker, a second heavy chain variable region for CD3 and a second heavy chain constant region.

While the bispecific embodiment above is one exemplary combination to achieve a multivalent binding molecule, it will be appreciated by one of ordinary skill in the art that in some embodiments, the antibody functional fragment disclosed herein can be, but is not limited to, a Fab, a Fab', a F(ab')₂, a scFV, a diabody, a triabody, a tetrabody, a minibody or a single-domain antibody (sdAB) and that many different configurations may combined to achieve an antibody binding molecule having specificity for both Tn/sTn and CD3 and/or any other co-inhibitory or a co-stimulatory molecule.

In yet another aspect, the bispecific antibody provided herein binds to Tn antigen or sTn antigen and a co-inhibitory molecule or a co-stimulatory molecule. In some embodiments, the co-inhibitory molecule is selected from the group consisting of VISTA, CD86, CD80, PDL-1, PDL-2, CTLA-4, PD1, LAGS, BTNL2, B7-H3, B7-H4, a butyrophilin, CD48, CD244, TIM-3, CD200R, CD200, CD160, BTLA, HVEM, LAIR1, TIM1, Galectin 9, TIM3, CD48, 2B4, CD155, CD112, CD113 and TIGIT. In some embodiments, the co-stimulatory molecule is selected from the group consisting of CD154, TNFRSF25, GITR, 4-1BB (TNFRSF9, CD137), OX40, CD27, TMIGD2, ICOS, CD28, CD40, TL1A, GITRL, 41BBL, OX40L, CD70, HHLA2, ICOSL, a cytokine, LIGHT, HVEM, CD30, CD3OL, B7-H2, CD80, CD86, CD40L, TIM4, TIM1, SLAM, CD48, CD58, CD155, CD112, DR3, GITR, CD2, and CD226.

Methods for generating such bispecific antibodies are well known in the art (see, e.g., Tomlinson and Holliger, *Methods in Enzymology*, 326: 461-479 (2000), Doppalapudi et al., *PNAS*, 107(52):22611-22616 (2010), and EP Patent 2606064).

In some embodiments, the present invention provides a method of producing an antibody or functional fragment thereof disclosed herein. The method disclosed herein can include introducing a polynucleotide disclosed herein into a host cell, culturing the host cell under conditions and for a sufficient period of time to produce the encoded heavy and/or light chain of an antibody or functional fragment disclosed herein, and purifying the heavy and/or light chain of an antibody or functional fragment. In other embodiments, the present invention provides a recombinant cell having a polynucleotide encoding an antibody or a functional fragment disclosed herein. In some aspects, the antibody or function fragment thereof has the variable heavy chain domain and the variable light chain domain of the clonal isolates 1A12b, 1A4, 1E2b, 1G10, 2A8, 2F3, 3A7 and 2F3 variants (e.g., Tables 5 and 6).

Recombinant expression of an antibody or functional fragment thereof disclosed herein that binds to a Tn antigen or sTn antigen can include construction of an expression vector containing a polynucleotide that encodes the heavy and/or light chain of an antibody or functional fragment disclosed herein. Once a polynucleotide encoding an antibody or functional fragment thereof (preferably, but not necessarily, containing the heavy and/or light chain variable domain) disclosed herein has been obtained, the vector for the production of the antibody or functional fragment can be produced by recombinant DNA technology using techniques well known in the art. Methods for preparing a protein by expressing a polynucleotide containing an antibody or a functional fragment thereof encoding nucleotide sequence are described herein.

Methods, which are well known to those skilled in the art, can be used to construct expression vectors containing antibody or functional fragments thereof coding sequences and appropriate transcriptional and translational control signals. These methods include, for example, in vitro recombinant DNA techniques, synthetic techniques, and in vivo genetic recombination. The invention, thus, provides replicable vectors including a nucleotide sequence encoding an antibody or functional fragment thereof disclosed herein operably linked to a promoter. Such vectors can include the nucleotide sequence encoding the constant region of the antibody molecule (see, e.g., International Publication Nos. WO 86/05807 and WO 89/01036; and U.S. Pat. No. 5,122,464) and the variable domain of the antibody can be cloned into such a vector for expression of the entire heavy, the entire light chain, or both the entire heavy and light chains.

The expression vector can be transferred to a host cell by conventional techniques and the transfected cells are then cultured by conventional techniques to produce an antibody or functional fragment thereof disclosed herein. Thus, the invention includes host cells containing a polynucleotide encoding an antibody or functional fragment thereof disclosed herein operably linked to a heterologous promoter. In some embodiments for the expression of double-chained antibodies, vectors encoding both the heavy and light chains can be co-expressed in the host cell for expression of the entire immunoglobulin molecule, as detailed below.

A variety of host-expression vector systems can be utilized to express the antibody or functional fragments thereof disclosed herein (see, e.g., U.S. Pat. No. 5,807,715). Such host-expression systems represent vehicles by which the coding sequences of interest can be produced and subsequently purified, but also represent cells which can, when transformed or transfected with the appropriate nucleotide coding sequences, express an antibody molecule disclosed herein in situ. These include but are not limited to microorganisms such as bacteria (e.g., *E. coli* and *B. subtilis*) transformed with recombinant bacteriophage DNA, plasmid DNA or cosmid DNA expression vectors containing antibody coding sequences; yeast (e.g., *Saccharomyces Pichia*) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BHK, 293, NS0, and 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). In some aspects, bacterial cells such as *Escherichia coli*, or eukaryotic cells, especially for the expression of whole recombinant antibody, are used for the expression of a recombinant antibody or functional fragment. For example, mammalian cells such as Chinese hamster ovary cells (CHO), in conjunction with a vector such as the major intermediate early gene promoter element from human cytomegalovirus is an effective expression system for antibodies (Foecking et al., 1986, *Gene* 45:101; and Cockett et al., 1990, *Bio/Technology* 8:2). In some embodiments, antibodies or fragments thereof disclosed herein are produced in CHO cells. In some embodiments, the expression of nucleotide sequences encoding antibodies or functional fragments thereof disclosed herein which bind to Tn antigen or sTn antigen is regulated by a constitutive promoter, inducible promoter or tissue specific promoter.

In bacterial systems, a number of expression vectors can be advantageously selected depending upon the use intended for the antibody molecule being expressed. For example, when a large quantity of such an antibody is to be produced, for the generation of pharmaceutical compositions of an antibody molecule, vectors which direct the expression of high levels of fusion protein products that are readily purified can be desirable. Such vectors include, but are not limited to, the *E. coli* expression vector pUR278 (Ruther et al., 1983, *EMBO* 12:1791), in which the antibody coding sequence can be ligated individually into the vector in frame with the lac Z coding region so that a fusion protein is produced; pIN vectors (Inouye & Inouye, 1985, *Nucleic Acids Res.* 13:3101-3109; Van Heeke & Schuster, 1989, *J. Biol. Chem.* 24:5503-5509); and the like. pGEX vectors can also be used to express foreign polypeptides as fusion proteins with glutathione 5-transferase (GST). In general, such fusion proteins are soluble and can easily be purified from lysed cells by adsorption and binding to matrix glutathione agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV) is used as a vector to express foreign genes. The virus grows in *Spodoptera frugiperda* cells. The antibody or functional fragment coding sequence can be cloned individually into non-essential regions (for example the polyhedrin gene) of the virus and placed under control of an AcNPV promoter (for example the polyhedrin promoter).

In mammalian host cells, a number of viral-based expression systems can be utilized. In cases where an adenovirus is used as an expression vector, the antibody coding sequence of interest can be ligated to an adenovirus transcription/translation control complex, e.g., the late promoter and tripartite leader sequence. This chimeric gene can then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts (e.g., see Logan & Shenk, 1984, *Proc. Natl. Acad. Sci. USA* 8 1:355-359). Specific initiation signals can also be used for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression can be enhanced by the inclusion of appropriate transcription enhancer elements, transcription terminators, etc. (see, e.g., Bittner et al., 1987, *Methods in Enzymol.* 153:51-544).

In addition, a host cell strain can be chosen which modulates the expression of the inserted sequences, or modifies and processes the gene product in the specific fashion desired. Such modifications (e.g., glycosylation) and processing (e.g., cleavage) of protein products can be important for the function of the antibody or functional fragment. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product can be used. Such mammalian host cells include but are not limited to CHO, VERY, BHK, Hela, COS, MDCK, 293, 3T3, W138, BT483, Hs578T, HTB2, BT2O and T47D, NS0 (a murine myeloma cell line that does not endogenously produce any immunoglobulin chains), CRL7O3O and HsS78Bst cells.

For long-term, high-yield production of recombinant proteins, stable expression is preferred. For example, cell lines which stably express the antibody or functional fragment disclosed herein can be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells can be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method can advantageously be used to engineer cell lines which express the antibody molecule.

A number of selection systems can be used, including but not limited to, the herpes simplex virus thymidine kinase (Wigler et al., 1977, *Cell* 11:223), hypoxanthineguanine phosphoribosyltransferase (Szybalska & Szybalski, 1992, *Proc. Natl. Acad. Sci. USA* 48:202), and adenine phosphoribosyltransferase (Lowy et al., 1980, *Cell* 22:8-17) genes can be employed in tk-, hgprt- or aprt-cells, respectively. Also, antimetabolite resistance can be used as the basis of selection for the following genes: dhfr, which confers resistance to methotrexate (Wigler et al., 1980, *Proc. Natl. Acad. Sci. USA.* 77(6):3567-70; O'Hare et al., 1981, *Proc. Natl. Acad. Sci. USA* 78:1527); glutamine synthetase (GS), which is an enzyme responsible for the biosynthesis of glutamine using glutamate and ammonia (Bebbington et al., 1992, *Biuotechnology* 10:169); gpt, which confers resistance to mycophenolic acid (Mulligan & Berg, 1981, *Proc. Natl. Acad. Sci. USA* 78:2072); neo, which confers resistance to the aminoglycoside G-418 (Wu and Wu, 1991, *Biotherapy* 3:87-95; Tolstoshev, 1993, *Ann. Rev. Pharmacol. Toxicol.* 32:573-596; Mulligan, 1993, *Science* 260:926-932; and Morgan and Anderson, 1993, *Ann. Rev. Biochem.* 62:191-217; May, 1993, *TIB TECH* 11(5):155-215); and hygro, which confers resistance to hygromycin (Santerre et al., 1984, *Gene* 30:147). Methods well known in the art of recombinant DNA technology can be routinely applied to select the desired recombinant clone, and such methods are described, for example, in Ausubel et al. (eds.), *Current Protocols in Molecular Biology*, John Wiley & Sons, N Y (1993); Kriegler, Gene Transfer and Expression, *A Laboratory Manual, Stockton Press, N Y* (1990); and in Chapters 12 and 13, Dracopoli et al. (eds.), *Current Protocols in Human Genetics*, John Wiley & Sons, N Y (1994); Colberre-Garapin et al., 1981, *J. Mol. Biol.* 150:1, which are incorporated by reference herein in their entireties.

The expression levels of an antibody molecule can be increased by vector amplification (for a review, see Bebbington and Hentschel, The use of vectors based on gene amplification for the expression of cloned genes in mammalian cells in DNA cloning, Vol. 3 (Academic Press, New York, 1987)). When a marker in the vector system expressing an antibody or functional fragment thereof is amplifiable, increase in the level of inhibitor present in culture of host cell will increase the number of copies of the marker gene. Since the amplified region is associated with the antibody gene, production of the antibody will also increase (Crouse et al., 1983, *Mol. Cell. Biol.* 3:257).

The host cell can be co-transfected with two expression vectors disclosed herein, the first vector encoding a heavy chain derived polypeptide and the second vector encoding a light chain derived polypeptide. The two vectors can contain identical selectable markers which enable equal expression of heavy and light chain polypeptides. Alternatively, a single vector can be used which encodes, and is capable of expressing, both heavy and light chain polypeptides. In such situations, the light chain can be placed before the heavy chain to avoid an excess of toxic free heavy chain (Proudfoot, 1986, *Nature* 322:52; and Kohler, 1980, *Proc. Natl. Acad. Sci. USA* 77:2197-2199). The coding sequences for the heavy and light chains can include cDNA or genomic DNA.

Additionally, polynucleotides encoding the heavy and/or light chains of the antibody or functional fragment disclosed herein can be subjected to codon optimization using techniques well known in the art to achieve optimized expression of an antibody or functional fragment disclosed herein in a desired host cell. For example, in one method of codon optimization, a native codon is substituted by the most frequent codon from a reference set of genes, wherein the rate of codon translation for each amino acid is designed to be high. Additional exemplary methods for generating codon optimized polynucleotides for expression of a desired protein, which can be applied to the heavy and/or light chains of the antibody or functional fragment disclosed herein, are described in Kanaya et al., *Gene,* 238:143-155

(1999), Wang et al., *Mol. Biol. Evol.*, 18(5):792-800 (2001), U.S. Pat. No. 5,795,737, U.S. Publication 2008/0076161 and WO 2008/000632.

Once an antibody molecule disclosed herein has been produced by recombinant expression, it can be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. Further, the antibodies or functional fragments of the present invention can be fused to heterologous polypeptide sequences provided herein or otherwise known in the art to facilitate purification. For example, an antibody or functional fragment disclosed herein can be purified through recombinantly adding a poly-histidine tag (His-tag), FLAG™-peptide fusion tag, hemagglutinin tag (HA-tag) or myc-tag among others that are commercially available and utilizing purification methods well known to those skilled in the art.

In some embodiments, the antibody functional fragment disclosed herein can be, but is not limited to, a Fab, a Fab', a F(ab')$_2$, a scFV, a diabody, a triabody, a tetrabody, a minibody or a single-domain antibody (sdAB). With respect to antibodies and functional fragments thereof, various forms, alterations and modifications are well known in the art. The Tn antigen or sTn antigen specific antibody fragments disclosed herein can include any of such various antibody forms, alterations and modifications. Examples of such various forms and terms as they are known in the art are set forth below.

A Fab fragment refers to a monovalent fragment consisting of the VL, VH, CL and CH1 domains; a F(ab')$_2$ fragment is a bivalent fragment including two Fab fragments linked by a disulfide bridge at the hinge region; a Fd fragment consists of the VH and CH1 domains; an Fv fragment consists of the VL and VH domains of a single arm of an antibody; and a dAb fragment (Ward et al., *Nature* 341:544-546, (1989)) consists of a VH domain.

An antibody can have one or more binding sites. If there is more than one binding site, the binding sites can be identical to one another or can be different. For example, a naturally occurring immunoglobulin has two identical binding sites, a single-chain antibody or Fab fragment has one binding site, while a "bispecific" or "bifunctional" antibody has two different binding sites.

A single-chain antibody (scFv) refers to an antibody in which a VL and a VH region are joined via a linker (e.g., a synthetic sequence of amino acid residues) to form a continuous polypeptide chain wherein the linker is long enough to allow the protein chain to fold back on itself and form a monovalent antigen binding site (see, e.g., Bird et al., *Science* 242:423-26 (1988) and Huston et al., *Proc. Natl. Acad. Sci. USA* 85:5879-83 (1988)). Diabodies refer to bivalent antibodies including two polypeptide chains, wherein each polypeptide chain includes VH and VL domains joined by a linker that is too short to allow for pairing between two domains on the same chain, thus allowing each domain to pair with a complementary domain on another polypeptide chain (see, e.g., Holliger et al., *Proc. Natl. Acad. Sci. USA* 90:6444-48 (1993), and Poljak et al., *Structure* 2:1121-23 (1994)). If the two polypeptide chains of a diabody are identical, then a diabody resulting from their pairing will have two identical antigen binding sites. Polypeptide chains having different sequences can be used to make a diabody with two different antigen binding sites. Similarly, tribodies and tetrabodies are antibodies including three and four polypeptide chains, respectively, and forming three and four antigen binding sites, respectively, which can be the same or different.

The present invention also provides an antibody or functional fragment thereof derivative of 1A4, 2F3, 3A7 or 2F3 variants disclosed herein, wherein the antibody or functional fragment binds to Tn antigen or sTn antigen. Standard techniques well known to those of skill in the art can be used to introduce mutations in the nucleotide sequence encoding an antibody or functional fragment thereof disclosed herein, including, for example, site-directed mutagenesis and PCR-mediated mutagenesis which results in amino acid substitutions. In some aspects, the derivative includes less than 25 amino acid substitutions, less than 20 amino acid substitutions, less than 15 amino acid substitutions, less than 10 amino acid substitutions, less than 5 amino acid substitutions, less than 4 amino acid substitutions, less than 3 amino acid substitutions, or less than 2 amino acid substitutions relative to the original molecule.

In some embodiments, the invention provides an antibody or functional fragment thereof having modified forms of naturally occurring amino acids, conservative substitutions, non-naturally occurring amino acids, amino acid analogues and mimetics so long as such the antibody or functional fragment retains functional activity as defined herein. In one embodiment, the derivative has conservative amino acid substitutions that are made at one or more predicted non-essential amino acid residues. A conservative amino acid substitution is one in which the amino acid residue is replaced with an amino acid residue having a side chain with a similar charge. Families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity. Following mutagenesis, the encoded antibody or functional fragment thereof can be expressed and the activity of the antibody or functional fragment can be determined.

In some embodiments, the invention provides an antibody or functional fragment thereof having modified fucosylation, galactosylation and/or sialylation of an Fc fragment contained within an antibody or functional fragment disclosed herein. Such modifications of an Fc fragment can affect Fc receptor-mediated activity as discussed in Peipp et al., *Blood*, 112(6):2390-2399 (2008). For example, glycoengineered therapeutic antibodies lacking core fucose residues from the Fc N-glycans exhibit strong ADCC at lower concentrations with much higher efficacy compared to fucosylated counterparts. Shields et al., *J. Biol. Chem.*, 277(30): 26733-40 (2002); Okazaki et al., *J Mol Biol.*, 336:1239-1249 (2004); Natsume et al., *J. Immunol. Methods.*, 306:93-103 (2005). Methods for modifying the fucosylation, galactosylation and/or sialylation of an antibody for functional fragment thereof are well known in the art. For example, defucosylation approaches can be grouped into three methodologies (1) conversion of the N-glycosylation pathway of nonmammalian cells to the 'humanized' non-fucosylation pathway; (2) inactivation of the N-glycan fucosylation pathway of mammalian cells and (3) in vitro chemical synthesis of non-fucosylated N-glycoprotein or enzymatic modification of N-glycans to non-fucosylated forms, as described in Yamane-Ohnuki et al., MAbs., 1(3):230-236 (2009). It is understood that any one of these methods or any other method that is well known in the art can be used to produce an antibody or functional fragment thereof having modified fucosylation, galactosylation and/or sialylation.

Antibodies or functional fragments thereof disclosed herein that bind to Tn antigen or sTn antigen can be produced by any method known in the art for the synthesis of antibodies, in particular, by chemical synthesis or by recombinant expression techniques. The practice disclosed herein employs, unless otherwise indicated, conventional techniques in molecular biology, microbiology, genetic analysis, recombinant DNA, organic chemistry, biochemistry, PCR, oligonucleotide synthesis and modification, nucleic acid hybridization, and related fields within the skill of the art. These techniques are described in the references cited herein and are fully explained in the literature. See, e.g., Maniatis et al. (1982) *Molecular Cloning: A Laboratory Manual*, Cold Spring Harbor Laboratory Press; Sambrook et al. (1989), *Molecular Cloning: A Laboratory Manual*, Second Edition, Cold Spring Harbor Laboratory Press; Sambrook et al. (2001) *Molecular Cloning: A Laboratory Manual*, Cold Spring Harbor Laboratory Press, Cold Spring Harbor, N.Y.; Ausubel et al., *Current Protocols in Molecular Biology*, John Wiley & Sons (1987 and annual updates); *Current Protocols in Immunology*, John Wiley & Sons (1987 and annual updates) Gait (ed.) (1984) *Oligonucleotide Synthesis: A Practical Approach*, IRL Press; Eckstein (ed.) (1991) *Oligonucleotides and Analogues: A Practical Approach*, IRL Press; Birren et al. (eds.) (1999) *Genome Analysis: A Laboratory Manual*, Cold Spring Harbor Laboratory Press; Borrebaeck (ed.) (1995) *Antibody Engineering*, Second Edition, Oxford University Press; Lo (ed.) (2006) *Antibody Engineering: Methods and Protocols* (Methods in Molecular Biology); Vol. 248, Humana Press, Inc; each of which is incorporated herein by reference in its entirety.

Monoclonal antibodies can be prepared using a wide variety of techniques known in the art including the use of hybridoma and recombinant technologies, or a combination thereof. For example, monoclonal antibodies can be produced using hybridoma techniques including those known in the art and taught, for example, in Harlow et al., *Antibodies: A Laboratory Manual*, (Cold Spring Harbor Laboratory Press, 2nd ed. 1988); Hammerling et al., in: *Monoclonal Antibodies and T-Cell Hybridomas* 563 681 (Elsevier, N.Y., 1981), each of which is incorporated herein by reference in its entirety. A monoclonal antibody is not limited to antibodies produced through hybridoma technology. Other exemplary methods of producing monoclonal antibodies are known in the art. Additional exemplary methods of producing monoclonal antibodies are provided in the Examples provided herein.

Antibody functional fragments, which bind Tn antigen or sTn antigen, can be generated by any technique well known to those of skill in the art. For example, Fab and F(ab')$_2$ fragments disclosed herein can be produced by proteolytic cleavage of immunoglobulin molecules, using enzymes such as papain (to produce Fab fragments) or pepsin (to produce F(ab')$_2$ fragments). F(ab')$_2$ fragments contain the variable region, the light chain constant region and the CH1 domain of the heavy chain.

The antibody functional fragments disclosed herein can also be generated using various phage display methods known in the art. For example, in phage display methods, functional antibody domains, such as the heavy and/or light chain variable regions having one, two, three, four, five or six CDRs provided herein, are displayed on the surface of phage particles which carry the polynucleotide sequences encoding them. The DNA encoding the VH and VL domains are recombined together with an scFv linker by PCR and cloned into a phagemid vector. The vector is electroporated in *E. coli* and the *E. coli* is infected with helper phage. Phage used in these methods are typically filamentous phage including fd and M13 and the VH and VL domains are usually recombinantly fused to either the phage gene III or gene VIII. Phage expressing an antigen binding domain that binds to a particular antigen, such as Tn antigen or sTn antigen, can be selected or identified with antigen, e.g., using labeled antigen or antigen bound or captured to a solid surface or bead. Examples of phage display methods that can be used to make the antibody functional fragments of the present invention include those disclosed in Brinkman et al., 1995, *J. Immunol. Methods* 182:41-50; Ames et al., 1995, *J. Immunol. Methods* 184:177-186; Kettleborough et al., 1994, *Eur. J. Immunol.* 24:952-958; Persic et al., 1997, *Gene* 187:9-18; Burton et al., 1994, *Advances in Immunology* 57:191-280; PCT Application No. PCT/GB91/01134; International Publication Nos. WO 90/02809, WO 91/10737, WO 92/01047, WO 92/18619, WO 93/1 1236, WO 95/15982, WO 95/20401, and WO97/13844; and U.S. Pat. Nos. 5,698,426, 5,223,409, 5,403,484, 5,580,717, 5,427,908, 5,750,753, 5,821,047, 5,571,698, 5,427,908, 5,516,637, 5,780,225, 5,658,727, 5,733,743 and 5,969,108; each of which is incorporated herein by reference in its entirety.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g., as described herein.

Techniques to recombinantly produce Fab, Fab' and F(ab')$_2$ fragments can also be employed using methods known in the art such as those disclosed in PCT publication No. WO 92/22324; Mullinax et al., 1992, *BioTechniques* 12(6):864-869; Sawai et al., 1995, *AJRI* 34:26-34; and Better et al., 1988, *Science* 240:1041-1043, each of which is incorporated by reference in its entirety.

To generate whole antibodies, PCR primers including VH or VL nucleotide sequences, a restriction site, and a flanking sequence to protect the restriction site can be used to amplify the VH or VL sequences in scFv clones. Utilizing cloning techniques well known to those of skill in the art, the PCR amplified VH domains can be cloned into vectors expressing a VH constant region, e.g., the human gamma 1 constant region, and the PCR amplified VL domains can be cloned into vectors expressing a VL constant region, e.g., human kappa or lambda constant regions. The VH and VL domains can also be cloned into one vector expressing the necessary constant regions. The heavy chain conversion vectors and light chain conversion vectors are then co-transfected into cell lines to generate stable or transient cell lines that express full-length antibodies, e.g., IgG, using techniques well known to those of skill in the art.

In some embodiments, an antibody or functional fragment disclosed herein is conjugated (covalent or non-covalent conjugations) or recombinantly fused to one or more localizing agent, detectable agent or therapeutic agent or any other desired molecule. The conjugated or recombinantly fused antibody or functional fragment can be useful for monitoring or diagnosing the onset, development, progression and/or severity of a disease associated with the expression of Tn antigen or sTn antigen, such as cancer or tumor formation, as part of a clinical testing procedure, such as determining the efficacy of a particular therapy.

In some aspects, an antibody or functional fragment thereof disclosed herein is conjugated with a localizing agent. It is well known in the art that an antibody can be appended with a localizing agent (e.g., a substituted alkene), which can then selectively react in a "click" fashion (formal cycloaddition) with a suitable substrate (e.g., an azide, tetrazine, or tetrazole appended with a detectable agent (e.g., positron-emitting radionuclide or a gamma-emitting radionuclide) or therapeutic agent (e.g., an alpha-emitting or beta-emitting radionuclide) to then bind the detectable or therapeutic agent to the antibody. Examples of such targeted therapy using click chemistry are disclosed, for example, in Houghton et. al., Mol Cancer Ther 16(1):124 (2017), U.S. Pat. Nos. 8,398,956, and 8,992,931.

Accordingly, in some embodiments, the localizing agent is an alkene or alkyne that is capable of undergoing a formal cycloaddition with a suitable substrate. The alkene or alkyne, in some aspects, is a strained alkene or strained alkyne. In some aspects, the strained alkene is a cycloalkane. In some aspects, the cycloalkane is a trans-cycloalkene. In some aspects, the trans-cycloalkene is cyclopentene, cyclohexene, trans-cycloheptane, trans-cyclooctene, or oxanorbornadiene. In some aspects, the suitable substrate is an azide, tetrazine, or tetrazole. In still further aspects, the formal cycloaddition is a click reaction, which can be followed by a retro formal cycloaddition.

In some aspects, an antibody or functional fragment thereof disclosed herein is conjugated with a detectable agent. Detection and diagnosis can be accomplished, for example, by coupling the antibody or functional fragment disclosed herein to detectable substances including: radioactive materials, such as a positron-emitting radionuclide or a gamma-emitting radionuclide (e.g., $^{78}$Br, $^{14}$C, $^{11}$C, $^{57}$Co, $^{64}$Cu, $^{51}$Cr, $^{18}$F $^{68}$Ga, $^{67}$Ga, $^{68}$Ge, $^{153}$Gd, $^{159}$Gd, $^{3}$H, $^{166}$Ho, $^{131}$I, $^{125}$I, $^{124}$I, $^{123}$I, $^{121}$I, $^{115}$In, $^{113}$In, $^{112}$In, $^{111}$In, $^{140}$La, $^{177}$Lu, $^{54}$Mn, $^{99}$Mo, $^{13}$N, $^{15}$O, $^{32}$P, $^{103}$Pd, $^{142}$Pr, $^{149}$Pm, $^{186}$Re, $^{188}$Re, $^{82}$Rb, $^{105}$Rh, $^{97}$Ru, $^{35}$S, $^{47}$Sc, $^{75}$Se, $^{153}$Sm, $^{113}$Sn, $^{117}$Sn, $^{85}$Sr, $^{94}$mTc, $^{99}$Tc, $^{201}$Ti, $^{133}$Xe, $^{86}$Y, $^{90}$Y, $^{169}$Yb, $^{175}$Yb, $^{65}$Zn, or $^{89}$Zr); an enzyme that catalyzes a detectable reaction (e.g., horseradish peroxidase, alkaline phosphatase, beta-galactosidase, or acetylcholinesterase); prosthetic groups (e.g., streptavidin/biotin or avidin/biotin); fluorescent materials (e.g., indocyanine green (ICG), an IRDye fluorescent dye (e.g., IRDye800), umbelliferone, fluorescein, fluorescein isothiocynate, rhodamine, dichlorotriazinylamine fluorescein, dansyl chloride or phycoerythrin); luminescent materials (e.g., luminol); bioluminescent materials (e.g., luciferase, luciferin, or aequorin), and non-radioactive paramagnetic metal ions.

The present invention further encompasses therapeutic uses of an antibody or functional fragment disclosed herein conjugated (covalent or non-covalent conjugations) or recombinantly fused to one or more therapeutic agent. In this context, for example, the antibody can be conjugated or recombinantly fused to a therapeutic agent such as a cytotoxin (e.g., a cytostatic or cytocidal agent). A cytotoxin or cytotoxic agent includes any agent that is detrimental to cells. A cytotoxin can be a radionuclide such as an alpha-emitting radionuclide (e.g., $^{211}$At, $^{212}$Bi, $^{213}$Bi, $^{225}$Ac, $^{223}$Ra, $^{212}$Pb, $^{227}$Th, and $^{149}$Tb) or a beta-emitting radionuclide (e.g., $^{90}$Y, $^{131}$I, $^{109}$Pd, $^{131}$Lu and $^{177}$Lu)). A cytotoxin can be a chemotherapeutic such as, but is not limited to: an anthracycline (e.g., doxorubicin and daunorubicin (formerly daunomycin)); a taxan (e.g., paclitaxel (TAXOL®) and docetaxel (TAXOTERE®); an antimetabolite (e.g., methotrexate, 6-mercaptopurine, 6-thioguanine, cytarabine, 5-fluorouracil and decarbazine); an alkylating agent (e.g., mechlorethamine, thioepa chlorambucil, melphalan, carmustine (BCNU), lomustine (CCNU), cyclothosphamide, busulfan, dibromomannitol, streptozotocin, mitomycin C, cisdichlorodiamine platinum (II) (DDP) and cisplatin); an antibiotic (e.g., actinomycin D, bleomycin, mithramycin, and anthramycin (AMC)); an Auristatin molecule (e.g., auristatin PHE, bryostatin 1, solastatin 10, monomethyl auristatin E (MMAE) and monomethylauristatin F (MMAF)); a hormone (e.g., glucocorticoids, progestins, androgens, and estrogens); a nucleoside analogue (e.g. Gemcitabine), a DNA-repair enzyme inhibitor (e.g., etoposide and topotecan), a kinase inhibitor (e.g., compound ST1571, also known as Gleevec or imatinib mesylate); a cytotoxic agent (e.g., maytansine, paclitaxel, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, 1-dehydrotestosterone, glucorticoids, procaine, tetracaine, lidocaine, propranolol, puromycin and analogs or homologs thereof, and those compounds disclosed in U.S. Pat. Nos. 6,245,759, 6,399,633, 6,383,790, 6,335,156, 6,271,242, 6,242,196, 6,218,410, 6,218,372, 6,057,300, 6,034,053, 5,985,877, 5,958,769, 5,925,376, 5,922,844, 5,911,995, 5,872,223, 5,863,904, 5,840,745, 5,728,868, 5,648,239, 5,587,459); a farnesyl transferase inhibitor (e.g., R115777, BMS-214662, and those disclosed by, for example, U.S. Pat. Nos. 6,458,935, 6,451,812, 6,440,974, 6,436,960, 6,432,959, 6,420,387, 6,414,145, 6,410,541, 6,410,539, 6,403,581, 6,399,615, 6,387,905, 6,372,747, 6,369,034, 6,362,188, 6,342,765, 6,342,487, 6,300,501, 6,268,363, 6,265,422, 6,248,756, 6,239,140, 6,232,338, 6,228,865, 6,228,856, 6,225,322, 6,218,406, 6,211,193, 6,187,786, 6,169,096, 6,159,984, 6,143,766, 6,133,303, 6,127,366, 6,124,465, 6,124,295, 6,103,723, 6,093,737, 6,090,948, 6,080,870, 6,077,853, 6,071,935, 6,066,738, 6,063,930, 6,054,466, 6,051,582, 6,051,574, and 6,040,305); a topoisomerase inhibitor (e.g., camptothecin, irinotecan, SN-38, topotecan, 9-aminocamptothecin, GG-211 (GI 147211), DX-8951f, IST-622, rubitecan, pyrazoloacridine, XR-5000, saintopin, UCE6, UCE1022, TAN-1518A, TAN 1518B, KT6006, KT6528, ED-110, NB-506, ED-110, NB-506, fagaronine, coralyne, beta-lapachone and rebeccamycin); a DNA minor groove binder (e.g., pyrrolobenzodiazepine, Hoescht dye 33342 and Hoechst dye 33258); an adenosine deaminase inhibitor (e.g., Fludarabine phosphate and 2-Chlorodeoxyadenosine); a microtubual disruptor (e.g., a maytansinoid); or pharmaceutically acceptable salts, solvates, clathrates, or prodrugs thereof. The cytotoxic agent described herein can be linked with chemical linkers well known in the art, including such linkers that are enzymatically cleaved upon entry into a cell to mediate its cytotoxic activity.

Further, an antibody or functional fragment disclosed herein can be conjugated (covalent or non-covalent conjugations) or recombinantly fused to a therapeutic agent that is an agent that modifies a given biological response. Thus, therapeutic agents are not to be construed as limited to classical chemical therapeutic agents. For example, the therapeutic agent can be a protein, peptide, or polypeptide possessing a desired biological activity. Such proteins can include, for example, a toxin (e.g., a-amanitin, abrin, ricin A, pseudomonas exotoxin, cholera toxin and diphtheria toxin);

a protein such as tumor necrosis factor, γ-interferon, α-interferon, nerve growth factor, platelet derived growth factor, tissue plasminogen activator, an apoptotic agent (e.g., TNF-γ, AIM I, AIM II, Fas Ligand and VEGF), an anti-angiogenic agent (e.g., angiostatin, endostatin and a component of the coagulation pathway such as tissue factor); a biological response modifier (e.g., a cytokine such as interferon gamma, interleukin-1, interleukin-2, interleukin-5, interleukin-6, interleukin-7, interleukin-9, interleukin-10, interleukin-12, interleukin-15, interleukin-23, granulocyte macrophage colony stimulating factor, and granulocyte colony stimulating factor); a growth factor (e.g., growth hormone), a coagulation agent (e.g., calcium, vitamin K, tissue factors, such as but not limited to, Hageman factor (factor XII), high-molecular-weight kininogen (HMWK), prekallikrein (PK), coagulation proteins-factors II (prothrombin), factor V, XIIa, VIII, XIIIa, XI, XIa, IX, IXa, X, phospholipid, and fibrin monomer), or a chimeric antigen receptor (CAR), which can be expressed by a T-cell and used in CAR T-Cell therapy (see, e.g., Posey et al., Immunity, 44(6):1444-1451 (2016).

The present invention encompasses antibodies or functional fragments disclosed herein recombinantly fused or chemically conjugated (covalent or non-covalent conjugations) to a heterologous protein or polypeptide to generate conjugate. In some aspects, such a polypeptide can be about 10, about 20, about 30, about 40, about 50, about 60, about 70, about 80, about 90 or about 100 amino acids in length. In some aspects, the invention provides conjugates having a functional fragment of an antibody disclosed herein (e.g., a Fab fragment, Fab' fragment, F(ab')$_2$ fragment, a VH domain, a VH CDR, a VL domain or a VL CDR) and a heterologous protein or polypeptide. In one embodiment, the heterologous protein or polypeptide that the antibody or functional fragment is fused to is useful for targeting the antibody or functional fragment to a particular cell type, such as a cell that expresses Tn antigen or sTn antigen.

A conjugated disclosed herein includes any antibody or functional fragment disclosed herein conjugated (covalent or non-covalent conjugations) or recombinantly fused to a localizing agent, detectable agent or therapeutic agent. In one embodiment, a conjugated disclosed herein includes an antibody or functional fragment thereof having the CDRs, VH and/or VL domains of a clonal isolate 1A12b, 1A4, 1E2b, 1G10, 2A8, 2F3, 3A7, or 2F3 variant described herein, and a localizing agent, detectable agent or therapeutic agent.

In some embodiments, a conjugated of the present invention includes one or more VH CDRs having the amino acid sequence of any one of the VH CDRs depicted in Tables 2-4 and a localizing agent, detectable agent or therapeutic agent. In another embodiment, a conjugated includes one or more VL CDRs having the amino acid sequence of any one of the VL CDRs depicted in Tables 2-4 or FIGS. 1-7 and a localizing agent, detectable agent or therapeutic agent.

In some other aspects, a conjugated disclosed herein includes a VH domain having an amino acid sequence depicted in Table 5 or 6 or FIG. 1, or 3-7, and a localizing agent, detectable agent or therapeutic agent.

In some other aspects, a conjugated disclosed herein includes a VL domain having an amino acid sequence depicted in Table 5 or FIG. 2, and a localizing agent, detectable agent or therapeutic agent.

In some embodiments, a conjugated disclosed herein includes a VH domain and a VL domain, wherein the VH domain has an amino acid sequence depicted in Table 5 or 6 or FIG. 1, or 3-7; and SEQ ID NO: 40; and the VL domain has an amino acid sequence depicted in Table 5 or FIG. 2, and a localizing agent, detectable agent or therapeutic agent.

Methods for fusing or conjugating localizing agents, detectable agents or therapeutic agents (including polypeptides) to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies 84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), Thorpe et al., 1982, Immunol. Rev. 62:119-58; U.S. Pat. Nos. 5,336,603, 5,622,929, 5,359,046, 5,349,053, 5,447,851, 5,723,125, 5,783,181, 5,908,626, 5,844,095, 5,112,946, 7,981,695, 8,039,273, 8,142,784; U.S. Publications 2009/0202536, 2010/0034837, 2011/0137017, 2011/0280891, 2012/0003247; EP 307,434; EP 367,166; EP 394, 827; PCT publications WO 91/06570, WO 96/04388, WO 96/22024, WO 97/34631, and WO 99/04813; Ashkenazi et al., Proc. Natl. Acad. Sci. USA, 88: 10535-10539, 1991; Traunecker et al., Nature, 331:84-86, 1988; Zheng et al., J. Immunol., 154:5590-5600, 1995; Vil et al., Proc. Natl. Acad. Sci. USA, 89:11337-11341, 1992; and Senter, Current Opinion in Chemical Biology, 13:235-244 (2009), which are incorporated herein by reference in their entireties.

In another aspect, a localizing agent, detectable agent or therapeutic agent can be attached at the hinge region of a reduced antibody component via disulfide bond formation. Alternatively, such agents can be attached to the antibody component using a heterobifunctional cross-linker, such as N-succinyl 3-(2-pyridyldithio)proprionate (SPDP). Yu et al., Int. J. Cancer 56: 244 (1994). General techniques for such conjugation are well known in the art. See, for example, Wong, CHEMISTRY OF PROTEIN CONJUGATION AND CROSS-LINKING (CRC Press 1991); Upeslacis et al., "Modification of Antibodies by Chemical Methods," in MONOCLONAL ANTIBODIES: PRINCIPLES AND APPLICATIONS, Birch et al. (eds.), pages 187-230 (Wiley-Liss, Inc. 1995); Price, "Production and Characterization of Synthetic Peptide-Derived Antibodies," in MONOCLONAL ANTIBODIES: PRODUCTION, ENGINEERING AND CLINICAL APPLICATION, Ritter et al. (eds.), pages 60-84 (Cambridge University Press 1995).

Alternatively, a localizing agent, detectable agent or therapeutic agent can be conjugated via a carbohydrate moiety in the Fc region of the antibody. Methods for conjugating peptides to antibody components via an antibody carbohydrate moiety are well known to those of skill in the art. See, for example, Shih et al., *Int. J. Cancer.* 41:832-839 (1988); Shih et al., *Int. J. Cancer.* 46:1101-1106 (1990); and Shih et al., U.S. Pat. No. 5,057,313, all of which are incorporated in their entirety by reference. The general method involves reacting an antibody component having an oxidized carbohydrate portion with a carrier polymer that has at least one free amine function and that is loaded with a plurality of peptide. This reaction results in an initial Schiff base (imine) linkage, which can be stabilized by reduction to a secondary amine to form the final conjugate.

However, if the Fc region is absent, for example, if an antibody functional fragment as provided herein is desirable, it is still possible to attach a localizing agent, a detectable agent or a therapeutic agent. A carbohydrate moiety can be introduced into the light chain variable region of a full-length antibody or antibody fragment. See, for example, Leung et al., *J. Immunol.*, 154: 5919 (1995); U.S. Pat. Nos. 5,443,953 and 6,254,868, all of which are incorporated in their entirety by reference. The engineered carbohydrate moiety is used to attach the localizing agent, detectable agent or therapeutic agent.

The therapeutic agent conjugated or recombinantly fused to an antibody or functional fragment disclosed herein that binds to Tn antigen or sTn antigen can be chosen to achieve the desired prophylactic or therapeutic effect(s). It is understood that it is within the skill level of a clinician or other medical personnel to consider the following when deciding which therapeutic agent to conjugate or recombinantly fuse to an antibody or functional fragment disclosed herein: the nature of the disease, the severity of the disease, and the condition of the subject.

A conjugate disclosed herein that is detectably labeled as provided herein and binds to Tn antigen or sTn antigen can be used for diagnostic purposes to detect, diagnose, or monitor a disease, wherein the cells that cause or are associated with the disease express Tn antigen or sTn antigen. A conjugate disclosed herein that is conjugated or fused with a therapeutic agent as provided herein and binds to Tn antigen or sTn antigen can be used for treating or preventing a disease, wherein the cells that cause or are associated with the disease express Tn antigen or sTn antigen. For example, as provided herein, cancer cells and tumors have been shown to express Tn antigen or sTn antigen, such as, but not limited to, breast cancer, ovarian cancer, colon cancer, lung cancer, prostate cancer, gastric cancer, endometrial cancer, and pancreatic cancer. A specific type of breast cancer that has been shown to express Tn antigen or sTn is triple negative breast cancer.

The present invention further includes an antibody or functional fragment thereof that binds preferentially or specifically to a Tn antigen or a sTn antigen on one or more serine residues. This preferential or specific binding to Tn or sTn on one or more serine residues may, for example, facilitate distinguishing target cells such as cancer compared to non-target cells such as normal immune cells. Additionally, the antibodies provided herein having preferential or specific to Tn or sTn on one or more serine residues are IgG isotypes, including IgG1 isotypes, which have distinguishing characteristics compared to, for example, IgM isotypes. Therefore, in some embodiments the present invention may, for example, facilitate target versus non-target selectivity using the antibodies or functional fragment thereof that binds preferentially or specifically to a Tn antigen or a sTn antigen on one or more serine residues to provide. In certain embodiments, the present invention provides a method to specifically target the cancer cell expressing Tn antigen through targeting serine linked Tn or sTn compared to theorine linked Tn or sTn.

Accordingly, the invention provides methods for detecting cancer or a tumor formation in a subject by administering an effective amount of an antibody, functional fragment thereof, or conjugate disclosed herein to a subject in need thereof. In some aspects, the detection method can further include assaying the expression of a Tn antigen or sTn antigen on the cells or a tissue sample of a subject using one or more conjugates or fusion antibodies or functional fragments disclosed herein that bind to Tn antigen or sTn antigen; and comparing the level of the Tn antigen or sTn antigen with a control level, e.g., levels in normal tissue samples (e.g., from a subject not having a disease, or from the same subject before disease onset), whereby an increase in the assayed level of Tn antigen or sTn antigen compared to the control level of the Tn antigen or sTn antigen is indicative of the disease. Such diagnostic methods can allow health professionals to employ preventative measures or aggressive treatment earlier than otherwise possible thereby preventing the development or further progression of the disease.

An antibody or functional fragment disclosed herein can also be used to assay Tn antigen or sTn antigen levels in a biological sample using classical immunohistological methods as provided herein or as well known to those of skill in the art (e.g., see Jalkanen et al., 1985, J. Cell. Biol. 101: 976-985; and Jalkanen et al., 1987, J. Cell. Biol. 105:3087-3096). Other antibody-based methods useful for detecting Tn antigen or sTn antigen include immunoassays, such as the enzyme linked immunosorbent assay (ELISA) and the radioimmunoassay (RIA). Suitable antibody assay labels are known in the art and include enzyme labels, such as, glucose oxidase; radioisotopes, such as iodine ($^{125}$I, $^{121}$I) carbon ($^{14}$C), sulfur ($^{35}$S), tritium ($^{3}$H), indium ($^{121}$In), and technetium ($^{99}$Tc); luminescent labels, such as luminol; and fluorescent labels, such as fluorescein and rhodamine, and biotin.

In one aspect, the invention provides for the detection and diagnosis of disease in a human. In one embodiment, diagnosis includes: a) administering (for example, parenterally, subcutaneously, or intraperitoneally) to a subject an effective amount of a conjugate or fusion protein disclosed herein that binds to Tn antigen or sTn antigen; b) waiting for a time interval following the administering for permitting the conjugate or fusion protein to preferentially concentrate at sites in the subject where Tn antigen or sTn antigen is expressed (and, in some aspects, for unbound conjugate or fusion protein to be cleared to background level); c) determining background level; and d) detecting the conjugate or fusion protein in the subject, such that detection of conjugate or fusion protein above the background level indicates that the subject has a disease. Background level can be determined by various methods including, comparing the amount of conjugate or fusion protein detected to a standard value previously determined for a particular system.

It is understood that the size of the subject and the imaging system used will determine the quantity of imaging moiety needed to produce diagnostic images and can be readily determined by one of skill in the art. For example, in the case of a radioisotope conjugated to an antibody or functional fragment disclosed herein, for a human subject, the quantity of radioactivity injected will normally range from about 5 to 20 millicuries of 99Tc. The conjugate will then preferentially accumulate at the location of cells which express Tn antigen or sTn antigen. In vivo tumor imaging is described in S. W. Burchiel et al., "Immunopharmacokinetics of Radiolabeled Antibodies and Their Fragments." (Chapter 13 in Tumor Imaging: The Radiochemical Detection of Cancer, S. W. Burchiel and B. A. Rhodes, eds., Masson Publishing Inc. (1982).

Depending on several variables, including the type of detectable agent used and the mode of administration, the time interval following the administration for permitting the conjugate to preferentially concentrate at sites in the subject and for unbound conjugate to be cleared to background level is 6 to 48 hours or 6 to 24 hours or 6 to 12 hours. In another embodiment, the time interval following administration is 5 to 20 days or 5 to 10 days. In one embodiment, monitoring of a disease is carried out by repeating the method for diagnosing as provided herein, for example, one month after initial diagnosis, six months after initial diagnosis, one year after initial diagnosis, or longer.

The presence of the conjugate or fusion protein can be detected in the subject using methods known in the art for in vivo scanning. These methods depend upon the type of detectable agent used. A skilled artisan will be able to determine the appropriate method for detecting a particular detectable agent. Methods and devices that can be used in the diagnostic methods disclosed herein include, but are not limited to, computed tomography (CT), whole body scan such as position emission tomography (PET), magnetic resonance imaging (MRI), and sonography. In one embodiment, an antibody or function fragment disclosed herein is conjugated to a radioisotope and is detected in the subject using a radiation responsive surgical instrument. In another embodiment, an antibody or function fragment disclosed herein is conjugated to a fluorescent compound and is detected in the subject using a fluorescence responsive scanning instrument. In another embodiment, an antibody or function fragment disclosed herein is conjugated to a positron emitting metal, such as zirconium ($^{89}$Zr) or any other positron emitting metal provided herein or that is well known in the art to be detectable by positron emission-tomography, and is detected in the subject using positron emission-tomography. In yet another embodiment, an antibody or function fragment disclosed herein is conjugated to a paramagnetic label and is detected in a subject using magnetic resonance imaging (MRI).

In one embodiment, the invention provides a pharmaceutical composition having an antibody or a functional fragment disclosed herein and a pharmaceutically acceptable carrier. A pharmaceutically acceptable carrier that can be used in the pharmaceutical compositions disclosed herein include any of the standard pharmaceutical carriers known in the art, such as phosphate buffered saline solution, water and emulsions such as an oil and water emulsion, and various types of wetting agents. These pharmaceutical compositions can be prepared in liquid unit dose forms or any other dosing form that is sufficient for delivery of the antibody or functional fragment disclosed herein to the target area of the subject in need of treatment. For example, the pharmaceutical compositions can be prepared in any manner appropriate for the chosen mode of administration, e.g., intravascular, intramuscular, sub-cutaneous, intraperitoneal, etc. Other optional components, e.g., pharmaceutical grade stabilizers, buffers, preservatives, excipients and the like can be readily selected by one of skill in the art. The preparation of a pharmaceutically composition, having due regard to pH, isotonicity, stability and the like, is within the level of skill in the art.

Pharmaceutical formulations containing one or more antibodies or functional fragments disclosed herein provided herein can be prepared for storage by mixing the antibody having the desired degree of purity with optional physiologically acceptable carriers, excipients or stabilizers (*Remington's Pharmaceutical Sciences* (1990) Mack Publishing Co., Easton, Pa.), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

In some embodiments, the invention provides a method for treating or preventing a disease in a subject in need thereof. The methods disclosed herein can include administering a therapeutically effective amount of a pharmaceutical composition provided herein to the subject. For example, the pharmaceutical composition can include one or more antibody or functional fragment provided herein. Diseases that can be treated or prevented using the methods disclosed herein include cancer, tumor formation and/or metastasis. In particular, the methods disclosed herein are useful for treating cancers or tumor formation wherein the cancer cells or tumor a protein having a Tn antigen and/or an sTn antigen. Non-limiting examples of cancers or tumors that can be treated or prevented using the methods disclosed herein include breast cancer, ovarian cancer, colon cancer, lung cancer, prostate cancer, gastric cancer, endometrial cancer, and pancreatic cancer. In a specific embodiment, the methods disclosed herein are useful for treating triple negative breast cancer. In a specific embodiment, the methods disclosed herein are useful for specifically targeting cancer cells.

In some embodiments, provided herein is a method for treating or preventing a disease comprising administering a therapeutically effective amount of an antibody or functional fragment thereof that binds to a Tn antigen or an sTn antigen, which also includes one or more of the following features:

binds to two Tn antigen molecules, wherein the two Tn antigen molecules are each located on an amino acid residue of a protein, and wherein the two Tn antigen molecules are separated by 10 or fewer consecutive amino acid residues;
  binds to two Tn antigen molecules, wherein the two Tn antigen molecules are located on adjacent amino acid residues of a protein;
  greater than 10 fold higher avidity for Tn antigen than sialyl Le$^a$, globo H, or a ganglioside selected from the group consisting of F-GM1, GM2, GM3, GD2, and GD3;
  greater than 10 fold higher avidity for Tn antigen than Thomsen-Friedenreich (TF) antigen;
  does not bind sialyl Le$^a$, globo H, or a ganglioside selected from the group consisting of F-GM1, GM2, GM3, GD2, and GD3 above a background control in an enzyme-linked immunosorbant assay;
  does not bind TF antigen above a background control in an enzyme-linked immunosorbant assay;
  has an EC50 value for binding to Tn antigen of less than 50 nM;
  has an EC50 value for binding to Tn antigen of less than 20 nM; or has an EC50 value for binding to Tn antigen of less than 10 nM;
  preferentially binds a Tn or sTn antigen, wherein the Tn or sTn antigen is on a serine residue;
  specifically binds a Tn or sTn antigen, wherein the Tn or sTn antigen is on a serine residue.

preferentially binds a Tn or sTn antigen, wherein the Tn or sTn antigen is on a cancer cell, and the Tn or sTn antigen is on a seine residue;

specifically binds a Tn or sTn antigen, wherein the Tn or sTn antigen is on a cancer cell, and the Tn or sTn antigen is on a seine residue.

Accordingly, in some embodiments, the invention provides a method for treating cancer or a tumor formation in a subject in need thereof by administering a therapeutically effective amount of a pharmaceutical composition having an antibody or functional fragment thereof or conjugate described herein, wherein the antibody heavy or light chain or functional fragment thereof has one or more of the CDRs from the clonal isolates named 1A12b, 1A4, 1E2b, 1G10, 2A8, 2F3, 3A7 and the 2F3 variants described herein. Accordingly, in some aspects, the antibody heavy or light chain or functional fragment thereof has one or more of the CDRs depicted in Table 2-4 and FIGS. 1-7.

In some embodiments, the method for treating cancer or a tumor formation in a subject in need thereof includes administering a therapeutically effective amount of a pharmaceutical composition having an antibody or functional fragment thereof or conjugate described herein, wherein an antibody or functional fragment thereof disclosed herein includes less than six CDRs. In some embodiments, the antibody or functional fragment or conjugate includes one, two, three, four, or five CDRs selected from the group consisting of VH CDR1, VH CDR2, VH CDR3, VL CDR1, VL CDR2, and/or VL CDR3. In specific embodiments, the antibody or functional fragment thereof or conjugate includes one, two, three, four, or five CDRs selected from the group consisting of VH CDR1, VH CDR2, VH CDR3, VL CDR1, VL CDR2, and/or VL CDR3 of clonal isolates 1A12b, 1A4, 1E2b, 1G10, 2A8, 2F3, or 3A7, including the 2F3 variants, described herein. Such CDRs are depicted in Table 2-4 and FIGS. 1-7.

In some embodiments, the method for treating cancer or a tumor formation in a subject in need thereof includes administering a therapeutically effective amount of a pharmaceutical composition having an antibody or functional fragment thereof or conjugate described herein, wherein the antibody or functional fragment thereof or conjugate includes: (a) a variable heavy chain (VH) domain, wherein the VH domain includes: a VH CDR1 having an amino acid sequence selected from the group consisting of SEQ ID NOS: 2, 5, 6, 8, 11, and 12; a VH CDR2 having an amino acid sequence selected from the group consisting of SEQ ID NOS: 14, 17, 18, 20, 23, 24, 149, 150, 151, 152, and 153; and a VH CDR3 having an amino acid sequence selected from the group consisting of SEQ ID NOS: 26, 30, 31, 33, 37, 38, and 154; and/or (b) a variable light chain (VL) domain, wherein the VL domain includes: a VL CDR1 having an amino acid sequence selected from the group consisting of SEQ ID NOS: 40, 44, 45, 47, 51, and 52; a VL CDR2 having an amino acid sequence selected from the group consisting of SEQ ID NOS: 54, 53, 59, 63, and 64; and a VL CDR3 having an amino acid sequence selected from the group consisting of SEQ ID NOS: 66, 70, and 71.

In some embodiments, the method for treating cancer or a tumor formation in a subject in need thereof includes administering a therapeutically effective amount of a pharmaceutical composition having an antibody or functional fragment thereof or conjugate described herein, wherein the antibody or functional fragment thereof or conjugate includes: (a) a variable heavy chain (VH) domain, wherein the VH domain includes: a VH CDR1 having an amino acid sequence selected from the group consisting of SEQ ID NOS: 2, 5, 6, 8, 11, and 12; a VH CDR2 having an amino acid sequence selected from the group consisting of SEQ ID NOS: 14, 17, 18, 20, 23, 24, 149, 150, 151, 152, and 153; and a VH CDR3 having an amino acid sequence selected from the group consisting of SEQ ID NOS: 26, 30, 31, 33, 37, 38, and 154.

In some embodiments, the method for treating cancer or a tumor formation in a subject in need thereof includes administering a therapeutically effective amount of a pharmaceutical composition having an antibody or functional fragment thereof or conjugate described herein, wherein the antibody or functional fragment thereof or conjugate includes: (a) a variable light chain (VL) domain, wherein the VL domain includes: a VL CDR1 having an amino acid sequence selected from the group consisting of SEQ ID NOS: 40, 44, 45, 47, 51, and 52; a VL CDR2 having an amino acid sequence selected from the group consisting of SEQ ID NOS: 54, 53, 59, 63, and 64; and a VL CDR3 having an amino acid sequence selected from the group consisting of SEQ ID NOS: 66, 70, and 71.

In some embodiments, the method for treating cancer or a tumor formation in a subject in need thereof includes administering a therapeutically effective amount of a pharmaceutical composition having an antibody or functional fragment thereof or conjugate described herein, wherein the antibody or functional fragment thereof or conjugate includes: a VH domain and a VL domain, wherein the VH domain includes: a VH CDR1 having an amino acid sequence selected from the group consisting of SEQ ID NOS: 2 and 8; a VH CDR2 having an amino acid sequence selected from the group consisting of SEQ ID NOS: 14 and 20; and a VH CDR3 having an amino acid sequence selected from the group consisting of SEQ ID NOS: 26 and 33; and the VL domain includes: a VL CDR1 having an amino acid sequence selected from the group consisting of SEQ ID NOS: 40 and 47; a VL CDR2 having an amino acid sequence selected from the group consisting of SEQ ID NOS: 54 and 59; and a VL CDR3 having an amino acid sequence of SEQ ID NO: 66.

In some embodiments, the method for treating cancer or a tumor formation in a subject in need thereof includes administering a therapeutically effective amount of a pharmaceutical composition having an antibody or functional fragment thereof or conjugate described herein, wherein the antibody or functional fragment thereof or conjugate includes: a VH domain and a VL domain, wherein the VH domain includes: a VH CDR1 having an amino acid sequence selected from the group consisting of SEQ ID NOS: 5 and 11; a VH CDR2 having an amino acid sequence selected from the group consisting of SEQ ID NOS: 17, 23, 149, 150, 151, 152, and 153; and a VH CDR3 having an amino acid sequence selected from the group consisting of SEQ ID NOS: 30, 37, and 154; and the VL domain includes: a VL CDR1 having an amino acid sequence selected from the group consisting of SEQ ID NOS: 44 and 51; a VL CDR2 having an amino acid sequence selected from the group consisting of SEQ ID NOS: 53 and 63; and a VL CDR3 having an amino acid of SEQ ID NO: 70.

In some embodiments, the method for treating cancer or a tumor formation in a subject in need thereof includes administering a therapeutically effective amount of a pharmaceutical composition having an antibody or functional fragment thereof or conjugate described herein, wherein the antibody or functional fragment thereof or conjugate includes: a VH domain and a VL domain, wherein the VH domain includes: a VH CDR1 having an amino acid sequence selected from the group consisting of SEQ ID NOS: 6 and 12; a VH CDR2 having an amino acid sequence selected from the group consisting of SEQ ID NOS: 18 and 24; and a VH CDR3 having an amino acid sequence selected from the group consisting of SEQ ID NOS: 31 and 38; and the VL domain includes: a VL CDR1 having an amino acid sequence selected from the group consisting of SEQ ID NOS: 45 and 52; a VL CDR2 having an amino acid sequence selected from the group consisting of SEQ ID NOS: 53 and 64; and a VL CDR3 having an amino acid sequence of SEQ ID NO: 71.

In some embodiments, the method for treating cancer or a tumor formation in a subject in need thereof includes administering a therapeutically effective amount of a pharmaceutical composition having an antibody or functional fragment thereof or conjugate described herein, wherein the antibody or functional fragment or conjugate has a VH domain with the amino acid sequence of the VH domain for the clonal isolate 1A12b, 1A4, 1E2b, 1G10, 2A8, 2F3, or 3A7, including the 2F3 variants, described herein. Such VH domain sequences are depicted in Tables 5 and 6 and FIGS. 1 and 3-7.

In some embodiments, the method for treating cancer or a tumor formation in a subject in need thereof includes administering a therapeutically effective amount of a pharmaceutical composition having an antibody or functional fragment thereof or conjugate described herein, wherein the antibody or functional fragment or conjugate has a VL domain with the amino acid sequence of the VL domain for the clonal isolate 1A12b, 1A4, 1E2b, 1G10, 2A8, 2F3, or 3A7, including the 2F3 variants, described herein. Such VL domain sequences are depicted in Table 5 and FIG. 2.

In some embodiments, the method for treating cancer or a tumor formation in a subject in need thereof includes administering a therapeutically effective amount of a pharmaceutical composition having an antibody or functional fragment thereof or conjugate described herein, wherein the antibody or functional fragment or conjugate has a VH domain and a VL domain with the amino acid sequence of the VH domain and VL domain for the clonal isolate 1A12b, 1A4, 1E2b, 1G10, 2A8, 2F3, or 3A7, including the 2F3 variants, described herein. Such VH domain and VL domain sequences are depicted in Table 5 and 6 and FIGS. 1-7.

In some embodiments, the method for treating cancer or a tumor formation in a subject in need thereof includes administering a therapeutically effective amount of a pharmaceutical composition having an antibody or functional fragment thereof or conjugate described herein, wherein the antibody or functional fragment thereof or conjugate includes a VH domain having an amino acid sequence selected from the group consisting of SEQ ID NOS: 101, 105, 106 and 114-130.

In some embodiments, the method for treating cancer or a tumor formation in a subject in need thereof includes administering a therapeutically effective amount of a pharmaceutical composition having an antibody or functional fragment thereof or conjugate described herein, wherein the antibody or functional fragment or conjugate thereof includes a VL domain having an amino acid sequence selected from the group consisting of SEQ ID NOS: 108, 112 and 113.

In some embodiments, the method for treating cancer or a tumor formation in a subject in need thereof includes administering a therapeutically effective amount of a pharmaceutical composition having an antibody or functional fragment thereof or conjugate described herein, wherein the antibody or functional fragment thereof or conjugate includes a VH domain and a VL domain, wherein the VH domain includes the amino acid sequence of SEQ ID NO: 101 and the VL domain includes the amino acid sequence of SEQ ID NO: 108.

In some embodiments, the method for treating cancer or a tumor formation in a subject in need thereof includes administering a therapeutically effective amount of a pharmaceutical composition having an antibody or functional fragment thereof or conjugate described herein, wherein the antibody or functional fragment thereof or conjugate includes a VH domain and a VL domain, wherein the VH domain includes an amino acid sequence selected from the group consisting of SEQ ID NOS: 105 and 114-130 and the VL domain includes the amino acid sequence of SEQ ID NO: 112.

In some embodiments, the method for treating cancer or a tumor formation in a subject in need thereof includes administering a therapeutically effective amount of a pharmaceutical composition having an antibody or functional fragment thereof or conjugate described herein, wherein the antibody or functional fragment thereof or conjugate includes a VH domain and a VL domain, wherein the VH domain includes the amino acid sequence of SEQ ID NOS: 106 and the VL domain includes the amino acid sequence of SEQ ID NO: 113.

Thus embodiments of the invention, include a method for treating or preventing a disease comprising administering a therapeutically effective amount of any of the above described antibodies or functional fragment thereof, the conjugate of any one of the above, or of the pharmaceutical composition of any of the above to a subject in need thereof.

Embodiments of the invention, also include the antibodies or functional fragment thereof of any the above described antibodies of the invention (e.g. bispecific antibodies), the conjugate of any one of the above, or of the pharmaceutical composition of any of the above for use in the treatment or prevention of a disease in a subject in need thereof.

Further aspects of the invention also include the use of the antibody or functional fragment thereof of any of the above described antibodies of the invention (e.g. bispecific antibodies), the conjugate of any one of above, or of the pharmaceutical composition of any of the aforementioned in the manufacture of a medicament for the treatment or prevention of a disease.

Formulations, such as those described herein, can also contain more than one active compound as necessary for the particular disease being treated. In certain embodiments, formulations include an antibody or functional fragment disclosed herein and one or more active compounds with complementary activities that do not adversely affect each other. Such molecules are suitably present in combination in amounts that are effective for the purpose intended. For example, an antibody or functional fragment disclosed herein can be combined with one or more other therapeutic agents. Such combined therapy can be administered to the subject concurrently or successively.

Thus, in some embodiments, invention provides a method for treating or preventing a disease by administering a therapeutically effective amount of a pharmaceutical composition provided herein to a subject in need thereof, wherein the pharmaceutical composition includes an antibody or functional fragment disclosed herein and a second therapeutic agent. The appropriate second therapeutic agent can be readily determined by one of ordinary skill in the art as discussed herein. In one aspect, the second therapeutic agent is a chemotherapeutic agent or an immunotherapeutic agent. An immunotherapeutic can be, but is not limited to, cetuximab, bevacizumab, heceptin, or rituximab.

The pharmaceutical compositions provided herein contain therapeutically effective amounts of one or more of the antibodies disclosed herein provided herein, and optionally one or more additional therapeutic agents, in a pharmaceutically acceptable carrier. Such pharmaceutical compositions are useful in the prevention, treatment, management or amelioration of a disease, such as cancer or tumor formation, or one or more of the symptoms thereof.

The pharmaceutical compositions can contain one or more antibodies or functional fragments disclosed herein. In one embodiment, the antibodies or functional fragments are formulated into suitable pharmaceutical preparations, such as sterile solutions or suspensions for parenteral administration. In one embodiment, the antibodies or functional fragments provided herein are formulated into pharmaceutical compositions using techniques and procedures well known in the art (see, e.g., Ansel (1985) *Introduction to Pharmaceutical Dosage Forms*, 4$^{th}$ Ed., p. 126).

An antibody or functional fragment disclosed herein can be included in the pharmaceutical composition in a therapeutically effective amount sufficient to exert a therapeutically useful effect in the absence of undesirable side effects on the subject treated. The therapeutically effective concentration can be determined empirically by testing the compounds in in vitro and in vivo systems using routine methods and then extrapolated therefrom for dosages for humans. The concentration of an antibody or functional fragment in the pharmaceutical composition will depend on, e.g., the physicochemical characteristics of the antibody or functional fragment, the dosage schedule, and amount administered as well as other factors well known to those of skill in the art.

In one embodiment, a therapeutically effective dosage produces a serum concentration of an antibody or functional fragment of from about 0.1 ng/ml to about 50-100 µg/ml. The pharmaceutical compositions, in another embodiment, provide a dosage of from about 0.001 mg to about 500 mg of antibody per kilogram of body weight per day. Pharmaceutical dosage unit forms can be prepared to provide from about 0.01 mg, 0.1 mg or 1 mg to about 30 mg, 100 mg or 500 mg, and in one embodiment from about 10 mg to about 500 mg of the antibody or functional fragment and/or a combination of other optional essential ingredients per dosage unit form.

The antibody or functional fragment disclosed herein can be administered at once, or can be divided into a number of smaller doses to be administered at intervals of time. It is understood that the precise dosage and duration of treatment is a function of the disease being treated and can be determined empirically using known testing protocols or by extrapolation from in vivo or in vitro test data. It is to be noted that concentrations and dosage values can also vary with the severity of the condition to be alleviated. It is to be further understood that for any particular subject, specific dosage regimens can be adjusted over time according to the individual need and the professional judgment of the person administering or supervising the administration of the compositions, and that the concentration ranges set forth herein are exemplary only and are not intended to limit the scope or practice of the claimed compositions.

Upon mixing or addition of the antibody or functional fragment disclosed herein, the resulting mixture can be a solution, suspension or the like. The form of the resulting mixture depends upon a number of factors, including the intended mode of administration and the solubility of the compound in the selected carrier or vehicle. The effective concentration is sufficient for ameliorating the symptoms of the disease, disorder or condition treated and can be empirically determined.

The pharmaceutical compositions are provided for administration to humans and animals in unit dosage forms, such as sterile parenteral solutions or suspensions containing suitable quantities of the compounds or pharmaceutically acceptable derivatives thereof. The antibody or functional fragment can be, in one embodiment, formulated and administered in unit-dosage forms or multiple-dosage forms. Unit-dose forms refers to physically discrete units suitable for human and animal subjects and packaged individually as is known in the art. Each unit-dose contains a predetermined quantity of the antibody or functional fragment disclosed herein sufficient to produce the desired therapeutic effect, in association with the required pharmaceutical carrier, vehicle or diluent. Examples of unit-dose forms include ampoules and syringes. Unit-dose forms can be administered in fractions or multiples thereof. A multiple-dose form is a plurality of identical unit-dosage forms packaged in a single container to be administered in segregated unit-dose form. Examples of multiple-dose forms include vials or bottles of pints or gallons. Hence, multiple dose form is a multiple of unit-doses that are not segregated in packaging.

In one embodiment, one or more antibody or functional fragment disclosed herein is in a liquid pharmaceutical formulation. Liquid pharmaceutically administrable compositions can, for example, be prepared by dissolving, dispersing, or otherwise mixing an antibody or functional fragment as provided herein and optional pharmaceutical adjuvants in a carrier, such as, for example, water, saline, aqueous dextrose, glycerol, glycols, ethanol, and the like, to thereby form a solution. If desired, the pharmaceutical composition to be administered can also contain minor amounts of nontoxic auxiliary substances such as wetting agents, emulsifying agents, solubilizing agents, pH buffering agents and the like, for example, acetate, sodium citrate, cyclodextrine derivatives, sorbitan monolaurate, triethanolamine sodium acetate, triethanolamine oleate, amino acids (e.g., histidine) and other such agents. Actual methods of preparing such dosage forms are known, or will be apparent, to those skilled in this art; for example, see *Remington's Pharmaceutical Sciences* (1990) Mack Publishing Co., Easton, Pa.

Methods for administering a pharmaceutical composition disclosed herein are well known in the art. It is understood that the appropriate route of administration of a pharmaceutical composition can be readily determined by a skilled clinician. Exemplary routes of administration include intravenous injection, intramuscular injection, intradermal injection or subcutaneous injection. Moreover, it is understood that the formulation of the pharmaceutical composition can be readily adjusted to accommodate the route of administration. The invention also provides that following administration of a pharmaceutical composition disclosed herein, delayed, successive and/or repeated dosages of one or more pharmaceutical composition as provided herein can be administered to the subject.

The methods disclosed herein for treating a disease is intended to include (1) preventing the disease, i.e., causing the clinical symptoms of the disease not to develop in a subject that can be predisposed to the disease but does not yet experience or display symptoms of the disease; (2) inhibiting the disease, i.e., arresting or reducing the development of the disease or its clinical symptoms; or (3) relieving the disease, i.e., causing regression of the disease or its clinical symptoms. The methods disclosed herein for preventing a disease is intended to include forestalling of a clinical symptom indicative of cancer or tumor formation. Such forestalling includes, for example, the maintenance of normal physiological indicators in a subject. Therefore, preventing can include the prophylactic treatment of a subject to guard them from the occurrence of tumor metastasis.

The therapeutically effective amount of the pharmaceutical composition used in the methods disclosed herein will vary depending on the pharmaceutical composition used, the disease and its severity and the age, weight, etc., of the subject to be treated, all of which is within the skill of the attending clinician. A subject that can be treated by the methods disclosed herein include a vertebrate, preferably a mammal, more preferably a human.

It is understood that modifications which do not substantially affect the activity of the various embodiments of this invention are also provided within the definition disclosed herein provided herein. Accordingly, the following examples are intended to illustrate but not limit the present invention.

Example I

Generation and Selection of Potent Human Monoclonal Antibodies to Tn Antigen or sTn Antigen The Tn antigen or sTn antigen has been found in a wide spectrum of human tumors. Accordingly, as described herein, fully human monoclonal antibodies (mAb) against Tn antigen or sTn antigen were generated. Several mAbs were selected from hybridomas based on Tn ELISA, further characterized for carbohydrate specificity, and purified.

Generation of Anti-Tn mAb Producing Hybridomas

Blood samples were obtained from patients in two ongoing vaccine trials. In the first trial, patients were vaccinated with Tn-modified-Muc1-KLH in the presence of other antigens (Globo H, GM2, and a peptide-assembled TF cluster) and treatment with bevacizumab (NCT01223235). In the second trial, a unimolecular vaccine comprising Globo H, GM2, sTn, TF, and Tn all conjugated to KLH was employed (NCT01248273). Both trials took place at MSKCC under an MSKCC- and FDA-approved IRB protocol and IND. Blood specimens were collected from 28 patients (14 patients from each trial) after 3-5 vaccinations, which showed antibody titers between 0 and 1/1280 against Tn. Peripheral blood mononuclear cells (PBMC) were isolated from approximately 80 to 90 mL of blood by gradient centrifugation on Histopaque-1077 (Sigma-Aldrich). B cells were isolated from PBMC using EasySep Memory B cell Isolation kit (StemCell Technologies).

B cells were cultured in RPMI-1640 medium supplemented with L-glutamine, nonessential amino acids, sodium pyruvate, vitamin, penicillin/streptomycin, 10% FBS (Omega Scientific), 10 ng/mL IL-10, 2000U/mL IL2, 5 ug/mL R-848 and 1 µg/mL anti-CD40 mAb (G28-5 hybridoma supernatant; ATCC). Twenty four to 48 hrs later B95-8 culture supernatant was added to B cells (30% V/V). Activated B cells were fused by electrofusion to P3×63Ag8.653 myeloma cells.

Screening of Anti-Tn mAb Producing Hybridomas by Tn ELISA

For the Tn ELISA, plates were coated with 5 µg/mL of polyvalent biotinylated Tn-PAA captured on Neutr-Avidin-coated and 0.25% BSA blocked plates. Neutr-Avidin coated wells were used as controls. Hybridoma supernatants (100 uL/well) were incubated at RT for 1 hour and washed with 3 times with 0.05% TWEEN™ non-ionic surfactant/PBS. Bound antibodies were initially detected with horseradish peroxidase (HRP)-labeled goat anti-human IgG+M (Jackson ImmunoResearch), and positive wells were subsequently probed with IgG-Fc- or IgM-specific secondary antibodies to determine isotypes.

Carbohydrate Specificity Analysis by ELISA

Polyvalent or monovalent biotinylated synthetic carbohydrates (Tn, sTn, TF, Tn-cluster, Globo-H, GD2, GM2 and GD3) were captured on Neutr-Avidin coated and 0.25% BSA blocked plates. MUC1-peptide(SEQ ID NO:157), MUC1-Di-Tn peptide (SEQ ID NO:156), MUC1-1-5G peptide (SEQ ID NO:155) and BSM (bovine submaxillary mucin) were coated directly on the plates and blocked with 0.25% BSA. Different concentration of purified mAbs (100 uL/well) were incubated at RT for 1 hr and washed 3 times with 0.5% TWEEN™ non-ionic surfactant/PBS. Bound antibodies were detected with horseradish peroxidase (HRP)-labeled goat anti-human IgG-Fc (Jackson ImmunoResearch) after washing 4 times with 0.05% TWEEN™ non-ionic surfactant/PBS using OPD as a substrate. Gangliosides GD2, GD3, fucosyl-GM1, GM2, and GM3 were diluted in EtOH at 5 ug/mL, incubated until the plates were dry. Plates were blocked with 2% human serum albumin and washed with PBS. Purified mAbs were incubated at RT for 1 hr and washed 2 times with PBS. After 3 tomes washing with 0.025% TWEEN™ non-ionic surfactant/PBS bound antibodies were detected with alkaline-phosphatase conjugated anti-human IgG-Fc (KPL) using dNPP as a substrate.

Immunoglobulin cDNA Cloning and Recombinant Antibody Expression

Variable region of human mAb heavy and light chain cDNA was recovered by RT-PCR from the individual hybridoma cell line and subcloned into IgG1 or IgM heavy chain or IgK or IgL light chain expression vectors as described before. Sawada-Hirai et al., J. Immune Based Ther. Vaccines, 2:5 (2004). Amino acid sequences and polynucleotide sequences of Fab heavy chain and light chain of the antibody clonal isolates 1A12b, 1A4, 1E2b, 1G10, 2A8, 2F3, and 3A7 are shown below in Tables 7 and 8, respectively. Recombinant mAbs were transiently expressed using EXPICHO™ Expression kit (Thermo Fisher).

Human mAb Purification

Antibodies were purified using the Äkta Explorer (GE Healthcare) system running Unicorn 5.0 software. Serum-free culture medium supernatant was clarified by centrifugation and filtration and stored refrigerated until used. Human IgG antibodies were purified on appropriate-sized protein A columns using 10 mmol/L PBS and 150 mmol/L NaCl running buffer. Human IgM antibodies were purified on a hydroxyapatite column, and IgM was eluted with a gradient of 500 mmol/L phosphate. The antibody concentrations were determined by OD280 using an E1% of 1.4 and 1.18 for IgG and IgM, respectively, and Protein A HPLC. The purity of each preparation was evaluated by SDS-PAGE analysis (1-5 µg per lane) under reducing conditions. Size exclusion chromatography was used to assess aggregation.

Human Cancer Tissue Mirroarray (TMA) Staining

Four tumor microarrays were obtained from US Biomax, Inc, stained with 2F3-G3 and scored for binding. A small cell lung cancer (SCLC) array (cat #LC818) contained 80 cases with a single core per case. An ovarian cancer array (cat #OV8011) containing 35 cases of serous adenocarcinoma, 15 cases of clear cell carcinoma, 15 cases of endometrioid adenocarcinoma, 10 cases of mucinous adenocarcinoma, 5 cases of cancer adjacent tissue had single cores from a total of 80 cases. A breast cancer tissue array (cat #BR1504b)

with cancer adjacent breast tissue as control, including TNM, clinical stage, pathology grade and IHC markers (ER, PR, Her-2, AR and Ki67) results contained duplicate cores from 75 different cases. 11 of these cases were triple negative in both cores, and these were further analyzed for 2F3 staining. 2F3 staining in at least one core was considered positive for the case. Finally, a colon disease spectrum tissue microarray (cat #BC05002a), containing 20 cases of each adenocarcinoma and metastatic carcinoma, 5 cases of each adenoma and polyp, 4 cases of crohn's disease, 1 case of tuberculosis, 5 cases of colonitis, 10 cases of each adjacent normal colonic tissue and normal tissue was stained.

The binding of 2F3v3G3 antibody to formalin fixed, paraffin embedded (FFPE) to sections of human tissues and tumor microarrays was evaluated by immunohistochemistry performed at Charles River Laboratories. TMA slides each containing 80 tissues from colon (BC05002a), breast (BR1504b), ovarian (OV8011) and small cell lung cancer (LC818) patients were acquired from US Biomax. The slides were dewaxed and brief treatment with citrate solution (pH6.0) was used for antigen retrieval. Non-specific protein binding was blocked with 0.5% casein, 1% BSA, 1.5% donkey serum in 2× phosphate buffered salt solution and residual peroxidase activity was blocked with 3% $H_2O_2$. Each TMA slides was incubated with 2F3V3G3 or human IgG1 isotype control antibodies at 2 mg/ml for 2 hours. After washing, binding of 2F3 to the TMAs was detected using precomplexed biotinylated F(ab')$_2$ donkey anti-human IgG (Fc specific) at a 1:1.5 primary:secondary antibody ratio. Binding was detected using the avidin-biotin complex (ABC) technique, a highly sensitive method for immunohistochemical detection with biotinylated secondary antibodies. In brief, the slides were rinsed twice with PBS, then treated for 30 minutes with Elite ABC reagent containing avidin and biotinylated horse radish peroxidase (HRP), rinsed twice with PBS, and then treated with 3,3'-diaminobenzidine (DAB) for 4 minutes as a substrate for the peroxidase reaction. All slides were rinsed with tap water, counterstained, dehydrated, and mounted. PBS+1% BSA served as the diluent for all antibodies and ABC reagent. Stained slides were evaluated by a trained Study Pathologist.

Results

Data from tumor microarray, together with evidence from literature, demonstrated broad expression of Tn antigen in a variety of tumor tissue types. In particular, ovary, breast and colon cancer all demonstrate approximately 50% or higher staining of primary human tumors. (FIG. 22). All 11 triple negative breast cancer cases stained positive for 2F3, with 10 of the 11 cases staining positive in both cores.

Given the tumor expression profile of the Tn antigen, hybridomas producing anti-Tn mAb were generated. Supernatants from 7 positive hybridomas tested interacted with Tn or sTn. V genes were isolated from these hybridomas and cloned in the context of human IgG1 or 3/kappa sequences. Amino acid sequences and polynucleotide sequences of Fab heavy chain and light chain of the antibody clonal isolates 2F3, 3A7, and 1A4 as well as the other 4 isolates are shown below in Tables 7 and 8, respectively. Purified antibodies were screened for reactivity with a panel of carbohydrate antigens to determine breadth of specificity (FIG. 8). Antigens were immobilized on ELISA plates as described in the methods section. The solvent for the first set of antigens, PBS, was tested as a negative control. The solvent for the second set of antigens, EtOH, was tested as a second negative control. Specificity of interaction is indicated in the "Specificity by ELISA" column of FIG. 8, and OD numbers indicating these specificities are indicated on the right-hand 15 columns of FIG. 8. 2F3 showed the best selectivity for Tn and STn. 3A7 and 1A4 also showed good selectivity for this set of antigens.

TABLE 7

Fab heavy chain and light chain amino acid sequences of the antibody clonal isolates 1A12b, 1A4, 1E2b, 1G10, 2A8, 2F3, and 3A7

| Clone | Heavy Chain | Light Chain |
|---|---|---|
| 1A12b | QVQLVESGGGLVQPGGSLRLSCAVSGFTF SDHYMDWVRQAPGKGLEWVGRIRNKAN SYTTEYAASVKGRFTISRDESKRSLYLQM NSLKTEDTAVYYCARVSYYAMDVWGQG TTVTVSSASTKGPSVFPLAPSSKSTSGGTA ALGCLVKDYFPEPVTVSWNSGALTSGVHT FPAVLQSSGLYSLSSVVTVPSSSLGTQTYIC NVNHKPSNTKVDKKVEPKS (SEQ ID NO: 72) | EIVLTQSPSSLSASVGDRVTITCRASQSISS YLNWYQQKPGKAPKLLIYAASSLQSGVPS RFSGSGSGTDFTLTISSLQPEDFATYYCQQ SYSTPRTFGQGTKVEIKRAVAAPSVFIFPPS DEQLKSGTASVVCLLNNFYPREAKVQWK VDNALQSGNSQESVTEQDSKDSTYSLSST LTLSKADYEKHKVYACEVTHQGLSSPVTK SFNRGEC (SEQ ID NO: 79) |
| 1A4 | QLQLVESGGGLVQPGGSLRLSCAASGFTF SDQYMDWIRQAPGKGLEWVGRIRNKANR YTTDYAASVKGRFIISRDDSKNSLYLQMN RLRIEDTAVYYCVRVTAVALDYWGQGTL VTVSSGSASAPTLFPLVSCENSPSDTSSVA VGCLAQDFLPDSITFSWKYKNNSDISSTRG FPSVLRGGKYAATSQVLLPSKDVMQGTDE HVVCKVQHPNGNKEKNVPLPV (SEQ ID NO: 73) | DVVMTQSPATLSLSPGERATLSCRASQSVS TYLAWYQQKPGQAPTLLIYDASNRATGIP ARFSGRGSGTDFTLTISSLEPEDFAVYYCH QRSDWPPVTFGQGTRLEIKRTVAAPSVFIF PPSDEQLKSGTASVVCLLNNFYPREAKVQ WKVDNALQSGNSQESVTEQDSKDSTYSLS STLTLSKADYEKHKVYACEVTHQGLSSPV TKSFNRGEC (SEQ ID NO: 80) |
| 1E2b | QVQLQQSGAEVKKPGASVKVSCKATGYT FTSYGISWVRQAPGQGLEWMGWISAYNG NTNYAQKLQGRVTMTTDTSTSTAYMELR SLRSDDTAVYYCARGGGTTVLDYYRYGM DVWGQGTTVTVSSGSASAPTLFPLVSCEN SPSDTSSVAVGCLAQDFLPDSITFSWKYKN NSDISSTRGFPSVLRGGKYAATSQVLLPSK DVMQGTDEHVVCKVQHPNGNKEKNVPLP V (SEQ ID NO: 74) | QSVLTQPPSLSASPGASASLTCTLRSGINV GTYRIYWYQQKPGSPPQYLLRYKSDSDKQ QGSGVPSRFSGSKDASANAGILLISGLQSE DEADYYCMIWHSSAVVFGGGTKLTVLGQ PKAAPSVTLFPPSSEELQANKATLVCLISDF YPGAVTVAWKADSSPVKAGVETTTPSKQ SNNKYAASSYLSLTPEQWKSHRSYSCQVT HEGSTVEKTVAPTEC (SEQ ID NO: 81) |

TABLE 7-continued

Fab heavy chain and light chain amino acid sequences of the antibody clonal isolates 1A12b, 1A4, 1E2b, 1G10, 2A8, 2F3, and 3A7

| Clone | Heavy Chain | Light Chain |
|---|---|---|
| 1G10 | QVQLVQSGAEVKKPGASVKVSCKASGYT FTSYDINWVRQATGQGLEWMGWMNPNS GNTGYAQKFQGRVTMTRNTSISTAYMELS SLRSEDTAVYYCARGWRYSSSWYRKVRF DPWGQGTLVTVSSGSASAPTLFPLVSCENS PSDTSSVXVGCLAQDFLPDSITFSWKYKN NSDISSTRGFPSVLRGGKYAATSQVLLPSK DVMQGTDEHVVCKVQHPNGNKEKNVPLP V (SEQ ID NO: 75) | ETTLTQSPLSLPVTPGEPASISCRSSQSLLHS NGYNYLDWYLQKPGQSPQLLIYLGSNRAS GVPDRFSGSGSGTDFTLKISRVEAEDVGV YYCMQALQTPITFGQGTRLEIKRTVAAPS VFIFPPSDEQLKSGTASVVCLLNNFYPREA KVQWKVDNALQSGNSQESVTEQDSKDST YSLSSTLTLSKADYEKHKVYACEVTHQGL SSPVTKSFNRGEC (SEQ ID NO: 82) |
| 2A8 | QVQLVGSGAEVKKPGASVKVSCKASGYT FTSYDINWVRQATGQGLEWMGWMNPNS GNTGYAQKFQGRVTMTRNTSISTAYMELS SLRSEDTAVYYCARANRKGARTRAFDYW GQGTLVTVSSGSASAPTLFPLVSCENSPSD TSSVAVGCLAQDFLPDSITFSWKYKNNSDI SSTRGFPSVLRGGKYAATSQVLLPSKDVM QGTDEHVVCKVQHPNGNKEKNVPLPV (SEQ ID NO: 76) | QSVLIQPPSVSAAPGQKVTISCSGSSSNIGN NYVSWYQQLPGTAPKLLIYDNNKRPSGIP VRFSGSKSGTSATLGITGLQTGDEADYYC GTWDSSLSAVFGTGTKVTVLGQPKANPTV TLFPPSSEELQANKATLVCLISDFYPGAVT VAWKADSSPVKAGVETTTPSKQSNNKYA ASSYLSLTPEQWKSHRSYSCQVTHEGSTV EKTVAPTECS (SEQ ID NO: 83) |
| 2F3 | EVQLLESGGGLVQPGGSLRLSCAASGFTF DSYAMSWVRQAPGKGLEWVSAISGSGDS TYYADSVKGRFSISRDNSKNTLYLQMNSL RAEDTAVYYCAIRREYSGYAPPDYWGQG TLVTVSSGSASAPTLFPLVSCENSPSDTSSV AVGCLAQDFLPDSITFSWKYKNNSDISSTR GFPSVLRGGKYAATSQVLLPSKDVMQGT DEHVVCKVQHPNGNKEKNVPLPV (SEQ ID NO: 77) | DIVMTQTPSSLSASVGDRVTITCRASQGISS WLAWYQQKPEKAPRSLIYAASSLQSGVPS RFSGSGSGTDFTLTISSLQPEDFATYYCQQ YISYPYTFGQGTKLEIKRTVAAPSVFIFPPS DEQLKSGTASVVCLLNNFYPREAKVQWK VDNALQSGNSQESVTEQDSKDSTYSLSST LTLSKADYEKHKVYACEVTHQGLSSPVTK SFNRGEC (SEQ ID NO: 84) |
| 3A7 | QVQLVQSGGGLVQPGETLRLSCEASGFTF RSYYMSWVRQAPRKGLEWVASINQHGSE KYYVDSVKGRFTISRDNAKNSLYLQMISL RAEDTAVYYCARDGDRTTDYWGQGTLV TVSSRSASAPTLFPLVSCENSPSDTSSVAV GCLAQDFLPDSITFSWKYKNNSDISSTRGF PSVLRGGKYAATSQVLLPSKDVMQGTDE HVVCKVQHPNGNKEKNVPLPV (SEQ ID NO: 78) | ETTLTQSPATLSLSPGDRATLSCRASQSVS SYLVWYQQKFGQAPRLLIYAASNRAAGIP ARFSGSGSGTDFTLTISSLEPEDFAVYYCQ QRSNWPITFGPGTKVDIKRTVAAPSVFIFPP SDEQLKSGTASVVCLLNNFYPREAKVQW KVDNALQSGNSQESVTEQDSKDSTYSLSS TLTLSKADYEKHKVYACEVTHQGLSSPVT KSFNRGEC (SEQ ID NO: 85) |

TABLE 8

Polynucleotide sequences encoding the fab heavy chain and light chain of the antibody clonal isolates 1A12b, 1A4, 1E2b, 1G10, 2A8, 2F3, and 3A7

| Clone | Heavy Chain | Light Chain |
|---|---|---|
| 1A12b | CAGGTGCAGCTGGTGGAGTCTGGGGGAG GCTTGGTCCAGCCTGGAGGGTCCCTGAGA CTCTCCTGTGCAGTCTCTGGATTCACCTTCCCATCACTTGCCGGGCAAGTCAGAGCATT AGTGACCACTACATGGACTGGGTCCGCCA GGCTCCAGGGAAGGGGCTGAGTGGGTT GGCCGTATTAGAAACAAAGCTAACAGTT ACACCACAGAATACGCCGCGTCTGTGAA AGGCAGATTCACCATCTCAAGAGATGAA TCAAAGAGGTCACTGTATCTGCAAATGAA CAGCCTGAAAACCGAGGACACAGCCGTG TATTACTGTGCTAGAGTATCCTACTACGC TATGGACGTCTGGGGCCAAGGGACCACG GTCACCGTCTCCTCA (SEQ ID NO: 86) | GAAATTGTGTTGACCCAGTCTCCATCCTC CCTGTCTGCATCTGTAGGAGACAGAGTCA CCATCAAGGTTCAGTGGCAGTGGATCTGG AGCAGCTATTTAAATTGGTATCAGCAGAA ACCAGGGAAAGCCCCTAAGCTCCTGATCT ATGCTGCATCCAGTTTGCAAAGTGGGGTC CCATCAAGGTTCAGTGGCAGTGGATCTGG GACAGATTTCACTCTCACCATCAGCAGTC TGCAACCTGAAGATTTTGCAACTTACTAC TGTCAACAGAGTTACAGTACCCCTCGGAC GTTCGGCCAAGGGACCAAGGTGGAAATC AAA (SEQ ID NO: 93) |
| 1A4 | CAGCTGCAGCTGGTGGAATCTGGGGGAG GCTTGGTCCAGCCTGGAGGGTCCCTGAGA CTCTCCTGTGCAGCCTCTGGATTCACCTTCCCCTCTCTTGCAGGGCCAGTCAGAGTGTT AGTGACCAATCATGGACTGGATCCGCC AGGCTCCAGGGAAGGGACTGGAGTGGGT TGGCCGTATTAGAAACAAAGCTAACAGG TATACCACAGACTACGCCGCGTCTGTGAA | GATGTTGTGATGACCCAGTCTCCAGCCAC CCTGTCTTTGTCTCCAGGGGAAAGAGCCA CCCTCTCCTGCAGGGCCAGTCAGAGTGTT AGTACCTACTTAGCCTGGTACCAGCAGAA ACCTGGCCAGGCTCCCACCCTCCTCATCT ATGATGCATCCAACAGGGCCACTGGCATC CCAGCCAGGTTCAGTGGCCGTGGGTCGG |

TABLE 8-continued

Polynucleotide sequences encoding the fab heavy chain and light chain of the antibody clonal isolates 1A12b, 1A4, 1E2b, 1G10, 2A8, 2F3, and 3A7

| Clone | Heavy Chain | Light Chain |
|---|---|---|
| | AGGCAGATTCATCATCTCAAGAGATGATT<br>CAAAGAACTCACTGTATCTGCAAATGAAC<br>AGGCTGAGAATTGAAGACACGGCCGTGT<br>ATTACTGTGTTAGAGTTACAGCAGTGGCT<br>CTAGACTATTGGGGCCAGGGAACCCTGGT<br>CACCGTCTCCTCA<br>(SEQ ID NO: 87) | GGACAGACTTCACTCTCACCATCAGCAGC<br>CTAGAGCCTGAAGATTTTGCAGTTTATTA<br>CTGTCACCAACGTAGCGACTGGCCTCCGG<br>TCACCTTCGGCCAAGGGACACGACTGGA<br>GATTAAA (SEQ ID NO: 94) |
| 1E2b | CAGGTGCAGCTGCAGCAGTCTGGAGCTG<br>AGGTGAAGAAGCCTGGGGCCTCAGTGAA<br>GGTCTCCTGCAAGGCTACTGGTTACACCT<br>TTACCAGCTATGGTATCAGCTGGGTGCGA<br>CAGGCCCCTGGACAAGGGCTTGAGTGGA<br>TGGGATGGATCAGCGCTTACAATGGTAAC<br>ACAAACTACGCACAGAAGCTCCAGGGCA<br>GGGTCACCATGACCACAGACACATCCAC<br>GAGCACAGCCTACATGGAGCTGAGGAGC<br>CTGAGATCTGACGACACGGCCGTGTATTA<br>CTGTGCGAGAGGCGGGGGGACTACGGTC<br>CTTGACTACTACCGCTACGGTATGGACGT<br>CTGGGGCCAAGGGACCACGGTCACCGTC<br>TCCTCA (SEQ ID NO: 88) | CAGTCTGTGTTGACGCAGCCGCCTTCCCT<br>CTCTGCATCTCCTGGAGCATCAGCCAGTC<br>TCACCTGCACCTTACGCAGTGGCATCAAT<br>GTTGGTACCTACAGGATATACTGGTACCA<br>GCAGAAGCCAGGGAGTCCTCCCCAGTAT<br>CTCCTGAGGTACAAATCAGACTCAGATAA<br>GCAGCAGGGCTCTGAGTCCCCAGCCGC<br>TTTCTCTGGATCCAAAGATGCTTCGGCCAA<br>TGCAGGGATTTTACTCATCTCTGGGCTCC<br>AGTCTGAGGATGAGGCTGACTATTACTGT<br>ATGATTTGGCACAGCAGCGCTGTGGTATT<br>CGGCGGAGGGACCAAGCTGACCGTCCTA<br>(SEQ ID NO: 95) |
| 1G10 | CAGGTGCAGCTGGTGCAGTCTGGGGCTG<br>AGGTGAAGAAGCCTGGGGCCTCAGTGAA<br>GGTCTCCTGCAAGGCTTCTGGATACACCT<br>TCACCAGTTATGATATCAACTGGGTGCGA<br>CAGGCCACTGGACAAGGGCTTGAGTGGA<br>TGGGATGGATGAACCCTAACAGTGGTAA<br>CACAGGCTATGCACAGAAGTTCCAGGGC<br>AGAGTCACCATGACCAGGAACACCTCCA<br>TAAGCACAGCCTACATGGAGCTGAGCAG<br>CCTGAGATCTGAGGACACGGCCGTGTATT<br>ACTGTGCGAGAGGGTGGAGGTATAGCAG<br>CAGCTGGTACCGGAAGGTCCGGTTCGACC<br>CCTGGGGCCAGGGAACCCTGGTCACCGT<br>CTCCTCA (SEQ ID NO: 89) | GAAACGACACTCACGCAGTCTCCACTCTC<br>CCTGCCCGTCACCCCTGGAGAGCCGGCCT<br>CCATCTCCTGCAGGTCTAGTCAGAGCCTC<br>CTGCATAGTAATGGATACAACTATTTGGA<br>TTGGTACCTGCAGAAGCCAGGGCAGTCTC<br>CACAGCTCCTGATCTATTTGGGTTCTAAT<br>CGGGCCTCCGGGGTCCCTGACAGGTTCAG<br>TGGCAGTGGATCAGGCACAGATTTTACAC<br>TGAAAATCAGCAGAGTGGAGGCTGAGGA<br>TGTTGGGGTTTATTACTGCATGCAAGCTC<br>TACAAACTCCGATCACCTTCGGCCAAGGG<br>ACACGACTGGAGATTAAA<br>(SEQ ID NO: 96) |
| 2A8 | CAGGTGCAGCTGGTGGGGTCTGGGGCTG<br>AGGTGAAGAAGCCTGGGGCCTCAGTGAA<br>GGTCTCCTGCAAGGCTTCTGGATACACCT<br>TCACCAGTTATGATATCAACTGGGTGCGA<br>CAGGCCACTGGACAAGGGCTTGAGTGGA<br>TGGGATGGATGAACCCTAACAGTGGTAA<br>CACAGGCTATGCACAGAAGTTCCAGGGC<br>AGAGTCACCATGACCAGGAACACCTCCA<br>TAAGCACAGCCTACATGGAGCTGAGCAG<br>CCTGAGATCTGAGGACACGGCCGTGTATT<br>ACTGTGCGAGAGCGAATAGGAAAGGGGC<br>ACGAACGCGGGCCTTTGACTACTGGGGCC<br>AGGGAACCCTGGTCACCGTCTCCTCA<br>(SEQ ID NO: 90) | CAGTCTGTCCTGATTCAGCCTCCCTCAGT<br>GTCTGCGGCCCCAGGACAGAAGGTCACC<br>ATCTCCTGCTCTGGAAGCAGCTCCAACAT<br>TGGGAATAATTATGTATCCTGGTACCAGC<br>AGCTCCCAGGAACAGCCCCCAAACTCCTC<br>ATTTATGACAATAATAAGCGACCCTAGGA<br>GATTCCTGTCCGATTCTCTGGCTCCAAGT<br>CTGGCACGTCAGCCACCCTGGGCATCACC<br>GGACTCCAGACTGGGGACGAGGCCGATT<br>ATTACTGCGGAACATGGGATAGCAGCCT<br>GAGTGCTGTCTTCGGAACTGGGACCAAG<br>GTCACCGTCCTA (SEQ ID NO: 97) |
| 2F3 | GAGGTGCAGCTGTTGGAGTCTGGGGGAG<br>GCTTGGTACAGCCTGGGGGGTCCCTGAGA<br>CTCTCCTGTGCAGCCTCTGGATTCACCTTTCCATCACTTGTGGGCGAGTCAGGGTATT<br>GATAGCTATGCCATGAGCTGGGTCCGCCA<br>GGCTCCAGGGAAGGGGCTGGAGTGGGTC<br>TCAGCTATTAGTGGTAGTGGTGATAGCAC<br>ATACTACGCAGACTCCGTGAAGGGCCGG<br>TTCAGCATCTCCAGAGACAATTCCAAGAA<br>CACGCTGTATCTGCAAATGAACAGCCTGA<br>GAGCCGAGGACACGGCCGTATATTACTGT<br>GCGATCAGACGTGAATATAGTGGCTACG<br>CTCCCTTTGACTACTGGGGCCAGGGAACC<br>CTGGTCACCGTCTCCTCA<br>(SEQ ID NO: 91) | GATATTGTGATGACTCAGACTCCATCCTC<br>ACTGTCTGCATCTGTAGGAGACAGAGTCA<br>CCATCACTTGTCGGGCGAGTCAGGGTATT<br>AGCAGCTGGTTAGCCTGGTATCAGCAGA<br>AACCAGAGAAAGCCCCTAGGTCCCTGAT<br>CTATGCTGCGTCCAGTTTGCAAAGTGGGG<br>TCCCATCAAGGTTCAGCGGCAGTGGATCT<br>GGGACAGATTTCACTCTCACCATCAGCAG<br>CCTGCAGCCTGAAGATTTTGCAACTTATT<br>ACTGCCAACAGTATATTAGTTACCCGTAC<br>ACTTTTGGCCAGGGGACCAAGCTGGAGA<br>TCAAA (SEQ ID NO: 98) |
| 3A7 | CAGGTACAGCTGGTGCAATCTGGGGGAG<br>GCTTGGTCCAGCCTGGGGGAGACCCTGAG<br>ACTCTCCTGTGAAGCCTCTGGATTCACTT<br>TTAGGAGCTACTACATGAGCTGGGTCCGC<br>CAGGCTCCACGGAAGGGGCTGGAGTGGG<br>TGGCCAGTATAAACCAACATGGAAGTGA | GAAACGACACTCACGCAGTCTCCAGCCA<br>CCCTGTCTTTGTCTCCAGGGGACAGAGCC<br>ACCCTCTCCTGCAGGGCCAGTCAGAGTGT<br>TAGCAGCTACTTAGTCTGGTACCAACAGA<br>AATTTGGTCAGGCTCCCAGGCTCCTCATC<br>TATGCTGCATCCAACAGGGCCGCTGGCAT |

TABLE 8-continued

Polynucleotide sequences encoding the fab heavy chain and light chain of the antibody clonal isolates 1A12b, 1A4, 1E2b, 1G10, 2A8, 2F3, and 3A7

| Clone | Heavy Chain | Light Chain |
|---|---|---|
|  | GAAATACTATGTGGACTCTGTGAAGGGCC GATTCACCATCTCCAGAGACAACGCCAA GAACTCACTCTATCTGCAAATGATCAGCC TGAGAGCCGAGGACACGGCCGTGTATTA CTGTGCGAGAGATGGGGACAGAACAACG GACTACTGGGGCCAGGGAACCCTGGTCA CCGTCTCCTCA (SEQ ID NO: 92) | CCCAGCCAGGTTCAGTGGCAGTGGGTCTG GGACAGACTTCACTCTCACCATCAGCAGC CTAGAGCCTGAAGATTTTGCAGTTTATTA CTGTCAGCAGCGTAGCAACTGGCCGATCA CTTTCGGCCCTGGGACCAAAGTGGATATC AAA (SEQ ID NO: 99) |

Example II

Generation and Optimization of Variants of a Potent Human Monoclonal Antibody to Tn Antigen or sTn Antigen, 2F3

One of the lead antibodies generated and identified in Example I, 2F3, was selected for generation of further variants and optimization. Error prone PCR was employed to generate mutants of 2F3 antibody and site directed mutagenesis and recombinant methods were subsequently employed to further optimize the generated 2F3 mutants. In a series of affinity maturation tests, favorable mutant antibodies were screened by ELISA and FACS for their improved binding affinity to model Tn antigens.

Generation of 2F3 Mutants Using Error-Prone PCR

2F3 VH region was amplified by PCR with GeneMorphII polymerase (Agilent) using VHF and CγR as primers as previously described (Sawada-Hirai et al., J. Immune Based Ther. Vaccines, 2:5 (2004)). VH fragments were purified and sub-cloned into an IgG expression vector. Plasmid DNAs from individual clones were purified and sequenced. Mutant heavy chains along with wild type 2F3 light chain were used to co-transfected Cos1 or Expi-CHO cells. Supernatants were evaluated by Tn specific ELISA and flow cytometry with Tn positive (T-47D and Jurkat) and negative (SK-MEL28) cell lines.

Generation of 2F3 Mutants by Site Directed Mutagenesis and Recombinant Methods.

Point mutations in CDRs were generated by overlapping PCR. First 5' and 3' fragments were amplified separately by PCR. The reverse primer for the N-term fragment and forward primer for the C-term fragment have overlapping complementary sequences with NNN sequence for targeting CDR position in the middle. Then entire VH region was amplified by PCR using 5' and 3' fragment as a mixed template with VHF and CγR primers. Purified VH fragment was sub-cloned into IgG expression cassette, expressed, and purified as described above.

Mutant combination variants between CDR2 and CDR3 were generated similarly by performing overlap PCR with a 5' fragment and a 3' fragment where the junction between the fragments is in FR3, between CDR2 and CDR3. The two fragments were mixed and used as template to amplify the VH region with two mutation with VHF and CγR primers. Purified VH fragment was sub-cloned into IgG expression cassette, expressed, and purified as described above.

Flow Cytometry

Tn-positive (T-47D, OVCAR3, MCF7, or Jurkat) tumor cell lines ($0.5 \times 10^6$ cells per condition) were washed in PBS/2% FBS (PBSF). Various concentration of test or control human mAb was added to the cells and incubated on ice for 30 minutes (Gilewski et al., Clin Cancer Res, 6:1693-701 (2000); Gilewski et al. Proc. Natl. Acad. Sci. U.S.A., 98:3270-5 (2001)). After washing in PBSF, the cells were incubated with ALEXAFLUOR™ 488 Reagent anti-human IgG-Fcγ or anti-human IgM-μ (Thermo Fisher) for 30 minutes on ice. Cells were washed twice in PBSF and fluorescence data were acquired by flow cytometry using the GUAVA® Personal Cell Analysis-96 (PCA-96) System (Millipore) and analyzed with GUAVA® ExpressPro Software.

Results

One of the lead antibodies, 2F3, was selected for affinity optimization. Error prone PCR was employed to generate mutants and mutants were screened by ELISA (FIG. 9). Unpurified cell supernatants were quantitated and used to bind to Tn-PAA to determine impact of mutations on binding. In this round, variants 17, 33, and 75 showed markedly improved binding compared to the parental sequence.

Figure 10:
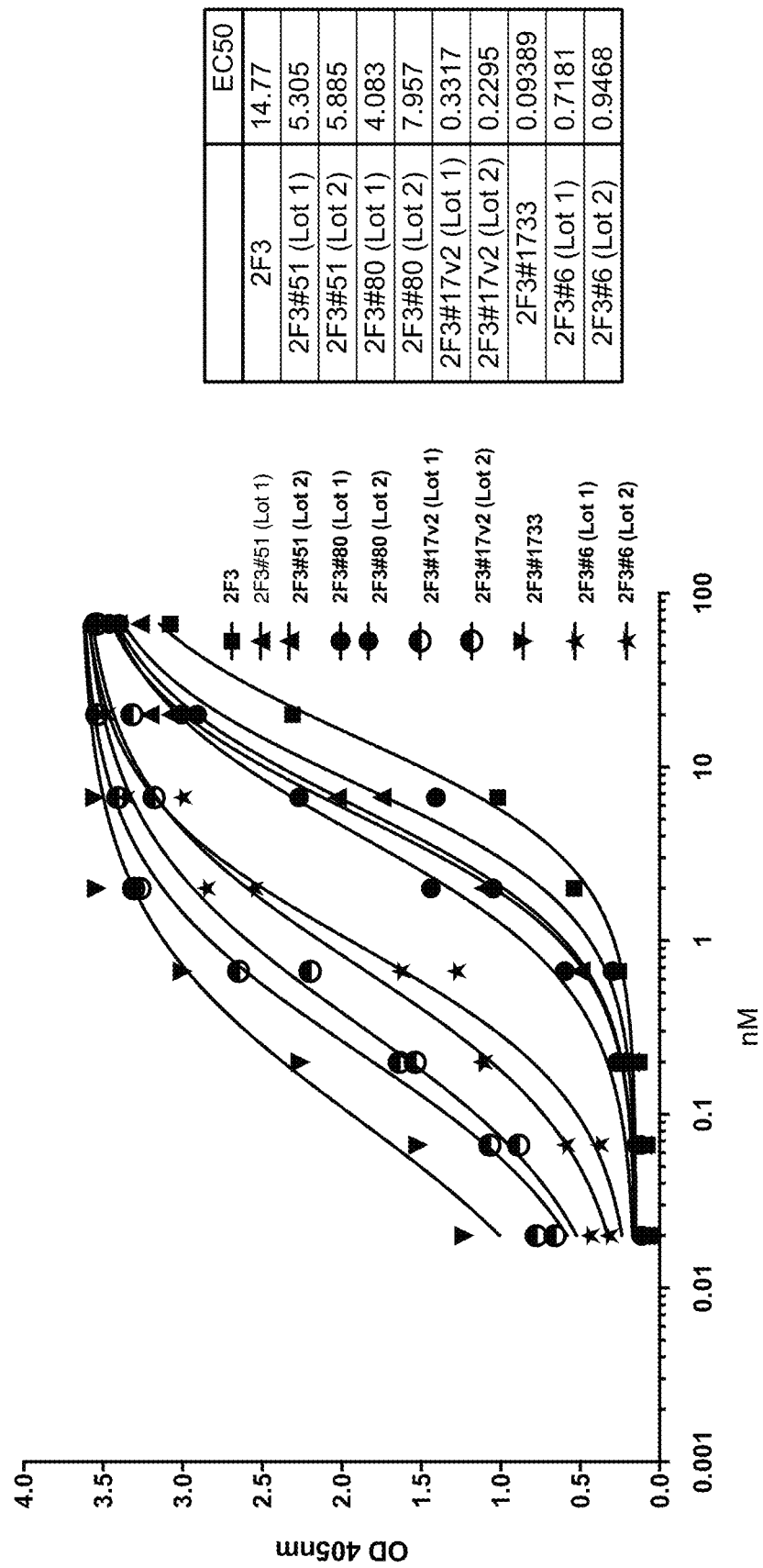
FIG. 10 shows modification of a subset of the lead optimized heavy chains, to remove sequence artifacts or combine two favorable mutants into a single construct. Multiple purified batches were assayed by ELISA and compared to the parent molecule for their binding affinities.

Further, a subset of the lead optimized heavy chains was modified slightly to remove sequence artifacts (clone 17) and in one case two favorable mutants were combined into a single construct (clone 1733) (FIG. 10). Multiple purified batches were assayed by ELISA and compared to the parent molecule. As shown in the table of FIG. 10, all optimized variants showed binding superior to the parent molecule, and clones 1733, 17v2, and 6 were the strongest binders to the Tn antigen among the tested variants.

Figure 11:
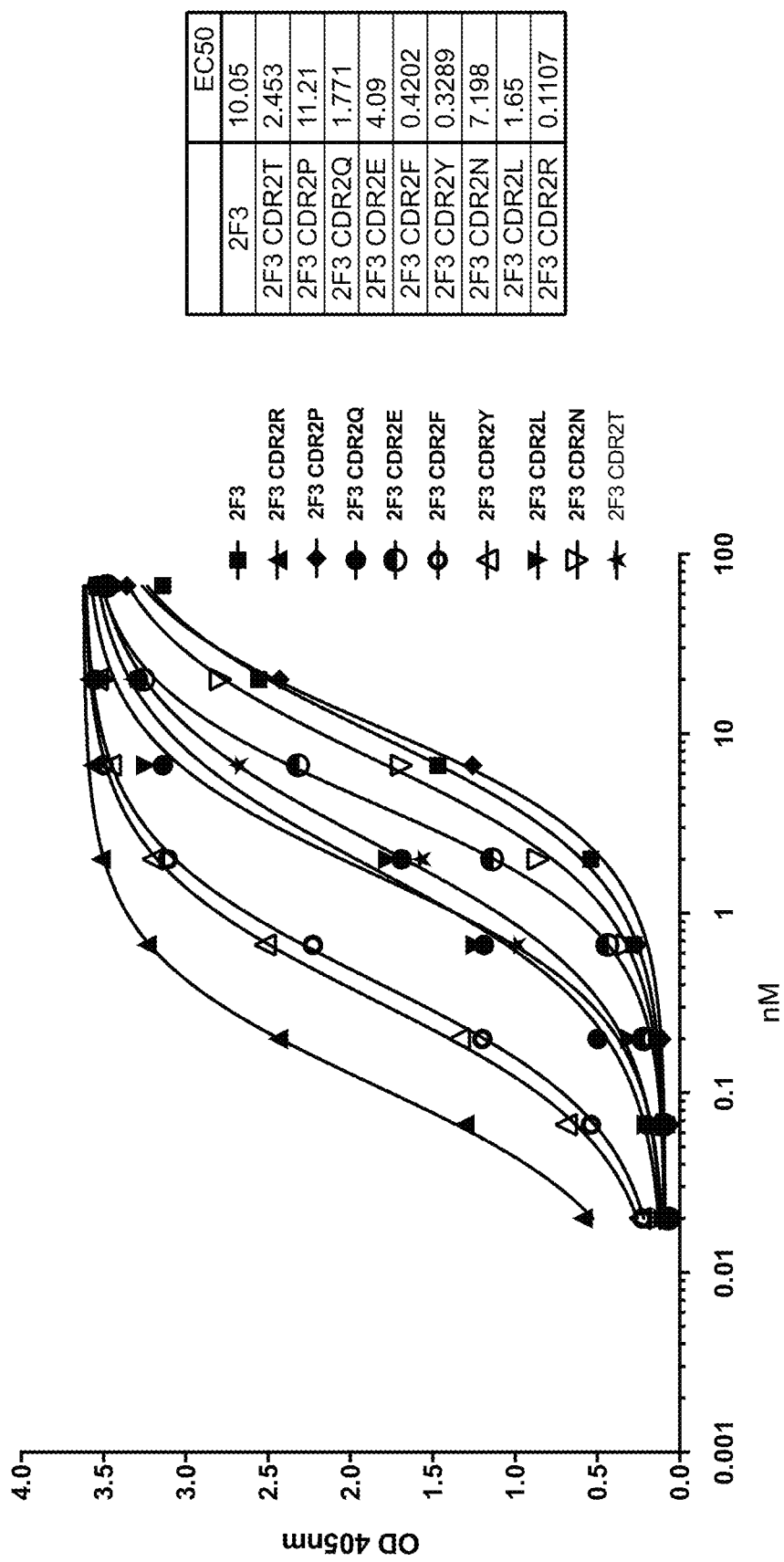
FIG. 11 shows introduction of additional mutations into position H55 (Kabat), which was found to contain two favorable mutations by the error prone PCR mutation process in variants 6 and 17, by randomizing the sequence for the codon encoding this position. Clones were picked and sequenced to achieve a sampling of all amino acids at this position, and mutant antibodies were generated and tested for their impact on binding affinity to Tn-PAA in comparison to the parent 2F3.
Figure 13A:
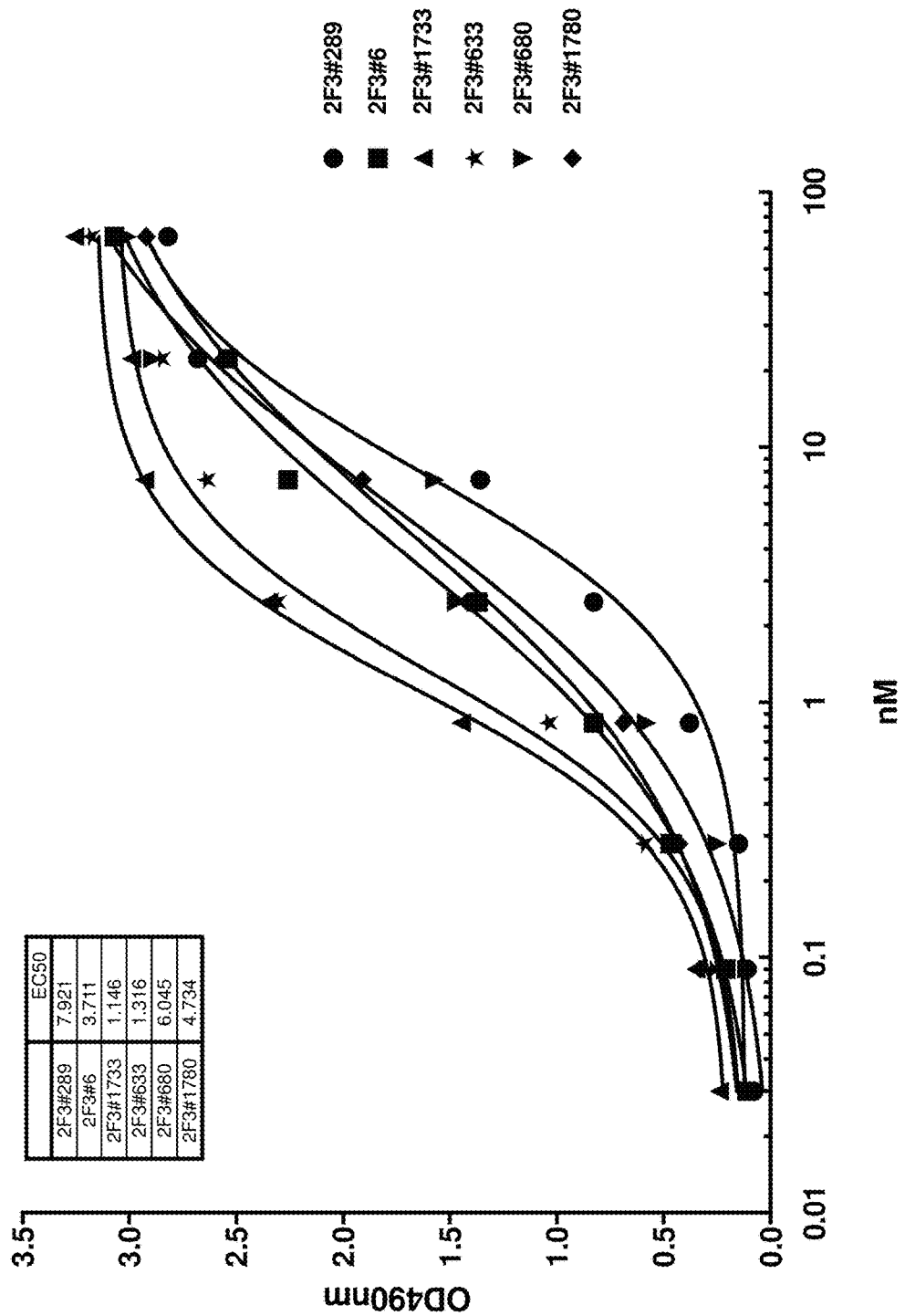
Figure 13C:
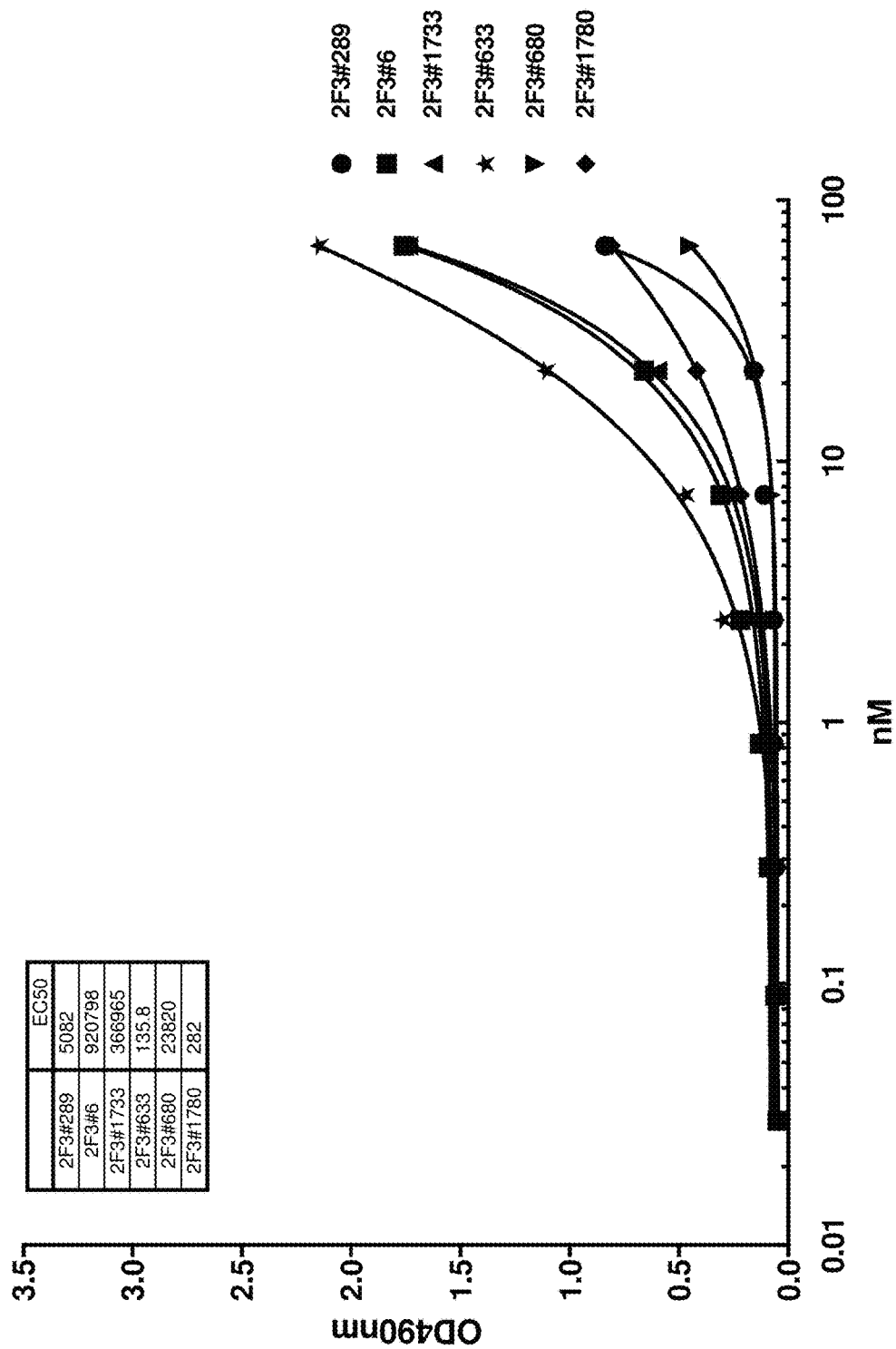
Figure 13D:
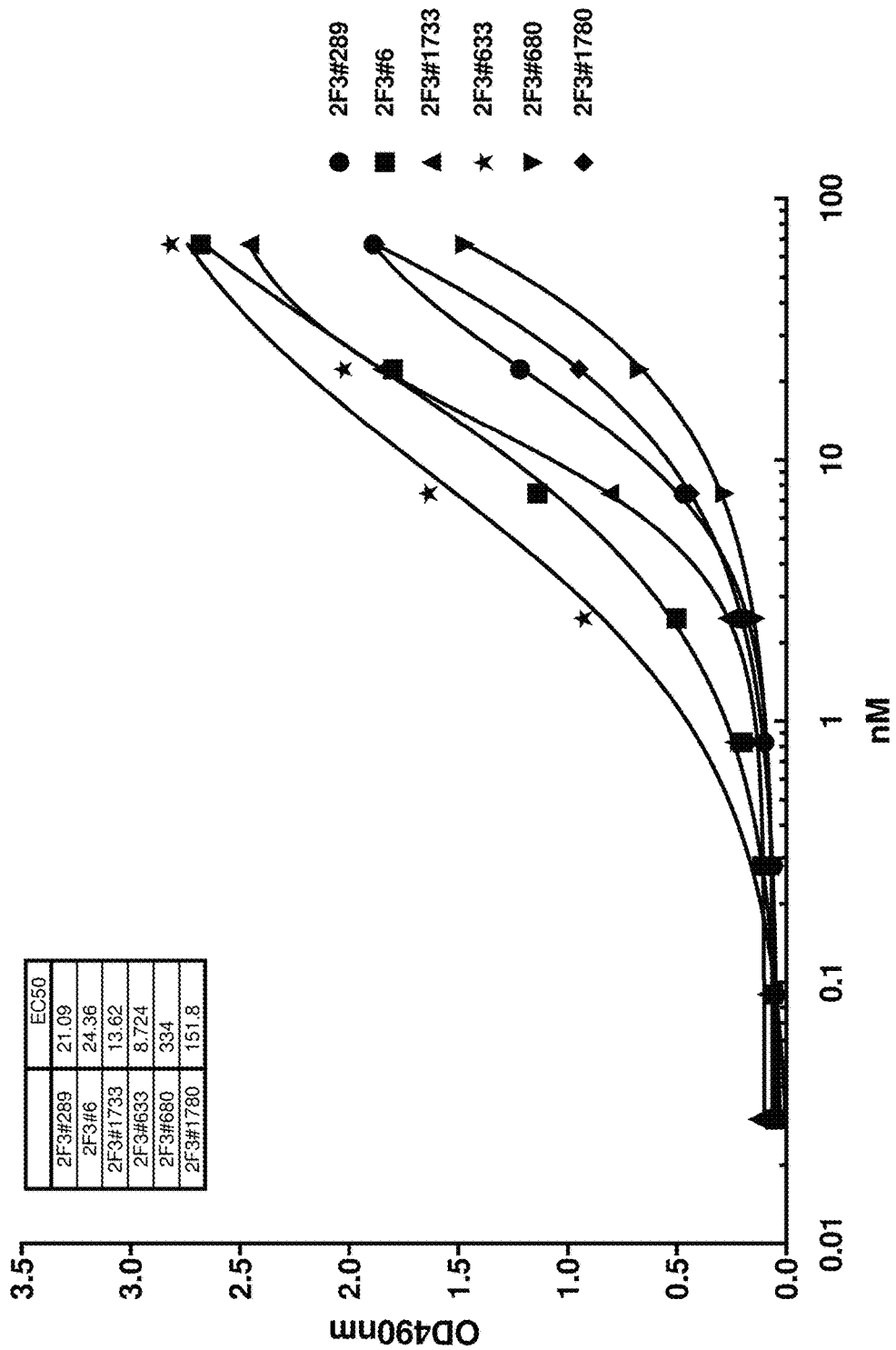

Position H55 (Kabat) was found to contain two favorable mutations by the error prone PCR mutation process in variants 6 and 17. Accordingly, additional mutations were made at these positions by randomizing the sequence for the codon encoding this position. Clones were picked and sequenced in order to achieve a sampling of all amino acids at this position, and mutant antibodies were generated and tested for their impact on binding to Tn-PAA antigen. As shown in the table of FIG. 11, a great majority of modifications at this position achieved superior binding compared to the parent 2F3. FIG. 12 summarizes the ELISA data for favorable 2F3 mutants from affinity maturation binding profiles to model antigens.

To determine relative improvement over parent and to determine if increased affinity had any impact on specificity, five mutants were selected and bound to model antigens (Tn-PAA, sTN-PAA, Tn-cluster, and dBSM) in ELISA assay (FIG. 13A-13D). Variants 6, 1733, and 633 all were among the best binders to all on-target antigens. On the other hand, no binding by any variants was observed with regard to TF-PAA, GalNac-beta-PAA (in which Tn is GalNac-alpha-linked), monomeric Tn, and monomeric sTn (data not shown).

Figures 14A, 14B:
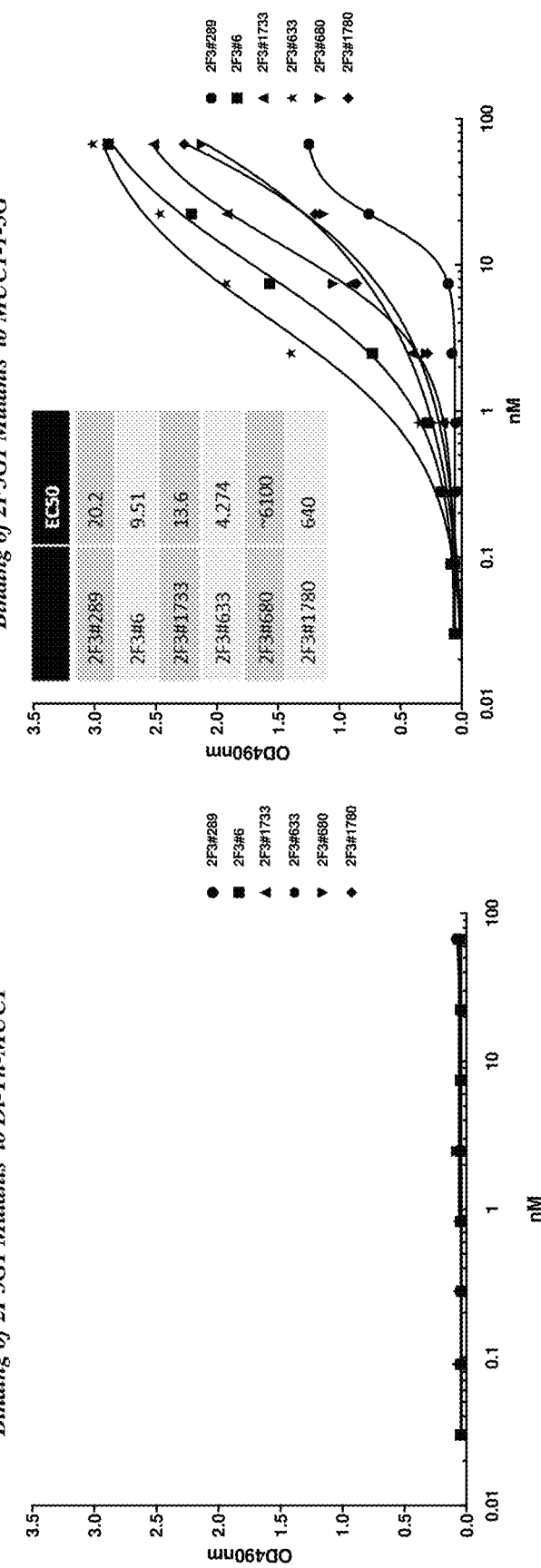
FIG. 14A-14B shows requirement of interaction with multiple Tn molecules in close proximity for high-affinity binding of the parent and variant Tn antibodies. Di-Tn Muc1 (SEQ ID NO:156) is a peptide derived from mucin-1 where the Tn modifications are separated by 12 non-modified residues, while 1-5G Muc1 (SEQ ID NO:155) is a peptide with multiple Tn modifications at adjacent residues.

Additionally, to confirm whether binding of Tn antibodies requires interaction with multiple Tn molecules in close proximity, two different forms of Muc1 peptides were tested as a model in ELISA assay. Di-Tn Muc1 (PAPGS TAPPAHGVTSAPDTRPAPG (SEQ ID NO:156), a peptide derived from mucin-1 where the Tn modifications are separated by 12 non-modified residues, did not show binding by any of the 2F3 variants (FIG. 14A). while a similar Mud peptide with multiple Tn modifications including Tn modification at adjacent residues (Muc1-1-5G; HGV TSAPDTRPAPGSTAPPA (SEQ ID NO: 155)), showed binding by 2F3 and its derivatives with high affinity (FIG. 14B).

Figure 15A:
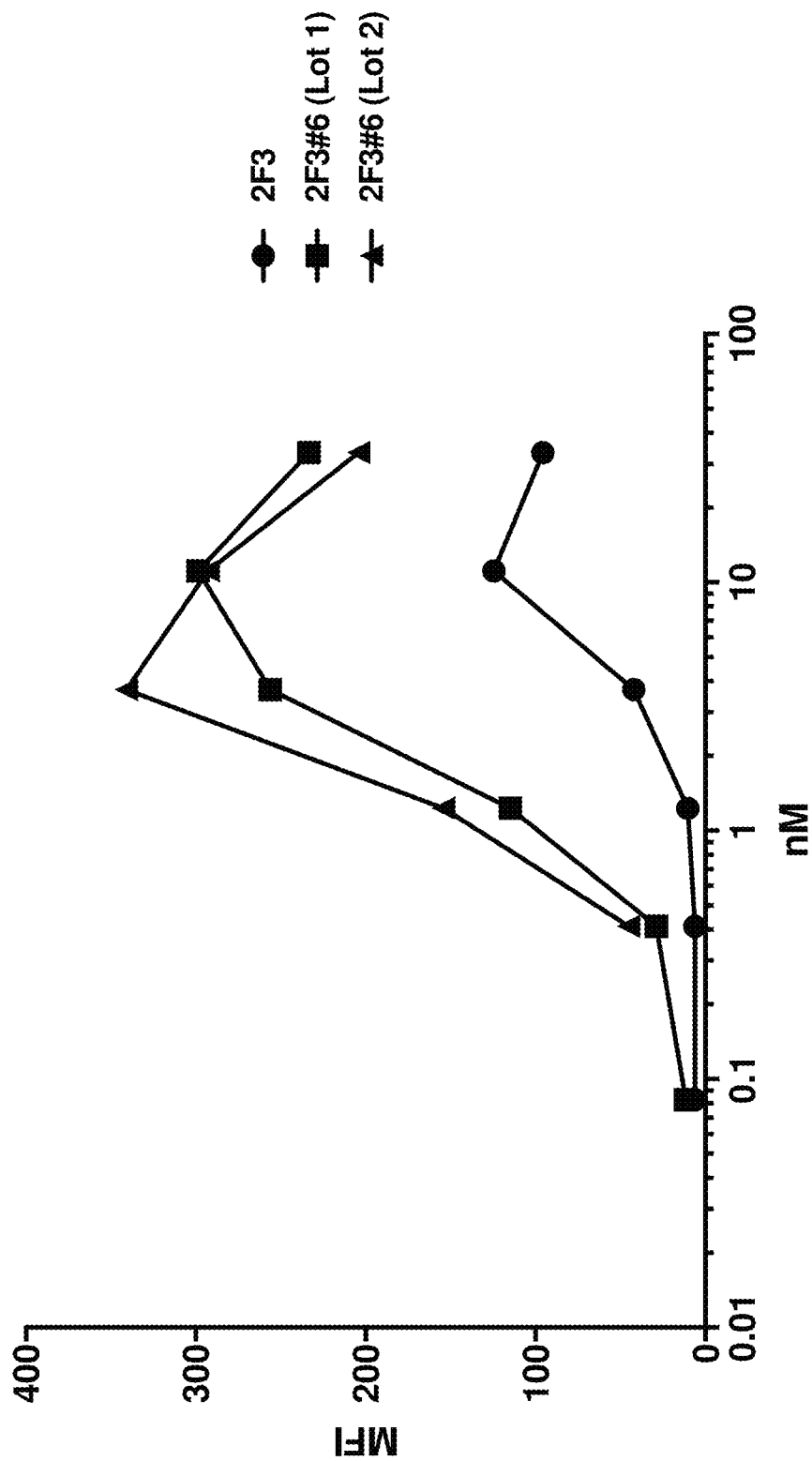
Figure 15B:
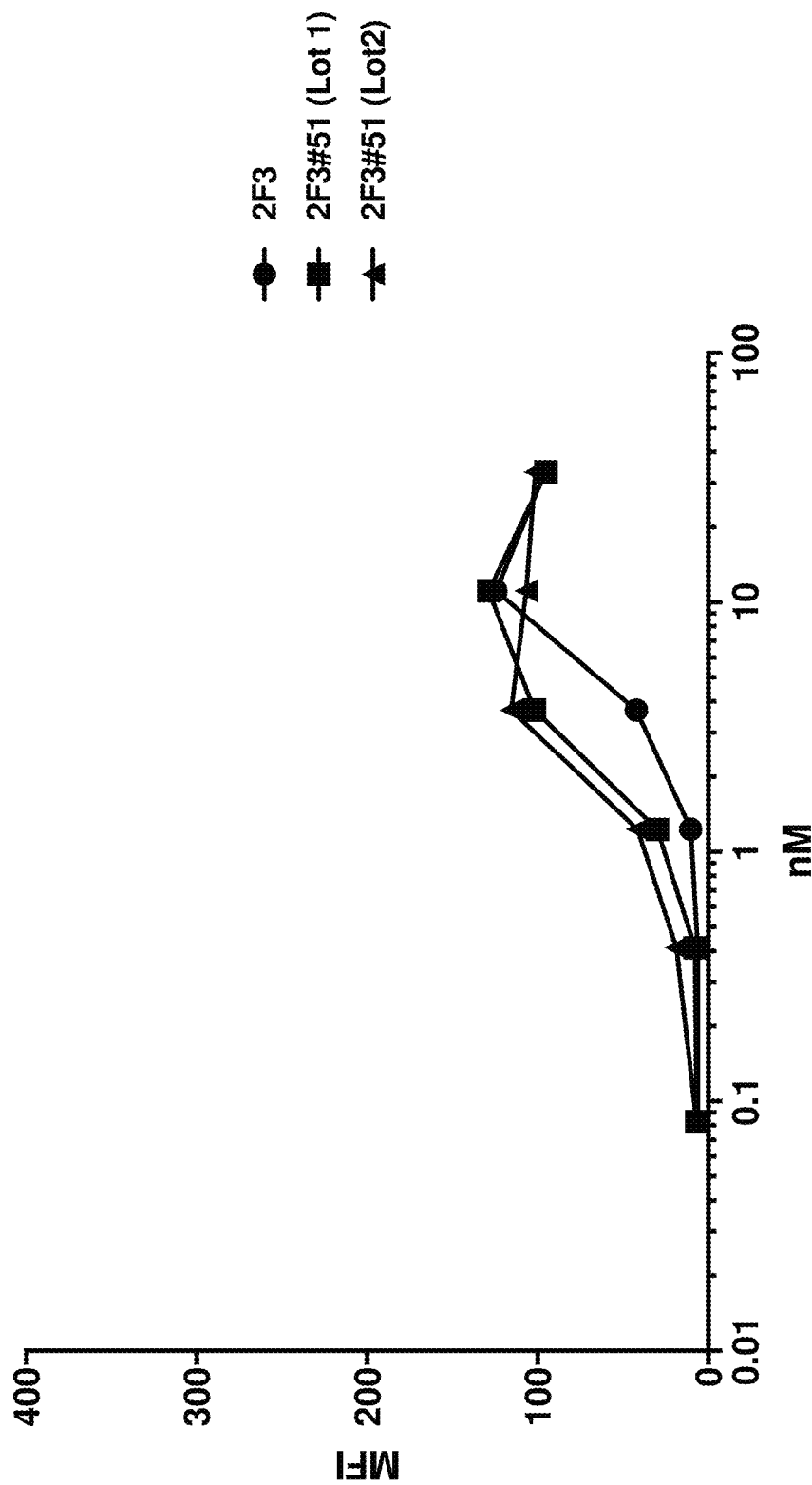
Figure 15D:
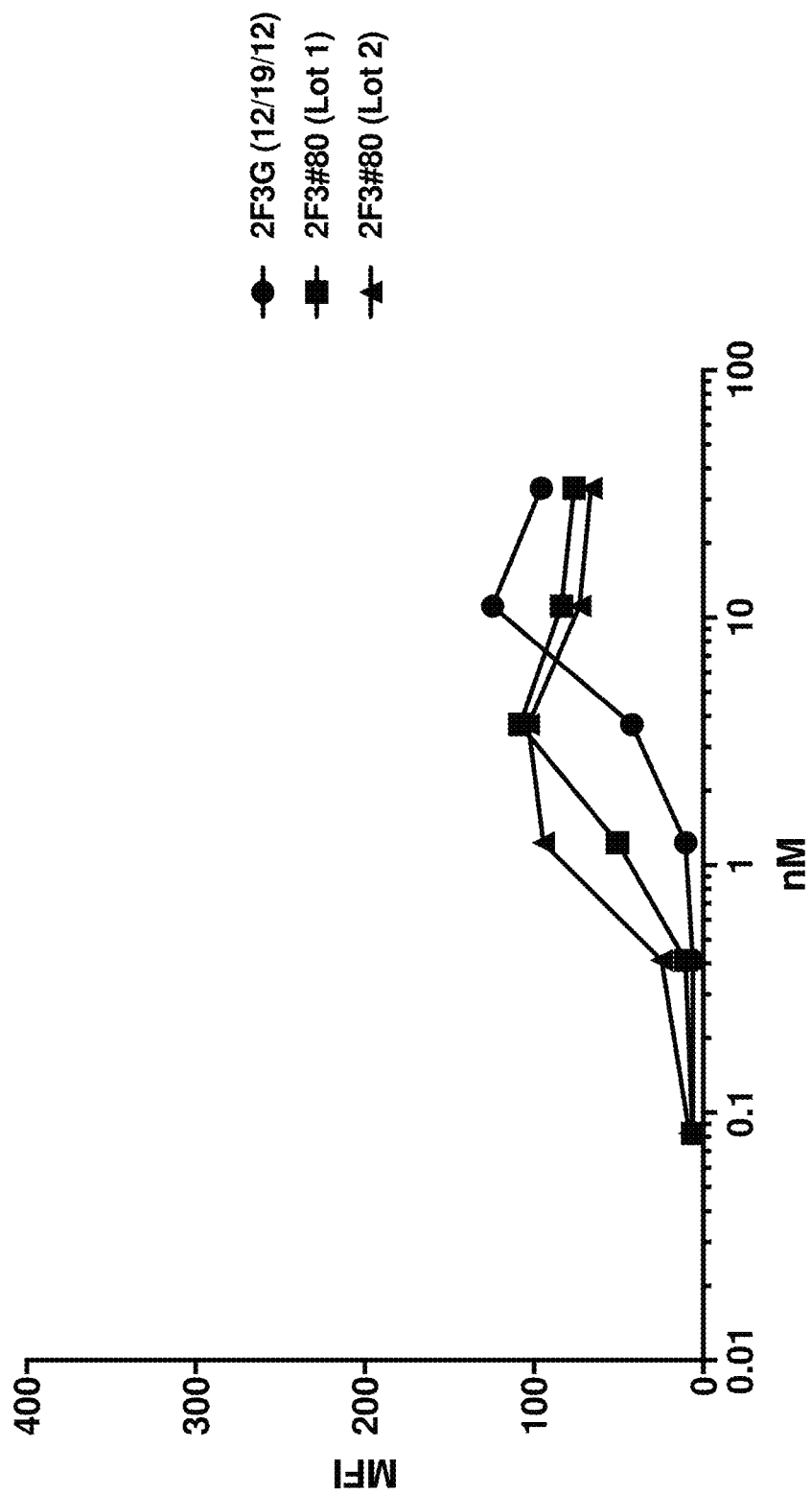
Figure 16A:
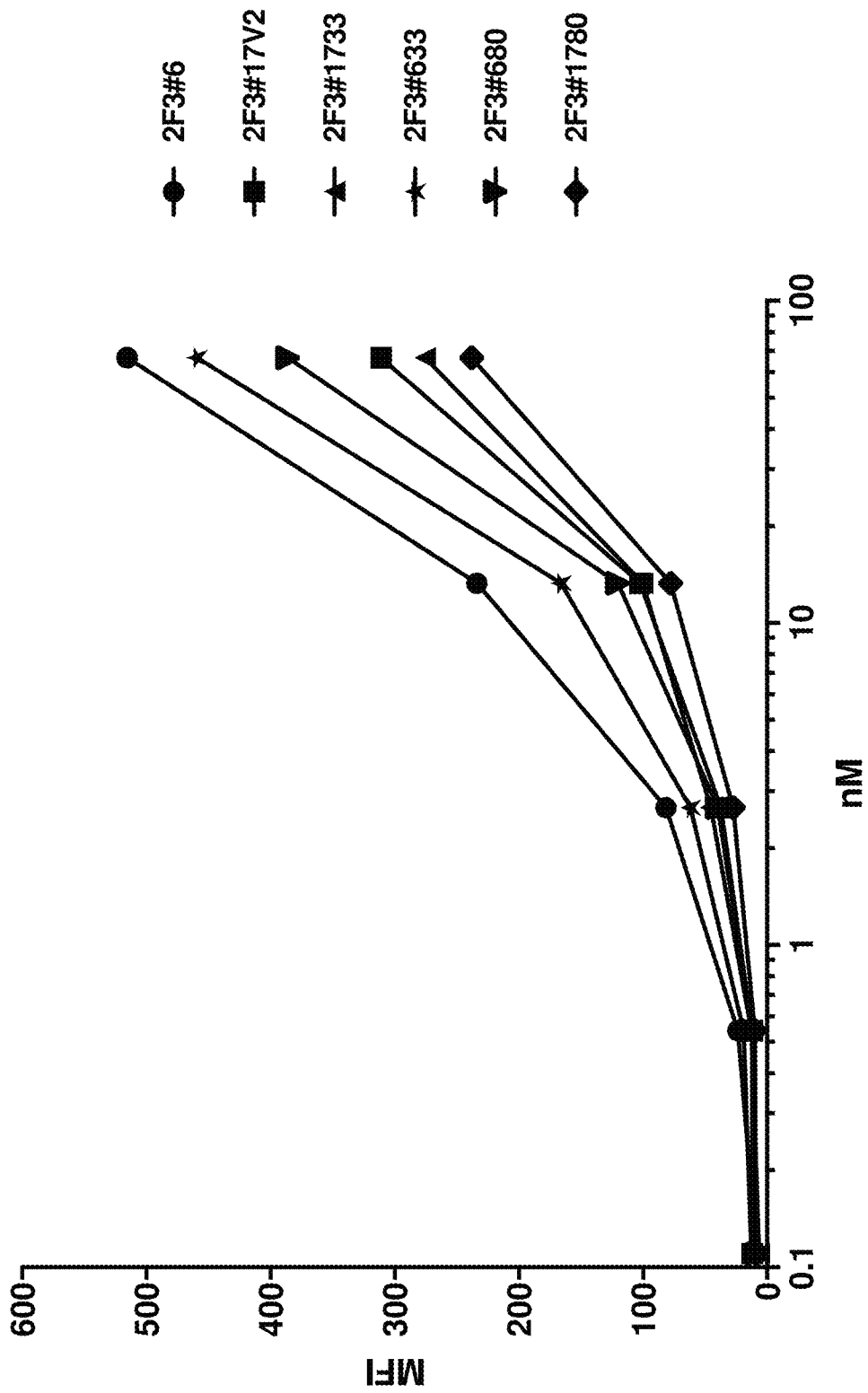
FIG. 16A-16D shows binding of original and variant 2F3 antibodies to additional multiple Tn-positive cell types demonstrated by FACS.
Figure 16B:
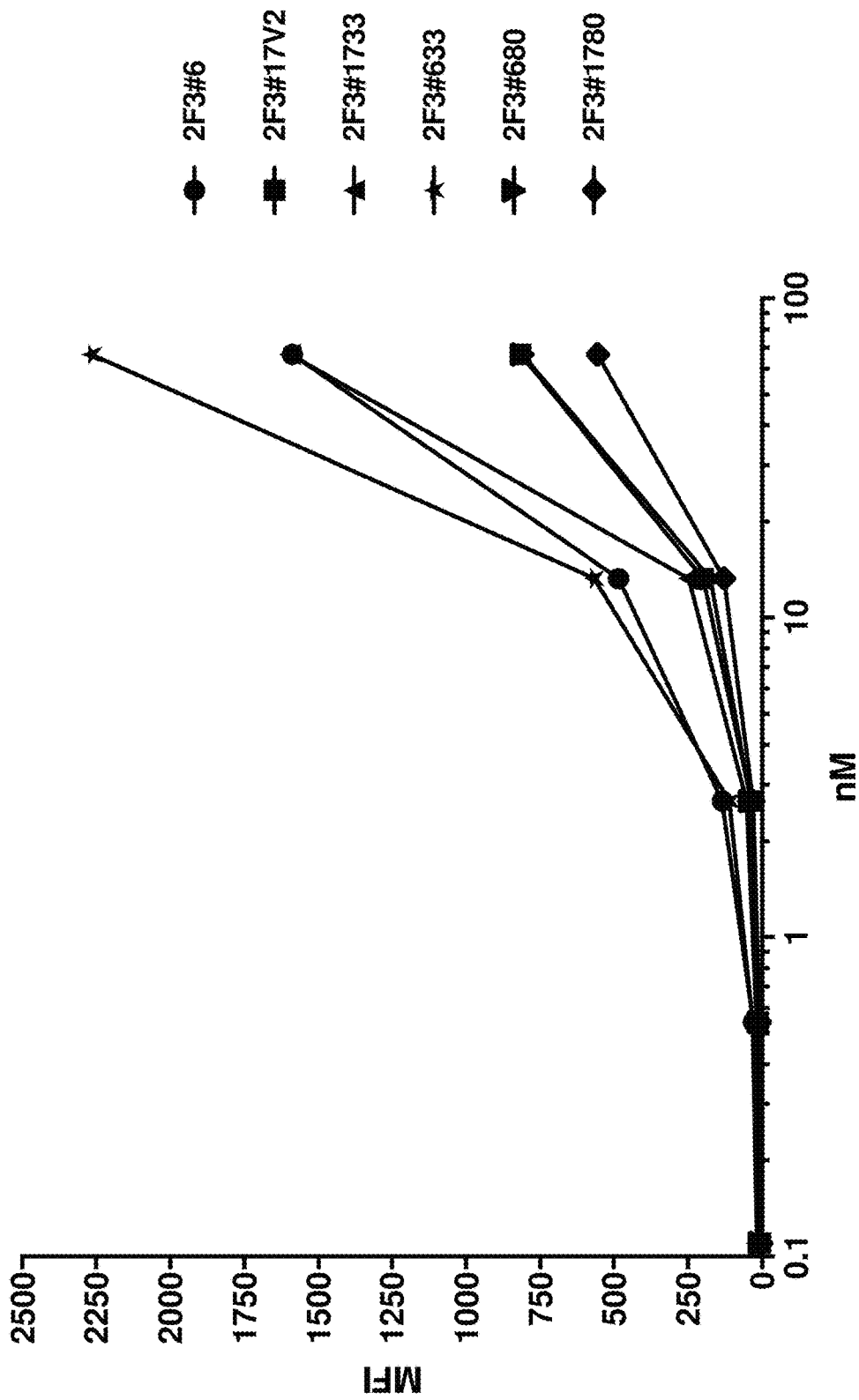
Figure 16C:
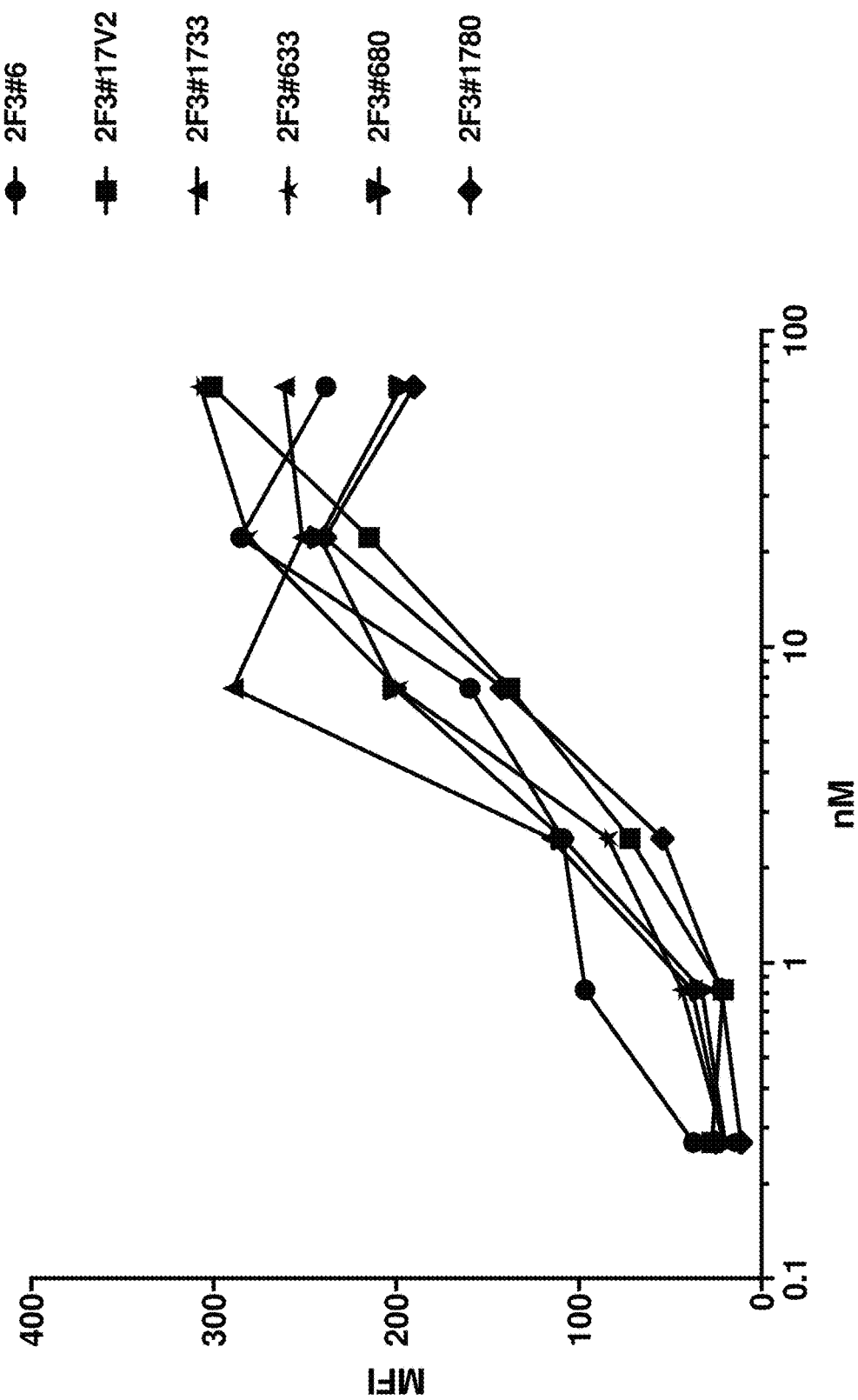
Figure 16D:
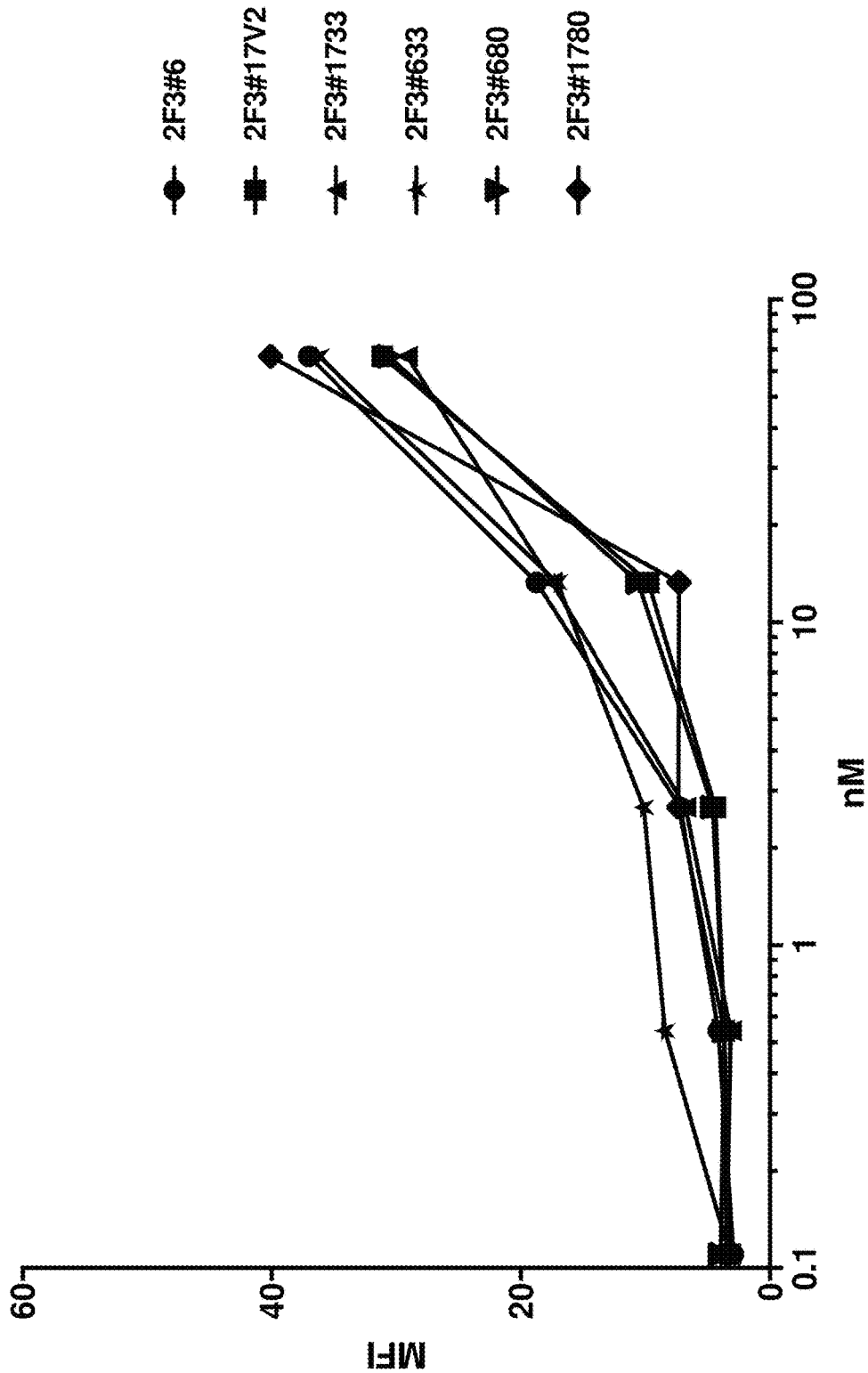

To confirm binding of the 2F3 and variant antibodies to the Tn antigens endogenously expressed by various cell lines under physiological conditions, original 2F3 parent and selected affinity variants were tested by FACS analysis. All of the tested 2F3 variants were shown to bind to Tn-positive T47-D cells with a strong shift in EC50 value compared with the 2F3 parent (FIG. 15A-15D). Variants 6 and 17 additionally showed a shift in the maximal binding, indicating their ability to occupy more available sites at equilibrium (FIGS. 15A and 15C). Similarly, original and variant 2F3 molecules were shown to bind to additional multiple Tn-positive cell types by FACS (FIG. 16A-16D).

Example III

Functional Characterization of 2F3 Antibody Variants

To assess cellular and physiological functionality of the 2F3 antibody variants that are suitable for therapeutic applications such as anti-cancer therapy, various functional assays were performed to measure: conjugation of fluorescent dyes; time-course cellular internalization profile; delivery of cytotoxic drugs into specific cell types; and antibody-dependent cell-mediated cytotoxicity (ADCC).

Conjugation of Antibodies to Fluorescent Dyes

Antibodies were first functionalized by conjugation with PEGylated N-succinimidyl S-acetylthioacetate (SAT (PEG)$_4$). Antibody was desalted into 50 mM NaHCO$_3$ via Zeba spin column (ThermoFisher) and then treated with four equivalents of PEGylated N-succinimidyl S-acetylthioacetate (SAT(PEG)$_4$) (ThermoFisher 26099) for >1 hour. After the reaction was complete the reaction mixture was desalted via Zeba spin column in to 1×PBS pH 7.4 and was treated with 10% by volume of deprotection buffer, allowed to react for 2 hours at room temperature, and buffer exchanged using a Zeba spin column into 1×PBS to yield the deprotected PEG thiol.

Conjugation with AF488 Maleimide. The PEG thiol antibody was treated with 4.4 equivalents of AF488 (ThemoFisher) with a maleimide group at room temperature for >1 hour. After the reaction was completed, the material was buffer exchanged into 1×PBS pH 7.4 using a Zeba Spin column.

Conjugation with pHAb Maleimide. The PEG thiol antibody was treated with 4.4 equivalents of pHAb (Promega) with a maleimide group at room temperature for >1 hour. After the reaction was completed the material was buffer exchanged into 1×PBS pH 7.4 using a Zeba Spin column.

Screening of 2F3 Mutants by pHAb-Dye Percent Internalization Assay

One hundred mL of T-47D cells (1×10$^6$ cells/mL in RPMI1640+10% FBS, final concentration at 0.5×106 cells/mL) were incubated with equal volume of pHAb conjugates mAb (40 ug/mL in PBS, final concentration at 20 ug/mL) at 37 C for 5 hrs. Cells were washed 2 times and divided into two tubes. Cells were re-suspended in 200 uL of pH7 (detecting internalized mAb only) or pH5.5 (detecting total mAb) medium and kept on ice. Sample data were acquired by Guava PCA-96 System and analyzed with Guava ExpressPro Software. % Internalized=MFI (pH7)/MFI (pH5.5)*100 (MFI values were corrected for background).

Internalization Time Course/Variant #6

Using pHAb dye. T-47D cells (0.5×106 cells/mL in medium) were incubated with 20 ug/mL of pHAb conjugated 2F3 #6 at 4C for 30 min. Cells were washed 2 times and re-suspended in the same volume and incubated at 37 C. At indicated time points 200 uL of cells were harvested and centrifuged. Cells were re-suspended in 200 uL of medium containing 10 mM NaN3 and 5 mM 2-deoxyglucose, divided into 2 wells (100 uL/well) and kept on ice. After final harvest at 240 min incubation period, 100 uL/well of medium was added to adjust to either pH7.0 or pH5.5 for each sample. Sample data were acquired by Guava PCA-96 System and analyzed with Guava ExpressPro Software. % internalized=MFI (pH7)/MFI (pH5.5)*100 (MFI values were corrected for background).

Using AF488 quencher. T-47D cells (0.5×106 cells/mL in medium) were incubated with 2 ug/mL of AlexaFluor-488 conjugated 2F3 #6 at 4C for 1 hr. Cells were washed 2 times and resuspended in the same volume and incubated at 37 C. At indicated time points 200 uL of cells were harvested and divided into 2 wells. One hundred mL of medium containing 10 mM NaN3 with or without AF488 Quencher antibody (final concentration at 25 ug/mL, Thermo Fisher) was added to the well. Cells were kept on ice until the final harvest (180 min at 37C and then 30 min at 4C). Sample data were acquired by Guava PCA-96 System and analyzed with Guava ExpressPro Software. % internalized=MFI (w/Quencher)/MFI (w/o quencher)*100 (MFI values were corrected for background).

Cytotoxicity Assay

Jurkat cells were seeded in 96 well plates at 1×10$^5$ cells/mL (0.5×10$^4$ cells/50 uL/well) in RPMI1640 medium with 10% FBS, L-Glu and P/S. Various concentrations of purified mAb (diluted with medium in separate 96 well plates) were incubated with 200 nM of Protein A-MMAE (LEV-AME-100) at RT for 20 min. Fifty mL of mAb and Protein A-MMAE complex was added to each well and incubated at 37 C for 3 days. CellTiter-Glo (70 uL/well, Promega) was added to teach well and incubated 5 min at RT. Chemiluminescent signal was measured using Gen5 software.

ADCC Assay

PBMCs were prepared from a healthy donor blood sample by Ficoll density gradient centrifugation. CAOV3 cells were labeled with Calcein-AM (Thermo Fisher) at 37 C for 30 min. After washing with media, labeled cells were added to a 96 well plate at 10,000 cells/well. PBMC (E/T at 20:1) and different concentrations of 2F3 variants were added to wells and incubated at 37 C for 3 hrs. Fluorescent signal was measured using a fluorometer. % Cytotoxicity=(Sample RFI–Mini release RFI)/(Max release RFI–Min release RFI) *100, CAOV3 lysed with NP40 was used as maximum release. CAOV3 cells with PB MC only was used as spontaneous (minimum) release.

Results

Figure 17:
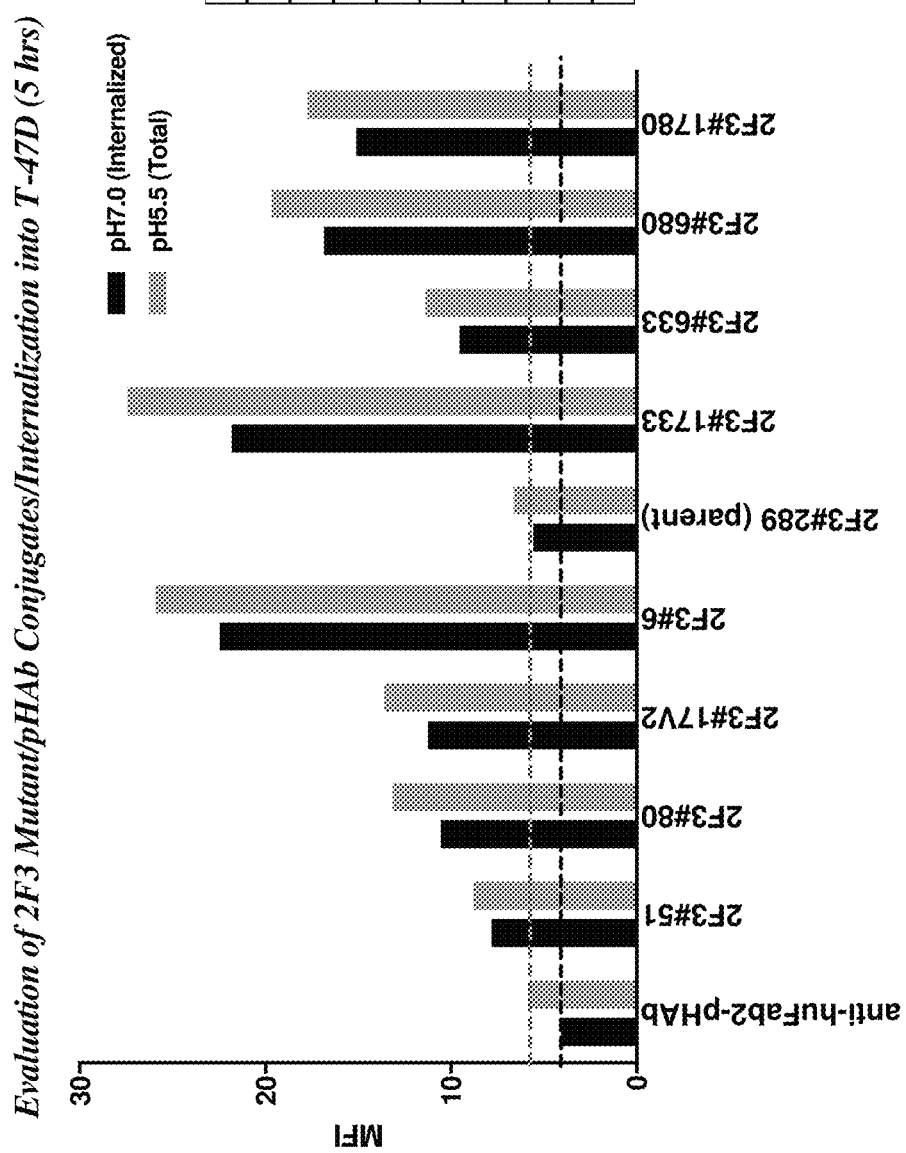
FIG. 17 shows internalization screen of the 2F3 parent and variants during 5-hour time period, with total amount of bound antibody determining the amount that can be internalized. Dotted lines indicate background levels for total and internalized fluorescence.
Figure 18A:
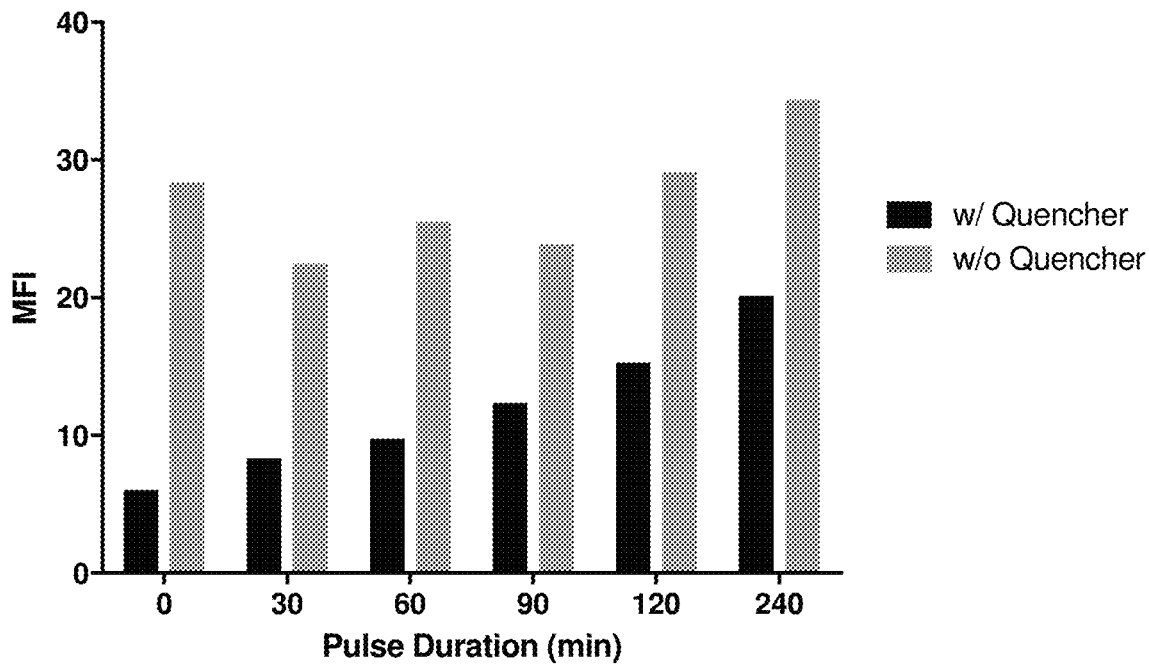
FIG. 18A-18B shows a time-course internalization study using orthogonal methods to measure internalization for highest binding lead with highest percent internalization chosen in the previous internalization assay. Cells were incubated with AF488 direct conjugate antibodies, washed, and transferred to 37° C. for indicated time to allow internalization. External signal was quenched with a secondary antibody, or unquenched fluorescence was measured. Percent internalization was calculated as a function of time.
Figure 18B:
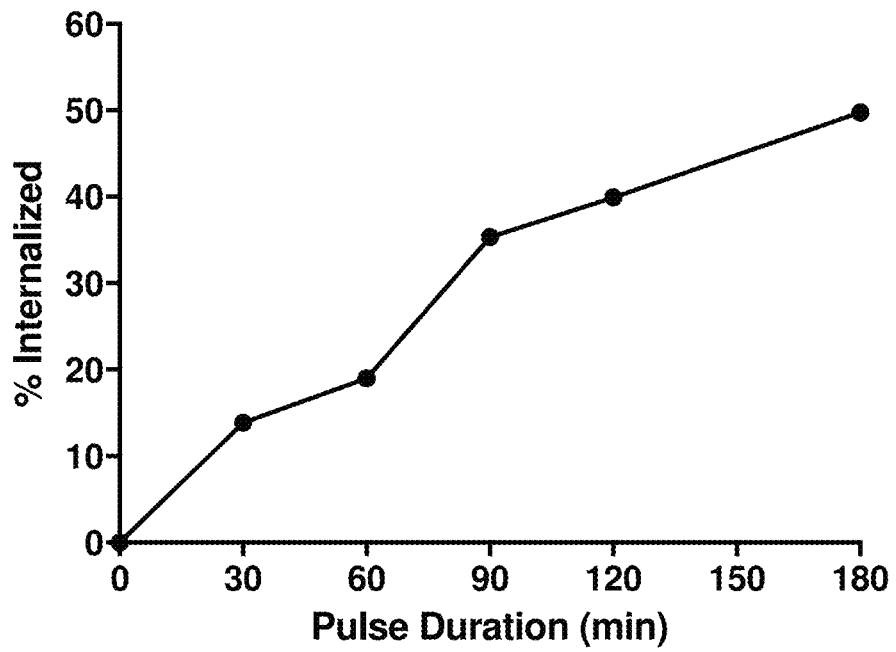

Percent cellular internalization of 2F3 variants were evaluated by measuring the ratio of median fluorescence intensity (MFI) of the variant antibodies conjugated with fluorescent dyes being internalized into T-47D cell line at pH 7.0 over the total amount of antibodies at pH 7.0 that can be internalized (FIG. 17). The results showed that all 2F3 variants internalized 74%-95% of bound antibody in 5 hours, and that variants 6 and 1733 were the best binders and internalizers in the internalization assay. For the highest binding lead with highest percent internalization, 2F3 variant clone 6, a time-course internalization study was additionally performed by using orthogonal methods to measure internalization over a time period of 3 hours (FIG. 18A). Percent internalization calculated as a function of time demonstrated proportional increase in the portion of the variant antibody internalized into the cell line that endogenously expresses Tn antigen (FIG. 18B).

Figure 19A:
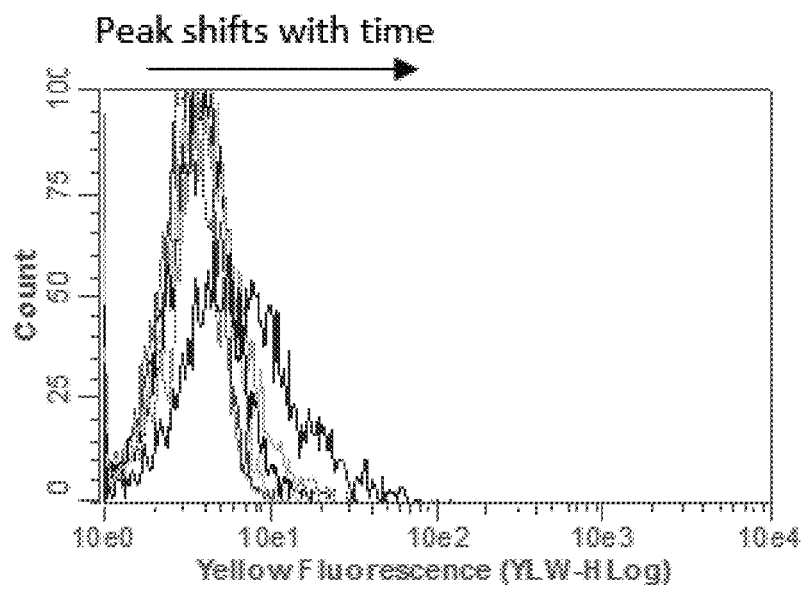
FIG. 19A-19C shows a second method used to calculate percent internalization as a function of time. pHAb is a fluorescent dye that efficiently fluoresces at pH<5.5, but does not fluoresce at neutral pH. Antibodies were directly conjugated with pHAb dye and allowed to internalize as a function of time. When the cells are incubated at pH 7, only internalized antibody fluoresces. When cells are incubated at pH 5.5, both the internal and external antibody fractions fluoresce (total). Accordingly, the ratio represents the percent internalized fluorescence.
Figure 19B:
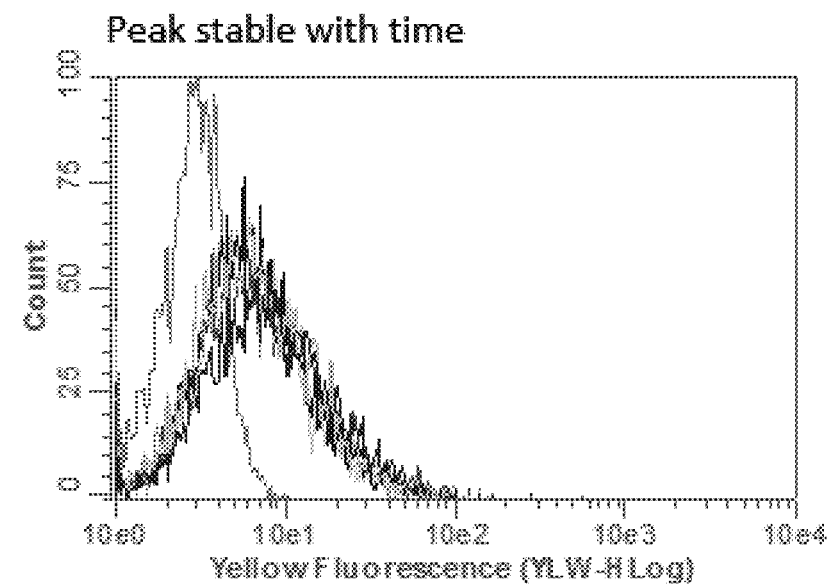
Figure 19C:
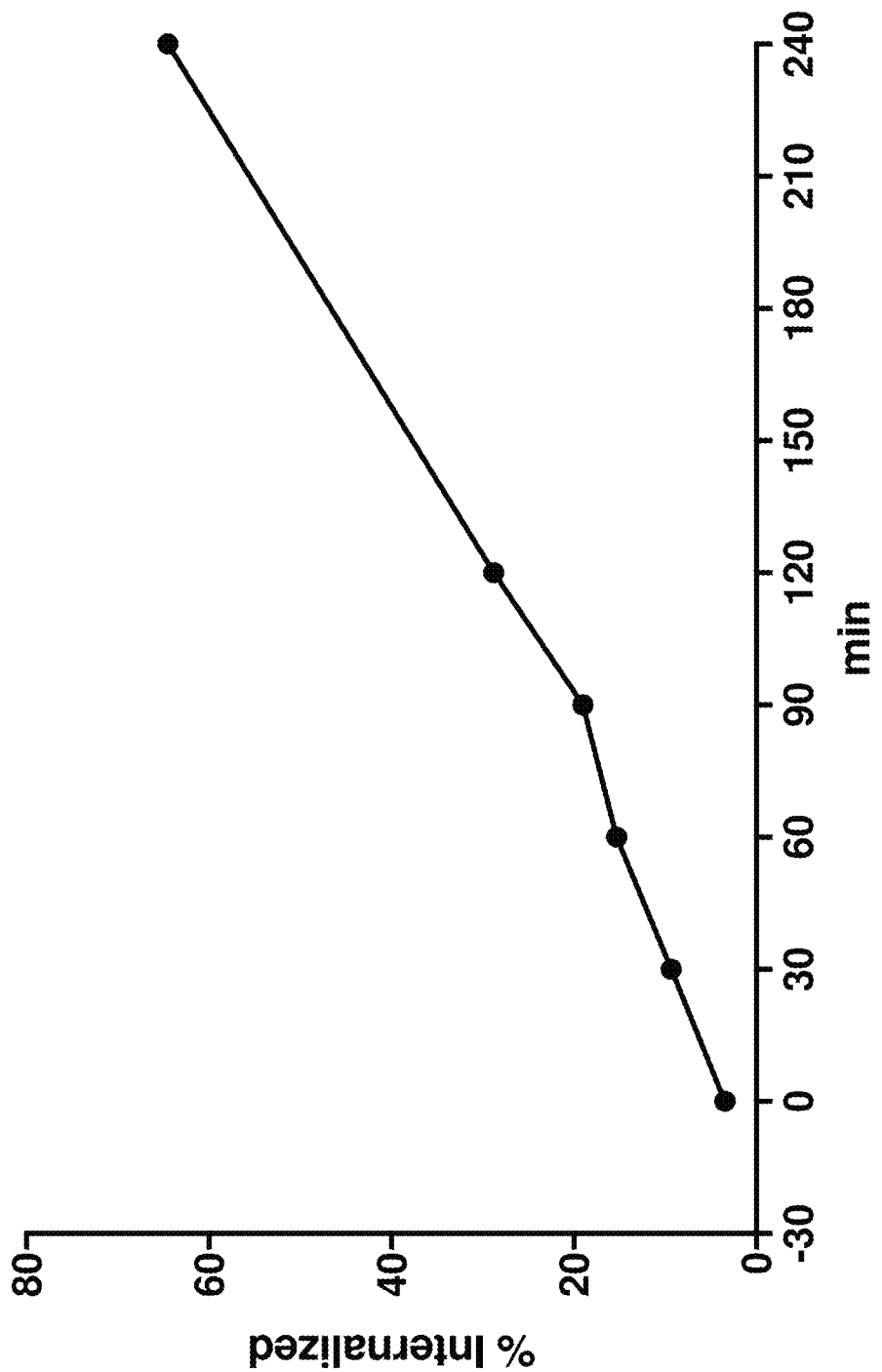

A second, orthogonal method was used to confirm the above results, by calculating percent internalization as a function of time with pHAb, a fluorescent dye that efficiently fluoresces at pH<5.5 but does not fluoresce at neutral pH. As shown in FIG. 19A-19C, when antibodies were directly conjugated with pHAb dye and allowed to internalize as a function of time, fluorescence from only the internalized antibodies was observed at pH 7, while fluorescence from both the internal and external antibody fractions (total) was observed at pH 5.5. The ratio of the former to the latter thus represented the percent internalized fluorescence, and showed results very similar to those obtained from the fluorescence dequenching studies described in FIG. 18.

Figure 20A:
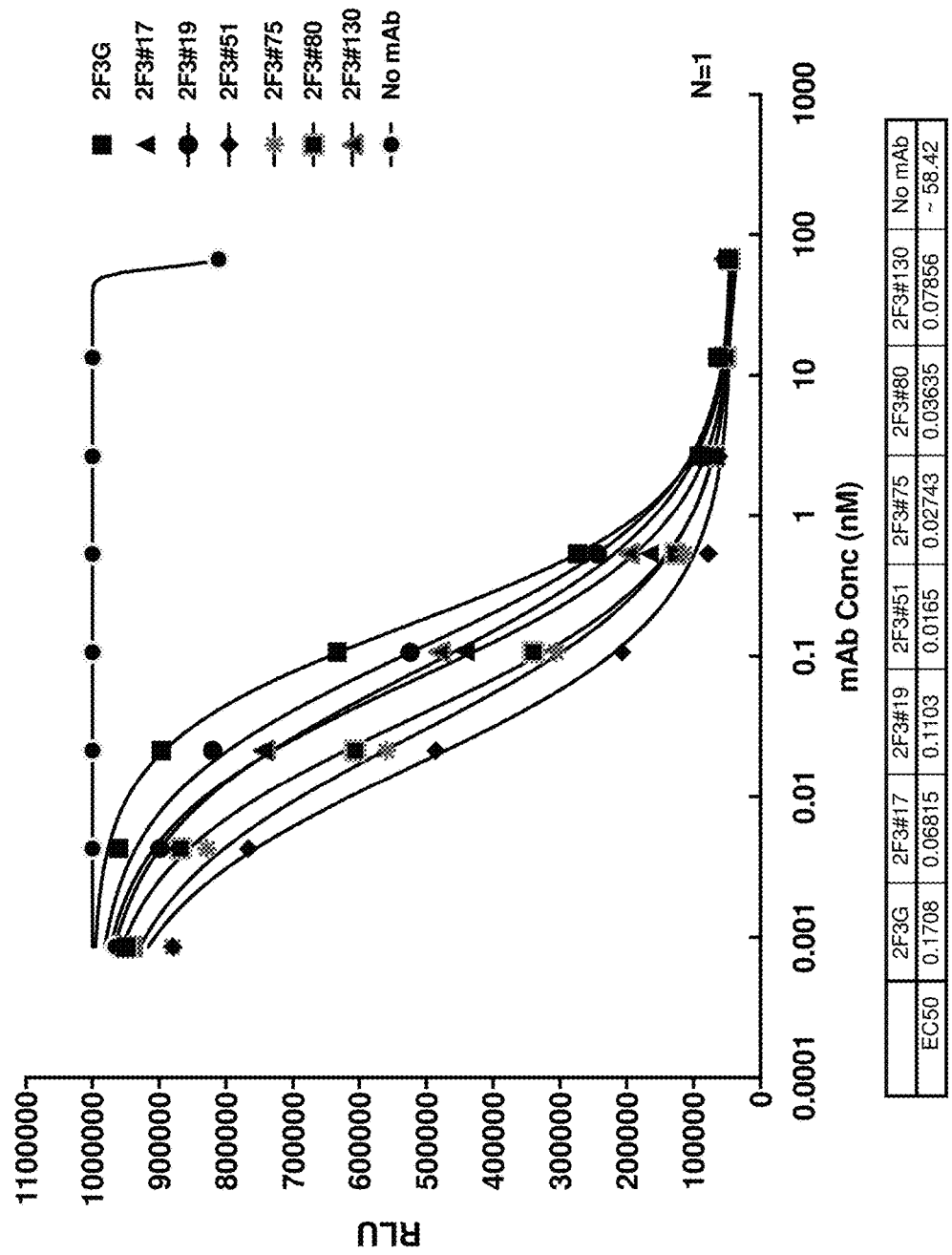
FIG. 20A-20B shows a screen for ability of 2F3 and variants to direct a cytotoxic agent into cells. Parent and variant 2F3 antibodies complexed with a protein A-MMAE conjugate were used to treat cells and cell viability was measured 3 days later to determine impact on the efficiency of target cell killing. Care was taken to avoid cytotoxic agent that can potentially alter the order of the antibody complex, because secondary antibodies armed with cytotoxic agents will also generate higher order complexes of the primary antibody, in some cases driving more efficient internalization than the primary antibody would typically accomplish on its own.
Figure 20B:
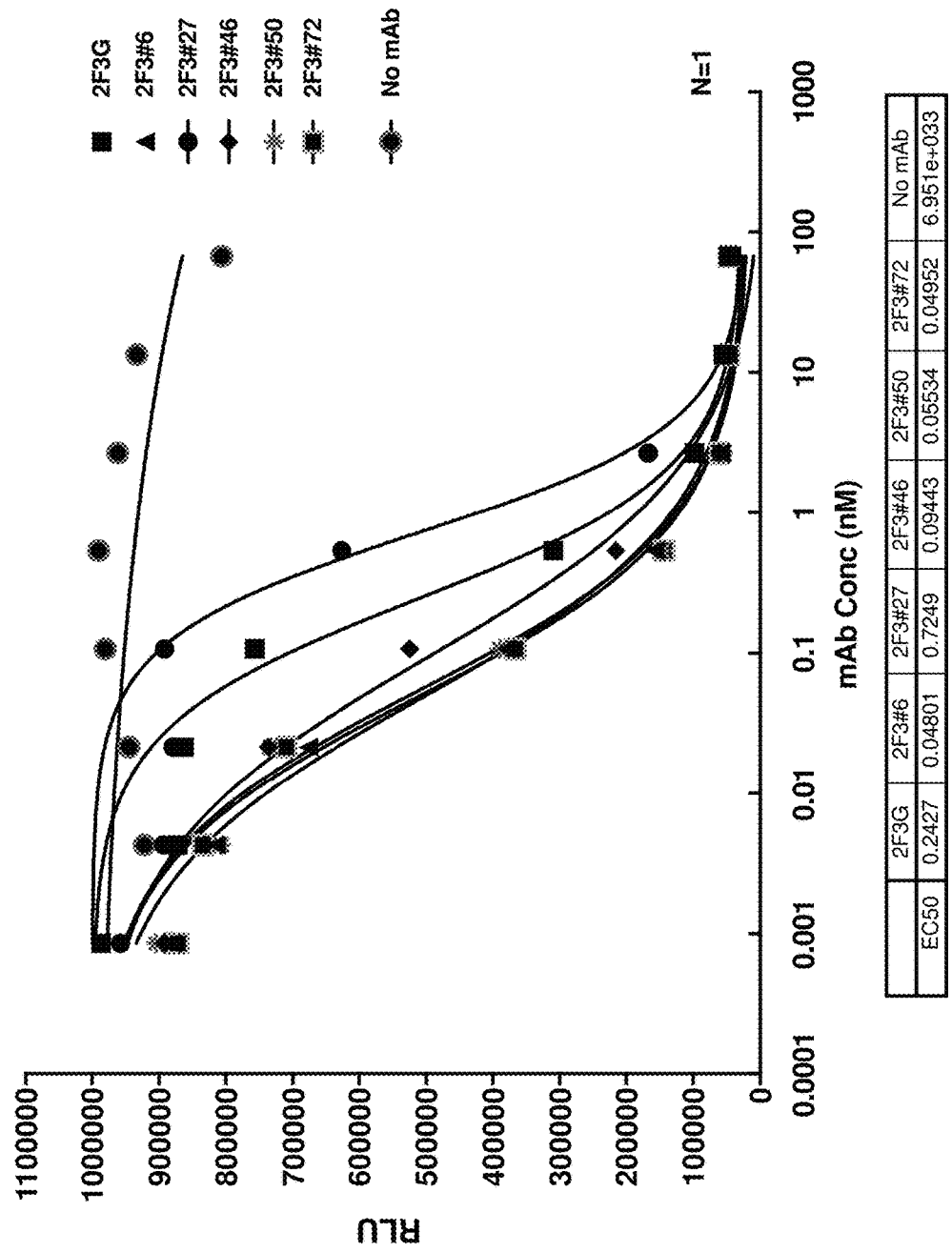

Next, internalizing anti-Tn antibody was evaluated for therapeutics that target cytotoxic drugs to specific cell types that bind and internalize said therapeutic. To screen for 2F3 variants that can direct a cytotoxic agent into cells, a complex of protein A-MMAE conjugate with antibodies was used to treat cells and cell viability was measured 3 days later (FIG. 20A-20B). Data from many variants demonstrated efficient killing, in many cases exceeding that of the parental clone by 3-10 times.

Figure 21:
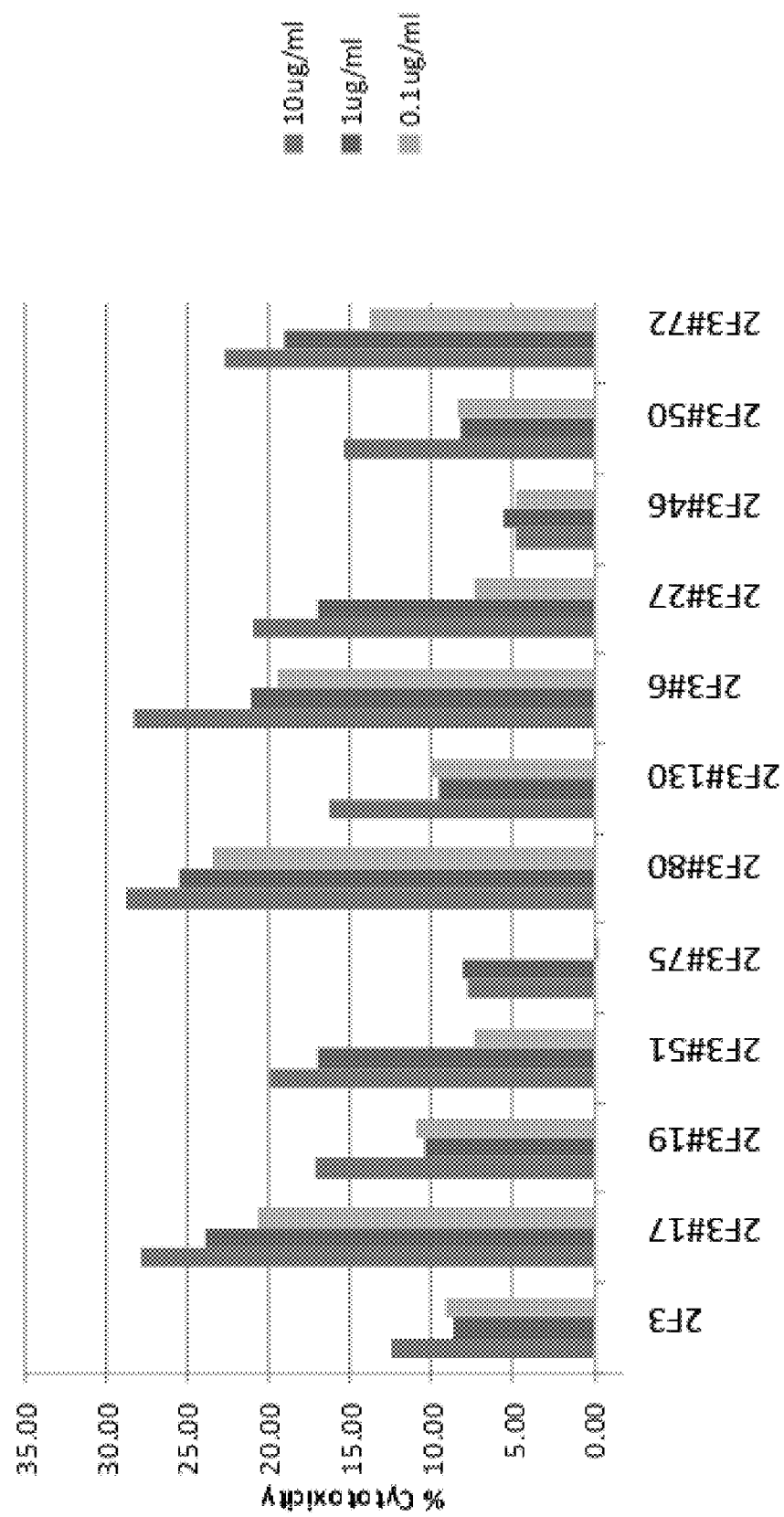
FIG. 21 shows results of antibody-dependent cell-mediated cytotoxicity (ADCC) assay to evaluate ability of affinity variants to mediate cytotoxic effects on tumor cells in the presence of effector cells.

Finally, to demonstrate ability of affinity variants to mediate cytotoxic effects on tumor cells in the presence of effector cells, ADCC assay was performed (FIG. 21). Variants 17, 80 and 6 demonstrate particularly high ADCC, with Clone 80 demonstrating the highest potency. Motivated by this result, combination mutants between clone 80 and clones 6 and 17 were generated.

Example IV

2F3 Anti-Tn/sTn Antibody Recognizes Tn Preferentially on Ser Residues

Figure 23A:
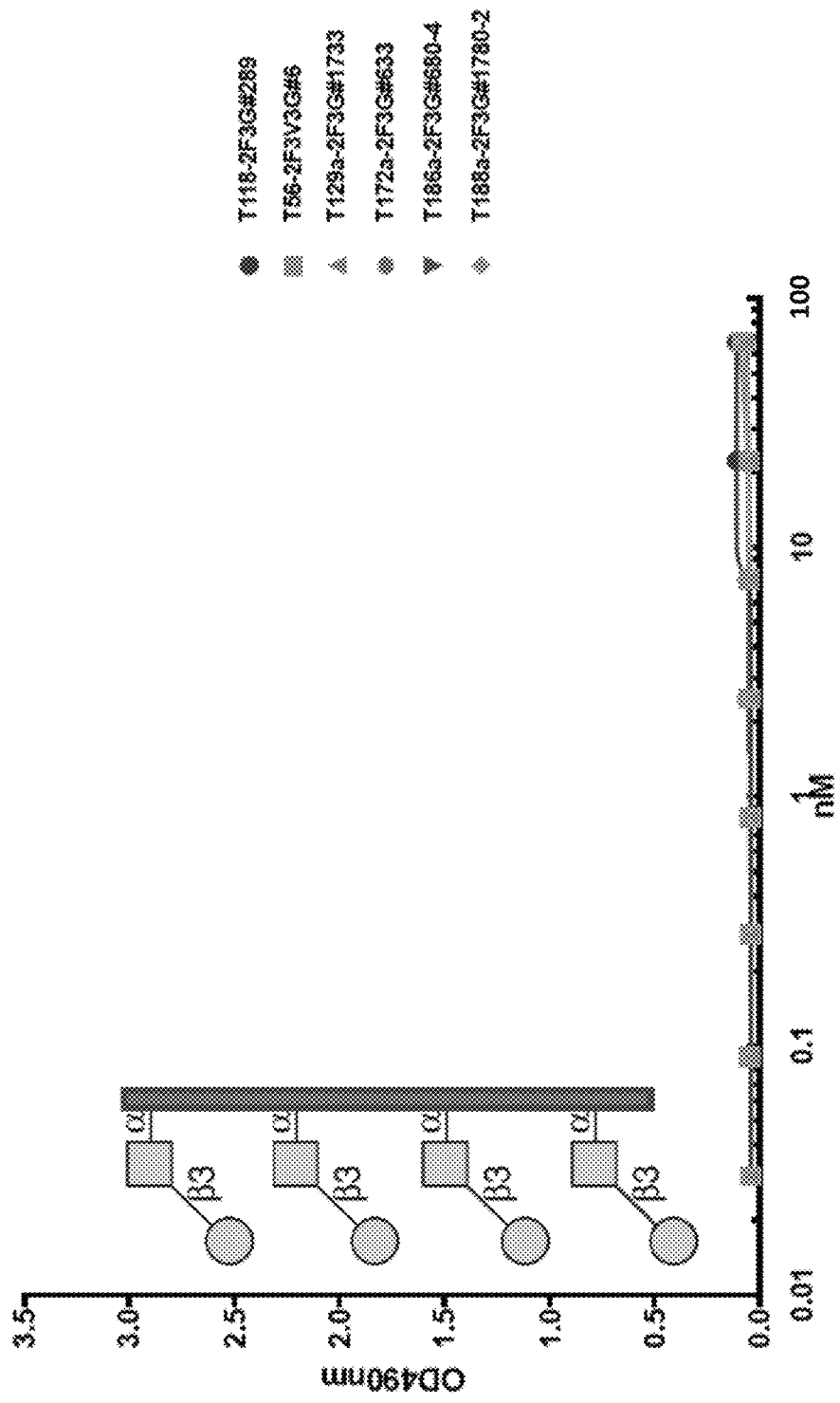
FIG. 23A-F shows binding of 2F3G1 mutants to synthetic antigens. Di-Tn Muc1 is a peptide derived from mucin-1 where the Tn modifications are separated by 12 non-modified residues, while 1-5G Muc1 is a peptide with multiple Tn modifications at adjacent residues.
Figure 23B:
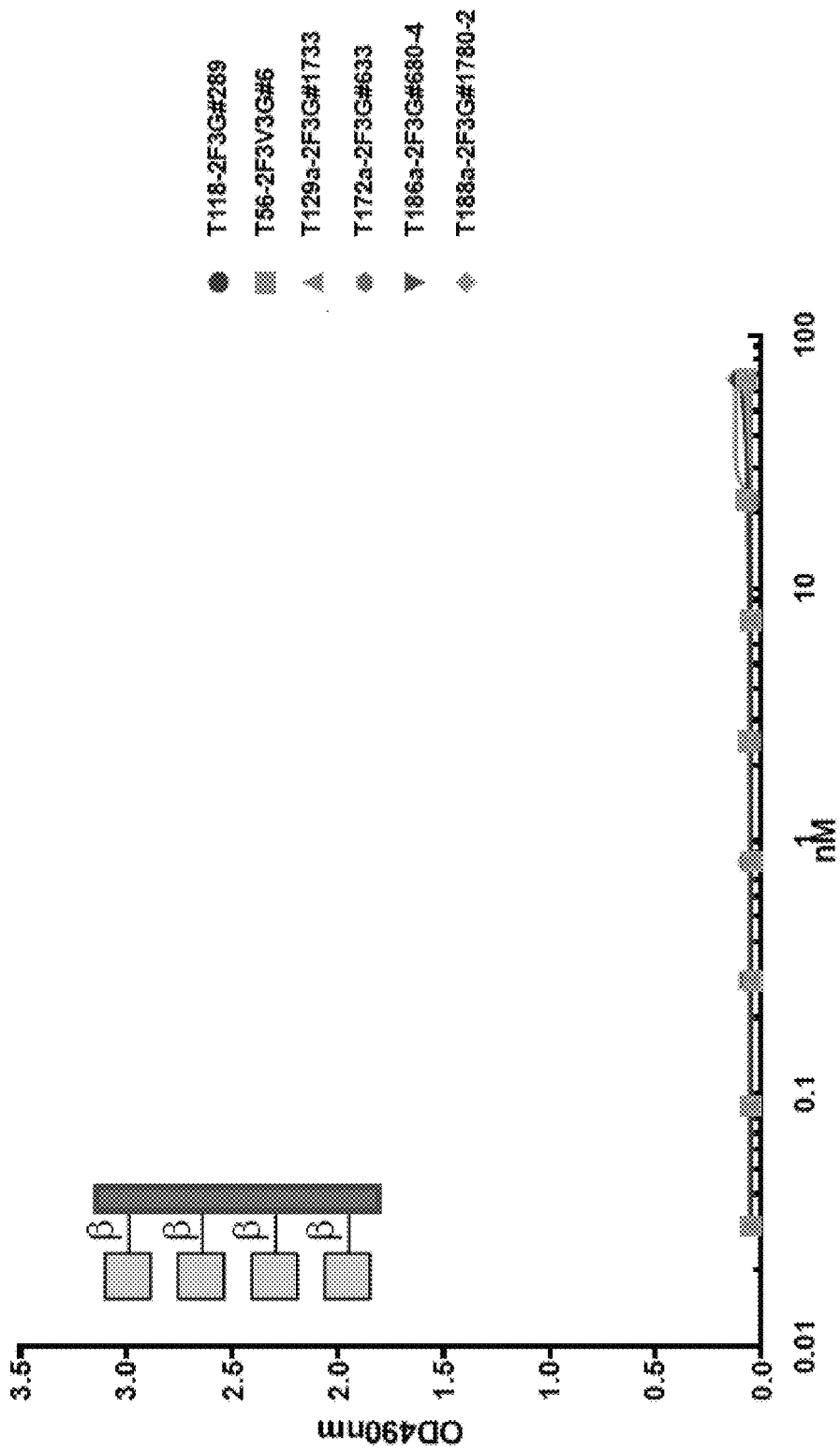
Figure 23C:
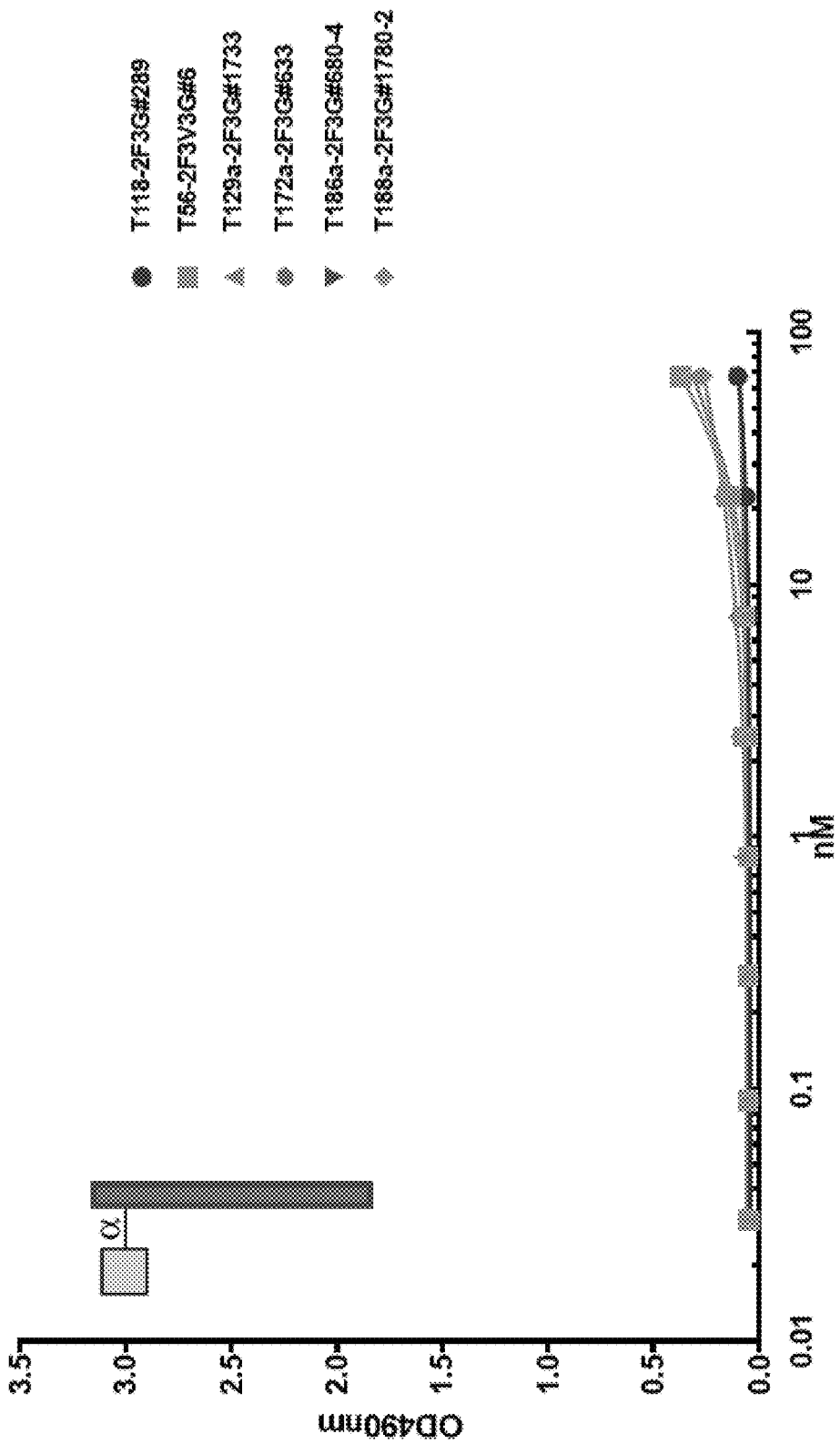
Figure 23D:
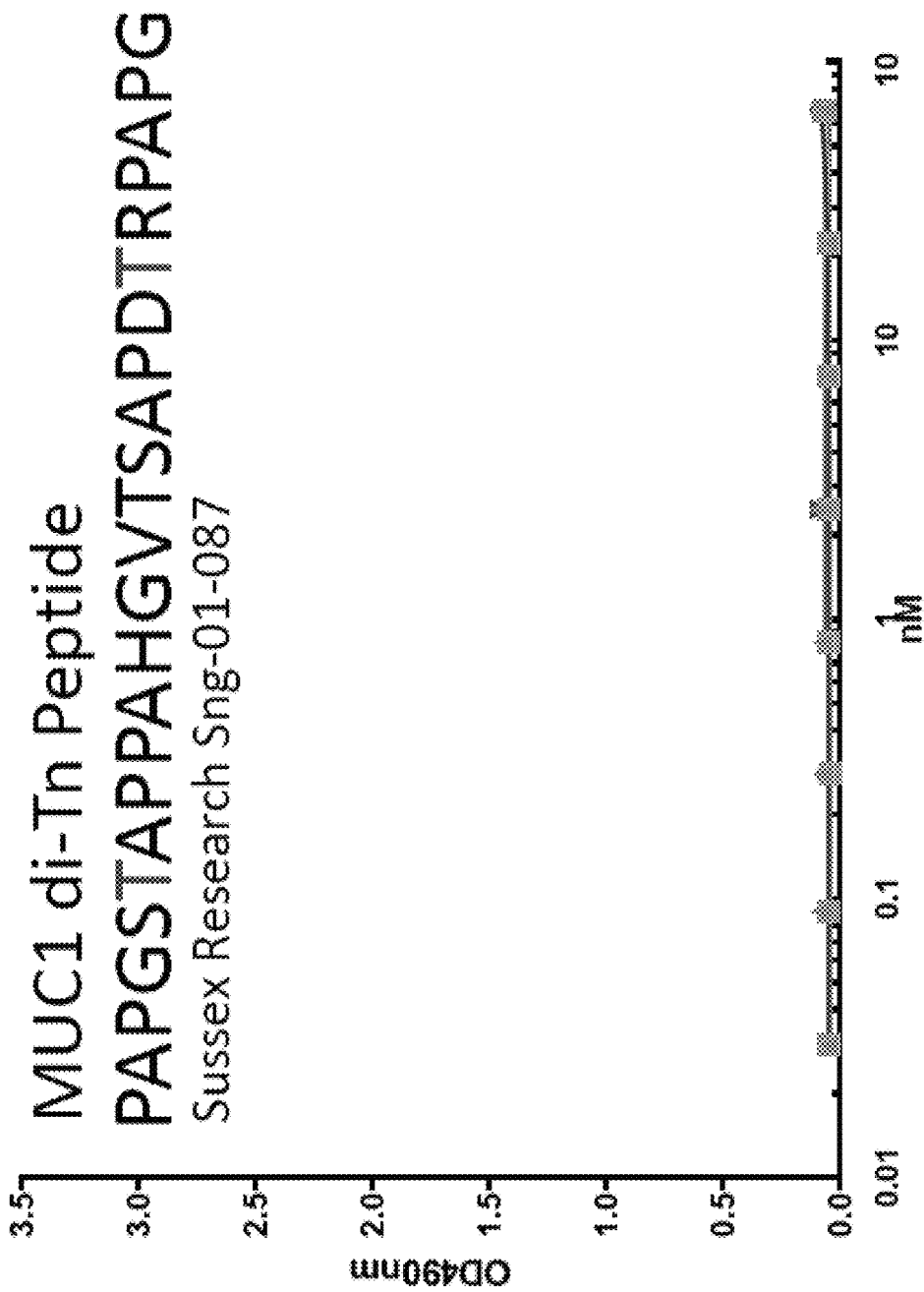

To determine the glycan epitope that the 2F3 antibody and its variants bind a series of experiments were performed using ELISA assays, as described above. In agreement with the experiments described above, binding of 2F3 variants for synthetic antigens other than Tn-PAA was not observed. For example, binding of the 2F3G1 mutants to the Thomsen-Friedenreich (TF)-polyacrylamide (PAA) glycogonjugate (TF-PAA), the Tn-β-PAA, or Tn-SP was not observed (FIG. 23A-C). To determine the epitope on Muc1, binding of the 2F3G1 mutants was assessed using a di-Tn-MUC1 peptide as the substrate, where the Tn antigens were linked to threonine (Thr) residues (PAPGST*APPAHGVTSAPDT*RPAPG)(SEQ ID NO:156). The results demonstrated that the antibodies did not bind the di-Tn-MUC1 peptide, indicating that the 2F3G1 mutants did not bind Thr modified MUC1 (FIG. 23D).)

Figure 23E:
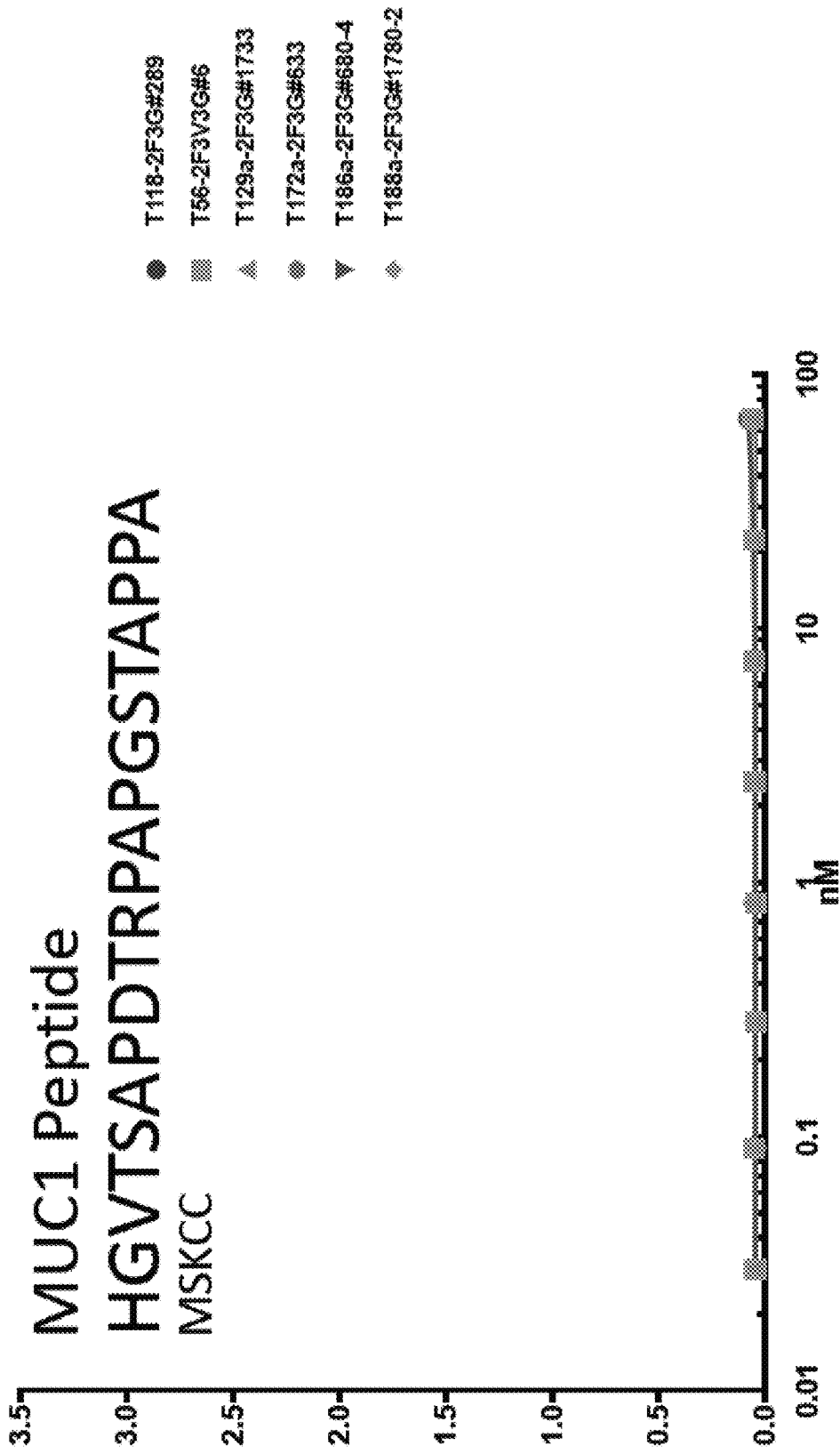
Figure 23F:
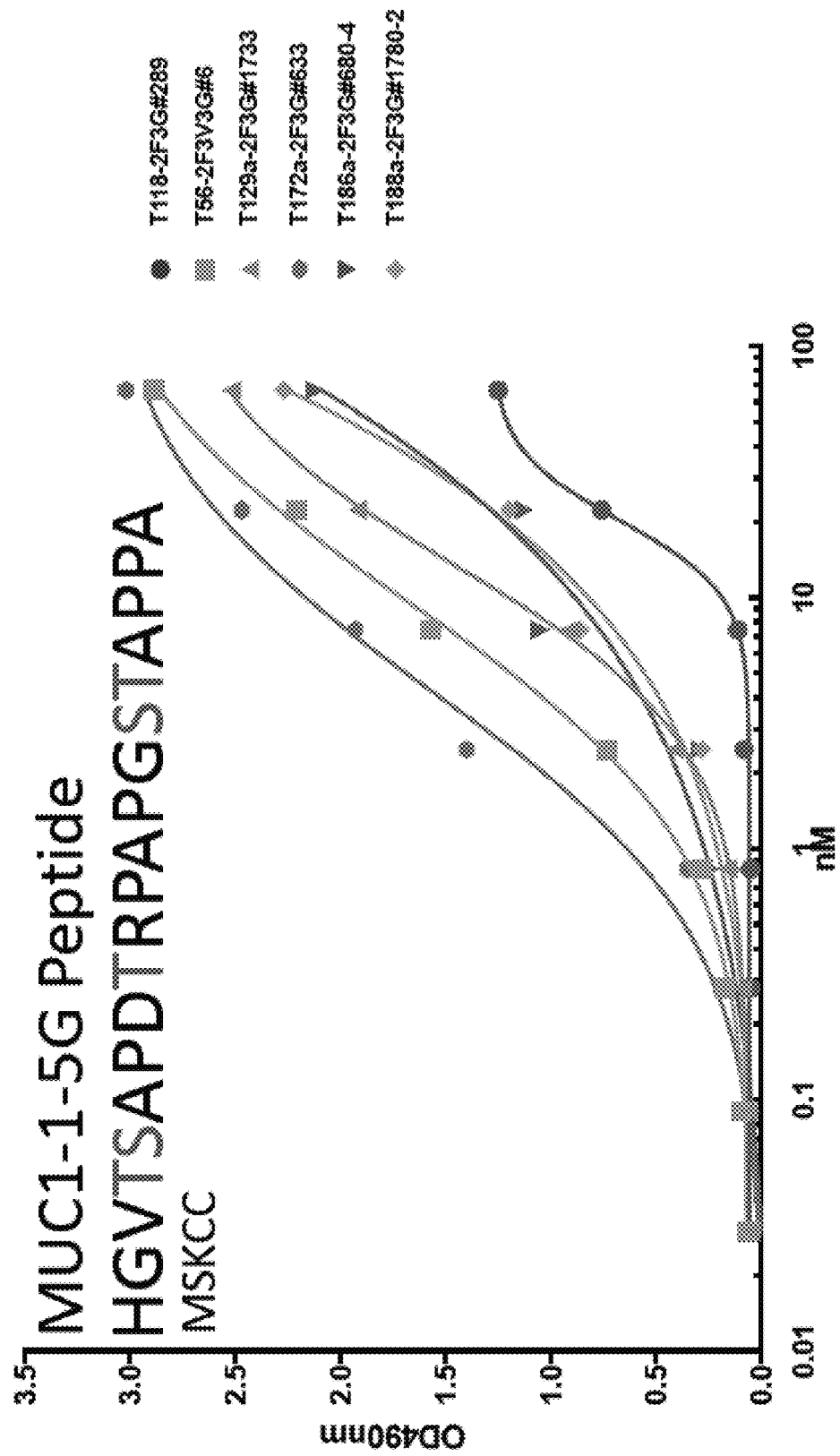

Next, the effect of Tn modification to Ser residues was tested. To this effect, binding of the 2F3G1 mutants to an unmodified MUC1 peptide (HGVTSAPDTRPAPGSTAPPA (SEQ ID NO: 157)), or to a MUC1 peptide with five Tn glycans attached to the peptide on Thr and Ser residues (HGVT*S*APDT*RPAPGS*T*APPA) (SEQ ID NO:155). While binding of the 2F3G1 mutants to MUC1 peptide containing unmodified residues was not observed, strong binding was observed in the modified MUC1 peptide (FIG. 23E-F). Given the lack of binding to MUC1 with Thr modified residues, and strong binding in the presence with Ser and Thr modified residues, these results indicate that 2F3G1 mutants bind to MUC1 peptides that are modified by Tn on a Ser residue.

Figure 24:
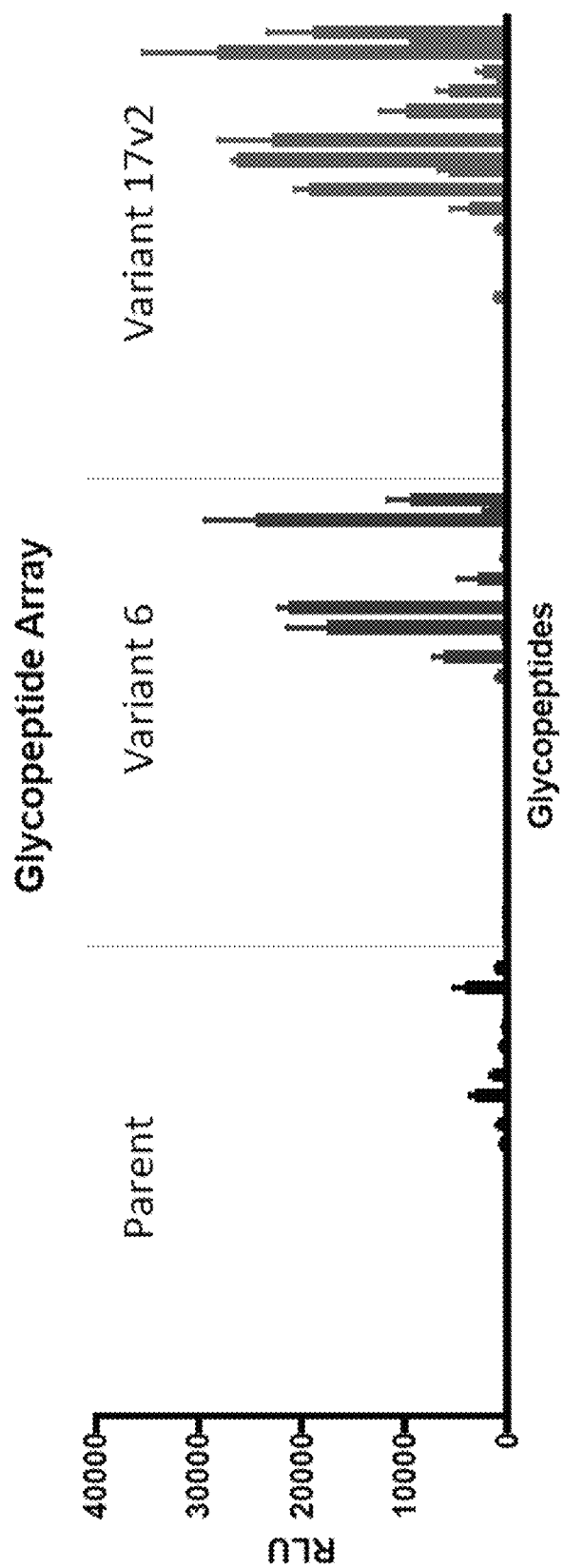
FIG. 24 shows a glyopeptide array for the 2F3 parent antibody and variants 6 and 17v2.

This was further confirmed by Tn glycan array analysis. The glycopeptide microarrays were prepared on N-hydroxysuccinimide (NHS) glass slides (Schott Nexterion), and immobilization of peptides and glycopeptides was achieved through amine functions. With concentrations adjusted to 100 μM in printing buffer (300 mM sodium phosphates, pH 8.5), 0.33 nL of each solution was spotted using a piezoelectric printer. The microarray was printed in spot replicates of 6. Arrays were interrogated with monoclonal anti-Tn antibodies 2F3 parent, 2F3V variant 6, or 2F3 variant 17-2 and detected with fluorescently labeled secondary antibodies and streptavidin as noted. Scanning and quantification were performed with ProScanArray scanner and ScanArray Express software (Perkin-Elmer). The assay examined a panel of ~50 Tn glycopeptides and addressed whether spacing, number of Tn modifications, specific residues modified, or sequence context contributed to the specificity of binding by 2F3. Efficient binding was observed to peptides that contained Ser-Tn, and those that were at least 5 amino acids from the attachment point to the solid matrix. Ser-Tn near free termini and multiple Ser-Tn in a single peptide increased binding. Using the 2F3 parent antibody ("parent"), Variant 6 and Variant 17, the binding of the antibodies to a panel of different glycoproteins was assayed to determine the preferred Tn context recognized by 2F3 and the 2F3G1 variants. Consistent with the ELISA assay described above, the parental 2F3 and 2F3G1 variants displayed strong binding when the glycopeptides were modified on serine residues (FIG. 24). Importantly, modification to Thr residues gave rise to little to no binding. However, linkage to just a single Ser residue was able to significantly increase binding. For example, the binding of all three antibodies tested was greatly enhanced for the Ser modified peptide IgA-Pep17 (H2N-KPSTPPTPSPS*C—OH (SEQ ID NO: 159)), relative to the same sequence peptide, IgA-Pep18, but with a Thr modification instead (H2N-KPST*PPTPSPSC-OH (SEQ ID NO: 160)) (Table 9). Furthermore, binding was observed not only to peptides that contained Ser-Tn, but specifically those that were at least 5 amino acids from the attachment point to the solid matrix. Ser-Tn near free termini and multiple Ser-Tn in a single peptide increased binding.

Figure 25:
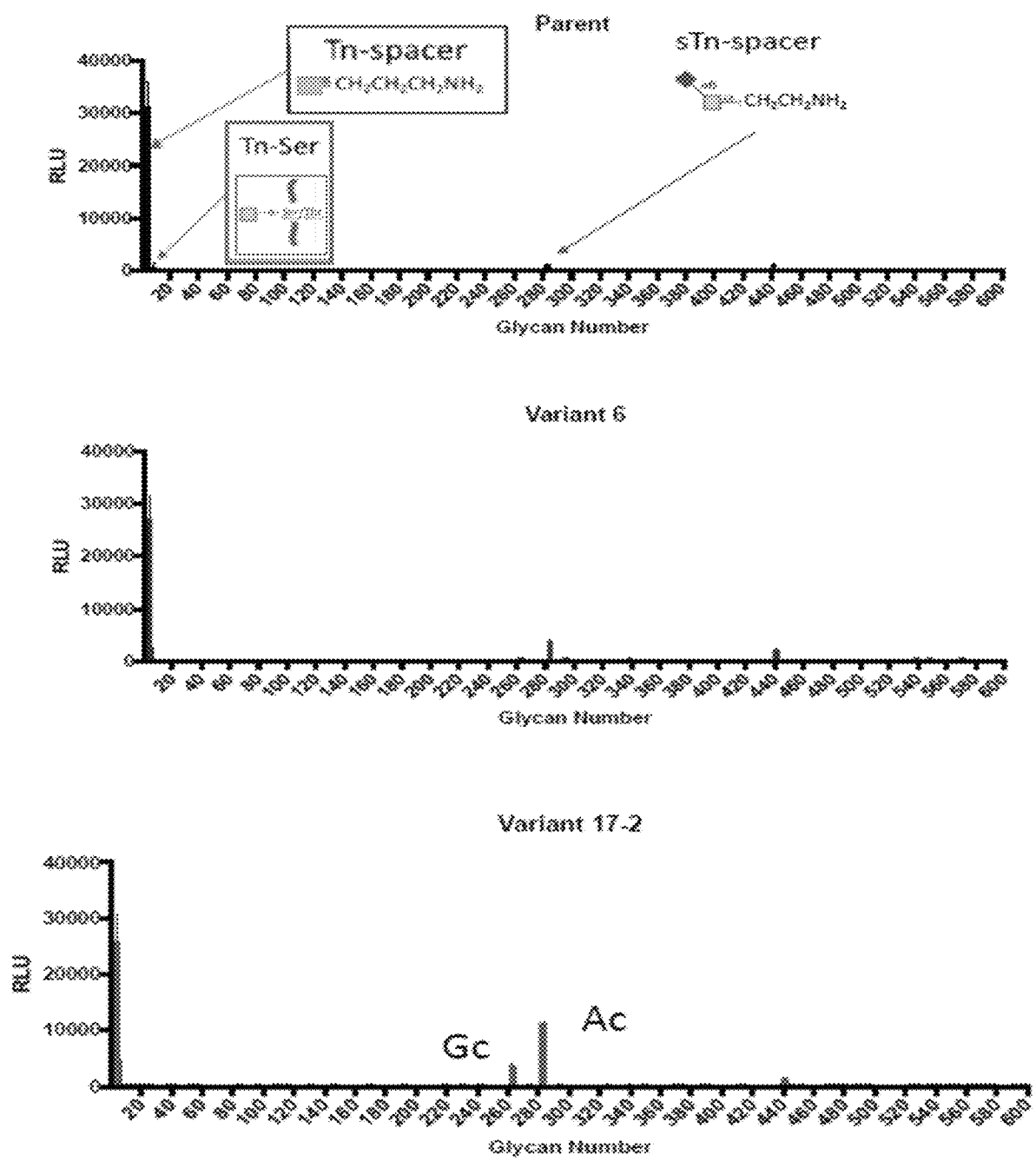
FIG. 25. shows a glycan array for 2F3 parent antibody and variants 6 and 17v2.
Figure 26:
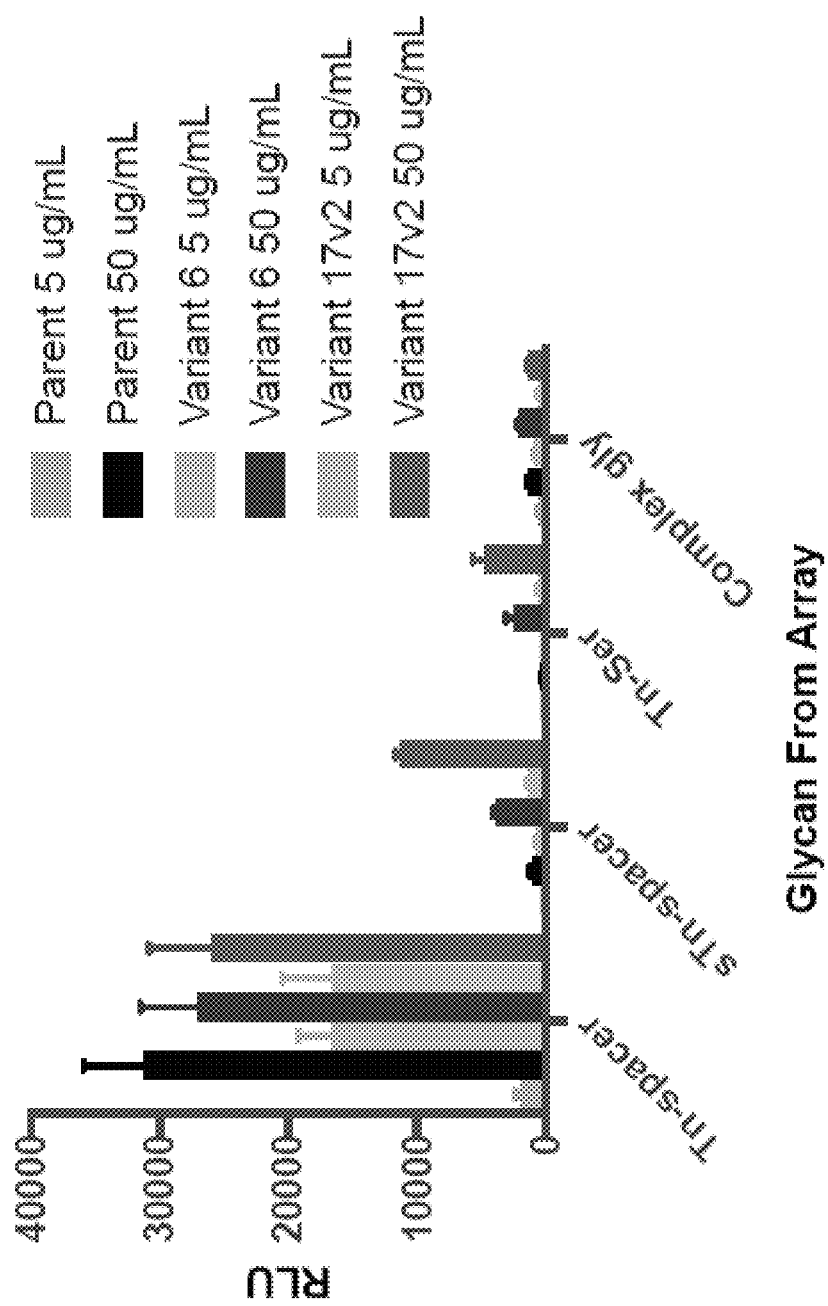
FIG. 26 shows a glycan array for 2F3 parent antibody and variants 6 and 17v2 using antibody concentrations of 5 μg/mL and 50 μg/mL.

In addition, a glycan array analysis consisting of 600 different mammalian glycans (version 5.3) demonstrated high specificity for Tn/sTn with no significant binding observed to almost 600 glycan structures found in mammals (FIG. 25). The two strongest hits were Tn connected to a spacer arm, and significant binding was also seen to Tn connected to a serine. Very weak binding to an unrelated complex N-linked glycan, even at the high antibody concentration was observed (FIG. 26). This could be further supported using different concentrations of the antibodies (FIG. 26). Moreover, affinity maturation of the parent 2F3 antibody resulted in two variants (2F3 #6 and 2F3 #17v2), which displayed dramatically increased affinity to Tn and sTn without losing specificity (FIG. 26).

The antibodies were applied to glycopeptide arrays at a concentration of 5 ug/mL (no data shown form this group) or 50 ug/mL (data shown in bar chart and in the table 9).

A structural analysis of the difference between Tn-Ser and Tn-Thr residues indicates that the Tn-Ser residues adopt a different conformation than the Tn-Thr residues (FIG. 27). While the favored conformation for Tn-Cer is parallel to the peptide backbone, the favored conformation for Tn-Thr is perpendicular. This difference shifts the face of the Tn molecule that is available to bind. Taken together, these results demonstrate that 2F3 anti-Tn/sTn antibody recognizes Tn preferentially on Ser residues that are in accessible contexts.

TABLE 9

Peptide description and sequences with the RLU units for binding 2F3, 2F3 variant 6, and 2F3 variant 17. Modification are noted with a "X".

| Description | Sequence | SEQ ID NO | Parent | Variant 6 | Variant 17 | At least 1 S | Only T | No Tn |
|---|---|---|---|---|---|---|---|---|
| Phosphate Buffer | buffer control | | 3 | 5 | 47 | | | X |
| Mannose5 (Man5) | glycan control | | 104 | 185 | 23 | | | X |
| Blood group A tetraose | GalNAca1-3(Fuca1-2)Galb1-3GlcNAc-AEAB | | 147 | 64 | 109 | | | |
| Blood group A pentaose | GalNAca1-3(Fuca1-2)Galb1-3GlcNAcb1-3Gal-AEAB | | 188 | 248 | 141 | | | |
| A-MUC2 | Ac-PT*TPLK-NH2 | 161 | 45 | 55 | 65 | | X | |
| B-MUC2 | Ac-PTT*TPLK-NH2 | 162 | 19 | 23 | 237 | | X | |
| C-MUC2 | Ac-PTTT*PLK-NH2 | 163 | 9 | 22 | 30 | | X | |
| D-MUC2 | Ac-PT*T*TPLK-NH2 | 164 | 12 | 12 | 179 | | X | |
| E-MUC2 | Ac-PT*TT*PLK-NH2 | 165 | 8 | 27 | 87 | | X | |
| F-MUC2 | Ac-PTT*T*PLK-NH2 | 166 | 11 | 54 | 70 | | X | |
| G-MUC2 | Ac-PT*T*T*PLK-NH2 | 167 | 10 | -39 | 51 | | X | |
| a-Dystroglycan | Ac-PPTTTTKKP-NH2 | 168 | 37 | -4 | 86 | | | X |
| MUC5AC | H2N-GTTPSPVPT*TSTTSAP-OH | 169 | 23 | -14 | 87 | X | | |
| EA2 | Ac-PTTDSTT*PAPTTK-NH2 | 170 | 11 | 18 | 16 | | X | |
| EA2-R | Ac-PTTDSTTPAPTTK-NH2 | 171 | 15 | 45 | 29 | | | X |
| a-Dystroglycan | Ac-PPT*T*T*T*KKP-HN2 | 172 | 24 | 28 | 51 | | X | |
| MUC1-1 | H2N-TSAPDT*RDAP-NH2 | 173 | 11 | 14 | 61 | | X | |
| MUC1-1R | H2N-TSAPDTRDAP-NH2 | 174 | 7 | 7 | 19 | | | X |
| MUC1-2 | H2N-APGS*T*APP-NH2 | 175 | 33 | 59 | 1121 | X | | |
| MUC1-2R | H2N-APGSTAPP-NH2 | 176 | 4 | 0 | 6 | | | X |
| PADRE Tn3b | H2N-GaKcVAAWTLKAAaT*T*T*G-CONH2 | | 13 | -84 | 49 | | X | |
| Tn3 linker | Ac-T*T*T*-NH(CH2)3NH2 | | 8 | 21 | 24 | | X | |
| Tn linker | Ac-T*-NH(CH2)3NH2 | | 34 | 2 | 70 | | X | |
| Peptide-4 | H2N-KTTT-CONH2 | 177 | 7 | 31 | 33 | | | X |
| Peptide-5 | H2N-KTTTG-CONH2 | 178 | 10 | -6 | 41 | | | X |

TABLE 9-continued

Peptide description and sequences with the RLU units for binding 2F3, 2F3 variant 6, and 2F3 variant 17. Modification are noted with a "X".

| Description | Sequence | SEQ ID NO | Parent | Variant 6 | Variant 17 | At least 1 S | Only T | No Tn |
|---|---|---|---|---|---|---|---|---|
| Ser-GalNAc1 | H2N-Ser(a-D-GalNAc)-NH2 | | 105 | −1 | 960 | X | | |
| Ser-GalNAc2 | H2N-Ser(a-D-GalNAc)-OH | | 10 | −3 | 42 | X | | |
| Thr-GalNAc1 | H2N-Thr(a-D-GalNAc)-NH2 | | 520 | 810 | 3674 | | X | |
| Thr-GalNAc2 | H2N-Thr(a-D-GalNAc)-OH | | 4 | 6 | 235 | | X | |
| IgA-Pep01 | **H2N-KPVPST\*PPT\*PS\*C-OH** | 179 | 939 | 6139 | 19275 | X | | |
| IgA-Pep02 | H2N-KPVPSTPPTPSC-OH | 180 | 26 | 35 | 75 | | | X |
| IgA-Pep03 | **H2N-KPVPS\*TPPTPSC-OH** | 181 | 58 | 353 | 5653 | X | | |
| IgA-Pep04 | **H2N-KPST\*PPT\*PS\*PS\*C-OH** | 182 | 3151 | 1749 | 26366 | X | | |
| IgA-Pep05 | H2N-KPSTPPTPSPSC-OH | 183 | 28 | 60 | 149 | | | X |
| IgA-Pep06 | **H2N-KT\*PPT\*PS\*PS\*TPC-OH** | 184 | 1373 | 21199 | 22880 | X | | |
| IgA-Pep07 | H2N-KTPPTPSPSTPC-OH | 185 | 20 | 30 | 144 | | | X |
| IgA-Pep08 | **H2N-KTPPTPSPST\*PC-OH** | 186 | 22 | −6 | 282 | | X | |
| IgA-Pep09 | **H2N-KPT\*PS\*PS\*TPPT\*C-OH** | 187 | 647 | 2844 | 9835 | X | | |
| IgA-Pep10 | H2N-KPSPSTPPTPSC-OH | 188 | 19 | −127 | 125 | | | X |
| IgA-Pep11 | **H2N-KPS\*PS\*TPPT\*PSC-OH** | 189 | 315 | 311 | 5649 | X | | |
| IgA-Pep12 | H2N-KPSTPPTPSPSC-OH | 183 | 20 | 83 | 457 | | | X |
| IgA-Pep13 | **H2N-KPS\*TPPT\*PSPSC-OH** | 190 | 40 | 253 | 2319 | X | | |
| IgA-Pep14 | H2N-KPSTPPTPSPSC-OH | 183 | 43 | 38 | 112 | | | X |
| IgA-Pep15 | **H2N-KPST\*PPTPS\*PS\*C-OH** | 191 | 4096 | 24378 | 28214 | X | | |
| IgA-Pep16 | **H2N-KPSTPPTPS\*PSC-OH** | 192 | 115 | 1649 | 8384 | X | | |
| IgA-Pep17 | **H2N-KPSTPPTPSPS\*C-OH** | 159 | 1010 | 9417 | 18803 | X | | |
| IgA-Pep18 | **H2N-KPST\*PPTPSPSC-OH** | 160 | 16 | 22 | 174 | | X | |

Throughout this application various publications have been referenced. The disclosures of these publications in their entireties are hereby incorporated by reference in this application in order to more fully describe the state of the art to which this invention pertains. Although the invention has been described with reference to the examples provided above, it should be understood that various modifications can be made without departing from the spirit of the invention.

The invention claimed is:

1. A monoclonal antibody that binds to a tumor glycoprotein containing a Thomsen-nouvelle (Tn) carbohydrate antigen, wherein said antibody comprises a variable heavy chain and a variable light chain, wherein the variable heavy chain (VH) domain comprises:
   (a) a VH CDR1 having an amino acid sequence comprising SEQ ID NO:11;
   (b) a VH CDR2 having an amino acid sequence comprising SEQ ID NO:141; and
   (c) a VH CDR3 having an amino acid sequence comprising SEQ ID NO: 37;
and wherein the variable light chain (VL) domain comprises:
   (d) a VL CDR1 having an amino acid sequence comprising SEQ ID NO:51;
   (e) a VL CDR2 having an amino acid sequence comprising SEQ ID NO:63; and
   (f) a VL CDR3 having an amino acid sequence comprising SEQ ID NO: 70.

2. The monoclonal antibody of claim 1, wherein the variable heavy chain (VH) domain comprises the amino acid sequence of SEQ ID NO: 122.

3. The monoclonal antibody of claim 1, wherein the variable light chain (VL) domain comprises the amino acid sequence of SEQ ID NO:112.

4. The monoclonal antibody of claim 1, wherein the variable heavy chain (VH) domain comprises the amino acid sequence of SEQ ID NO: 122 and the variable light chain (VL) domain comprises the amino acid sequence of SEQ ID NO: 112.

5. The monoclonal antibody of claim 1, wherein the antibody is a human antibody.

6. The monoclonal antibody of claim 1, wherein the antibody is an IgG.

7. The monoclonal antibody of claim 6, wherein the IgG antibody is an IgG1 subclass.

8. A purified expression vector that encodes the variable heavy chain (VH) domain of the antibody of claim 1, or the variable light chain (VL) domain of claim 1, or both the VH domain of the antibody of claim 1 and the VL domain of the antibody of claim 1.

9. An isolated host cell comprising
   (a) at least two expression vectors of claim 8 wherein a first expression vector encodes the VH domain of the antibody of claim 1, and a second expression vector encodes the VL domain of the antibody of claim 1; or (b) a single expression vector encoding both the VH domain and the VL domain of the antibody of claim 1;

wherein the host cell is a prokaryotic cell or a eukaryotic cell present in an in vitro cell culture.

10. A method of making the monoclonal antibody of claim 1 that binds to a Thomsen-nouvelle (Tn) antigen comprising:

(a) culturing an isolated host cell comprising a purified expression vector encoding both the VH and VL domains of the monoclonal antibody of claim 1 in a medium under conditions that allow expression of an antibody having both a variable heavy chain and a variable light chain according to claim 1, and (b) obtaining said monoclonal antibody comprising both a VH and VL domain derived from step (a) expressed therein.

11. A conjugate comprising the monoclonal antibody of claim 1 conjugated or recombinantly fused to a therapeutic agent wherein the therapeutic agent is an agent that modifies a biological response or is a cytotoxin.

12. The conjugate of claim 11, wherein the cytotoxin is a chemotherapeutic.

13. The conjugate of claim 12, wherein the chemotherapeutic is an Auristatin molecule.

14. A pharmaceutical composition comprising the monoclonal antibody of claim 1 and a pharmaceutically acceptable carrier.

15. A pharmaceutical composition comprising the conjugate of claim 11 and a pharmaceutically acceptable carrier.

* * * * *

```
                          SEQUENCE LISTING

<160> NUMBER OF SEQ ID NOS: 192

<210> SEQ ID NO 1
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gly Phe Thr Phe Ser Asp His Tyr
1               5

<210> SEQ ID NO 2
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gly Phe Thr Phe Ser Asp Gln Tyr
1               5

<210> SEQ ID NO 3
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gly Tyr Thr Phe Thr Ser Tyr Gly
1               5

<210> SEQ ID NO 4
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gly Tyr Thr Phe Thr Ser Tyr Asp
1               5

<210> SEQ ID NO 5
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 5

Gly Phe Thr Phe Asp Ser Tyr Ala
1               5

<210> SEQ ID NO 6
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gly Phe Thr Phe Arg Ser Tyr Tyr
1               5

<210> SEQ ID NO 7
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Asp His Tyr Met Asp
1               5

<210> SEQ ID NO 8
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Asp Gln Tyr Met Asp
1               5

<210> SEQ ID NO 9
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Ser Tyr Gly Ile Ser
1               5

<210> SEQ ID NO 10
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Ser Tyr Asp Ile Asn
1               5

<210> SEQ ID NO 11
<211> LENGTH: 5
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 11

Ser Tyr Ala Met Ser
1               5

<210> SEQ ID NO 12
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Ser Tyr Tyr Met Ser
1               5

<210> SEQ ID NO 13
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Ile Arg Asn Lys Ala Asn Ser Tyr Thr Thr
1               5                   10

<210> SEQ ID NO 14
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Ile Arg Asn Lys Ala Asn Arg Tyr Thr Thr
1               5                   10

<210> SEQ ID NO 15
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Ile Ser Ala Tyr Asn Gly Asn Thr
1               5

<210> SEQ ID NO 16
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Met Asn Pro Asn Ser Gly Asn Thr
1               5
```

```
<210> SEQ ID NO 17
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Ile Ser Gly Ser Gly Asp Ser Thr
1               5

<210> SEQ ID NO 18
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Ile Asn Gln His Gly Ser Glu Lys
1               5

<210> SEQ ID NO 19
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Arg Ile Arg Asn Lys Ala Asn Ser Tyr Thr Thr Glu Tyr Ala Ala Ser
1               5                   10                  15

Val Lys Gly

<210> SEQ ID NO 20
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Arg Ile Arg Asn Lys Ala Asn Arg Tyr Thr Thr Asp Tyr Ala Ala Ser
1               5                   10                  15

Val Lys Gly

<210> SEQ ID NO 21
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Trp Ile Ser Ala Tyr Asn Gly Asn Thr Asn Tyr Ala Gln Lys Leu Gln
1               5                   10                  15

Gly

<210> SEQ ID NO 22
```

```
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Trp Met Asn Pro Asn Ser Gly Asn Thr Gly Tyr Ala Gln Lys Phe Gln
1               5                   10                  15
Gly

<210> SEQ ID NO 23
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Ala Ile Ser Gly Ser Gly Asp Ser Thr Tyr Tyr Ala Asp Ser Val Lys
1               5                   10                  15
Gly

<210> SEQ ID NO 24
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Ser Ile Asn Gln His Gly Ser Glu Lys Tyr Tyr Val Asp Ser Val Lys
1               5                   10                  15
Gly

<210> SEQ ID NO 25
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Ala Arg Val Ser Tyr Tyr Ala Met Asp Val
1               5                   10

<210> SEQ ID NO 26
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Val Arg Val Thr Ala Val Ala Leu Asp Tyr
1               5                   10

<210> SEQ ID NO 27
<211> LENGTH: 18
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 27

Ala Arg Gly Gly Gly Thr Thr Val Leu Asp Tyr Tyr Arg Tyr Gly Met
1               5                   10                  15

Asp Val

<210> SEQ ID NO 28
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Ala Arg Gly Trp Arg Tyr Ser Ser Ser Trp Tyr Arg Lys Val Arg Phe
1               5                   10                  15

Asp Pro

<210> SEQ ID NO 29
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Ala Arg Ala Asn Arg Lys Gly Ala Arg Thr Arg Ala Phe Asp Tyr
1               5                   10                  15

<210> SEQ ID NO 30
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Ala Ile Arg Arg Glu Tyr Ser Gly Tyr Ala Pro Phe Asp Tyr
1               5                   10

<210> SEQ ID NO 31
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Ala Arg Asp Gly Asp Arg Thr Thr Asp Tyr
1               5                   10

<210> SEQ ID NO 32
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32
```

```
Val Ser Tyr Tyr Ala Met Asp Val
1               5

<210> SEQ ID NO 33
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Val Thr Ala Val Ala Leu Asp Tyr
1               5

<210> SEQ ID NO 34
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Gly Gly Gly Thr Thr Val Leu Asp Tyr Tyr Arg Tyr Gly Met Asp Val
1               5                   10                  15

<210> SEQ ID NO 35
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Gly Trp Arg Tyr Ser Ser Ser Trp Tyr Arg Lys Val Arg Phe Asp Pro
1               5                   10                  15

<210> SEQ ID NO 36
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Ala Asn Arg Lys Gly Ala Arg Thr Arg Ala Phe Asp Tyr
1               5                   10

<210> SEQ ID NO 37
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Arg Arg Glu Tyr Ser Gly Tyr Ala Pro Phe Asp Tyr
1               5                   10

<210> SEQ ID NO 38
<211> LENGTH: 8
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 38

Asp Gly Asp Arg Thr Thr Asp Tyr
1               5

<210> SEQ ID NO 39
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Gln Ser Ile Ser Ser Tyr
1               5

<210> SEQ ID NO 40
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Gln Ser Val Ser Thr Tyr
1               5

<210> SEQ ID NO 41
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Ser Gly Ile Asn Val Gly Thr Tyr Arg
1               5

<210> SEQ ID NO 42
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Gln Ser Leu Leu His Ser Asn Gly Tyr Asn Tyr
1               5                   10

<210> SEQ ID NO 43
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Ser Ser Ser Asn Ile Gly Asn Asn Tyr
1               5
```

```
<210> SEQ ID NO 44
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Gln Gly Ile Ser Ser Trp
1               5

<210> SEQ ID NO 45
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Gln Ser Val Ser Ser Tyr
1               5

<210> SEQ ID NO 46
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Arg Ala Ser Gln Ser Ile Ser Ser Tyr Leu Asn
1               5                   10

<210> SEQ ID NO 47
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Arg Ala Ser Gln Ser Val Ser Thr Tyr Leu Ala
1               5                   10

<210> SEQ ID NO 48
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Thr Leu Arg Ser Gly Ile Asn Val Gly Thr Tyr Arg Ile Tyr
1               5                   10

<210> SEQ ID NO 49
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 49

Arg Ser Ser Gln Ser Leu Leu His Ser Asn Gly Tyr Asn Tyr Leu Asp
1               5                   10                  15

<210> SEQ ID NO 50
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Ser Gly Ser Ser Ser Asn Ile Gly Asn Asn Tyr Val Ser
1               5                   10

<210> SEQ ID NO 51
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Arg Ala Ser Gln Gly Ile Ser Ser Trp Leu Ala
1               5                   10

<210> SEQ ID NO 52
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Arg Ala Ser Gln Ser Val Ser Ser Tyr Leu Val
1               5                   10

<210> SEQ ID NO 53
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Ala Ala Ser
1

<210> SEQ ID NO 54
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Asp Ala Ser
1

<210> SEQ ID NO 55
<211> LENGTH: 7
<212> TYPE: PRT
```

<213> ORGANISM: Artificial Sequence
<220> FEATURE:
<223> OTHER INFORMATION: Description of Artificial Sequence: Synthetic
    peptide

<400> SEQUENCE: 55

Tyr Lys Ser Asp Ser Asp Lys
1               5

<210> SEQ ID NO 56
<211> LENGTH: 3
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 56

Leu Gly Ser
1

<210> SEQ ID NO 57
<211> LENGTH: 3
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 57

Asp Asn Asn
1

<210> SEQ ID NO 58
<211> LENGTH: 7
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 58

Ala Ala Ser Ser Leu Gln Ser
1               5

<210> SEQ ID NO 59
<211> LENGTH: 7
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 59

Asp Ala Ser Asn Arg Ala Thr
1               5

<210> SEQ ID NO 60
<211> LENGTH: 11
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 60

Tyr Lys Ser Asp Ser Asp Lys Gln Gln Gly Ser
1               5                   10

```
<210> SEQ ID NO 61
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Leu Gly Ser Asn Arg Ala Ser
1               5

<210> SEQ ID NO 62
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Asp Asn Asn Lys Arg Pro Ser
1               5

<210> SEQ ID NO 63
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Ala Ala Ser Ser Leu Gln Ser
1               5

<210> SEQ ID NO 64
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Ala Ala Ser Asn Arg Ala Ala
1               5

<210> SEQ ID NO 65
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Gln Gln Ser Tyr Ser Thr Pro Arg Thr
1               5

<210> SEQ ID NO 66
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 66

His Gln Arg Ser Asp Trp Pro Pro Val Thr
1               5                   10

<210> SEQ ID NO 67
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Met Ile Trp His Ser Ser Ala Val Val
1               5

<210> SEQ ID NO 68
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Met Gln Ala Leu Gln Thr Pro Ile Thr
1               5

<210> SEQ ID NO 69
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Gly Thr Trp Asp Ser Ser Leu Ser Ala Val
1               5                   10

<210> SEQ ID NO 70
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Gln Gln Tyr Ile Ser Tyr Pro Tyr Thr
1               5

<210> SEQ ID NO 71
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Gln Gln Arg Ser Asn Trp Pro Ile Thr
1               5

<210> SEQ ID NO 72
<211> LENGTH: 221
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Gln Val Gln Leu Val Glu Ser Gly Gly Gly Leu Val Gln Pro Gly Gly
1               5                   10                  15

Ser Leu Arg Leu Ser Cys Ala Val Ser Gly Phe Thr Phe Ser Asp His
            20                  25                  30

Tyr Met Asp Trp Val Arg Gln Ala Pro Gly Lys Gly Leu Glu Trp Val
        35                  40                  45

Gly Arg Ile Arg Asn Lys Ala Asn Ser Tyr Thr Thr Glu Tyr Ala Ala
50                  55                  60

Ser Val Lys Gly Arg Phe Thr Ile Ser Arg Asp Glu Ser Lys Arg Ser
65                  70                  75                  80

Leu Tyr Leu Gln Met Asn Ser Leu Lys Thr Glu Asp Thr Ala Val Tyr
                85                  90                  95

Tyr Cys Ala Arg Val Ser Tyr Tyr Ala Met Asp Val Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser
    210                 215                 220

<210> SEQ ID NO 73
<211> LENGTH: 224
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Gln Leu Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Gln
            20                  25                  30

Tyr Met Asp Trp Ile Arg Gln Ala Pro Gly Lys Gly Leu Glu Trp Val
        35                  40                  45

Gly Arg Ile Arg Asn Lys Ala Asn Arg Tyr Thr Thr Asp Tyr Ala Ala
50                  55                  60

Ser Val Lys Gly Arg Phe Ile Ile Ser Arg Asp Asp Ser Lys Asn Ser
65                  70                  75                  80

Leu Tyr Leu Gln Met Asn Arg Leu Arg Ile Glu Asp Thr Ala Val Tyr
                85                  90                  95
```

```
Tyr Cys Val Arg Val Thr Ala Val Ala Leu Asp Tyr Trp Gly Gln Gly
                100                 105                 110

Thr Leu Val Thr Val Ser Ser Gly Ser Ala Ser Ala Pro Thr Leu Phe
            115                 120                 125

Pro Leu Val Ser Cys Glu Asn Ser Pro Ser Asp Thr Ser Ser Val Ala
        130                 135                 140

Val Gly Cys Leu Ala Gln Asp Phe Leu Pro Asp Ser Ile Thr Phe Ser
145                 150                 155                 160

Trp Lys Tyr Lys Asn Asn Ser Asp Ile Ser Ser Thr Arg Gly Phe Pro
                165                 170                 175

Ser Val Leu Arg Gly Gly Lys Tyr Ala Ala Thr Ser Gln Val Leu Leu
            180                 185                 190

Pro Ser Lys Asp Val Met Gln Gly Thr Asp Glu His Val Val Cys Lys
        195                 200                 205

Val Gln His Pro Asn Gly Asn Lys Glu Lys Asn Val Pro Leu Pro Val
210                 215                 220
```

<210> SEQ ID NO 74
<211> LENGTH: 230
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 74

```
Gln Val Gln Leu Gln Gln Ser Gly Ala Glu Val Lys Lys Pro Gly Ala
1               5                   10                  15

Ser Val Lys Val Ser Cys Lys Ala Thr Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Gly Gly Thr Thr Val Leu Asp Tyr Arg Tyr Gly Met
                100                 105                 110

Asp Val Trp Gly Gln Gly Thr Thr Val Thr Val Ser Ser Gly Ser Ala
            115                 120                 125

Ser Ala Pro Thr Leu Phe Pro Leu Val Ser Cys Glu Asn Ser Pro Ser
        130                 135                 140

Asp Thr Ser Ser Val Ala Val Gly Cys Leu Ala Gln Asp Phe Leu Pro
145                 150                 155                 160

Asp Ser Ile Thr Phe Ser Trp Lys Tyr Lys Asn Asn Ser Asp Ile Ser
                165                 170                 175

Ser Thr Arg Gly Phe Pro Ser Val Leu Arg Gly Gly Lys Tyr Ala Ala
            180                 185                 190

Thr Ser Gln Val Leu Leu Pro Ser Lys Asp Val Met Gln Gly Thr Asp
        195                 200                 205

Glu His Val Val Cys Lys Val Gln His Pro Asn Gly Asn Lys Glu Lys
    210                 215                 220

Asn Val Pro Leu Pro Val
225                 230
```

<210> SEQ ID NO 75
<211> LENGTH: 230
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (150)..(150)
<223> OTHER INFORMATION: Any amino acid

<400> SEQUENCE: 75

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asp Ile Asn Trp Val Arg Gln Ala Thr Gly Gln Gly Leu Glu Trp Met
        35                  40                  45

Gly Trp Met Asn Pro Asn Ser Gly Asn Thr Gly Tyr Ala Gln Lys Phe
    50                  55                  60

Gln Gly Arg Val Thr Met Thr Arg Asn Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Trp Arg Tyr Ser Ser Ser Trp Tyr Arg Lys Val Arg Phe
            100                 105                 110

Asp Pro Trp Gly Gln Gly Thr Leu Val Thr Val Ser Ser Gly Ser Ala
        115                 120                 125

Ser Ala Pro Thr Leu Phe Pro Leu Val Ser Cys Glu Asn Ser Pro Ser
    130                 135                 140

Asp Thr Ser Ser Val Xaa Val Gly Cys Leu Ala Gln Asp Phe Leu Pro
145                 150                 155                 160

Asp Ser Ile Thr Phe Ser Trp Lys Tyr Lys Asn Asn Ser Asp Ile Ser
                165                 170                 175

Ser Thr Arg Gly Phe Pro Ser Val Leu Arg Gly Gly Lys Tyr Ala Ala
            180                 185                 190

Thr Ser Gln Val Leu Leu Pro Ser Lys Asp Val Met Gln Gly Thr Asp
        195                 200                 205

Glu His Val Val Cys Lys Val Gln His Pro Asn Gly Asn Lys Glu Lys
    210                 215                 220

Asn Val Pro Leu Pro Val
225                 230

<210> SEQ ID NO 76
<211> LENGTH: 227
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Gln Val Gln Leu Val Gly Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asp Ile Asn Trp Val Arg Gln Ala Thr Gly Gln Gly Leu Glu Trp Met

```
            35                  40                  45
Gly Trp Met Asn Pro Asn Ser Gly Asn Thr Gly Tyr Ala Gln Lys Phe
 50                  55                  60

Gln Gly Arg Val Thr Met Thr Arg Asn Thr Ser Ile Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Ala Asn Arg Lys Gly Ala Arg Thr Arg Ala Phe Asp Tyr Trp
                100                 105                 110

Gly Gln Gly Thr Leu Val Thr Val Ser Ser Gly Ser Ala Ser Ala Pro
                115                 120                 125

Thr Leu Phe Pro Leu Val Ser Cys Glu Asn Ser Pro Ser Asp Thr Ser
                130                 135                 140

Ser Val Ala Val Gly Cys Leu Ala Gln Asp Phe Leu Pro Asp Ser Ile
145                 150                 155                 160

Thr Phe Ser Trp Lys Tyr Lys Asn Asn Ser Asp Ile Ser Ser Thr Arg
                165                 170                 175

Gly Phe Pro Ser Val Leu Arg Gly Gly Lys Tyr Ala Ala Thr Ser Gln
                180                 185                 190

Val Leu Leu Pro Ser Lys Asp Val Met Gln Gly Thr Asp Glu His Val
                195                 200                 205

Val Cys Lys Val Gln His Pro Asn Gly Asn Lys Glu Lys Asn Val Pro
210                 215                 220

Leu Pro Val
225

<210> SEQ ID NO 77
<211> LENGTH: 226
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Asp Ser Tyr
                 20                  25                  30

Ala Met Ser Trp Val Arg Gln Ala Pro Gly Lys Gly Leu Glu Trp Val
                 35                  40                  45

Ser Ala Ile Ser Gly Ser Gly Asp Ser Thr Tyr Tyr Ala Asp Ser Val
 50                  55                  60

Lys Gly Arg Phe Ser Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Ile Arg Arg Glu Tyr Ser Gly Tyr Ala Pro Phe Asp Tyr Trp Gly
                100                 105                 110

Gln Gly Thr Leu Val Thr Val Ser Ser Gly Ser Ala Ser Ala Pro Thr
                115                 120                 125

Leu Phe Pro Leu Val Ser Cys Glu Asn Ser Pro Ser Asp Thr Ser Ser
                130                 135                 140

Val Ala Val Gly Cys Leu Ala Gln Asp Phe Leu Pro Asp Ser Ile Thr
145                 150                 155                 160
```

Phe Ser Trp Lys Tyr Lys Asn Asn Ser Asp Ile Ser Ser Thr Arg Gly
              165                 170                 175

Phe Pro Ser Val Leu Arg Gly Gly Lys Tyr Ala Ala Thr Ser Gln Val
            180                 185                 190

Leu Leu Pro Ser Lys Asp Val Met Gln Gly Thr Asp Glu His Val Val
        195                 200                 205

Cys Lys Val Gln His Pro Asn Gly Asn Lys Glu Lys Asn Val Pro Leu
210                 215                 220

Pro Val
225

<210> SEQ ID NO 78
<211> LENGTH: 222
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

Gln Val Gln Leu Val Gln Ser Gly Gly Gly Leu Val Gln Pro Gly Glu
1               5                   10                  15

Thr Leu Arg Leu Ser Cys Glu Ala Ser Gly Phe Thr Phe Arg Ser Tyr
            20                  25                  30

Tyr Met Ser Trp Val Arg Gln Ala Pro Arg Lys Gly Leu Glu Trp Val
        35                  40                  45

Ala Ser Ile Asn Gln His Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Ile Ser Leu Arg Ala Glu Asp Thr Ala Val Tyr Tyr Cys
                85                  90                  95

Ala Arg Asp Gly Asp Arg Thr Thr Asp Tyr Trp Gly Gln Gly Thr Leu
            100                 105                 110

Val Thr Val Ser Ser Arg Ser Ala Ser Ala Pro Thr Leu Phe Pro Leu
        115                 120                 125

Val Ser Cys Glu Asn Ser Pro Ser Asp Thr Ser Ser Val Ala Val Gly
    130                 135                 140

Cys Leu Ala Gln Asp Phe Leu Pro Asp Ser Ile Thr Phe Ser Trp Lys
145                 150                 155                 160

Tyr Lys Asn Asn Ser Asp Ile Ser Ser Thr Arg Gly Phe Pro Ser Val
                165                 170                 175

Leu Arg Gly Gly Lys Tyr Ala Ala Thr Ser Gln Val Leu Leu Pro Ser
            180                 185                 190

Lys Asp Val Met Gln Gly Thr Asp Glu His Val Val Cys Lys Val Gln
        195                 200                 205

His Pro Asn Gly Asn Lys Glu Lys Asn Val Pro Leu Pro Val
    210                 215                 220

<210> SEQ ID NO 79
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

Glu Ile Val Leu Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Arg
                85                  90                  95

Thr Phe Gly Gln Gly Thr Lys Val Glu Ile Lys Arg Ala Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 80
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

Asp Val Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Thr Tyr
            20                  25                  30

Leu Ala Trp Tyr Gln Gln Lys Pro Gly Gln Ala Pro Thr Leu Leu Ile
        35                  40                  45

Tyr Asp Ala Ser Asn Arg Ala Thr Gly Ile Pro Ala Arg Phe Ser Gly
    50                  55                  60

Arg Gly Ser Gly Thr Asp Phe Thr Leu Thr Ile Ser Ser Leu Glu Pro
65                  70                  75                  80

Glu Asp Phe Ala Val Tyr Tyr Cys His Gln Arg Ser Asp Trp Pro Pro
                85                  90                  95

Val Thr Phe Gly Gln Gly Thr Arg Leu Glu Ile Lys Arg Thr Val Ala
                100                 105                 110

Ala Pro Ser Val Phe Ile Phe Pro Pro Ser Asp Glu Gln Leu Lys Ser
            115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 81
<211> LENGTH: 220
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

Gln Ser Val Leu Thr Gln Pro Pro Ser Leu Ser Ala Ser Pro Gly Ala
1               5                   10                  15

Ser Ala Ser Leu Thr Cys Thr Leu Arg Ser Gly Ile Asn Val Gly Thr
            20                  25                  30

Tyr Arg Ile Tyr Trp Tyr Gln Gln Lys Pro Gly Ser Pro Pro Gln Tyr
        35                  40                  45

Leu Leu Arg Tyr Lys Ser Asp Ser Asp Lys Gln Gly Ser Gly Val
50                  55                  60

Pro Ser Arg Phe Ser Gly Ser Lys Asp Ala Ser Ala Asn Ala Gly Ile
65                  70                  75                  80

Leu Leu Ile Ser Gly Leu Gln Ser Glu Asp Glu Ala Asp Tyr Tyr Cys
                85                  90                  95

Met Ile Trp His Ser Ser Ala Val Val Phe Gly Gly Gly Thr Lys Leu
            100                 105                 110

Thr Val Leu Gly Gln Pro Lys Ala Ala Pro Ser Val Thr Leu Phe Pro
        115                 120                 125

Pro Ser Ser Glu Glu Leu Gln Ala Asn Lys Ala Thr Leu Val Cys Leu
130                 135                 140

Ile Ser Asp Phe Tyr Pro Gly Ala Val Thr Val Ala Trp Lys Ala Asp
145                 150                 155                 160

Ser Ser Pro Val Lys Ala Gly Val Glu Thr Thr Thr Pro Ser Lys Gln
                165                 170                 175

Ser Asn Asn Lys Tyr Ala Ala Ser Ser Tyr Leu Ser Leu Thr Pro Glu
            180                 185                 190

Gln Trp Lys Ser His Arg Ser Tyr Ser Cys Gln Val Thr His Glu Gly
        195                 200                 205

Ser Thr Val Glu Lys Thr Val Ala Pro Thr Glu Cys
210                 215                 220

<210> SEQ ID NO 82
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

Glu Thr Thr Leu Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Ile Thr Phe Gly Gln Gly Thr Arg Leu Glu Ile Lys
            100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 83
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83

Gln Ser Val Leu Ile Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
            35                  40                  45

Ile Tyr Asp Asn Asn Lys Arg Pro Ser Gly Ile Pro Val Arg Phe Ser
        50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Val Phe Gly Thr Gly Thr Lys Val Thr Val Leu Gly Gln Pro
            100                 105                 110

Lys Ala Asn Pro Thr Val Thr Leu Phe Pro Pro Ser Ser Glu Glu Leu
            115                 120                 125

Gln Ala Asn Lys Ala Thr Leu Val Cys Leu Ile Ser Asp Phe Tyr Pro

```
                130                 135                 140
Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
                180                 185                 190

Ser Tyr Ser Cys Gln Val Thr His Glu Gly Ser Thr Val Glu Lys Thr
                195                 200                 205

Val Ala Pro Thr Glu Cys Ser
    210                 215

<210> SEQ ID NO 84
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

Asp Ile Val Met Thr Gln Thr Pro Ser Ser Leu Ser Ala Ser Val Gly
1               5                   10                  15

Asp Arg Val Thr Ile Thr Cys Arg Ala Ser Gln Gly Ile Ser Ser Trp
                20                  25                  30

Leu Ala Trp Tyr Gln Gln Lys Pro Glu Lys Ala Pro Arg Ser Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ile Ser Tyr Pro Tyr
                85                  90                  95

Thr Phe Gly Gln Gly Thr Lys Leu Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
    210

<210> SEQ ID NO 85
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 85

Glu Thr Thr Leu Thr Gln Ser Pro Ala Thr Leu Ser Leu Ser Pro Gly
1               5                   10                  15

Asp Arg Ala Thr Leu Ser Cys Arg Ala Ser Gln Ser Val Ser Ser Tyr
            20                  25                  30

Leu Val Trp Tyr Gln Gln Lys Phe Gly Gln Ala Pro Arg Leu Leu Ile
        35                  40                  45

Tyr Ala Ala Ser Asn Arg Ala Ala Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Ile
                85                  90                  95

Thr Phe Gly Pro Gly Thr Lys Val Asp Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 86
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 86
caggtgcagc tggtggagtc tgggggaggc ttggtccagc ctggagggtc cctgagactc      60
tcctgtgcag tctctggatt caccttcagt gaccactaca tggactgggt ccgccaggct    120
ccagggaagg ggctggagtg ggttggccgt attagaaaca agctaacag ttacaccaca     180 gaatacgccg cgtctgtgaa aggcagattc accatctcaa gagatgaatc aaagaggtca    240
ctgtatctgc aaatgaacag cctgaaaacc gaggacacag ccgtgtatta ctgtgctaga    300
gtatcctact acgctatgga cgtctggggc caagggacca cggtcaccgt ctcctca       357

<210> SEQ ID NO 87
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 87
cagctgcagc tggtggaatc tgggggaggc ttggtccagc ctggagggtc cctgagactc      60

```
tcctgtgcag cctctggatt caccttcagt gaccaataca tggactggat ccgccaggct    120
ccagggaagg gactggagtg ggttggccgt attagaaaca aagctaacag gtataccaca    180
gactacgccg cgtctgtgaa aggcagattc atcatctcaa gagatgattc aaagaactca    240
ctgtatctgc aaatgaacag gctgagaatt gaagacacgg ccgtgtatta ctgtgttaga    300
gttacagcag tggctctaga ctattggggc cagggaaccc tggtcaccgt ctcctca       357
```

<210> SEQ ID NO 88
<211> LENGTH: 375
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 88

```
caggtgcagc tgcagcagtc tggagctgag gtgaagaagc ctggggcctc agtgaaggtc    60
tcctgcaagg ctactggtta cacctttacc agctatggta tcagctgggt gcgacaggcc    120
cctggacaag ggcttgagtg gatgggatgg atcagcgctt acaatggtaa cacaaactac    180
gcacagaagc tccagggcag ggtcaccatg accacagaca tccacgag cacagcctac    240 atggagctga ggagcctgag atctgacgac acggccgtgt attactgtgc gagaggcggg    300
gggactacgg tccttgacta ctaccgctac ggtatggacg tctggggcca agggaccacg    360
gtcaccgtct cctca                                                    375
```

<210> SEQ ID NO 89
<211> LENGTH: 375
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 89

```
caggtgcagc tggtgcagtc tggggctgag gtgaagaagc ctggggcctc agtgaaggtc    60
tcctgcaagg cttctggata caccttcacc agttatgata tcaactgggt gcgacaggcc    120
actggacaag ggcttgagtg gatgggatgg atgaaccta acagtggtaa cacaggctat    180
gcacagaagt tccagggcag agtcaccatg accaggaaca cctccataag cacagcctac    240
atggagctga gcagcctgag atctgaggac acggccgtgt attactgtgc gagagggtgg    300
aggtatagca gcagctggta ccggaaggtc cggttcgacc cctggggcca gggaaccctg    360
gtcaccgtct cctca                                                    375
```

<210> SEQ ID NO 90
<211> LENGTH: 366
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 90

```
caggtgcagc tggtggggtc tggggctgag gtgaagaagc ctggggcctc agtgaaggtc    60
tcctgcaagg cttctggata caccttcacc agttatgata tcaactgggt gcgacaggcc    120
actggacaag ggcttgagtg gatgggatgg atgaaccta acagtggtaa cacaggctat    180
gcacagaagt tccagggcag agtcaccatg accaggaaca cctccataag cacagcctac    240
```

```
atggagctga gcagcctgag atctgaggac acggccgtgt attactgtgc gagagcgaat      300
aggaaagggg cacgaacgcg ggcctttgac tactggggcc agggaaccct ggtcaccgtc      360
tcctca                                                                 366
```

<210> SEQ ID NO 91
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 91

```
gaggtgcagc tgttggagtc tgggggaggc ttggtacagc ctgggggtc cctgagactc       60 tcctgtgcag cctctggatt cacctttgat agctatgcca tgagctgggt ccgccaggct     120
ccagggaagg ggctggagtg ggtctcagct attagtggta gtggtgatag cacatactac     180
gcagactccg tgaagggccg gttcagcatc tccagagaca attccaagaa cacgctgtat     240
ctgcaaatga acagcctgag agccgaggac acggccgtat attactgtgc gatcagacgt     300
gaatatagtg gctacgctcc ctttgactac tggggccagg gaaccctggt caccgtctcc     360
tca                                                                   363
```

<210> SEQ ID NO 92
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 92

```
caggtacagc tggtgcaatc tggggggaggc ttggtccagc ctggggagac cctgagactc      60
tcctgtgaag cctctggatt cacttttagg agctactaca tgagctgggt ccgccaggct     120
ccacggaagg ggctggagtg ggtggccagt ataaaccaac atggaagtga gaaatactat     180
gtggactctg tgaagggccg attcaccatc tccagagaca cgccaagaa ctcactctat      240 ctgcaaatga tcagcctgag agccgaggac acggccgtgt attactgtgc gagagatggg     300
gacagaacaa cggactactg ggggccaggga accctggtca ccgtctcctc a             351
```

<210> SEQ ID NO 93
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 93

```
gaaattgtgt tgacccagtc tccatcctcc ctgtctgcat ctgtaggaga cagagtcacc       60
atcacttgcc gggcaagtca gagcattagc agctatttaa attggtatca gcagaaacca     120
gggaaagccc ctaagctcct gatctatgct gcatccagtt tgcaaagtgg ggtcccatca     180
aggttcagtg gcagtggatc tgggacagat ttcactctca ccatcagcag tctgcaacct     240
gaagattttg caacttacta ctgtcaacag agttacagta cccctcggac gttcggccaa     300
gggaccaagg tggaaatcaa a                                                321
```

```
<210> SEQ ID NO 94
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 94
gatgttgtga tgacccagtc tccagccacc ctgtctttgt ctccagggga aagagccacc    60
ctctcttgca gggccagtca gagtgttagt acctacttag cctggtacca gcagaaacct   120
ggccaggctc ccaccctcct catctatgat gcatccaaca gggccactgg catcccagcc   180
aggttcagtg gccgtgggtc ggggacagac ttcactctca ccatcagcag cctagagcct   240
gaagattttg cagtttatta ctgtcaccaa cgtagcgact ggcctccggt caccttcggc   300
caagggacac gactggagat taaa                                          324

<210> SEQ ID NO 95
<211> LENGTH: 345
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 95
cagtctgtgt tgacgcagcc gccttccctc tctgcatctc ctggagcatc agccagtctc    60
acctgcacct tacgcagtgg catcaatgtt ggtacctaca ggatatactg gtaccagcag   120
aagccaggga gtcctcccca gtatctcctg aggtacaaat cagactcaga taagcagcag   180
ggctctggag tccccagccg cttctctgga tccaaagatg cttcggccaa tgcagggatt   240
ttactcatct ctgggctcca gtctgaggat gaggctgact attactgtat gatttggcac   300
agcagcgctg tggtattcgg cggagggacc aagctgaccg tccta                   345

<210> SEQ ID NO 96
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 96
gaaacgacac tcacgcagtc tccactctcc ctgcccgtca cccctggaga gccggcctcc    60
atctcctgca ggtctagtca gagcctcctg catagtaatg gatacaacta tttggattgg   120
tacctgcaga agccagggca gtctccacag ctcctgatct atttgggttc taatcgggcc   180
tccggggtcc ctgacaggtt cagtggcagt ggatcaggca cagattttac actgaaaatc   240
agcagagtgg aggctgagga tgttggggtt tattactgca tgcaagctct acaaactccg   300
atcaccttcg gccaagggac acgactggag attaaa                             336

<210> SEQ ID NO 97
<211> LENGTH: 327
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 97
```

```
cagtctgtcc tgattcagcc tccctcagtg tctgcggccc caggacagaa ggtcaccatc    60
tcctgctctg gaagcagctc caacattggg aataattatg tatcctggta ccagcagctc   120
ccaggaacag cccccaaact cctcatttat gacaataata gcgaccctca gggattcct   180 gtccgattct ctggctccaa gtctggcacg tcagccaccc tgggcatcac cggactccag   240
actggggacg aggccgatta ttactgcgga acatgggata gcagcctgag tgctgtcttc   300
ggaactggga ccaaggtcac cgtccta                                       327
```

<210> SEQ ID NO 98
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 98

```
gatattgtga tgactcagac tccatcctca ctgtctgcat ctgtaggaga cagagtcacc    60
atcacttgtc gggcgagtca gggtattagc agctggttag cctggtatca gcagaaacca   120
gagaaagccc ctaggtccct gatctatgct gcgtccagtt tgcaaagtgg ggtcccatca   180
aggttcagcg gcagtggatc tgggacagat ttcactctca ccatcagcag cctgcagcct   240
gaagattttg caacttatta ctgccaacag tatattagtt acccgtacac ttttggccag   300
gggaccaagc tggagatcaa a                                             321
```

<210> SEQ ID NO 99
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 99

```
gaaacgacac tcacgcagtc tccagccacc ctgtctttgt ctccagggga cagagccacc    60
ctctcctgca gggccagtca gagtgttagc agctacttag tctggtacca acagaaattt   120
ggtcaggctc ccaggctcct catctatgct gcatccaaca gggccgctgg catcccagcc   180
aggttcagtg gcagtgggtc tgggacagac ttcactctca ccatcagcag cctagagcct   240
gaagattttg cagtttatta ctgtcagcag cgtagcaact ggccgatcac tttcggccct   300
gggaccaaag tggatatcaa a                                             321
```

<210> SEQ ID NO 100
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 100

```
Gln Val Gln Leu Val Glu Ser Gly Gly Gly Leu Val Gln Pro Gly Gly
1               5                   10                  15

Ser Leu Arg Leu Ser Cys Ala Val Ser Gly Phe Thr Phe Ser Asp His
            20                  25                  30

Tyr Met Asp Trp Val Arg Gln Ala Pro Gly Lys Gly Leu Glu Trp Val
        35                  40                  45

Gly Arg Ile Arg Asn Lys Ala Asn Ser Tyr Thr Thr Glu Tyr Ala Ala
```

```
                    50                  55                  60
Ser Val Lys Gly Arg Phe Thr Ile Ser Arg Asp Glu Ser Lys Arg Ser
 65                  70                  75                  80

Leu Tyr Leu Gln Met Asn Ser Leu Lys Thr Glu Asp Thr Ala Val Tyr
                    85                  90                  95

Tyr Cys Ala Arg Val Ser Tyr Tyr Ala Met Asp Val Trp Gly Gln Gly
                100                 105                 110

Thr Thr Val Thr Val Ser Ser
            115

<210> SEQ ID NO 101
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 101

Gln Leu Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Asp Gln
                 20                  25                  30

Tyr Met Asp Trp Ile Arg Gln Ala Pro Gly Lys Gly Leu Glu Trp Val
             35                  40                  45

Gly Arg Ile Arg Asn Lys Ala Asn Arg Tyr Thr Thr Asp Tyr Ala Ala
         50                  55                  60

Ser Val Lys Gly Arg Phe Ile Ile Ser Arg Asp Asp Ser Lys Asn Ser
 65                  70                  75                  80

Leu Tyr Leu Gln Met Asn Arg Leu Arg Ile Glu Asp Thr Ala Val Tyr
                    85                  90                  95

Tyr Cys Val Arg Val Thr Ala Val Ala Leu Asp Tyr Trp Gly Gln Gly
                100                 105                 110

Thr Leu Val Thr Val Ser Ser
            115

<210> SEQ ID NO 102
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 102

Gln Val Gln Leu Gln Gln Ser Gly Ala Glu Val Lys Lys Pro Gly Ala
  1               5                  10                  15

Ser Val Lys Val Ser Cys Lys Ala Thr Gly Tyr Thr Phe Thr Ser Tyr
                 20                  25                  30

Gly Ile Ser Trp Val Arg Gln Ala Pro Gly Gln Gly Leu Glu Trp Met
             35                  40                  45

Gly Trp Ile Ser Ala Tyr Asn Gly Asn Thr Asn Tyr Ala Gln Lys Leu
         50                  55                  60

Gln Gly Arg Val Thr Met Thr Thr Asp Thr Ser Thr Ser Thr Ala Tyr
 65                  70                  75                  80

Met Glu Leu Arg Ser Leu Arg Ser Asp Asp Thr Ala Val Tyr Tyr Cys
                    85                  90                  95

Ala Arg Gly Gly Gly Thr Thr Val Leu Asp Tyr Tyr Arg Tyr Gly Met
```

```
                100               105               110
Asp Val Trp Gly Gln Gly Thr Thr Val Thr Val Ser Ser
            115               120               125

<210> SEQ ID NO 103
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 103

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asp Ile Asn Trp Val Arg Gln Ala Thr Gly Gln Gly Leu Glu Trp Met
        35                  40                  45

Gly Trp Met Asn Pro Asn Ser Gly Asn Thr Gly Tyr Ala Gln Lys Phe
    50                  55                  60

Gln Gly Arg Val Thr Met Thr Arg Asn Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Trp Arg Tyr Ser Ser Ser Trp Tyr Arg Lys Val Arg Phe
            100                 105                 110

Asp Pro Trp Gly Gln Gly Thr Leu Val Thr Val Ser Ser
        115                 120                 125

<210> SEQ ID NO 104
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 104

Gln Val Gln Leu Val Gly Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asp Ile Asn Trp Val Arg Gln Ala Thr Gly Gln Gly Leu Glu Trp Met
        35                  40                  45

Gly Trp Met Asn Pro Asn Ser Gly Asn Thr Gly Tyr Ala Gln Lys Phe
    50                  55                  60

Gln Gly Arg Val Thr Met Thr Arg Asn Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Asn Arg Lys Gly Ala Arg Thr Arg Ala Phe Asp Tyr Trp
            100                 105                 110

Gly Gln Gly Thr Leu Val Thr Val Ser Ser
        115                 120

<210> SEQ ID NO 105
<211> LENGTH: 121
<212> TYPE: PRT
```

```
<213> ORGANISM: Artificial Sequence
<220> FEATURE:
<223> OTHER INFORMATION: Description of Artificial Sequence: Synthetic
      polypeptide

<400> SEQUENCE: 105

Gln Ile Thr Leu Arg Glu Ser Gly Gly Gly Leu Val Gln Pro Gly Gly
1               5                   10                  15

Ser Leu Arg Leu Ser Cys Ala Ala Ser Gly Phe Thr Phe Asp Ser Tyr
                20                  25                  30

Ala Met Ser Trp Val Arg Gln Ala Pro Gly Lys Gly Leu Glu Trp Val
            35                  40                  45

Ser Ala Ile Ser Gly Ser Gly Asp Ser Thr Tyr Tyr Ala Asp Ser Val
        50                  55                  60

Lys Gly Arg Phe Ser Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Arg Arg Glu Tyr Ser Gly Tyr Ala Pro Phe Asp Tyr Trp Gly
                100                 105                 110

Gln Gly Thr Leu Val Thr Val Ser Ser
            115                 120

<210> SEQ ID NO 106
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 106

Gln Val Gln Leu Val Gln Ser Gly Gly Gly Leu Val Gln Pro Gly Glu
1               5                   10                  15

Thr Leu Arg Leu Ser Cys Glu Ala Ser Gly Phe Thr Phe Arg Ser Tyr
                20                  25                  30

Tyr Met Ser Trp Val Arg Gln Ala Pro Arg Lys Gly Leu Glu Trp Val
            35                  40                  45

Ala Ser Ile Asn Gln His Gly Ser Glu Lys Tyr Tyr Val Asp Ser Val
        50                  55                  60

Lys Gly Arg Phe Thr Ile Ser Arg Asp Asn Ala Lys Asn Ser Leu Tyr
65                  70                  75                  80

Leu Gln Met Ile Ser Leu Arg Ala Glu Asp Thr Ala Val Tyr Tyr Cys
                85                  90                  95

Ala Arg Asp Gly Asp Arg Thr Thr Asp Tyr Trp Gly Gln Gly Thr Leu
                100                 105                 110

Val Thr Val Ser Ser
            115

<210> SEQ ID NO 107
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 107

Glu Ile Val Leu Thr Gln Ser Pro Ser Ser Leu Ser Ala Ser Val Gly
1               5                   10                  15
```

```
Asp Arg Val Thr Ile Thr Cys Arg Ala Ser Gln Ser Ile Ser Ser Tyr
                20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Pro Arg
                85                  90                  95

Thr Phe Gly Gln Gly Thr Lys Val Glu Ile Lys
                100                 105
```

<210> SEQ ID NO 108
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 108

```
Asp Val Val Met Thr Gln Ser Pro Ala Thr Leu Ser Leu Ser Pro Gly
1               5                  10                  15

Glu Arg Ala Thr Leu Ser Cys Arg Ala Ser Gln Ser Val Ser Thr Tyr
                20                  25                  30

Leu Ala Trp Tyr Gln Gln Lys Pro Gly Gln Ala Pro Thr Leu Leu Ile
            35                  40                  45

Tyr Asp Ala Ser Asn Arg Ala Thr Gly Ile Pro Ala Arg Phe Ser Gly
 50                  55                  60

Arg Gly Ser Gly Thr Asp Phe Thr Leu Thr Ile Ser Ser Leu Glu Pro
 65                  70                  75                  80

Glu Asp Phe Ala Val Tyr Tyr Cys His Gln Arg Ser Asp Trp Pro Pro
                85                  90                  95

Val Thr Phe Gly Gln Gly Thr Arg Leu Glu Ile Lys
                100                 105
```

<210> SEQ ID NO 109
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 109

```
Gln Ser Val Leu Thr Gln Pro Pro Ser Leu Ser Ala Ser Pro Gly Ala
1               5                  10                  15

Ser Ala Ser Leu Thr Cys Thr Leu Arg Ser Gly Ile Asn Val Gly Thr
                20                  25                  30

Tyr Arg Ile Tyr Trp Tyr Gln Gln Lys Pro Gly Ser Pro Pro Gln Tyr
            35                  40                  45

Leu Leu Arg Tyr Lys Ser Asp Ser Asp Lys Gln Gly Ser Gly Val
 50                  55                  60

Pro Ser Arg Phe Ser Gly Ser Lys Asp Ala Ser Ala Asn Ala Gly Ile
 65                  70                  75                  80

Leu Leu Ile Ser Gly Leu Gln Ser Glu Asp Glu Ala Asp Tyr Tyr Cys
                85                  90                  95
```

```
Met Ile Trp His Ser Ser Ala Val Val Phe Gly Gly Gly Thr Lys Leu
            100                 105                 110

Thr Val Leu
        115

<210> SEQ ID NO 110
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 110

Glu Thr Thr Leu Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Ile Thr Phe Gly Gln Gly Thr Arg Leu Glu Ile Lys
            100                 105                 110

<210> SEQ ID NO 111
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 111

Gln Ser Val Leu Ile Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Val Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Val Phe Gly Thr Gly Thr Lys Val Thr Val Leu
            100                 105

<210> SEQ ID NO 112
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 112

Asp Ile Val Met Thr Gln Thr Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Arg Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ile Ser Tyr Pro Tyr
                85                  90                  95

Thr Phe Gly Gln Gly Thr Lys Leu Glu Ile Lys
            100                 105

<210> SEQ ID NO 113
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 113

Glu Thr Thr Leu Thr Gln Ser Pro Ala Thr Leu Ser Leu Ser Pro Gly
1               5                   10                  15

Asp Arg Ala Thr Leu Ser Cys Arg Ala Ser Gln Ser Val Ser Ser Tyr
            20                  25                  30

Leu Val Trp Tyr Gln Gln Lys Phe Gly Gln Ala Pro Arg Leu Leu Ile
        35                  40                  45

Tyr Ala Ala Ser Asn Arg Ala Ala Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Ile
                85                  90                  95

Thr Phe Gly Pro Gly Thr Lys Val Asp Ile Lys
            100                 105

<210> SEQ ID NO 114
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 114

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asp Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Asp Ser Thr Tyr Tyr Ala Asp Ser Val
    50                  55                  60

-continued

```
Lys Gly Arg Phe Ser Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Ile Arg Arg Glu Tyr Ser Gly Tyr Ala Pro Phe Asp Tyr Trp Gly
            100                 105                 110

Gln Gly Thr Leu Val Thr Val Ser Ser
        115                 120

<210> SEQ ID NO 115
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 115

Gln Val Thr Leu Lys Glu Ser Gly Gly Gly Leu Val Gln Pro Gly Gly
  1               5                  10                  15

Phe Leu Arg Leu Ser Cys Ala Ala Ser Gly Phe Thr Phe Asp Ser Tyr
                 20                  25                  30

Ala Met Ser Trp Val Arg Gln Ala Pro Gly Lys Gly Leu Glu Trp Val
             35                  40                  45

Ser Ala Ile Ser Gly Ser Gly Asp Ser Thr Tyr Tyr Ala Asp Ser Val
     50                  55                  60

Lys Gly Arg Phe Ser Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Ile Arg Arg Glu Tyr Ser Gly Tyr Ala Pro Phe Asp Tyr Trp Gly
            100                 105                 110

Gln Gly Thr Leu Val Thr Val Ser Ser
        115                 120

<210> SEQ ID NO 116
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 116

Gln Val Thr Leu Lys Glu Ser Gly Gly Gly Leu Val Gln Pro Gly Gly
  1               5                  10                  15

Ser Leu Arg Leu Ser Cys Ala Ala Ser Gly Phe Thr Phe Asp Ser Tyr
                 20                  25                  30

Ala Met Ser Trp Val Arg Gln Ala Pro Gly Lys Gly Leu Glu Trp Val
             35                  40                  45

Ser Ala Ile Ser Gly Ser Gly Asp Ser Thr Tyr Tyr Ala Asp Ser Val
     50                  55                  60

Lys Gly Arg Phe Ser Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Ile Arg Arg Glu Tyr Ser Gly Tyr Ala Pro Phe Asp Tyr Trp Gly
            100                 105                 110
```

```
Lys Gly Thr Leu Val Thr Val Ser Ser
        115                 120
```

<210> SEQ ID NO 117
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 117

```
Gln Ile Thr Leu Arg Glu Ser Gly Gly Leu Val Gln Pro Gly Gly
1               5                   10                  15

Ser Leu Arg Leu Ser Cys Ala Ala Ser Gly Phe Thr Phe Asp Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly His Ser Thr Tyr Tyr Ala Asp Ser Val
    50                  55                  60

Lys Gly Arg Phe Ser Ile Ser Arg Asp Asn Ser Lys Asn Thr Leu Tyr
65                  70                  75                  80

Leu Gln Met Asn Asn Leu Arg Ala Glu Asp Thr Ala Val Tyr Tyr Cys
                85                  90                  95

Ala Ile Arg Arg Glu Tyr Ser Gly Tyr Ala Pro Phe Asp Tyr Trp Gly
            100                 105                 110

Gln Gly Thr Leu Val Thr
        115
```

<210> SEQ ID NO 118
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 118

```
Gln Ile Thr Leu Arg Glu Ser Gly Gly Gly Leu Val Gln Pro Gly Gly
1               5                   10                  15

Ser Leu Arg Leu Ser Cys Ala Ala Ser Gly Phe Thr Phe Asp Ser Tyr
            20                  25                  30

Ala Met Ser Trp Val Cys Gln Ala Pro Gly Lys Gly Leu Glu Trp Val
        35                  40                  45

Ser Ala Ile Ser Gly Ser Gly Asp Ser Thr Tyr Tyr Ala Asp Ser Val
    50                  55                  60

Lys Gly Arg Phe Ser Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Arg Arg Glu Tyr Ser Gly Tyr Thr Pro Phe Asp Tyr Trp Gly
            100                 105                 110

Gln Gly Thr Leu Val Thr Val Ser Ser
        115                 120
```

<210> SEQ ID NO 119
<211> LENGTH: 121
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 119

Gln Ile Thr Leu Lys Glu Ser Gly Gly Gly Leu Val Gln Pro Gly Gly
1               5                   10                  15

Ser Leu Arg Leu Ser Cys Ala Ala Ser Gly Phe Thr Phe Asp Ser Tyr
            20                  25                  30

Ala Met Ser Trp Ile Arg Gln Ala Pro Gly Lys Gly Leu Glu Trp Val
        35                  40                  45

Ser Ala Ile Ser Gly Ser Gly Asp Ser Thr Tyr Tyr Ala Tyr Ser Val
    50                  55                  60

Lys Gly Arg Phe Ser Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Arg Arg Glu Tyr Ser Gly Tyr Ala Pro Phe Asp Tyr Trp Gly
            100                 105                 110

Gln Gly Thr Leu Val Thr Val Ser Ser
        115                 120

<210> SEQ ID NO 120
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 120

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asp Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Asp Ser Thr Tyr Tyr Ala Asp Ser Val
    50                  55                  60

Lys Gly Arg Phe Ser Ile Ser Arg Asp Asn Ser Lys Asn Thr Leu Tyr
65                  70                  75                  80

Leu Gln Met Asn Ser Leu Arg Ala Glu Asp Ala Ala Val Tyr Tyr Cys
                85                  90                  95

Ala Ile Arg Arg Glu Tyr Ser Gly Tyr Ala Pro Phe Asp Tyr Trp Gly
            100                 105                 110

Gln Gly Thr Leu Val Thr Val Ser Ser
        115                 120

<210> SEQ ID NO 121
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 121

Gln Val Thr Leu Arg Glu Ser Val Gly Gly Leu Val Gln Pro Gly Gly
1               5                   10                  15

Ser Leu Arg Leu Ser Cys Ala Ala Ser Gly Phe Thr Phe Asp Ser Tyr

```
            20                  25                  30
Ala Met Ser Trp Val Arg Gln Ala Pro Gly Lys Gly Leu Glu Trp Val
                35                  40                  45
Ser Ala Ile Ser Gly Ser Gly Asp Ser Thr Tyr Tyr Ala Asp Ser Met
         50                  55                  60
Lys Gly Arg Phe Ser Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Ile Arg Arg Glu Tyr Ser Gly Tyr Ala Pro Phe Asp Tyr Trp Gly
            100                 105                 110
Gln Gly Thr Leu Val Thr Val Ser Ser
            115                 120

<210> SEQ ID NO 122
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 122

Gln Val Gln Leu Leu Glu Ser Gly Gly Gly Leu Val Gln Pro Gly Gly
 1               5                  10                  15
Ser Leu Arg Leu Ser Cys Ala Ala Ser Gly Phe Thr Phe Asp Ser Tyr
            20                  25                  30
Ala Met Ser Trp Val Arg Gln Ala Pro Gly Lys Gly Leu Glu Trp Val
                35                  40                  45
Ser Ala Ile Ser Gly Ser Gly Ala Ser Thr Tyr Tyr Ala Asp Ser Val
         50                  55                  60
Lys Gly Arg Phe Ser Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Ile Arg Arg Glu Tyr Ser Gly Tyr Ala Pro Phe Asp Tyr Trp Gly
            100                 105                 110
Gln Gly Thr Leu Val Ile Val Ser Ser
            115                 120

<210> SEQ ID NO 123
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 123

Gln Ile Thr Leu Arg Glu Ser Gly Gly Gly Leu Val Gln Pro Gly Gly
 1               5                  10                  15
Ser Leu Arg Leu Ser Cys Ala Ala Ser Gly Phe Thr Phe Asp Ser Tyr
            20                  25                  30
Ala Met Ser Trp Val Arg Gln Ala Pro Gly Lys Gly Leu Glu Trp Val
                35                  40                  45
Ser Ala Ile Ser Gly Ser Gly His Ser Thr Tyr Tyr Ala Asp Ser Val
         50                  55                  60
Lys Gly Arg Phe Ser Ile Ser Arg Asp Asn Ser Lys Asn Thr Leu Tyr
```

```
                65                  70                  75                  80
Leu Gln Met Asn Asn Leu Arg Ala Glu Asp Thr Ala Val Tyr Tyr Cys
                    85                  90                  95

Ala Ile Arg Arg Glu Tyr Ser Gly Tyr Ala Pro Phe Asp Tyr Trp Gly
                100                 105                 110

Gln Gly Thr Leu Val Thr Val Ser Ser
        115                 120

<210> SEQ ID NO 124
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 124

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asp Ser Tyr
                20                  25                  30

Ala Met Ser Trp Val Arg Gln Ala Pro Gly Lys Gly Leu Glu Trp Val
            35                  40                  45

Ser Ala Ile Ser Gly Ser Gly Arg Ser Thr Tyr Tyr Ala Asp Ser Val
        50                  55                  60

Lys Gly Arg Phe Ser Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                    85                  90                  95

Ala Ile Arg Arg Glu Tyr Ser Gly Tyr Ala Pro Phe Asp Tyr Trp Gly
                100                 105                 110

Gln Gly Thr Leu Val Thr Val Ser Ser
        115                 120

<210> SEQ ID NO 125
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 125

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asp Ser Tyr
                20                  25                  30

Ala Met Ser Trp Val Arg Gln Ala Pro Gly Lys Gly Leu Glu Trp Val
            35                  40                  45

Ser Ala Ile Ser Gly Ser Gly Tyr Ser Thr Tyr Tyr Ala Asp Ser Val
        50                  55                  60

Lys Gly Arg Phe Ser Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                    85                  90                  95

Ala Ile Arg Arg Glu Tyr Ser Gly Tyr Ala Pro Phe Asp Tyr Trp Gly
                100                 105                 110

Gln Gly Thr Leu Val Thr Val Ser Ser
```

<210> SEQ ID NO 126
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 126

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asp Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Phe Ser Thr Tyr Tyr Ala Asp Ser Val
    50                  55                  60

Lys Gly Arg Phe Ser Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Arg Arg Glu Tyr Ser Gly Tyr Ala Pro Phe Asp Tyr Trp Gly
            100                 105                 110

Gln Gly Thr Leu Val Thr Val Ser Ser
        115                 120

<210> SEQ ID NO 127
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 127

Gln Ile Thr Leu Arg Glu Ser Gly Gly Gly Leu Val Gln Pro Gly Gly
1               5                   10                  15

Ser Leu Arg Leu Ser Cys Ala Ala Ser Gly Phe Thr Phe Asp Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly His Ser Thr Tyr Tyr Ala Asp Ser Val
    50                  55                  60

Lys Gly Arg Phe Ser Ile Ser Arg Asp Asn Ser Lys Asn Thr Leu Tyr
65                  70                  75                  80

Leu Gln Met Asn Asn Leu Arg Ala Glu Asp Thr Ala Val Tyr Tyr Cys
                85                  90                  95

Ala Ile Arg Arg Glu Tyr Ser Gly Tyr Thr Pro Phe Asp Tyr Trp Gly
            100                 105                 110

Gln Gly Thr Leu Val Thr Val Ser Ser
        115                 120

<210> SEQ ID NO 128
<211> LENGTH: 121
<212> TYPE: PRT
<213> ORGANISM: Artificial Sequence
<220> FEATURE:
<223> OTHER INFORMATION: Description of Artificial Sequence: Synthetic -continued polypeptide

<400> SEQUENCE: 128

Gln Ile Thr Leu Lys Glu Ser Gly Gly Gly Leu Val Gln Pro Gly Gly
1               5                   10                  15

Ser Leu Arg Leu Ser Cys Ala Ala Ser Gly Phe Thr Phe Asp Ser Tyr
            20                  25                  30

Ala Met Ser Trp Ile Arg Gln Ala Pro Gly Lys Gly Leu Glu Trp Val
        35                  40                  45

Ser Ala Ile Ser Gly Ser Gly Ala Ser Thr Tyr Tyr Ala Tyr Ser Val
    50                  55                  60

Lys Gly Arg Phe Ser Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Arg Arg Glu Tyr Ser Gly Tyr Ala Pro Phe Asp Tyr Trp Gly
            100                 105                 110

Gln Gly Thr Leu Val Thr Val Ser Ser
        115                 120

<210> SEQ ID NO 129
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 129

Gln Ile Thr Leu Lys Glu Ser Gly Gly Gly Leu Val Gln Pro Gly Gly
1               5                   10                  15

Ser Leu Arg Leu Ser Cys Ala Ala Ser Gly Phe Thr Phe Asp Ser Tyr
            20                  25                  30

Ala Met Ser Trp Ile Arg Gln Ala Pro Gly Lys Gly Leu Glu Trp Val
        35                  40                  45

Ser Ala Ile Ser Gly Ser Gly His Ser Thr Tyr Tyr Ala Tyr Ser Val
    50                  55                  60

Lys Gly Arg Phe Ser Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Arg Arg Glu Tyr Ser Gly Tyr Ala Pro Phe Asp Tyr Trp Gly
            100                 105                 110

Gln Gly Thr Leu Val Thr Val Ser Ser
        115                 120

<210> SEQ ID NO 130
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 130

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asp Ser Tyr
            20                  25                  30

Ala Met Ser Trp Val Arg Gln Ala Pro Gly Lys Gly Leu Glu Trp Val
            35                  40                  45

Ser Ala Ile Ser Gly Ser Gly Ala Ser Thr Tyr Tyr Ala Asp Ser Val
    50                  55                  60

Lys Gly Arg Phe Ser Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Arg Arg Glu Tyr Ser Gly Tyr Thr Pro Phe Asp Tyr Trp Gly
                100                 105                 110

Gln Gly Thr Leu Val Thr Val Ser Ser
            115                 120

<210> SEQ ID NO 131

<400> SEQUENCE: 131

000

<210> SEQ ID NO 132

<400> SEQUENCE: 132

000

<210> SEQ ID NO 133

<400> SEQUENCE: 133

000

<210> SEQ ID NO 134

<400> SEQUENCE: 134

000

<210> SEQ ID NO 135

<400> SEQUENCE: 135

000

<210> SEQ ID NO 136

<400> SEQUENCE: 136

000

<210> SEQ ID NO 137

<400> SEQUENCE: 137

000

<210> SEQ ID NO 138

<400> SEQUENCE: 138

000

<210> SEQ ID NO 139

<400> SEQUENCE: 139

000

<210> SEQ ID NO 140

<400> SEQUENCE: 140

000

<210> SEQ ID NO 141
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Ala Ile Ser Gly Ser Gly Ala Ser Thr Tyr Tyr Ala Asp Ser Val Lys
1               5                   10                  15

Gly

<210> SEQ ID NO 142
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term NH2
<220> FEATURE:
<221> NAME/KEY: MOD_RES
<222> LOCATION: (2)..(2)
<223> OTHER INFORMATION: D-alanine
<220> FEATURE:
<221> NAME/KEY: MOD_RES
<222> LOCATION: (4)..(4)
<223> OTHER INFORMATION: Cyclohexylalanine
<220> FEATURE:
<221> NAME/KEY: MOD_RES
<222> LOCATION: (14)..(14)
<223> OTHER INFORMATION: D-alanine
<220> FEATURE:
<221> NAME/KEY: MOD_RES
<222> LOCATION: (15)..(15)
<223> OTHER INFORMATION: n-Acetylgalactosamine modified residue
<220> FEATURE:
<221> NAME/KEY: MOD_RES
<222> LOCATION: (16)..(16)
<223> OTHER INFORMATION: n-Acetylgalactosamine modified residue
<220> FEATURE:
<221> NAME/KEY: MOD_RES
<222> LOCATION: (17)..(17)
<223> OTHER INFORMATION: n-Acetylgalactosamine modified residue
<220> FEATURE:
<223> OTHER INFORMATION: C-term CONH2

<400> SEQUENCE: 142

Gly Ala Lys Ala Val Ala Ala Trp Thr Leu Lys Ala Ala Ala Thr Thr
1               5                   10                  15

Thr Gly

<210> SEQ ID NO 143

<400> SEQUENCE: 143

000

<210> SEQ ID NO 144

```
<400> SEQUENCE: 144

000

<210> SEQ ID NO 145

<400> SEQUENCE: 145

000

<210> SEQ ID NO 146

<400> SEQUENCE: 146

000

<210> SEQ ID NO 147

<400> SEQUENCE: 147

000

<210> SEQ ID NO 148

<400> SEQUENCE: 148

000

<210> SEQ ID NO 149
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

Ile Ser Gly Ser Gly His Ser Thr
1               5

<210> SEQ ID NO 150
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Ile Ser Gly Ser Gly Ala Ser Thr
1               5

<210> SEQ ID NO 151
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Ile Ser Gly Ser Gly Arg Ser Thr
1               5

<210> SEQ ID NO 152
<211> LENGTH: 8
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 152

Ile Ser Gly Ser Gly Tyr Ser Thr
1               5

<210> SEQ ID NO 153
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

Ile Ser Gly Ser Gly Phe Ser Thr
1               5

<210> SEQ ID NO 154
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

Ala Ile Arg Arg Glu Tyr Ser Gly Tyr Thr Pro Phe Asp Tyr
1               5                   10

<210> SEQ ID NO 155
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(5)
<223> OTHER INFORMATION: N-acetylgalactosamine modified residue
<220> FEATURE:
<221> NAME/KEY: MOD_RES
<222> LOCATION: (9)..(9)
<223> OTHER INFORMATION: N-acetylgalactosamine modified residue
<220> FEATURE:
<221> NAME/KEY: MOD_RES
<222> LOCATION: (15)..(16)
<223> OTHER INFORMATION: N-acetylgalactosamine modified residue

<400> SEQUENCE: 155

His Gly Val Thr Ser Ala Pro Asp Thr Arg Pro Ala Pro Gly Ser Thr
1               5                   10                  15

Ala Pro Pro Ala
            20

<210> SEQ ID NO 156
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: N-acetylgalactosamine modified residue
```

```
<220> FEATURE:
<221> NAME/KEY: MOD_RES
<222> LOCATION: (19)..(19)
<223> OTHER INFORMATION: N-acetylgalactosamine modified residue

<400> SEQUENCE: 156

Pro Ala Pro Gly Ser Thr Ala Pro Pro Ala His Gly Val Thr Ser Ala
1               5                   10                  15

Pro Asp Thr Arg Pro Ala Pro Gly
            20

<210> SEQ ID NO 157
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 157

His Gly Val Thr Ser Ala Pro Asp Thr Arg Pro Ala Pro Gly Ser Thr
1               5                   10                  15

Ala Pro Pro Ala
            20

<210> SEQ ID NO 158
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 158

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asp Ser Tyr
            20                  25                  30

Ala Met Ser Trp Val Cys Gln Ala Pro Gly Lys Gly Leu Glu Trp Val
        35                  40                  45

Ser Ala Ile Ser Gly Ser Gly Asp Ser Thr Tyr Tyr Ala Asp Ser Val
    50                  55                  60

Lys Gly Arg Phe Ser Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ile Arg Arg Glu Tyr Ser Gly Tyr Thr Pro Phe Asp Tyr Trp Gly
            100                 105                 110

Gln Gly Thr Leu Val Thr Val Ser Ser
        115                 120

<210> SEQ ID NO 159
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H2N
<220> FEATURE:
<221> NAME/KEY: MOD_RES
<222> LOCATION: (11)..(11)
<223> OTHER INFORMATION: N-acetylgalactosamine modified residue
```

```
<220> FEATURE:
<223> OTHER INFORMATION: C-term OH

<400> SEQUENCE: 159

Lys Pro Ser Thr Pro Pro Thr Pro Ser Pro Ser Cys
1               5                   10

<210> SEQ ID NO 160
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H2N
<220> FEATURE:
<221> NAME/KEY: MOD_RES
<222> LOCATION: (4)..(4)
<223> OTHER INFORMATION: N-acetylgalactosamine modified residue
<220> FEATURE:
<223> OTHER INFORMATION: C-term OH

<400> SEQUENCE: 160

Lys Pro Ser Thr Pro Pro Thr Pro Ser Pro Ser Cys
1               5                   10

<210> SEQ ID NO 161
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (2)..(2)
<223> OTHER INFORMATION: N-acetylgalactosamine modified residue
<220> FEATURE:
<223> OTHER INFORMATION: C-term NH2

<400> SEQUENCE: 161

Pro Thr Thr Thr Pro Leu Lys
1               5

<210> SEQ ID NO 162
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (3)..(3)
<223> OTHER INFORMATION: N-acetylgalactosamine modified residue
<220> FEATURE:
<223> OTHER INFORMATION: C-term NH2

<400> SEQUENCE: 162

Pro Thr Thr Thr Pro Leu Lys
1               5

<210> SEQ ID NO 163
<211> LENGTH: 7
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (4)..(4)
<223> OTHER INFORMATION: N-acetylgalactosamine modified residue
<220> FEATURE:
<223> OTHER INFORMATION: C-term NH2

<400> SEQUENCE: 163

Pro Thr Thr Thr Pro Leu Lys
1               5

<210> SEQ ID NO 164
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (2)..(3)
<223> OTHER INFORMATION: N-acetylgalactosamine modified residue
<220> FEATURE:
<223> OTHER INFORMATION: C-term NH2

<400> SEQUENCE: 164

Pro Thr Thr Thr Pro Leu Lys
1               5

<210> SEQ ID NO 165
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (2)..(2)
<223> OTHER INFORMATION: N-acetylgalactosamine modified residue
<220> FEATURE:
<221> NAME/KEY: MOD_RES
<222> LOCATION: (4)..(4)
<223> OTHER INFORMATION: N-acetylgalactosamine modified residue
<220> FEATURE:
<223> OTHER INFORMATION: C-term NH2

<400> SEQUENCE: 165

Pro Thr Thr Thr Pro Leu Lys
1               5

<210> SEQ ID NO 166
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (3)..(4)
<223> OTHER INFORMATION: N-acetylgalactosamine modified residue
```

```
<220> FEATURE:
<223> OTHER INFORMATION: C-term NH2

<400> SEQUENCE: 166

Pro Thr Thr Thr Pro Leu Lys
1               5

<210> SEQ ID NO 167
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (2)..(4)
<223> OTHER INFORMATION: N-acetylgalactosamine modified residue
<220> FEATURE:
<223> OTHER INFORMATION: C-term NH2

<400> SEQUENCE: 167

Pro Thr Thr Thr Pro Leu Lys
1               5

<210> SEQ ID NO 168
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term NH2

<400> SEQUENCE: 168

Pro Pro Thr Thr Thr Thr Lys Lys Pro
1               5

<210> SEQ ID NO 169
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H2N
<220> FEATURE:
<221> NAME/KEY: MOD_RES
<222> LOCATION: (9)..(9)
<223> OTHER INFORMATION: N-acetylgalactosamine modified residue
<220> FEATURE:
<223> OTHER INFORMATION: C-term OH

<400> SEQUENCE: 169

Gly Thr Thr Pro Ser Pro Val Pro Thr Thr Ser Thr Thr Ser Ala Pro
1               5                   10                  15

<210> SEQ ID NO 170
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<223> OTHER INFORMATION: N-term Ac
<220> FEATURE:
<221> NAME/KEY: MOD_RES
<222> LOCATION: (7)..(7)
<223> OTHER INFORMATION: N-acetylgalactosamine modified residue
<220> FEATURE:
<223> OTHER INFORMATION: C-term NH2

<400> SEQUENCE: 170

Pro Thr Thr Asp Ser Thr Thr Pro Ala Pro Thr Thr Lys
1               5                   10

<210> SEQ ID NO 171
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term NH2

<400> SEQUENCE: 171

Pro Thr Thr Asp Ser Thr Thr Pro Ala Pro Thr Thr Lys
1               5                   10

<210> SEQ ID NO 172
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<221> NAME/KEY: MOD_RES
<222> LOCATION: (3)..(6)
<223> OTHER INFORMATION: N-acetylgalactosamine modified residue
<220> FEATURE:
<223> OTHER INFORMATION: C-term NH2

<400> SEQUENCE: 172

Pro Pro Thr Thr Thr Thr Lys Lys Pro
1               5

<210> SEQ ID NO 173
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H2N
<220> FEATURE:
<221> NAME/KEY: MOD_RES
<222> LOCATION: (6)..(6)
<223> OTHER INFORMATION: N-acetylgalactosamine modified residue
<220> FEATURE:
<223> OTHER INFORMATION: C-term NH2

<400> SEQUENCE: 173

Thr Ser Ala Pro Asp Thr Arg Asp Ala Pro
1               5                   10

<210> SEQ ID NO 174
<211> LENGTH: 10
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H2N
<220> FEATURE:
<223> OTHER INFORMATION: C-term NH2

<400> SEQUENCE: 174

Thr Ser Ala Pro Asp Thr Arg Asp Ala Pro
1               5                   10

<210> SEQ ID NO 175
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H2N
<220> FEATURE:
<221> NAME/KEY: MOD_RES
<222> LOCATION: (4)..(5)
<223> OTHER INFORMATION: N-acetylgalactosamine modified residue
<220> FEATURE:
<223> OTHER INFORMATION: C-term NH2

<400> SEQUENCE: 175

Ala Pro Gly Ser Thr Ala Pro Pro
1               5

<210> SEQ ID NO 176
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H2N
<220> FEATURE:
<223> OTHER INFORMATION: C-term NH2

<400> SEQUENCE: 176

Ala Pro Gly Ser Thr Ala Pro Pro
1               5

<210> SEQ ID NO 177
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H2N
<220> FEATURE:
<223> OTHER INFORMATION: C-term CONH2

<400> SEQUENCE: 177

Lys Thr Thr Thr
1

<210> SEQ ID NO 178
<211> LENGTH: 5
<212> TYPE: PRT
<213> ORGANISM: Artificial Sequence
<220> FEATURE:
<223> OTHER INFORMATION: Description of Artificial Sequence: Synthetic
```

```
           peptide
<220> FEATURE:
<223> OTHER INFORMATION: N-term H2N
<220> FEATURE:
<223> OTHER INFORMATION: C-term CONH2

<400> SEQUENCE: 178

Lys Thr Thr Thr Gly
1               5

<210> SEQ ID NO 179
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H2N
<220> FEATURE:
<221> NAME/KEY: MOD_RES
<222> LOCATION: (6)..(6)
<223> OTHER INFORMATION: N-acetylgalactosamine modified residue
<220> FEATURE:
<221> NAME/KEY: MOD_RES
<222> LOCATION: (9)..(9)
<223> OTHER INFORMATION: N-acetylgalactosamine modified residue
<220> FEATURE:
<221> NAME/KEY: MOD_RES
<222> LOCATION: (11)..(11)
<223> OTHER INFORMATION: N-acetylgalactosamine modified residue
<220> FEATURE:
<223> OTHER INFORMATION: C-term OH

<400> SEQUENCE: 179

Lys Pro Val Pro Ser Thr Pro Pro Thr Pro Ser Cys
1               5                   10

<210> SEQ ID NO 180
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H2N
<220> FEATURE:
<223> OTHER INFORMATION: C-term OH

<400> SEQUENCE: 180

Lys Pro Val Pro Ser Thr Pro Pro Thr Pro Ser Cys
1               5                   10

<210> SEQ ID NO 181
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H2N
<220> FEATURE:
<221> NAME/KEY: MOD_RES
<222> LOCATION: (5)..(5)
<223> OTHER INFORMATION: N-acetylgalactosamine modified residue
<220> FEATURE:
<223> OTHER INFORMATION: C-term OH

<400> SEQUENCE: 181

Lys Pro Val Pro Ser Thr Pro Pro Thr Pro Ser Cys
```

```
                1               5                    10

<210> SEQ ID NO 182
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H2N
<220> FEATURE:
<221> NAME/KEY: MOD_RES
<222> LOCATION: (4)..(4)
<223> OTHER INFORMATION: N-acetylgalactosamine modified residue
<220> FEATURE:
<221> NAME/KEY: MOD_RES
<222> LOCATION: (7)..(7)
<223> OTHER INFORMATION: N-acetylgalactosamine modified residue
<220> FEATURE:
<221> NAME/KEY: MOD_RES
<222> LOCATION: (9)..(9)
<223> OTHER INFORMATION: N-acetylgalactosamine modified residue
<220> FEATURE:
<221> NAME/KEY: MOD_RES
<222> LOCATION: (11)..(11)
<223> OTHER INFORMATION: N-acetylgalactosamine modified residue
<220> FEATURE:
<223> OTHER INFORMATION: C-term OH

<400> SEQUENCE: 182

Lys Pro Ser Thr Pro Pro Thr Pro Ser Pro Ser Cys
1               5                   10

<210> SEQ ID NO 183
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H2N
<220> FEATURE:
<223> OTHER INFORMATION: C-term OH

<400> SEQUENCE: 183

Lys Pro Ser Thr Pro Pro Thr Pro Ser Pro Ser Cys
1               5                   10

<210> SEQ ID NO 184
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H2N
<220> FEATURE:
<221> NAME/KEY: MOD_RES
<222> LOCATION: (2)..(2)
<223> OTHER INFORMATION: N-acetylgalactosamine modified residue
<220> FEATURE:
<221> NAME/KEY: MOD_RES
<222> LOCATION: (5)..(5)
<223> OTHER INFORMATION: N-acetylgalactosamine modified residue
<220> FEATURE:
<221> NAME/KEY: MOD_RES
<222> LOCATION: (7)..(7)
<223> OTHER INFORMATION: N-acetylgalactosamine modified residue
<220> FEATURE:
<221> NAME/KEY: MOD_RES
<222> LOCATION: (9)..(9)
```

<223> OTHER INFORMATION: N-acetylgalactosamine modified residue
<220> FEATURE:
<223> OTHER INFORMATION: C-term OH

<400> SEQUENCE: 184

Lys Thr Pro Pro Thr Pro Ser Pro Ser Thr Pro Cys
1               5                   10

<210> SEQ ID NO 185
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H2N
<220> FEATURE:
<223> OTHER INFORMATION: C-term OH

<400> SEQUENCE: 185

Lys Thr Pro Pro Thr Pro Ser Pro Ser Thr Pro Cys
1               5                   10

<210> SEQ ID NO 186
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H2N
<220> FEATURE:
<221> NAME/KEY: MOD_RES
<222> LOCATION: (10)..(10)
<223> OTHER INFORMATION: N-acetylgalactosamine modified residue
<220> FEATURE:
<223> OTHER INFORMATION: C-term OH

<400> SEQUENCE: 186

Lys Thr Pro Pro Thr Pro Ser Pro Ser Thr Pro Cys
1               5                   10

<210> SEQ ID NO 187
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H2N
<220> FEATURE:
<221> NAME/KEY: MOD_RES
<222> LOCATION: (3)..(3)
<223> OTHER INFORMATION: N-acetylgalactosamine modified residue
<220> FEATURE:
<221> NAME/KEY: MOD_RES
<222> LOCATION: (5)..(5)
<223> OTHER INFORMATION: N-acetylgalactosamine modified residue
<220> FEATURE:
<221> NAME/KEY: MOD_RES
<222> LOCATION: (7)..(7)
<223> OTHER INFORMATION: N-acetylgalactosamine modified residue
<220> FEATURE:
<221> NAME/KEY: MOD_RES
<222> LOCATION: (11)..(11)
<223> OTHER INFORMATION: N-acetylgalactosamine modified residue
<220> FEATURE:
<223> OTHER INFORMATION: C-term OH

<400> SEQUENCE: 187

```
Lys Pro Thr Pro Ser Pro Ser Thr Pro Pro Thr Cys
1               5                   10
```

<210> SEQ ID NO 188
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H2N
<220> FEATURE:
<223> OTHER INFORMATION: C-term OH

<400> SEQUENCE: 188

```
Lys Pro Ser Pro Ser Thr Pro Pro Thr Pro Ser Cys
1               5                   10
```

<210> SEQ ID NO 189
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H2N
<220> FEATURE:
<221> NAME/KEY: MOD_RES
<222> LOCATION: (3)..(3)
<223> OTHER INFORMATION: N-acetylgalactosamine modified residue
<220> FEATURE:
<221> NAME/KEY: MOD_RES
<222> LOCATION: (5)..(5)
<223> OTHER INFORMATION: N-acetylgalactosamine modified residue
<220> FEATURE:
<221> NAME/KEY: MOD_RES
<222> LOCATION: (9)..(9)
<223> OTHER INFORMATION: N-acetylgalactosamine modified residue
<220> FEATURE:
<223> OTHER INFORMATION: C-term OH

<400> SEQUENCE: 189

```
Lys Pro Ser Pro Ser Thr Pro Pro Thr Pro Ser Cys
1               5                   10
```

<210> SEQ ID NO 190
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H2N
<220> FEATURE:
<221> NAME/KEY: MOD_RES
<222> LOCATION: (3)..(3)
<223> OTHER INFORMATION: N-acetylgalactosamine modified residue
<220> FEATURE:
<221> NAME/KEY: MOD_RES
<222> LOCATION: (7)..(7)
<223> OTHER INFORMATION: N-acetylgalactosamine modified residue
<220> FEATURE:
<223> OTHER INFORMATION: C-term OH

<400> SEQUENCE: 190

```
Lys Pro Ser Thr Pro Pro Thr Pro Ser Pro Ser Cys
1               5                   10
```

```
<210> SEQ ID NO 191
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H2N
<220> FEATURE:
<221> NAME/KEY: MOD_RES
<222> LOCATION: (4)..(4)
<223> OTHER INFORMATION: N-acetylgalactosamine modified residue
<220> FEATURE:
<221> NAME/KEY: MOD_RES
<222> LOCATION: (9)..(9)
<223> OTHER INFORMATION: N-acetylgalactosamine modified residue
<220> FEATURE:
<221> NAME/KEY: MOD_RES
<222> LOCATION: (11)..(11)
<223> OTHER INFORMATION: N-acetylgalactosamine modified residue
<220> FEATURE:
<223> OTHER INFORMATION: C-term OH

<400> SEQUENCE: 191

Lys Pro Ser Thr Pro Pro Thr Pro Ser Pro Ser Cys
1               5                   10

<210> SEQ ID NO 192
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H2N
<220> FEATURE:
<221> NAME/KEY: MOD_RES
<222> LOCATION: (9)..(9)
<223> OTHER INFORMATION: N-acetylgalactosamine modified residue
<220> FEATURE:
<223> OTHER INFORMATION: C-term OH

<400> SEQUENCE: 192

Lys Pro Ser Thr Pro Pro Thr Pro Ser Pro Ser Cys
1               5                   10
```